US012473282B2

(12) United States Patent
Zhang et al.

(10) Patent No.: US 12,473,282 B2
(45) Date of Patent: Nov. 18, 2025

(54) BIPHENYL FLUORINE DOUBLE BOND DERIVATIVE, PREPARATION METHOD THEREFOR, AND PHARMACEUTICAL APPLICATION THEREOF

(71) Applicant: Abbisko Therapeutics Co., Ltd., Shanghai (CN)

(72) Inventors: Mingming Zhang, Shanghai (CN); Baowei Zhao, Shanghai (CN); Fei Yang, Shanghai (CN); Haiyan Ying, Pudong New Area Shanghai (CN); Yongxian Zhang, Shanghai (CN); Hongping Yu, Shanghai (CN); Zhui Chen, Shanghai (CN); Yaochang Xu, Shanghai (CN)

(73) Assignee: ABBISKO THERAPEUTICS CO., LTD., Shanghai (CN)

( * ) Notice: Subject to any disclaimer, the term of this patent is extended or adjusted under 35 U.S.C. 154(b) by 844 days.

(21) Appl. No.: 17/777,767

(22) PCT Filed: Jan. 5, 2021

(86) PCT No.: PCT/CN2021/070300
§ 371 (c)(1),
(2) Date: May 18, 2022

(87) PCT Pub. No.: WO2021/139647
PCT Pub. Date: Jul. 15, 2021

(65) Prior Publication Data

US 2023/0014651 A1 Jan. 19, 2023

(30) Foreign Application Priority Data

Jan. 7, 2020 (CN) ......................... 202010015333.7
Aug. 27, 2020 (CN) ......................... 202010878389.5

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ............................ C07D 471/04; C07D 519/00
See application file for complete search history.

(56) References Cited

U.S. PATENT DOCUMENTS

2018/0177870 A1* 6/2018 Liu ...................... C07D 413/06
2019/0345170 A1 11/2019 Wu et al.

FOREIGN PATENT DOCUMENTS

| | | | |
|---|---|---|---|
| CN | 109890819 | A | 6/2019 |
| CN | 110267953 | A | 9/2019 |
| CN | 110582493 | A | 12/2019 |
| CN | 111039942 | A | 4/2020 |
| WO | 2018119286 | A1 | 6/2018 |
| WO | 2020011209 | A1 | 1/2020 |

OTHER PUBLICATIONS

Int'l Search Report & Written Opinion sent Apr. 2, 2021 in Int'l Application No. PCT/CN2021/070300.

* cited by examiner

*Primary Examiner* — Matthew P Coughlin
(74) *Attorney, Agent, or Firm* — Panitch Schwarze Belisario & Nadel LLP

(57) ABSTRACT

A biphenyl fluorine double bond derivative having a structure as represented by formula (I), a preparation method therefor, and a pharmaceutical application thereof. The biphenyl fluorine double bond derivative having the structure as represented by formula (I) can be widely applied in the preparation of medicaments for preventing and/or treating cancers or tumors, immune-related diseases and disorders, communicable diseases, infectious diseases or metabolic diseases mediated by PD-1/PD-L1 signal pathways, and is expected to be developed into a new generation of PD-1/PD-L1 inhibitors.

(I)

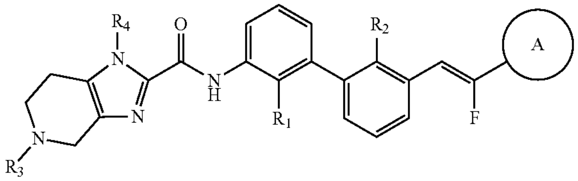

15 Claims, No Drawings

BIPHENYL FLUORINE DOUBLE BOND DERIVATIVE, PREPARATION METHOD THEREFOR, AND PHARMACEUTICAL APPLICATION THEREOF

CROSS-REFERENCE TO RELATED APPLICATIONS

This application is a Section 371 National Stage of International Application No. PCT/CN2021/070300, filed Jan. 5, 2021, which was published in the Chinese language on Jul. 15, 2021 under International Publication No. WO 2021/139647 A1, which claims priority under 35 U.S.C. § 119(b) to Chinese Application No. 202010015333.7, filed on Jan. 7, 2020, and Chinese Application No. 202010878389.5, filed on Aug. 27, 2020, the disclosures of which are incorporated herein by reference in their entireties.

TECHNICAL FIELD

The present invention belongs to the field of medicament synthesis, and in particular relates to a biphenyl fluoine double bond derivative, preparation method therefor, and pharmaceutical use thereof.

BACKGROUND

The immune system plays a very important role in controlling and eliminating diseases, such as cancer. However, tumor cells are often able to develop a strategy for escaping or suppressing the monitoring of the immune system to promote their malignant growth. One very important mechanism is to change the expression of co-stimulatory and co-inhibitory immune checkpoint molecules on immunocytes. Blocking the signal pathway of immune checkpoint molecules, such as PD1, has been proved to be an extremely promising and effective therapy.

Programmed cell death protein 1 (PD-1), also known as CD279, is a receptor expressed on the surfaces of activated T cells, natural killer T cells, B cells and macrophages. The structure of PD-1 contains an extracellular domain similar to an immunoglobulin variable region, a transmembrane domain and an intracellular domain, wherein the intracellular domain contains two phosphorylation sites located in an immunoreceptor tyrosine kinase-based inhibitory domain and an immunoreceptor tyrosine kinase-based transduction domain, suggesting that PD1 can down-regulate T cell receptor-mediated signal pathways.

PD1 has two ligands: PD-L1 and PDL2, and they are different in their expression profile. The expression of PDL1 will be up-regulated in macrophages and dendritic cells after treatment with lipopolysaccharide (LPS) and granulocyte-macrophage colony-stimulating factor (GM-CSF), and will also be up-regulated in T cells and B cells after stimulation of T cell receptor and B cell receptor signal pathways. PD-L1 is also highly expressed in almost all tumor cells, and the expression will be up-regulated after stimulation of interferon (IFN) gamma. As a matter of fact, the expression of PDL1 in a variety of tumors is considered to have prognostic relevance, but the expression of PD-L2 is relatively concentrated, and mainly on dendritic cells.

When T cells expressing PD-1 come into contact with cells expressing the ligands of PD-1, those antigen-stimulated functional activities, such as cell proliferation, cytokine release and cell lysis activity, are all inhibited. Therefore, the interaction between PD1 and its ligands thereof can function as an intrinsic negative feedback regulation mechanism to prevent T cell hyperactivation during infection, immune tolerance or tumorigenesis, thus reducing the occurrence of autoimmune diseases and promoting self tolerance. Long-term antigen stimulation, e.g., in tumor or long-term infection, will cause T cells to express high level of PD-1, gradually lose activities in response to these long-term antigens, and eventually become nonfunctional, namely, the so-called T cell exhaustion. B cells also have the inhibitory effect caused by PD1 and ligands thereof and corresponding functional exhaustion.

Some evidence from preclinical animal studies have indicated that PD-1 and its ligands thereof can down-regulate the immunoreaction. PD-1-deficient mice will develop lupus erythematosus-like acute proliferative glomerulonephritis and dilated cardiomyopathy. Utilizing the antibody of PDL1 to block the interaction between PD-1 and PDL1 has been proved to be able to restore and enhance T cell activation in many systems. The monoclonal antibody of PDL1 can also benefit patients with advanced cancers. In some preclinical animal tumor models, it was also shown that blocking the signal pathway of PD-1/PD-L1 with a monoclonal antibody can enhance the immunoreaction and lead to immunoreactions to a series of histologically different tumors. With the long-term infection LCMV model, the interaction between PD-1 and PD-L1 has been found to be able to inhibit the activation and proliferation of virus-specific CD8 T cells and the acquisition of effector cell functions. Besides being capable of enhancing the immunoreaction to long-term antigens, blocking the pathway of PD-1/PDL1 was also discovered to be able to enhance response to vaccines, including response to a therapeutic vaccine in long-term infection.

To sum up, if, besides the existing monoclonal antibody, a compound for blocking the interaction between PD1 and PDL1 can be developed, it can serve as an effective therapeutic means for blocking the PD-1/PDL1-mediated inhibitory signal pathway to enhance or restore the function of T cells. Therefore, the compound specifically blocking the interaction between PD-1 and PD-L1 will achieve a good therapeutic effect in immunotherapies for a variety of cancers and other immunity-associated diseases.

SUMMARY OF THE INVENTION

The object of the present invention is to provide a biphenyl fluorine double bond derivative for blocking the interaction between PD-1 and PD-L1, and thus to hopefully develop a new generation of PD-1/PD-L1 inhibitors.

The first aspect of the invention provides a compound of formula (I), a stereoisomer, prodrug or pharmaceutically acceptable salt thereof:

(I)

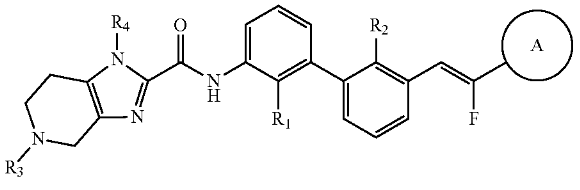

wherein, ring A is selected from the group consisting of:

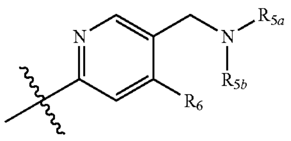

or

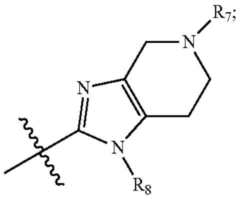

$R_1$ and $R_2$ are each independently selected from the group consisting of hydrogen, deuterium, halogen, cyano, hydroxy, carboxyl, $C_{1-10}$ alkyl, $C_{3-10}$ cycloalkyl and $C_{1-10}$ alkoxy, above groups are optionally further substituted by one or more substituents selected from the group consisting of deuterium, halogen, cyano, cyclopropyl, hydroxy and $C_{1-4}$ alkoxy;

$R_3$ is selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$, above groups are optionally more further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_1$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$;

$R_4$ is selected from the group consisting of hydrogen, deuterium, hydroxy, $C_{1-10}$ alkyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, cyano, cyclopropyl, hydroxy and $C_{1-4}$ alkoxy;

$R_{5a}$ and $R_{5b}$ are each independently selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl and 5-10 membered heteroaryl, or, $R_{5a}$ and $R_{5b}$, together with the nitrogen atom directly attached thereto, form 4-10 membered heterocyclyl, or, the formed 4-10 membered heterocyclyl is fused to $C_{5-10}$ aryl or 5-10 membered heteroaryl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)$ $R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$, above groups are optionally more further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$;

$R_6$ is selected from the group consisting of hydrogen, deuterium, halogen, cyano, hydroxy, carboxyl, $C_{1-10}$ alkyl, $C_{3-10}$ cycloalkyl and $C_{1-10}$ alkoxy, above groups are optionally further substituted by one or more substituents selected from the group consisting of deuterium, halogen, cyano, cyclopropyl, hydroxy and $C_{1-4}$ alkoxy;

$R_7$ is selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$, above groups are optionally more further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$;

$R_8$ is selected from the group consisting of hydrogen, deuterium, hydroxy, $C_{1-10}$ alkyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, cyano, cyclopropyl, hydroxy and $C_{1-4}$ alkoxy;

each $R_9$ is independently selected from the group consisting of hydrogen, deuterium, hydroxy, $C_{1-10}$ alkyl, $C_{2-10}$ alkenyl, $C_{3-10}$ cycloalkyl, 3-10 membered heterocyclyl, $C_{5-10}$ aryl, 5-10 membered heteroaryl and $-NR_{12}R_{13}$, above groups are optionally further substituted by one or more substituents selected from the group consisting of deuterium, halogen, hydroxy, oxo, cyano, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $-NR_{12}R_{13}$;

each $R_{10}$ is independently selected from the group consisting of hydrogen, deuterium, $C_{1-10}$ alkyl, $C_{2-10}$ alkenyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, hydroxy, oxo, cyano, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $—NR_{12}R_{13}$;

each $R_1$ is independently selected from the group consisting of hydrogen, deuterium, hydroxy, $C_{1-10}$ alkyl, $C_{1-10}$ alkoxy, $C_{2-10}$ alkenyl, $C_{2-10}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $—NR_{12}R_{13}$, above groups are optionally further substituted by one or more substituents selected from the group consisting of deuterium, halogen, hydroxy, cyano, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $—NR_{12}R_{13}$; each of $R_{12}$ and $R_{13}$ is independently selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, sulfonyl, methanesulfonyl, isopropylsulfonyl, cyclopropylsulfonyl, p-toluenesulfonyl, amino, $C_{1-10}$ monoalkylamino, di($C_{1-10}$ alkyl)amino and $C_{1-10}$ alkanoyl, above groups are optionally further substituted by one or more substituents selected from the group consisting of deuterium, halogen, hydroxy, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, $C_{1-10}$ monoalkylamino, di($C_{1-10}$ alkyl)amino and $C_{1-10}$ alkanoyl;

or, $R_{12}$ and $R_{13}$, together with the nitrogen atom directly attached thereto, form 4-10 membered heterocyclyl, above group is optionally further substituted by one or more substituents selected from the group consisting of deuterium, halogen, hydroxy, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, $C_{1-10}$ monoalkylamino, di($C_{1-10}$ alkyl)amino and $C_{1-10}$ alkanoyl;

each r is independently 0, 1 or 2.

In a preferred embodiment, in the compound of formula (I), the stereoisomer, prodrug or pharmaceutically acceptable salt thereof, $R_1$ and $R_2$ are each independently selected from the group consisting of hydrogen, deuterium, halogen, cyano, hydroxy, carboxyl, $C_{1-4}$ alkyl, $C_{3-6}$ cycloalkyl and $C_{1-4}$ alkoxy, above groups are optionally further substituted by one or more substituents selected from the group consisting of deuterium, halogen, cyano, cyclopropyl, hydroxy and $C_{1-4}$ alkoxy.

In a preferred embodiment, in the compound of formula (I), the stereoisomer, prodrug or pharmaceutically acceptable salt thereof, $R_4$ is selected from the group consisting of hydrogen, deuterium, hydroxy, $C_{1-4}$ alkyl, $C_{3-6}$ cycloalkyl, 3-6 membered heterocyclyl, $C_{5-8}$ aryl and 5-8 membered heteroaryl, above groups are optionally further substituted by one or more substituents selected from the group consisting of deuterium, halogen, cyano, cyclopropyl, hydroxy and $C_{1-4}$ alkoxy.

In a preferred embodiment, in the compound of formula (I), the stereoisomer, prodrug or pharmaceutically acceptable salt thereof, $R_8$ is selected from the group consisting of hydrogen, deuterium, hydroxy, $C_{1-4}$ alkyl, and $C_{3-6}$ cycloalkyl, above groups are optionally further substituted by one or more substituents selected from the group consisting of deuterium, halogen, cyano, cyclopropyl, hydroxy and $C_{1-4}$ alkoxy.

In a preferred embodiment, in the compound of formula (I), the stereoisomer, prodrug or pharmaceutically acceptable salt thereof, $R_6$ is selected from the group consisting of hydrogen, deuterium, halogen, cyano, hydroxy, carboxyl, $C_{1-4}$ alkyl, $C_{3-6}$ cycloalkyl and $C_{1-4}$ alkoxy, above groups are optionally further substituted by one or more substituents selected from the group consisting of deuterium, halogen, cyano, cyclopropyl, hydroxy and $C_{1-4}$ alkoxy.

In a preferred embodiment, in the compound of formula (I), the stereoisomer, prodrug, or pharmaceutically acceptable salt thereof, $R_3$ is selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, $=O$, $—C_{0-4}—S(O)_rR_9$, $—C_{0-4}—O—R_{10}$, $—C_{0-4}—C(O)OR_{10}$, $—C_{0-4}—C(O)R_{11}$, $—C_{0-4}—O—C(O)R_{11}$, $—C_{0-4}—NR_{12}R_{13}$, $—C_{0-4}—C(=NR_{12})R_{11}$, $—C_{0-4}—N(R_{12})—C(=NR_{13})R_{11}$, $—C_{0-4}—C(O)NR_{12}R_{13}$ and $—C_{0-4}—N(R_{12})—C(O)R_{11}$, above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, $=O$, $—C_{0-4}—S(O)_rR_9$, $—C_{0-4}—O—R_{10}$, $—C_{0-4}—C(O)OR_{10}$, $—C_{0-4}—C(O)R_{11}$, $—C_{0-4}—O—C(O)R_{11}$, $—C_{0-4}—NR_{12}R_{13}$, $—C_{0-4}—C(=NR_{12})R_{11}$, $—C_{0-4}—N(R_{12})—C(=NR_{13})R_{11}$, $—C_{0-4}—C(O)NR_{12}R_{13}$ and $—C_{0-4}—N(R_{12})—C(O)R_{11}$;

wherein, $R_9$, $R_{10}$, $R_{11}$, $R_{12}$, $R_{13}$ and r are defined as those in the compound of formula (I).

In a preferred embodiment, in the compound of formula (I), the stereoisomer, prodrug, or pharmaceutically acceptable salt thereof, $R_7$ is selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, $=O$, $—C_{0-4}—S(O)_rR_9$, $—C_{0-4}—O—R_{10}$, $—C_{0-4}—C(O)OR_{10}$, $—C_{0-4}—C(O)R_{11}$, $—C_{0-4}—O—C(O)R_{11}$, $—C_{0-4}—NR_{12}R_{13}$, $—C_{0-4}—C(=NR_{12})R_{11}$, $—C_{0-4}—N(R_{12})—C(=NR_{13})R_{11}$, $—C_{0-4}—C(O)NR_{12}R_{13}$ and $—C_{0-4}—N(R_{12})—C(O)R_{11}$, above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, $=O$, $-C_{0-4}-S(O)_rR_9$, $-C_{0-4}-O-R_{10}$, $-C_{0-4}-C(O)OR_{10}$, $-C_{0-4}-C(O)R_{11}$, $-C_{0-4}-O-C(O)R_{11}$, $-C_{0-4}-NR_{12}R_{13}$, $-C_{0-4}-C(=NR_{12})R_{11}$, $-C_{0-4}-N(R_{12})-C(=NR_{13})R_{11}$, $-C_{0-4}-C(O)NR_{12}R_{13}$ and $-C_{0-4}-N(R_{12})-C(O)R_{11}$;

wherein, $R_9$, $R_{10}$, $R_{11}$, $R_{12}$, $R_{13}$ and r are defined as those in the compound of formula (I).

In a preferred embodiment, in the compound of formula (I), the stereoisomer, prodrug, or pharmaceutically acceptable salt thereof, $R_{5a}$ and $R_{5b}$ are each independently selected from the group consisting of hydrogen, deuterium, hydroxy, $C_{1-4}$ alkyl, $C_{2-4}$ alkenyl, $C_{2-4}$ alkynyl, $C_{3-10}$ cycloalkyl, 3-10 membered heterocyclyl, $C_{5-8}$ aryl and 5-8 membered heteroaryl, or, $R_{5a}$ and $R_{5b}$, together with the nitrogen atom directly attached thereto, form 4-8 membered heterocyclyl, or, the formed 4-8 membered heterocyclyl is fused to $C_{5-8}$ aryl or 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, =O, $-C_{0-4}-S(O)_rR_9$, $-C_{0-4}-O-R_{10}$, $-C_{0-4}-C(O)OR_{10}$, $-C_{0-4}-C(O)R_{11}$, $-C_{0-4}-O-C(O)R_{11}$, $-C_{0-4}-NR_{12}R_{13}$, $-C_{0-4}-C(=NR_{12})R_{11}$, $-C_{0-4}-N(R_{12})-C(=NR_{13})R_{11}$, $-C_{0-4}-C(O)NR_{12}R_{13}$ and $-C_{0-4}-N(R_{12})-C(O)R_{11}$, above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, $-C_{0-4}-S(O)_rR_9$, $-C_{0-4}-O-R_{10}$, $-C_{0-4}-C(O)OR_{10}$, $-C_{0-4}-C(O)R_{11}$, $-C_{0-4}-O-C(O)R_{11}$, $-C_{0-4}-NR_{12}R_{13}$, $-C_{0-4}-C(=NR_{12})R_{11}$, $-C_{0-4}-N(R_{12})-C(=NR_{13})R_{11}$, $-C_{0-4}-C(O)NR_{12}R_{13}$ and $-C_{0-4}-N(R_{12})-C(O)R_{11}$;

wherein, $R_9$, $R_{10}$, $R_{11}$, $R_{12}$, $R_{13}$ and r are defined as those in the compound of formula (I).

In a preferred embodiment, in the compound of formula (I), the stereoisomer, prodrug, or pharmaceutically acceptable salt thereof, $R_{5a}$ is hydrogen or $C_{1-4}$ alkyl, $R_{5b}$ is selected from the group consisting of hydrogen, deuterium, hydroxy, $C_{1-4}$ alkyl, $C_{2-4}$ alkenyl, $C_{2-4}$ alkynyl, $C_{3-10}$ cycloalkyl, 3-10 membered heterocyclyl, $C_{5-8}$ aryl and 5-8 membered heteroaryl, or, $R_{5a}$ and $R_{5b}$, together with the nitrogen atom directly attached thereto, form 4-8 membered heterocyclyl, the formed 4-8 membered heterocyclyl is fused to $C_{5a}$ aryl or 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, =O, $-S(O)_rR_9$, $-O-R_{10}$, $-C(O)OR_{10}$, $-C(O)R_{11}$, $-O-C(O)R_{11}$, $-NR_{12}R_{13}$, $-C(=NR_{12})R_{11}$, $-N(R_{12})-C(=NR_{13})R_{11}$, $-C(O)NR_{12}R_{13}$ and $-N(R_{12})-C(O)R_{11}$, above groups are optionally more further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, $-S(O)_rR_9$, $-O-R_{10}$, $-C(O)OR_{10}$, $-C(O)R_{11}$, $-O-C(O)R_{11}$, $-NR_{12}R_{13}$, $-C(=NR_{12})R_{11}$, $-N(R_{12})-C(=NR_{13})R_{11}$, $-C(O)NR_{12}R_{13}$ and $-N(R_{12})-C(O)R_{11}$;

wherein, $R_9$, $R_{10}$, $R_{11}$, $R_{12}$, $R_{13}$ and r are defined as those in the compound of formula (I).

In a further preferred embodiment, in the compound of formula (I), the stereoisomer, prodrug, or pharmaceutically acceptable salt thereof, the compound of formula (I) is a compound with the structure shown as formula (IIa):

(IIa)

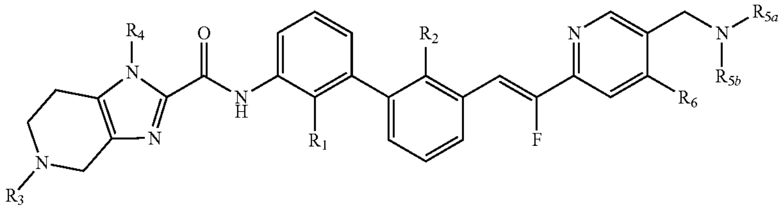

wherein, $R_1$ and $R_2$ are each independently selected from the group consisting of hydrogen, deuterium, halogen, cyano, hydroxy, carboxyl, $C_{1-4}$ alkyl, $C_{3-6}$ cycloalkyl and $C_{1-4}$ alkoxy;

$R_3$ is selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are optionally further substituted by one or more substituents selected from the group consisting of deuterium, halogen, cyano, $C_{1-4}$ alkyl, $C_{3-8}$ cycloalkyl, 3-8 membered heterocyclyl, $C_{5-8}$ aryl, 5-8 membered heteroaryl, =O, $-S(O)_rR_9$, $-O-R_{10}$, $-C(O)OR_{10}$, $-C(O)R_{11}$, $-O-C(O)R_{11}$, $-NR_{12}R_{13}$, $-C(=NR_{12})R_{11}$, $-N(R_{12})-C(=NR_{13})R_{11}$, $-C(O)NR_{12}R_{13}$ and $-N(R_{12})-C(O)R_{11}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, $-S(O)_rR_9$, $-O-R_{10}$, $-C(O)OR_{10}$, $-C(O)R_{11}$, $-O-C(O)R_{11}$, $-NR_{12}R_{13}$, $-C(=NR_{12})R_{11}$, $-N(R_{12})-C(=NR_{13})R_{11}$, $-C(O)NR_{12}R_{13}$ and $-N(R_{12})-C(O)R_{11}$;

$R_4$ is selected from the group consisting of hydrogen, deuterium, hydroxy, methyl, ethyl, isopropyl, difluoromethyl, dideuteriomethyl, trifluoromethyl, trideuteriomethyl, cyclopropyl and cyclobutyl;

$R_{5a}$ is hydrogen or $C_{1-4}$ alkyl, $R_{5b}$ is selected from the group consisting of hydrogen, deuterium, hydroxy, $C_{1-4}$ alkyl, $C_{2-4}$ alkenyl, $C_{2-4}$ alkynyl, $C_{3-10}$ cycloalkyl, 3-10 membered heterocyclyl, $C_{5-8}$ aryl and 5-8 membered heteroaryl, or, $R_{5a}$ and $R_{5b}$, together with the nitrogen atom directly attached thereto, form 4-8 membered heterocyclyl, or, $R_{5a}$ and $R_{5b}$, together with the nitrogen atom directly attached thereto, form the following group:

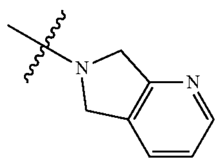

or

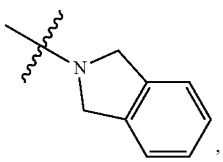

, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, and —NR$_{12}$R$_{13}$, above groups are optionally more further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, and —NR$_{12}$R$_{13}$;

$R_6$ is selected from the group consisting of hydrogen, deuterium, halogen, cyano, hydroxy, carboxyl, methyl, ethyl, isopropyl, difluoromethyl, dideuteriomethyl, trifluoromethyl, trideuteriomethyl, cyclopropyl, cyclobutyl, methoxy, ethyoxy and isopropoxy;

wherein, $R_9$, $R_{10}$, $R_{11}$, $R_{12}$, $R_{13}$ and r are defined as those in the compound of formula (I).

In a further preferred embodiment, in the compound of formula (I), the stereoisomer, prodrug, or pharmaceutically acceptable salt thereof, the compound of formula (I) is a compound with the structure shown as formula (IIb):

(IIb)

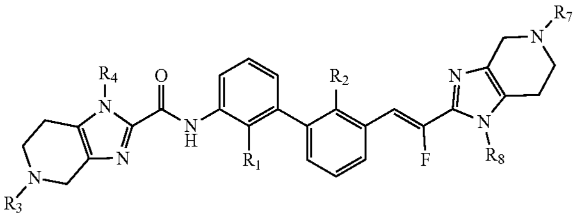

wherein, $R_1$ and $R_2$ are each independently selected from the group consisting of hydrogen, deuterium, halogen, cyano, hydroxy, carboxyl, $C_{1-4}$ alkyl, $C_{3-6}$ cycloalkyl and $C_{1-4}$ alkoxy;

$R_3$ is selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are optionally further substituted by one or more substituents selected from the group consisting of deuterium, halogen, cyano, $C_{1-4}$ alkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, —NR$_{12}$R$_{13}$, —C(=NR$_{12}$)R$_{11}$, —N(R$_{12}$)—C(=NR$_{13}$)R$_{11}$, —C(O)NR$_{12}$R$_{13}$ and —N(R$_{12}$)—C(O)R$_{11}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, —NR$_{12}$R$_{13}$, —C(=NR$_{12}$)R$_{11}$, —N(R$_{12}$)—C(=NR$_{13}$) R$_{11}$, —C(O)NR$_{12}$R$_{13}$ and —N(R$_{12}$)—C(O)R$_{11}$;

$R_4$ is selected from the group consisting of hydrogen, deuterium, hydroxy, methyl, ethyl, isopropyl, difluoromethyl, dideuteriomethyl, trifluoromethyl, trideuteriomethyl, cyclopropyl and cyclobutyl;

$R_7$ is selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are optionally further substituted by one or more substituents selected from the group consisting of deuterium, halogen, cyano, $C_{1-4}$ alkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, —NR$_{12}$R$_{13}$, —C(=NR$_{12}$)R$_{11}$, —N(R$_{12}$)—C(=NR$_{13}$)R$_{11}$, —C(O)NR$_{12}$R$_{13}$ and —N(R$_{12}$)—C(O)R$_{11}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, —NR$_{12}$R$_{13}$, —C(=NR$_{12}$)R$_{11}$, —N(R$_{12}$)—C(=NR$_{13}$) R$_{11}$, —C(O)NR$_{12}$R$_{13}$ and —N(R$_{12}$)—C(O)R$_{11}$;

$R_8$ is selected from the group consisting of hydrogen, deuterium, hydroxy, methyl, ethyl, isopropyl, difluoromethyl, dideuteriomethyl, trifluoromethyl, trideuteriomethyl, cyclopropyl and cyclobutyl;

wherein, $R_9$, $R_{10}$, $R_{11}$, $R_{12}$, $R_{13}$ and r are defined as those in the compound of formula (I).

In a preferred embodiment, in the compound of formula (I), the stereoisomer, prodrug, or pharmaceutically acceptable salt thereof, $R_3$ is selected from the group consisting of hydrogen, deuterium, $C_{1-4}$ alkyl, $C_{3-8}$ cycloalkyl and 3-8 membered heterocyclyl, above groups are optionally further substituted by one or more substituents selected from the group consisting of deuterium, halogen, cyano, $C_{1-4}$ alkyl, $C_{3-8}$ cycloalkyl, 3-8 membered heterocyclyl, =O, —O—R$_{10}$, —C(O)OR$_{10}$, —C(O)R$_{11}$ and —O—C(O)R$_{11}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, =O, —O—R$_{10}$, —C(O)OR$_{10}$, —C(O)R$_{11}$, and —O—C(O) R$_{11}$;

$R_4$ is selected from the group consisting of hydrogen, deuterium, methyl, difluoromethyl, dideuteriomethyl, trifluoromethyl, trideuteriomethyl, and cyclopropyl;

wherein, $R_{10}$ and $R_{11}$ are defined as those in the compound of formula (I).

In a preferred embodiment, in the compound of formula (I), the stereoisomer, prodrug, or pharmaceutically acceptable salt thereof, $R_{5a}$ is hydrogen or methyl, $R_{5b}$ is selected from the group consisting of hydrogen, deuterium, $C_{1-4}$ alkyl, $C_{3-10}$ cycloalkyl and 3-10 membered heterocyclyl, or, $R_{5a}$ and $R_{5b}$, together with the nitrogen atom directly attached thereto, form 4-8 membered nitrogen-containing heterocyclyl, or, $R_{5a}$ and $R_{5b}$, together with the nitrogen atom directly attached thereto, form the following group:

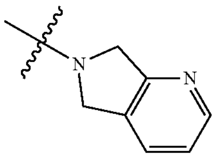

or

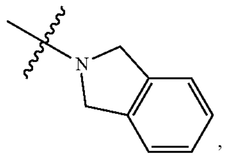

, above groups are optionally further substituted by one or more substituents selected from the group consisting of deuterium, halogen, cyano, $C_{1-4}$ alkyl, $C_{3-8}$ cycloalkyl, 3-8 membered heterocyclyl, =O, —O—$R_{10}$, —C(O)O$R_{10}$, —C(O)$R_{11}$, —O—C(O)$R_{11}$ and —N$R_{12}R_{13}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, =O, —O—$R_{10}$, —C(O)O$R_{10}$, —C(O)$R_{11}$, —O—C(O)$R_{11}$, and —N$R_{12}R_{13}$;

$R_6$ is selected from the group consisting of hydrogen, deuterium, methyl, difluoromethyl, dideuteriomethyl, trifluoromethyl, trideuteriomethyl, cyclopropyl methoxy, and ethyoxy;

wherein, $R_{10}$, $R_{11}$, $R_{12}$ and $R_{13}$ are defined as those in the compound of formula (I).

In a preferred embodiment, in the compound of formula (I), the stereoisomer, prodrug, or pharmaceutically acceptable salt thereof, $R_7$ is selected from the group consisting of hydrogen, deuterium, $C_{1-4}$ alkyl, $C_{3-8}$ cycloalkyl and 3-8 membered heterocyclyl, above groups are optionally further substituted by one or more substituents selected from the group consisting of deuterium, halogen, cyano, $C_{1-4}$ alkyl, $C_{3-8}$ cycloalkyl, 3-8 membered heterocyclyl, =O, —O—$R_{10}$, —C(O)O$R_{10}$, —C(O)$R_{11}$ and —O—C(O)$R_{11}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, =O, —O—$R_{10}$, —C(O)O$R_{10}$, —C(O)$R_{11}$, and —O—C(O)$R_{11}$;

$R_8$ is selected from the group consisting of hydrogen, deuterium, methyl, difluoromethyl, dideuteriomethyl, trifluoromethyl, trideuteriomethyl, and cyclopropyl;

wherein, $R_{10}$ and $R_{11}$ are defined as those in the compound of formula (I).

In a preferred embodiment, in the compound of formula (I), the stereoisomer, prodrug, or pharmaceutically acceptable salt thereof, each $R_9$ is independently selected from the group consisting of hydrogen, deuterium, hydroxy, $C_{1-4}$ alkyl, $C_{2-4}$ alkenyl, $C_{3-6}$ cycloalkyl, 3-6 membered heterocyclyl, $C_{5-8}$ aryl, 5-8 membered heteroaryl and —N$R_{12}R_{13}$, above groups are optionally further substituted by one or more substituents selected from the group consisting of deuterium, halogen, hydroxy, oxo, cyano, $C_{1-4}$ alkyl, $C_{1-4}$ alkoxy, $C_{3-6}$ cycloalkyl, $C_{3-6}$ cycloalkyloxy, 3-8 membered heterocyclyl, 3-8 membered heterocyclyloxy, $C_{5-8}$ aryl, $C_{5-8}$ aryloxy, 5-8 membered heteroaryl, 5-8 membered heteroaryloxy and —N$R_{12}R_{13}$;

each $R_{10}$ is independently selected from the group consisting of hydrogen, deuterium, $C_{1-4}$ alkyl, $C_{2-4}$ alkenyl, $C_{3-4}$ cycloalkyl, 3-6 membered heterocyclyl, $C_{5-8}$ aryl and 5-8 membered heteroaryl, above groups are optionally further substituted by one or more substituents selected from the group consisting of deuterium, halogen, hydroxy, oxo, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —N$R_{12}R_{13}$;

each $R_{11}$ is independently selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —N$R_{12}R_{13}$, above groups are optionally further substituted by one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —N$R_{12}R_{13}$;

each of $R_{12}$ and $R_{13}$ is independently selected from the group consisting of hydrogen, deuterium, hydroxy, $C_{1-4}$ alkyl, $C_{2-4}$ alkenyl, $C_{2-4}$ alkynyl, $C_{3-6}$ cycloalkyl, 3-6 membered heterocyclyl, $C_{5-8}$ aryl, 5-8 membered heteroaryl, sulfonyl, methanesulfonyl, isopropylsulfonyl, cyclopropylsulfonyl, p-toluenesulfonyl, amino, $C_{1-4}$ monoalkylamino, di($C_{1-4}$ alkyl)amino and $C_{1-4}$ alkanoyl, above groups are optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy, amino, $C_{1-4}$ monoalkylamino, di($C_{1-4}$ alkyl)amino and $C_{1-4}$ alkanoyl;

or, $R_{12}$ and $R_{13}$, together with the nitrogen atom directly attached thereto, form 4-6 membered heterocyclyl, above group is optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy, amino, $C_{1-4}$ monoalkylamino, di($C_{1-4}$ alkyl)amino and $C_{1-4}$ alkanoyl.

In a preferred embodiment, the compound of formula (I), the stereoisomer, prodrug, or pharmaceutically acceptable salt thereof, includes, but is not limited to, the following compounds:

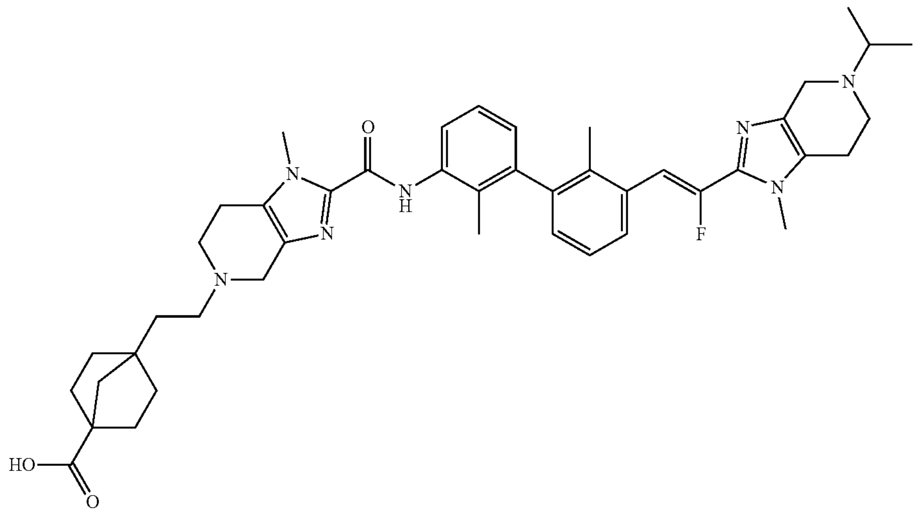
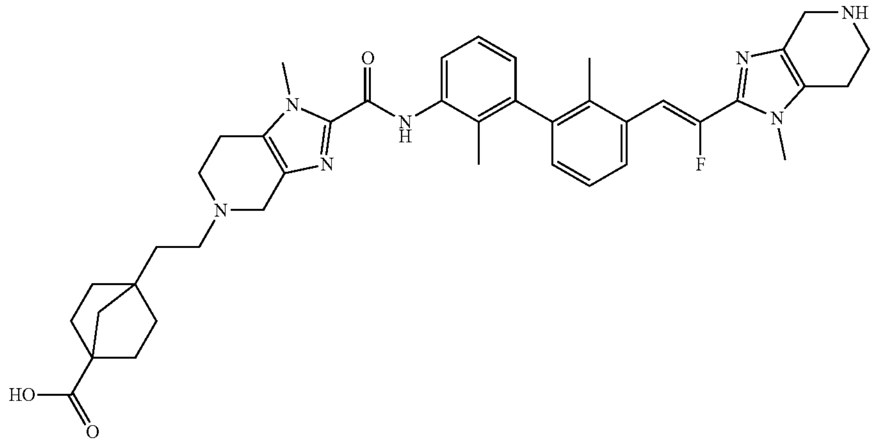
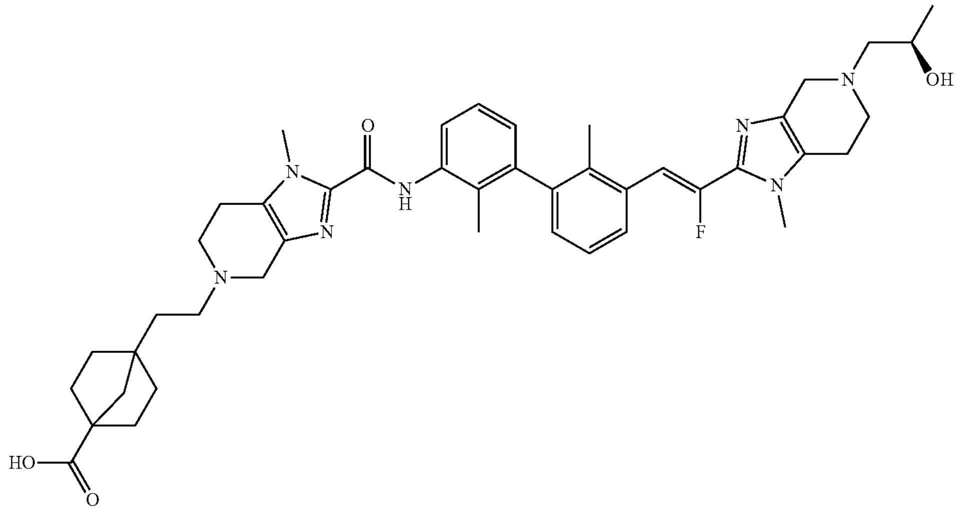

-continued
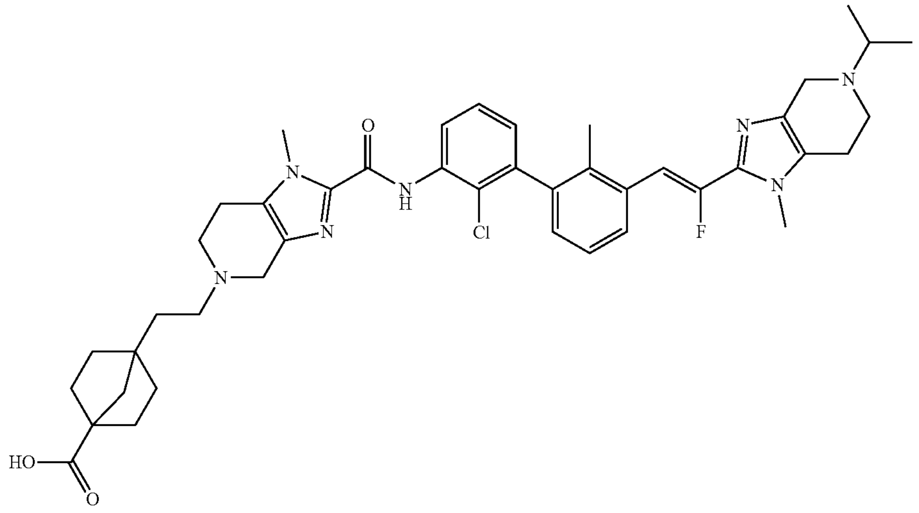
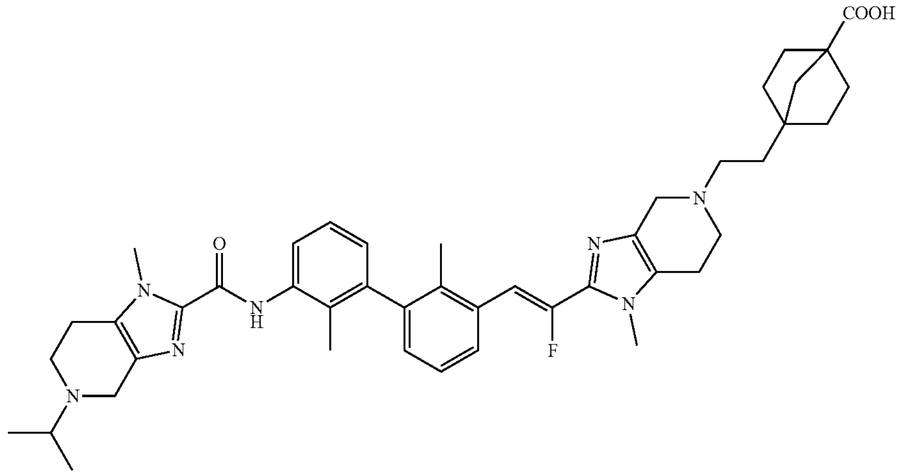
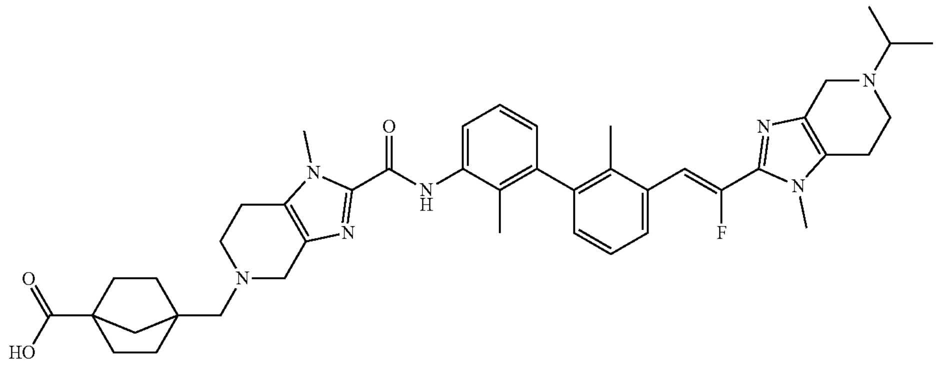

-continued
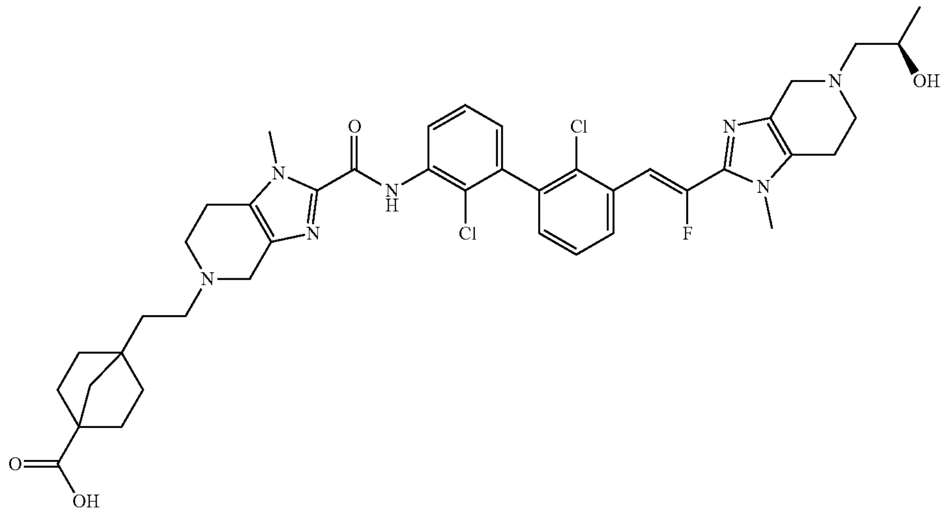
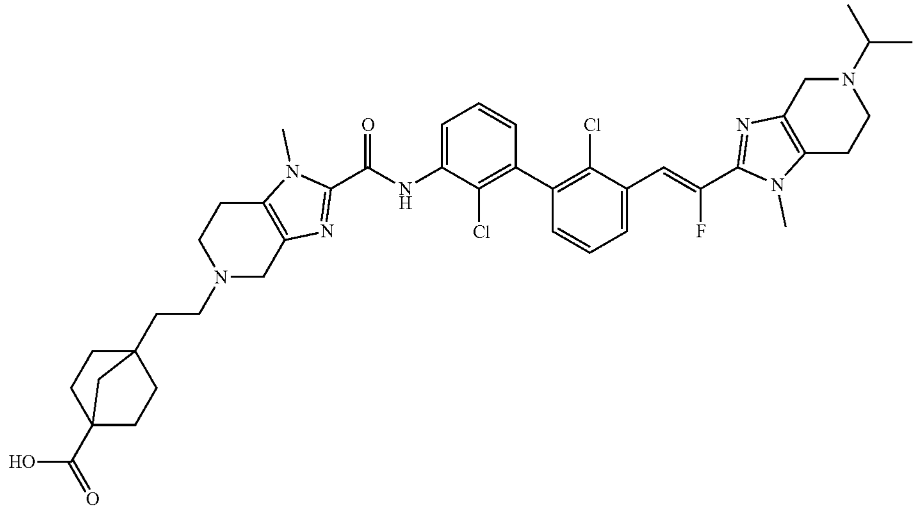
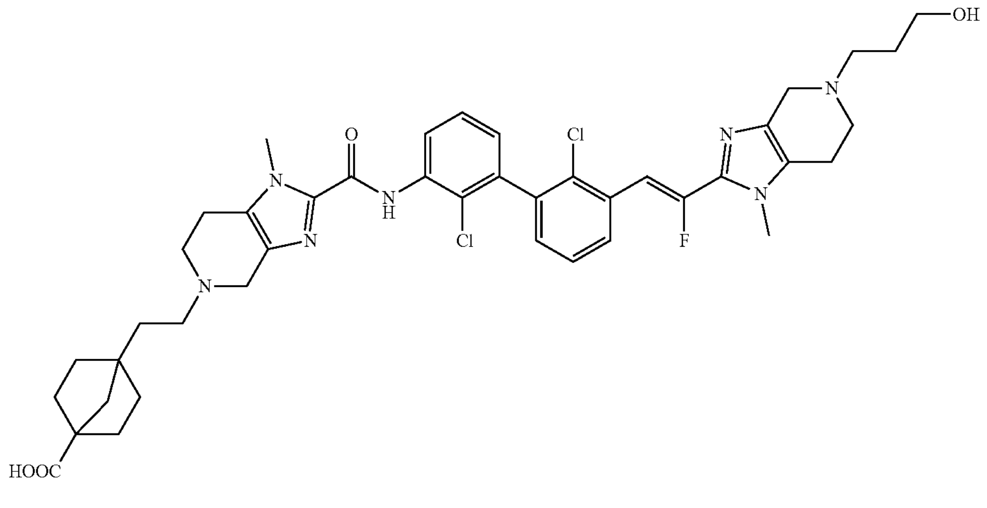

-continued
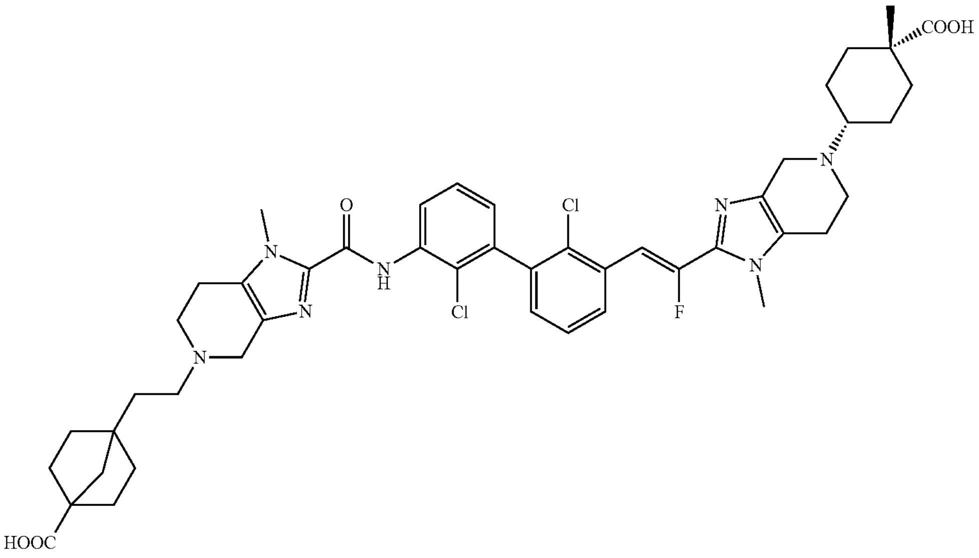
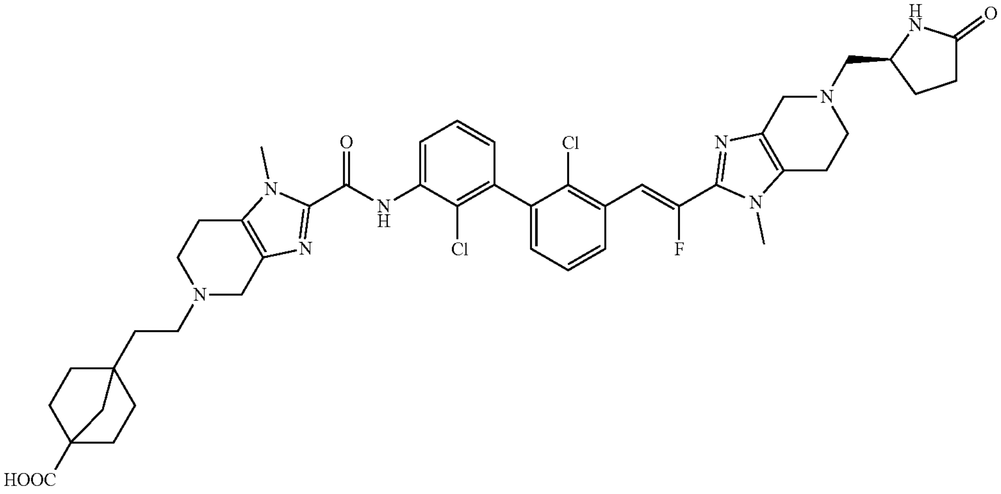
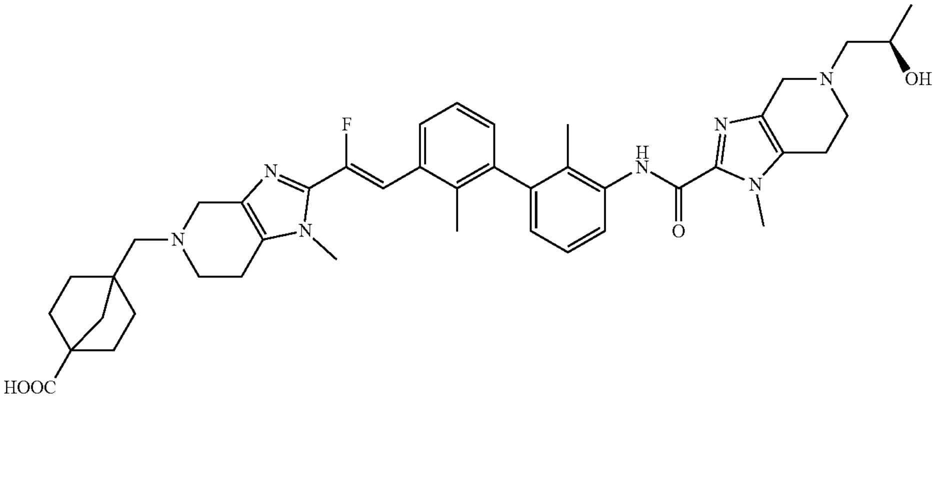

-continued
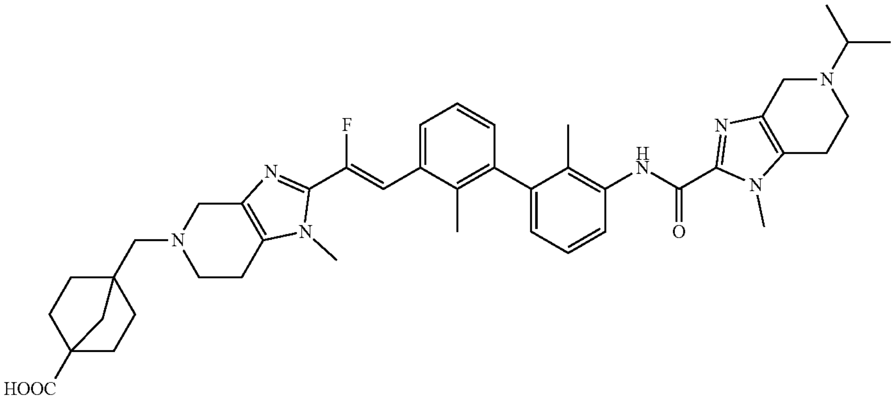
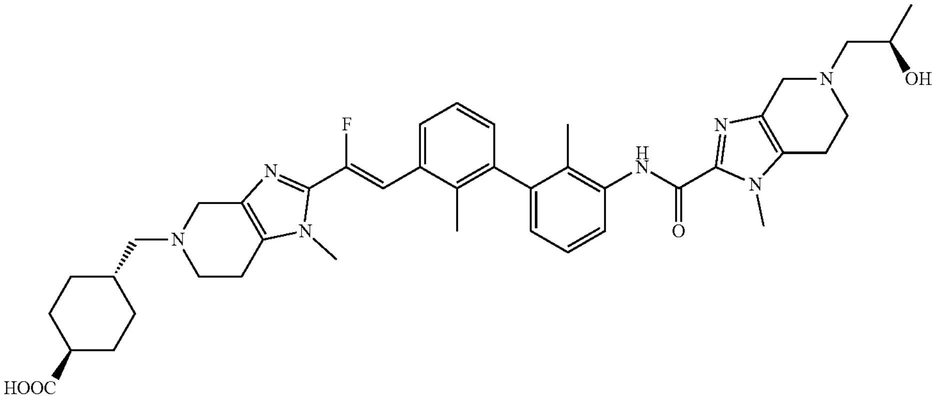
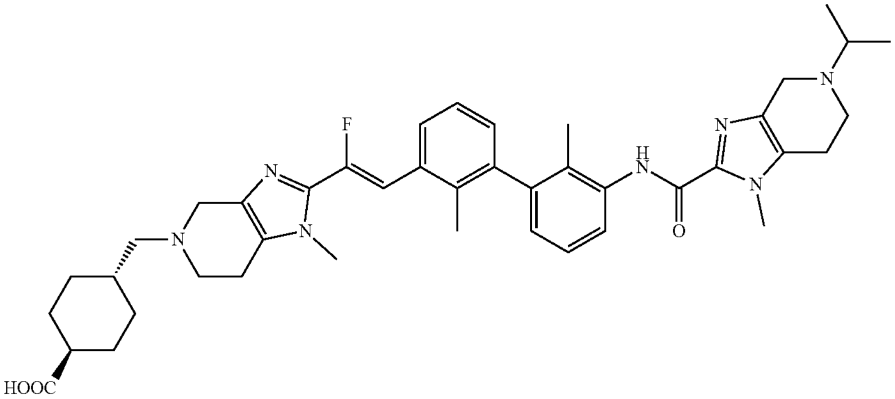
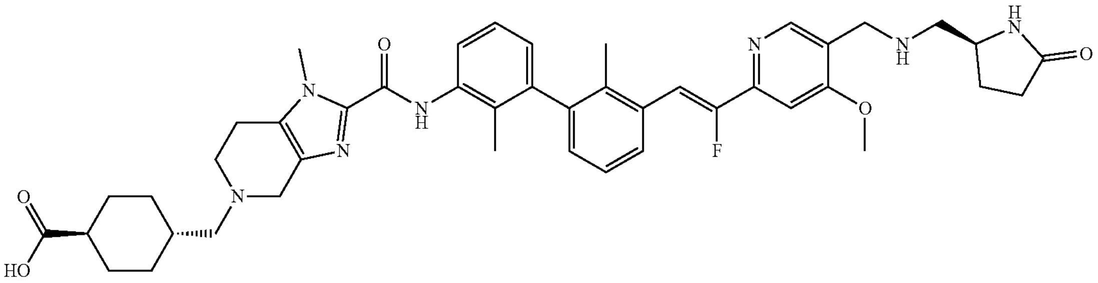

-continued
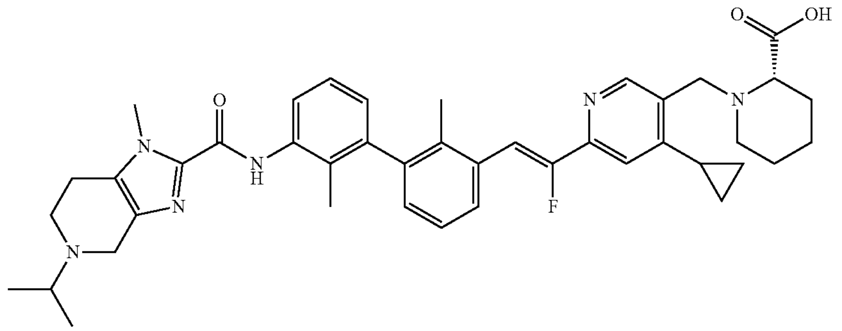
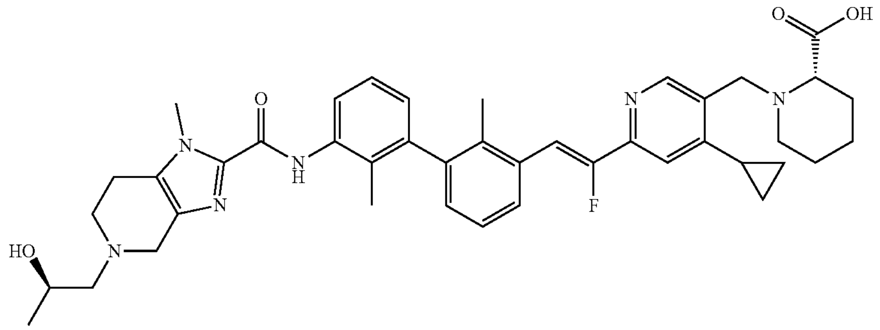
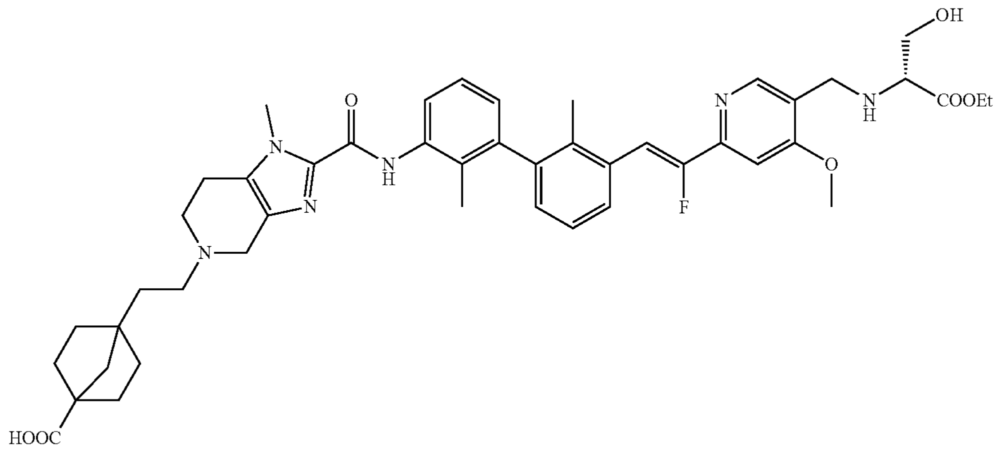
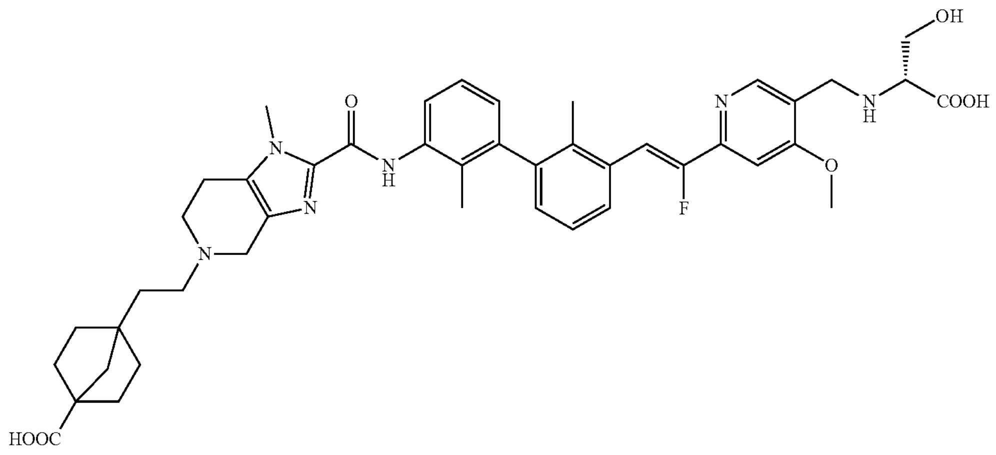

-continued
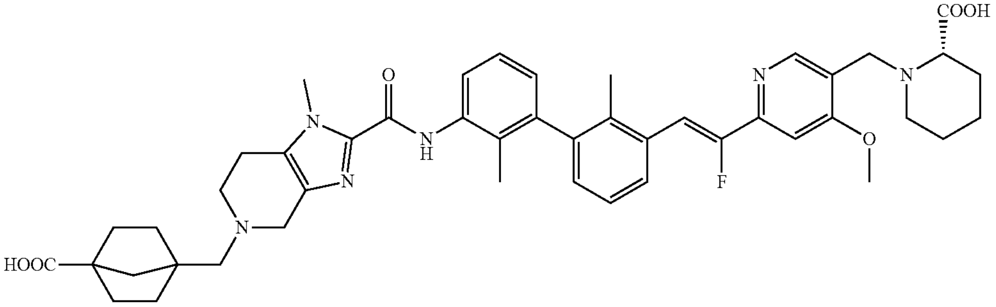
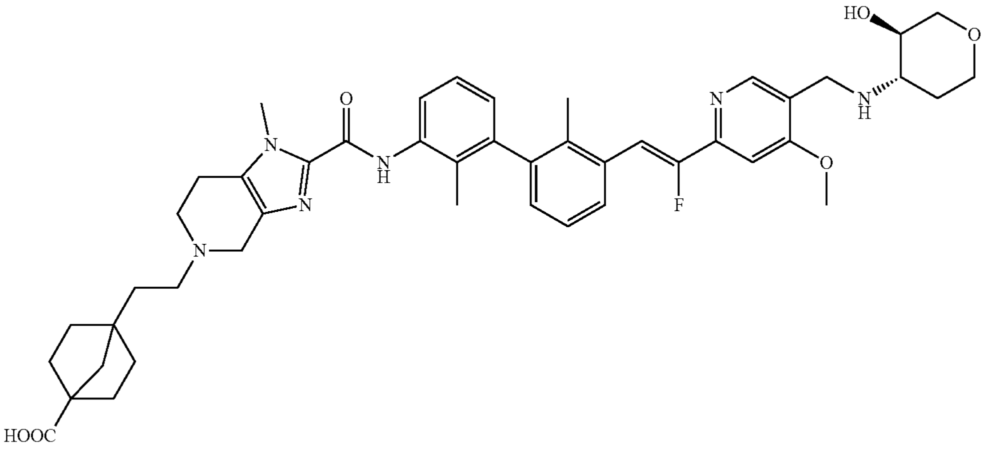
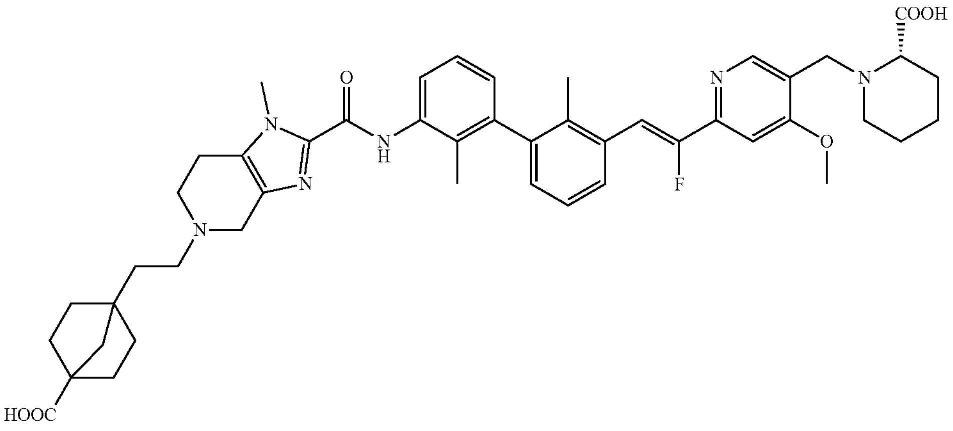
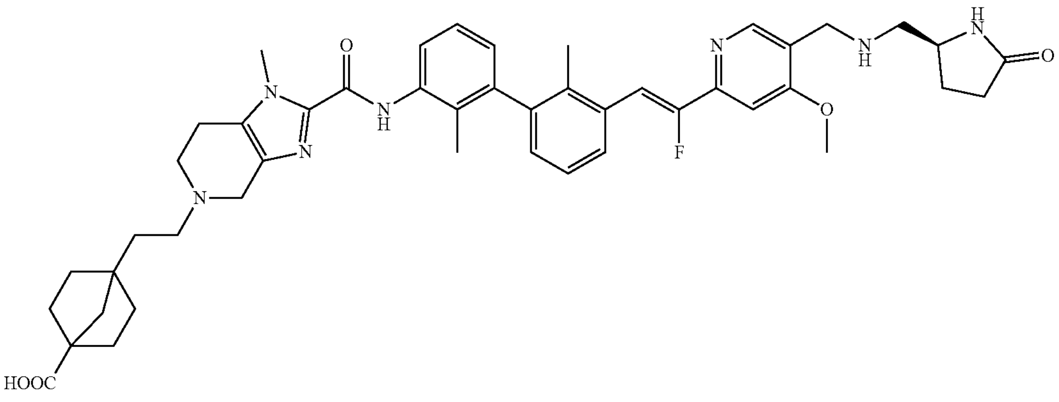

-continued
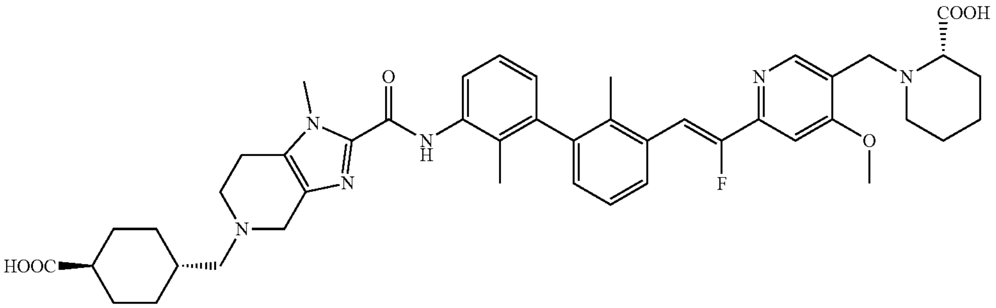
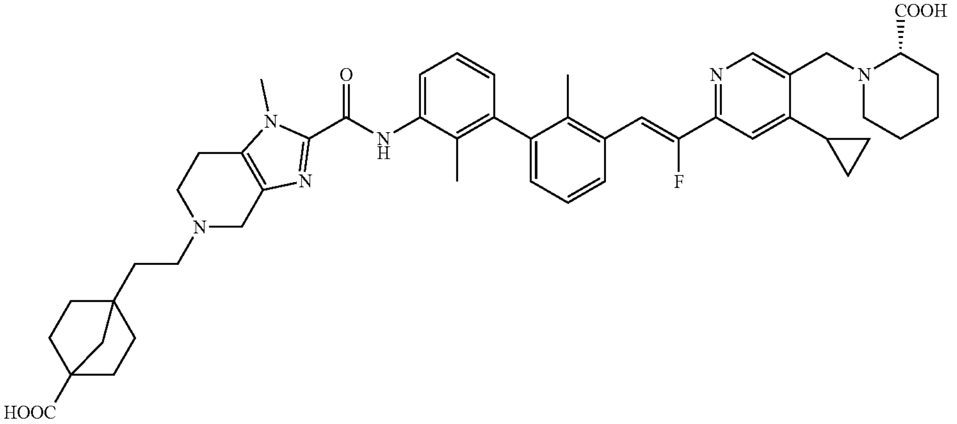
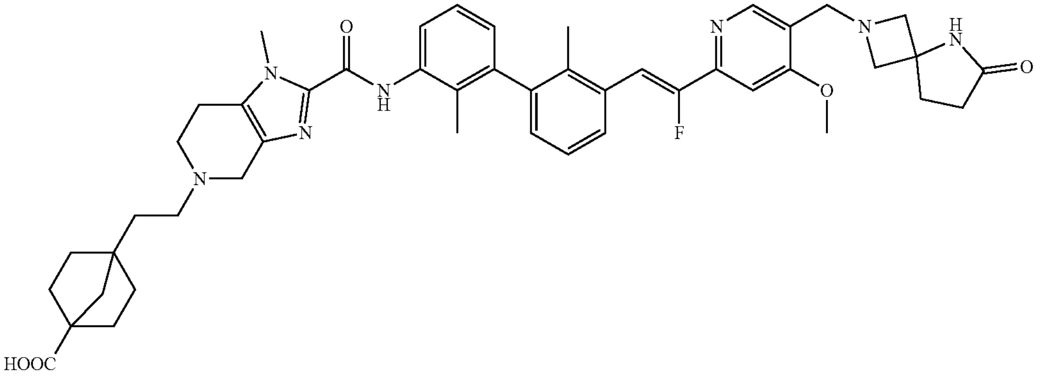
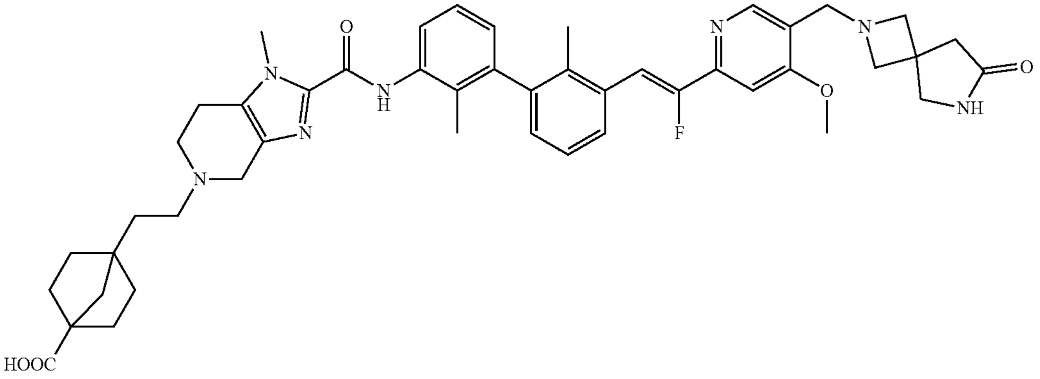

-continued
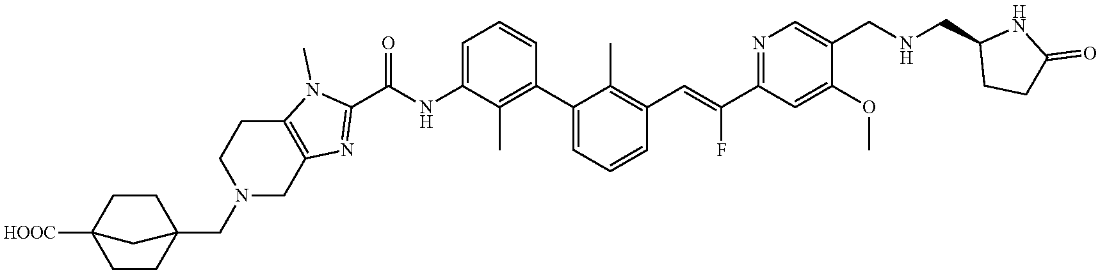
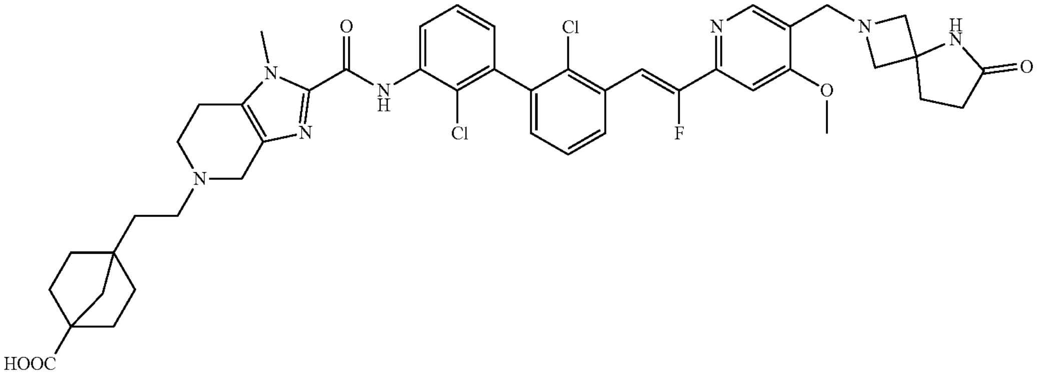
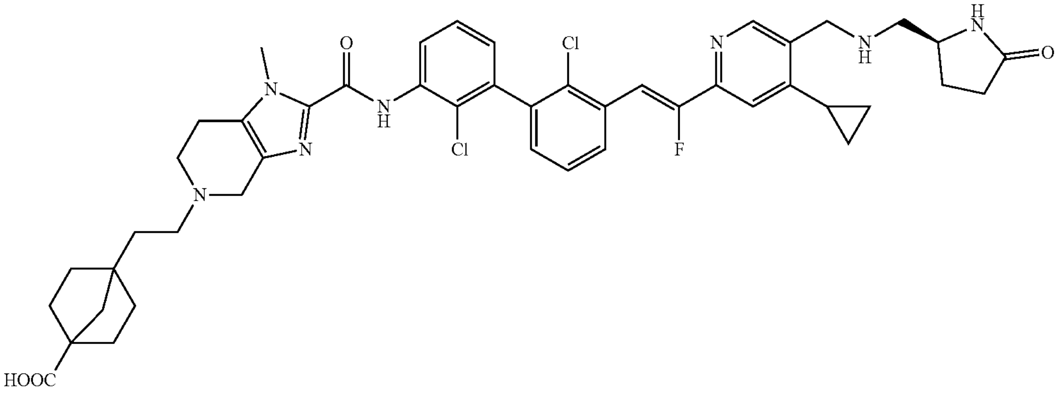
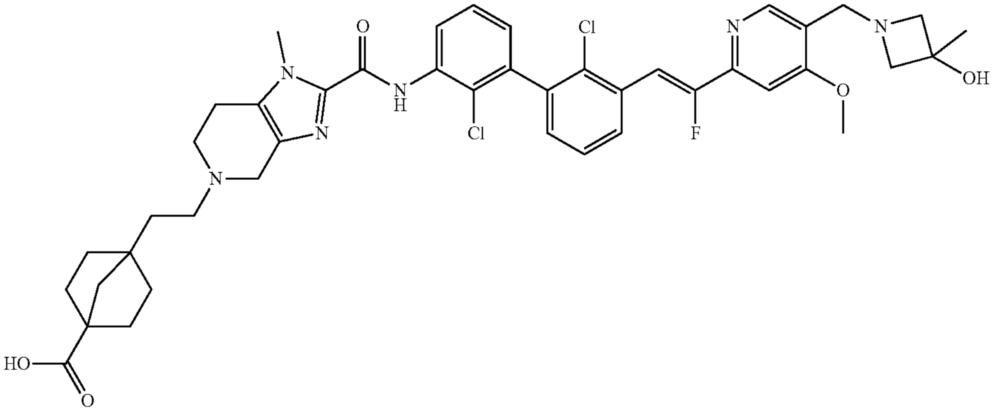

-continued
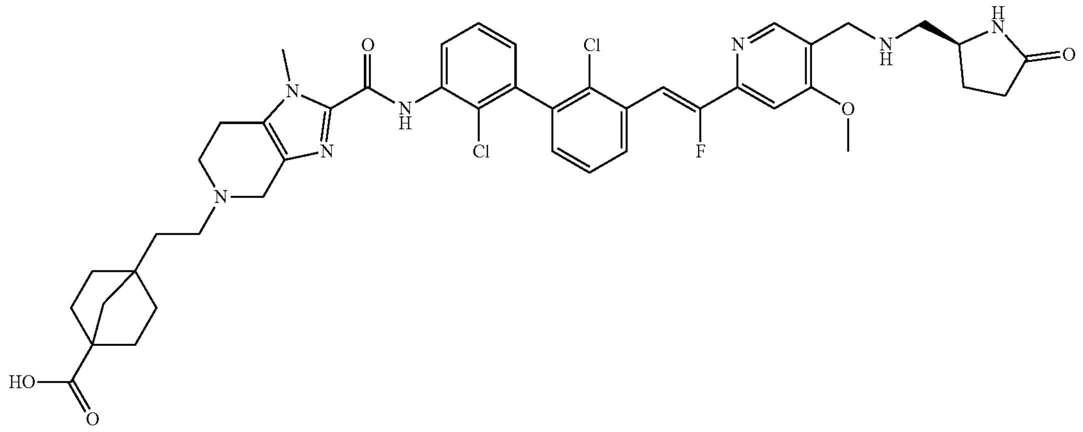
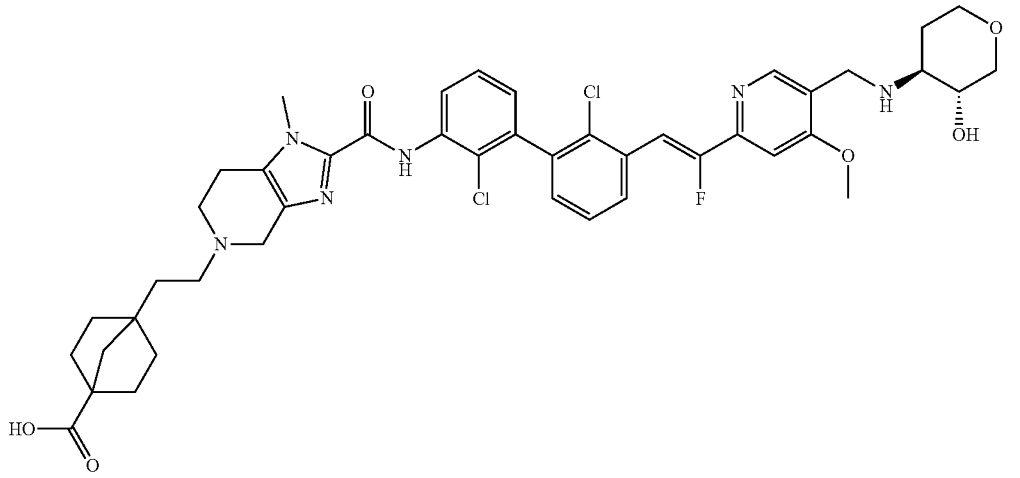
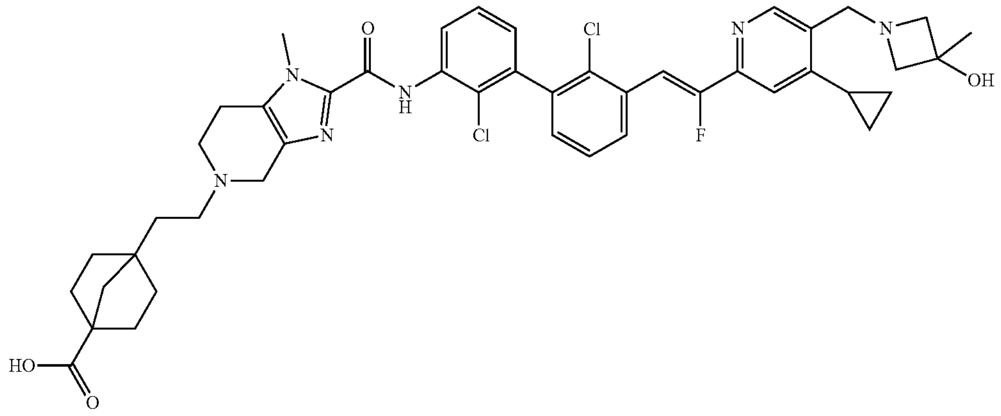

-continued
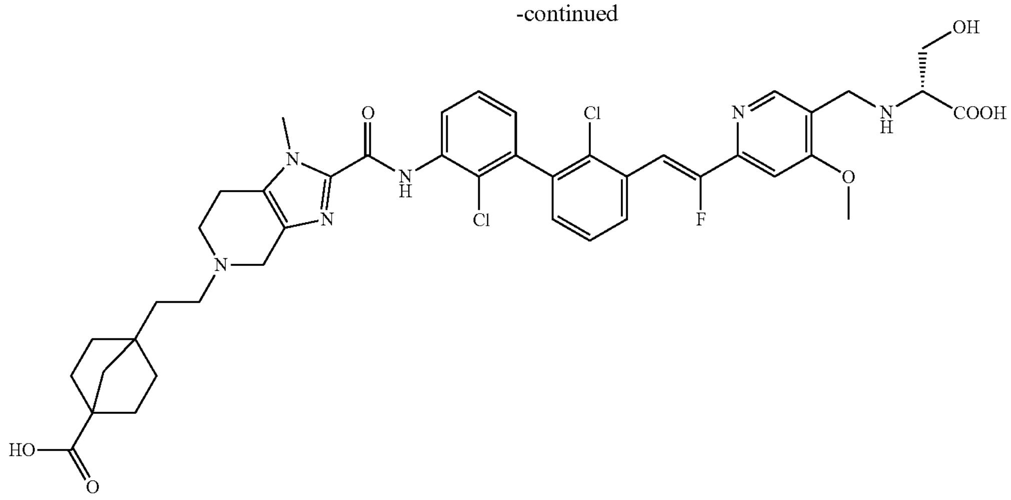
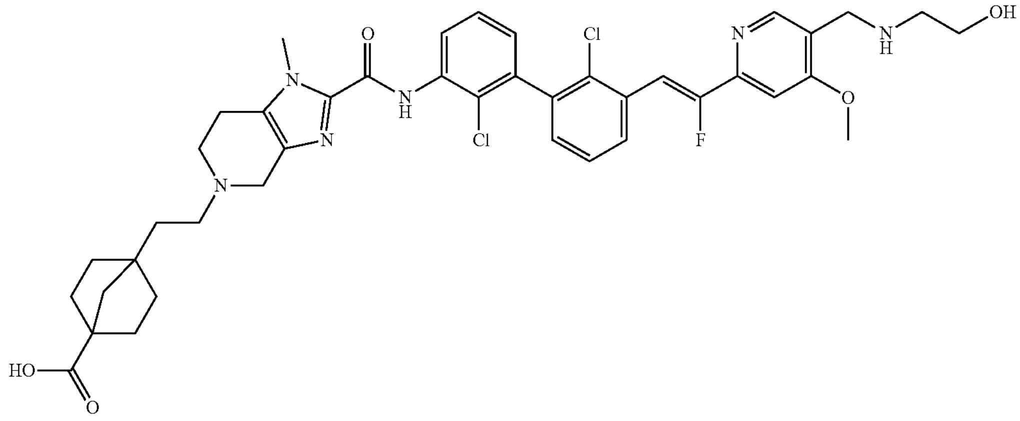
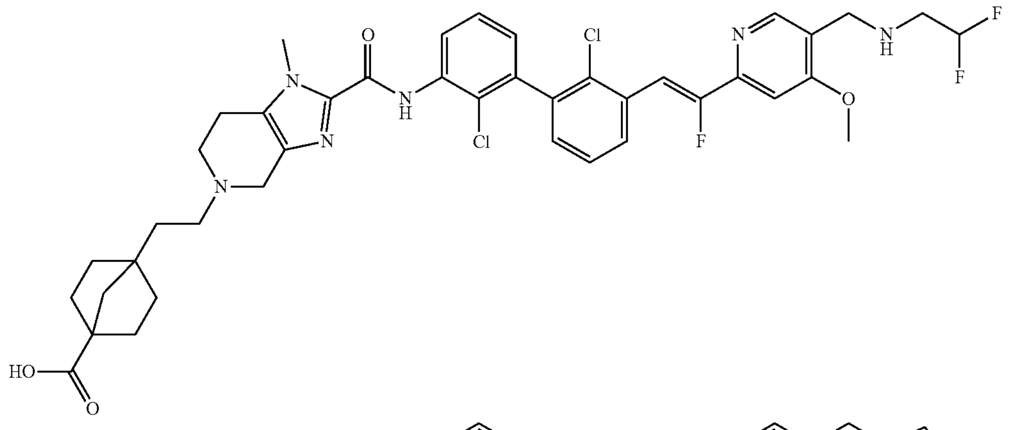
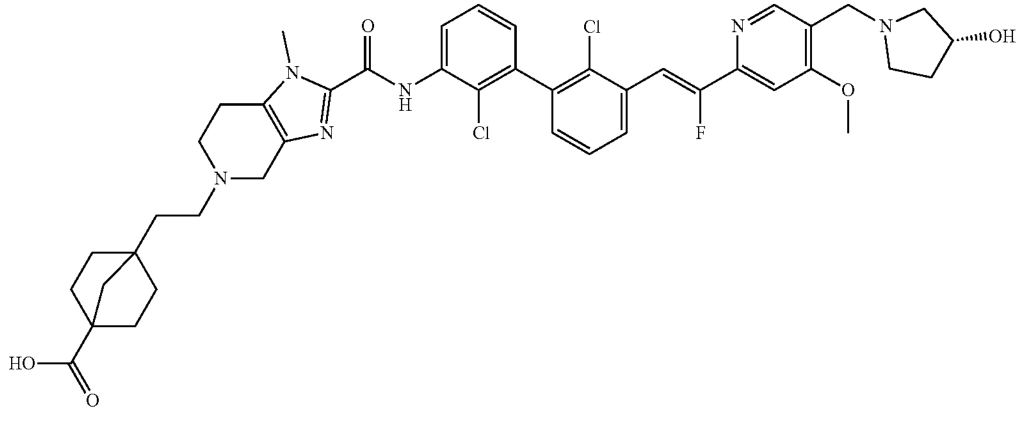

-continued
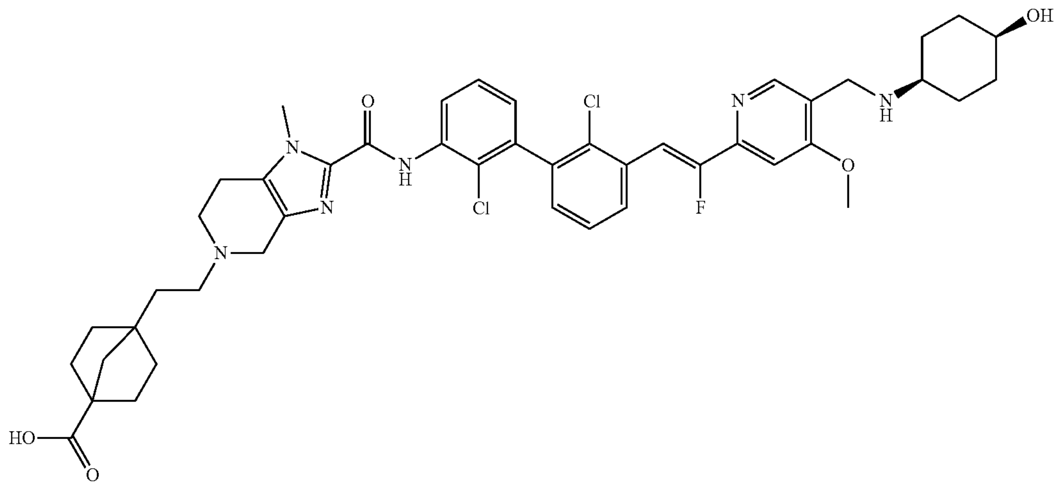
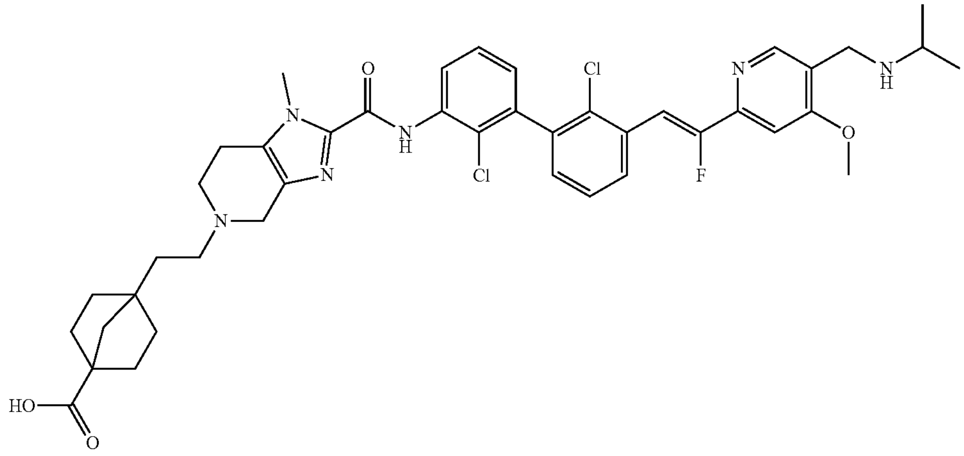
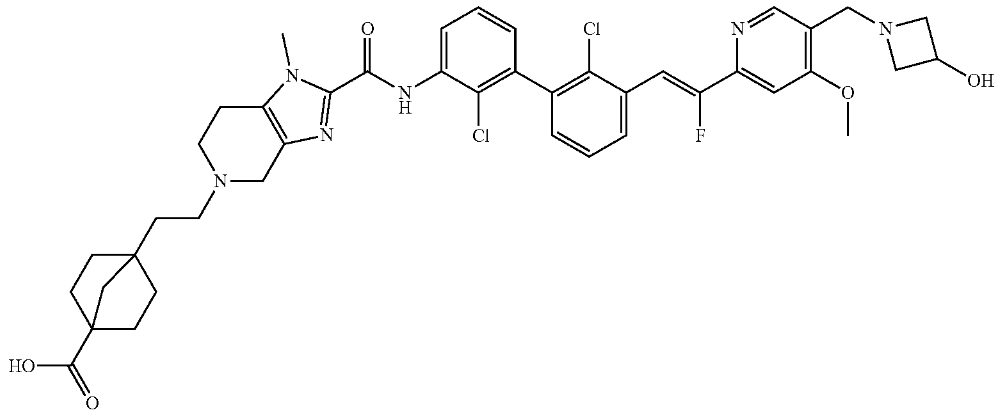

-continued
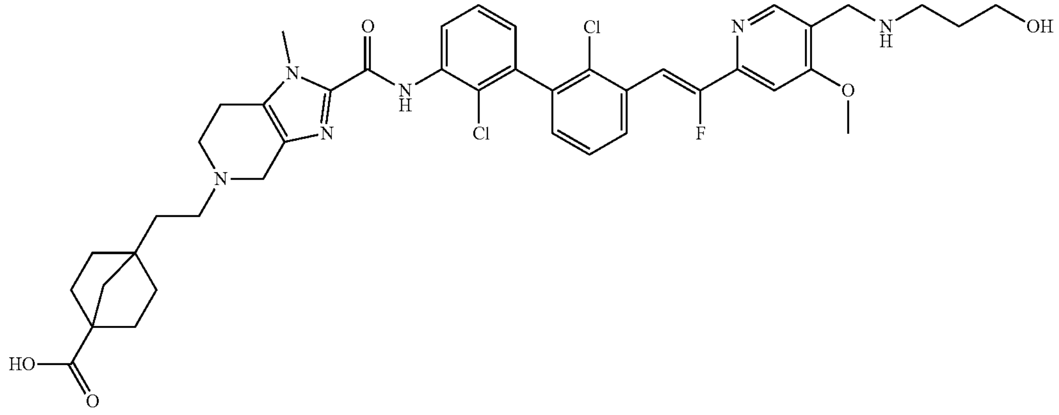
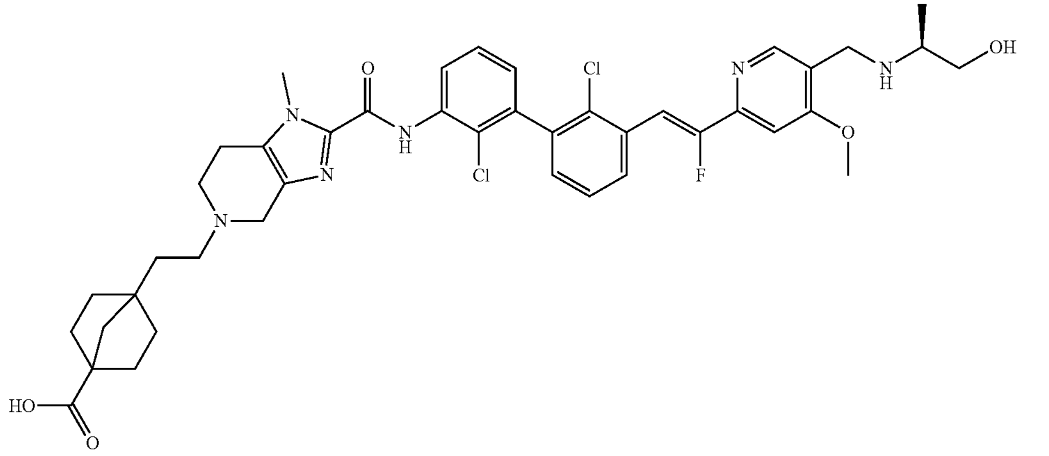
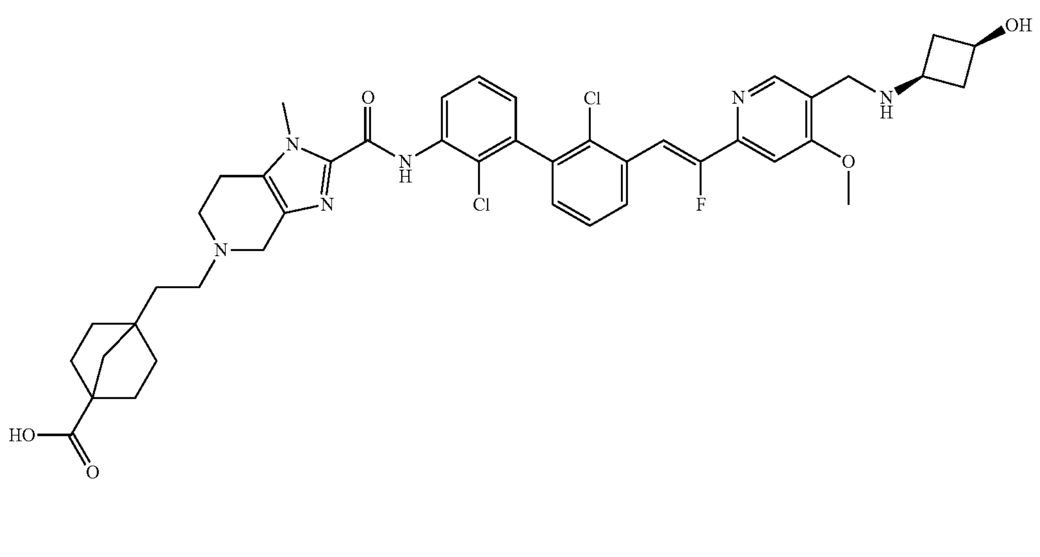

-continued
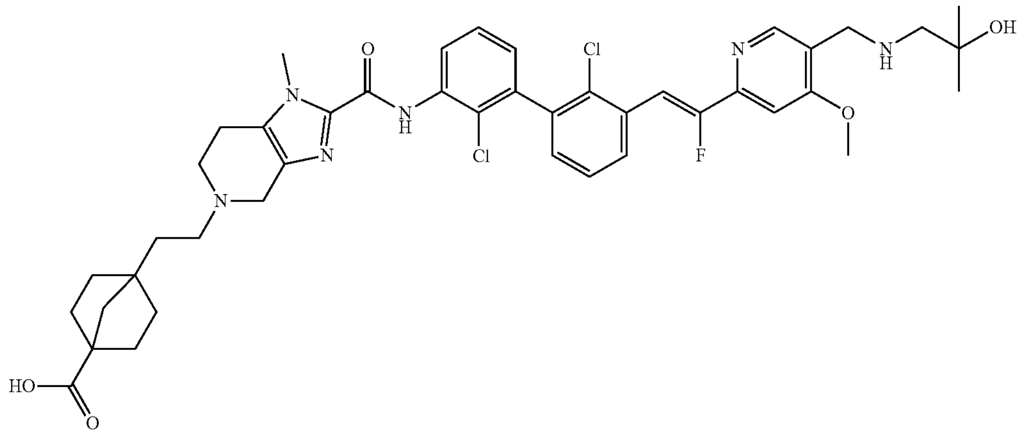
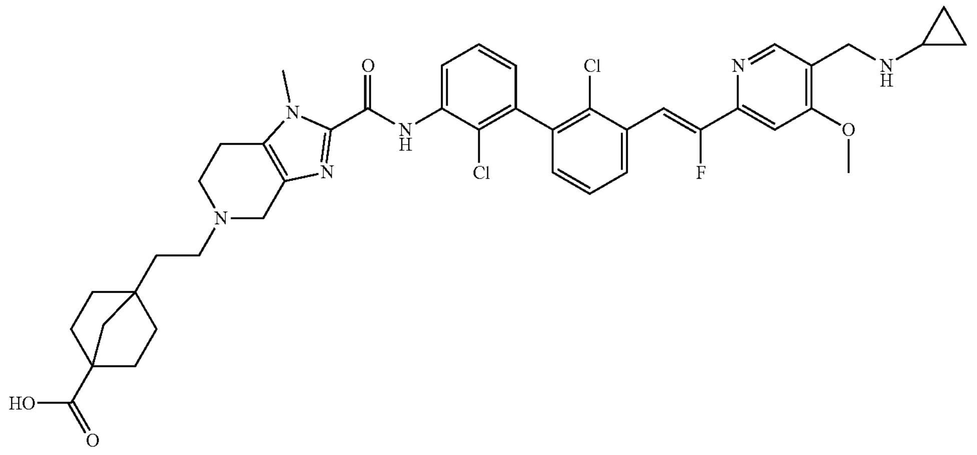
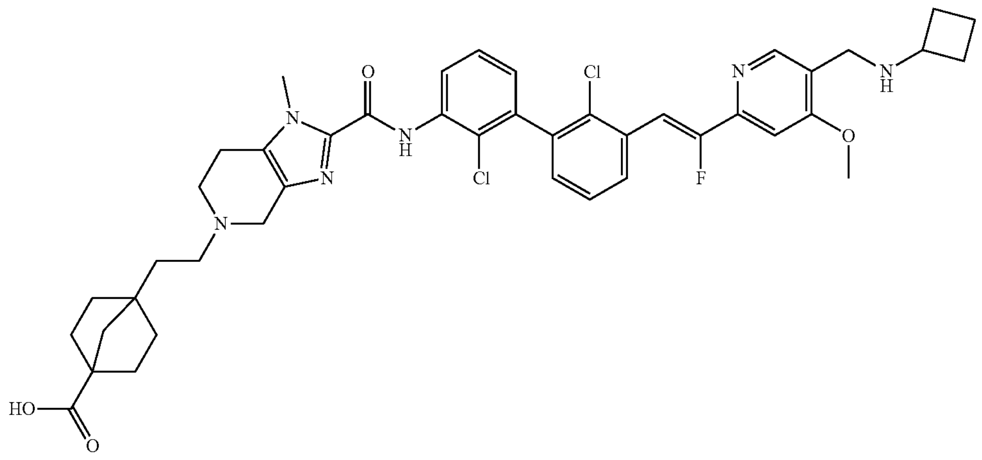

-continued
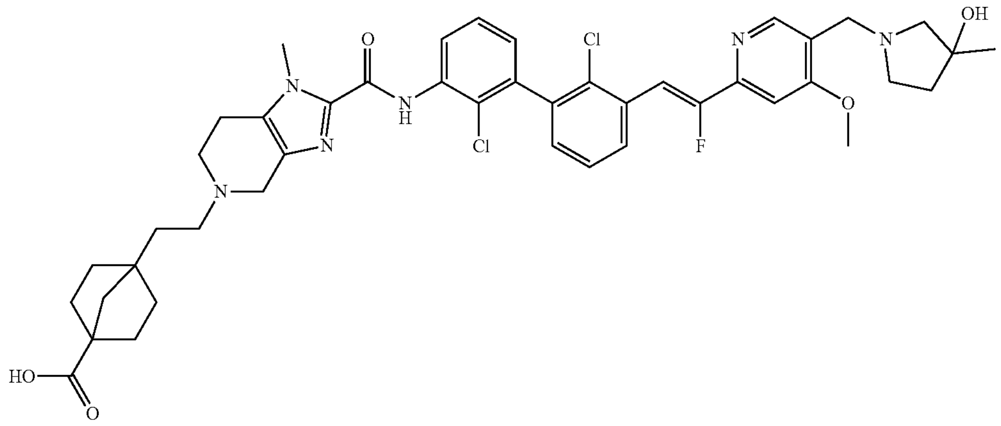
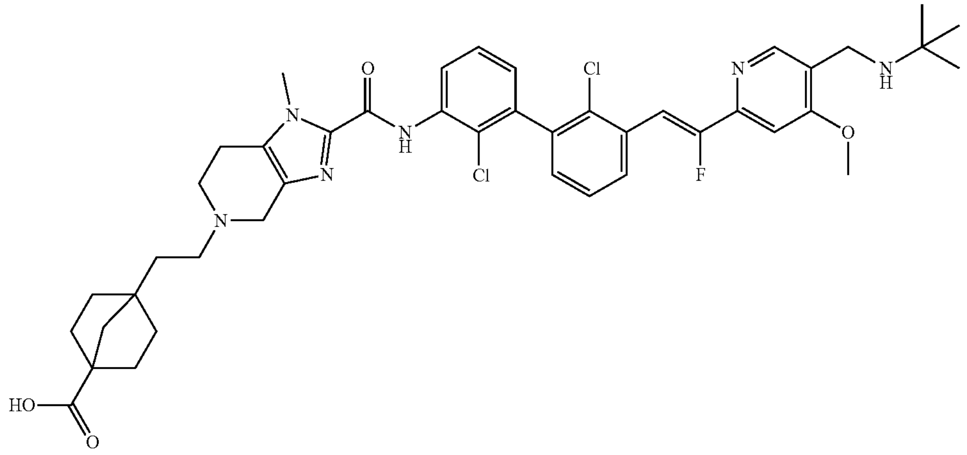
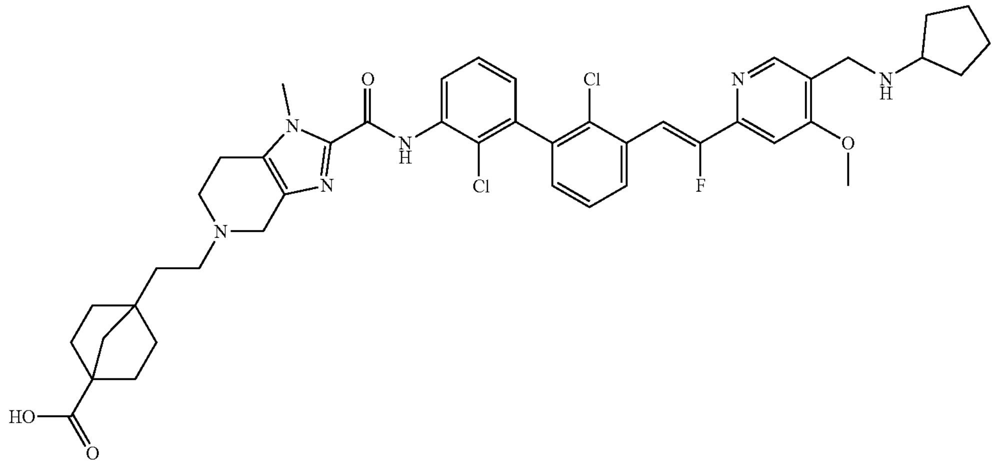

-continued
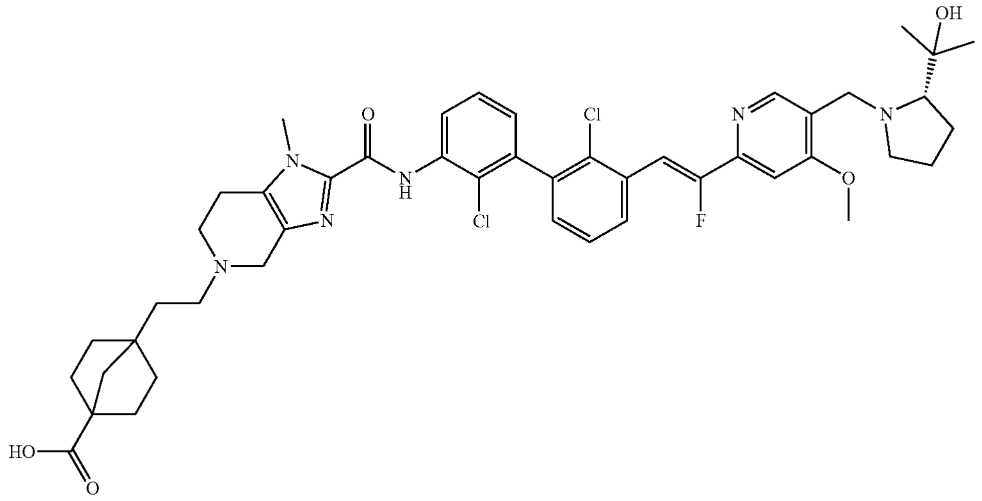
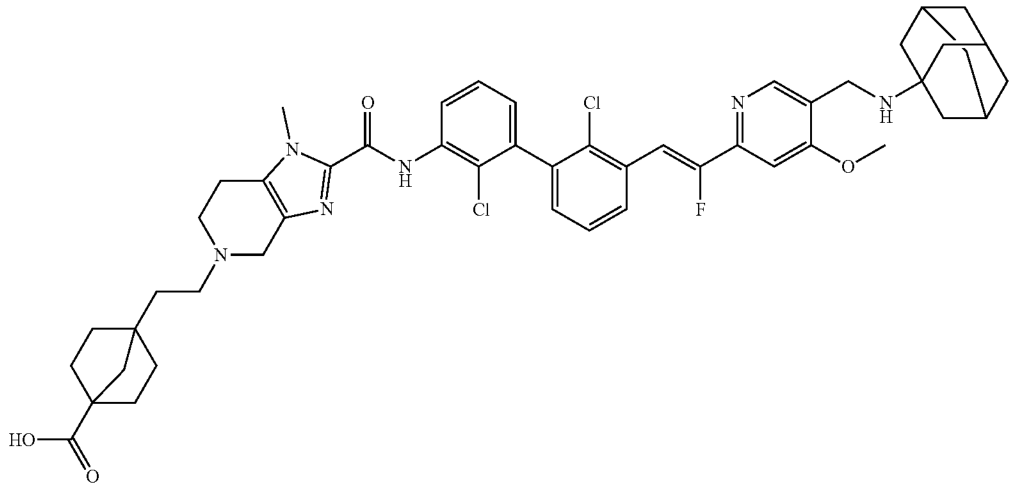
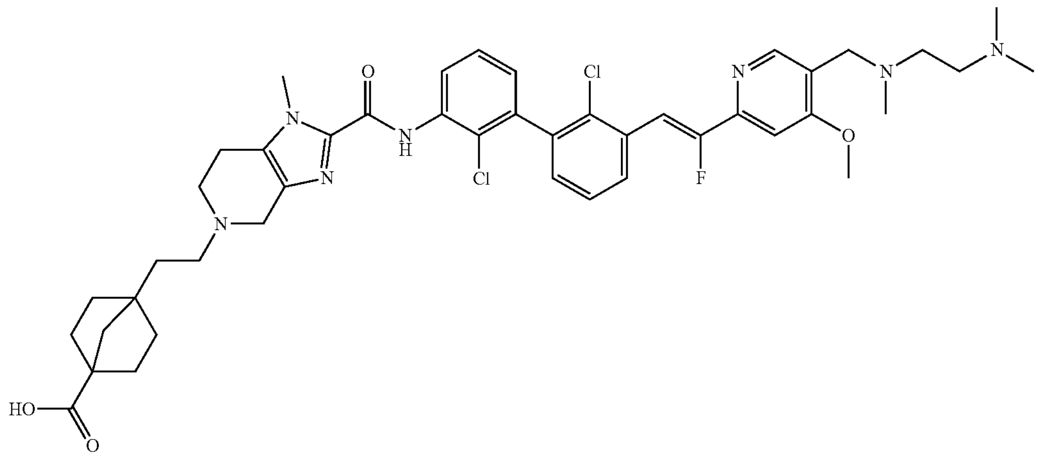

-continued
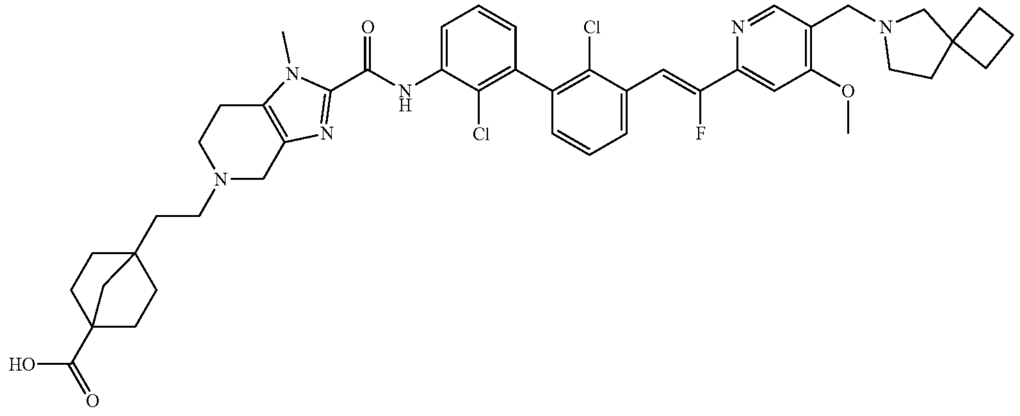
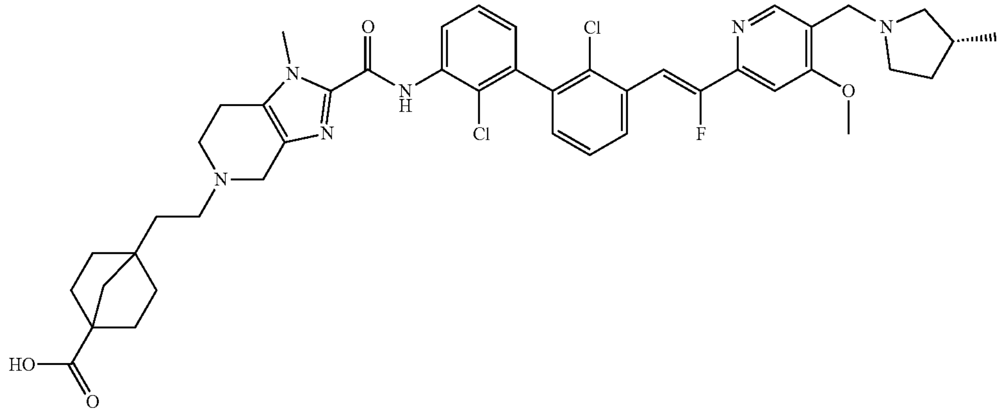
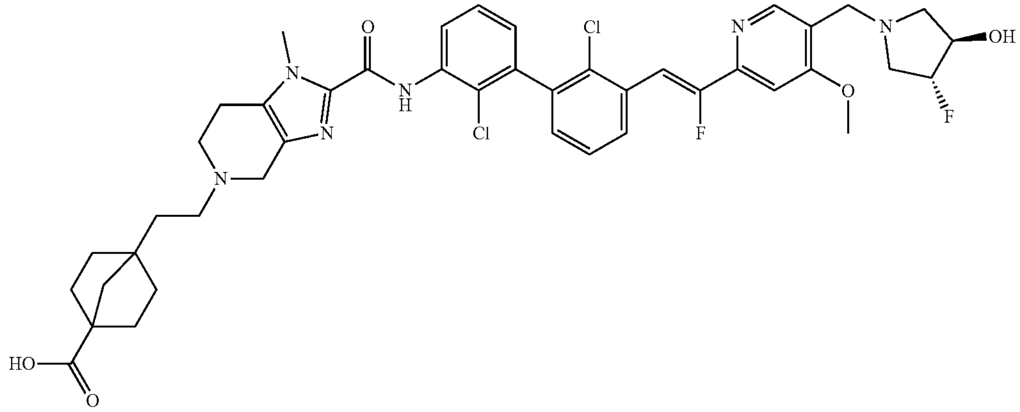
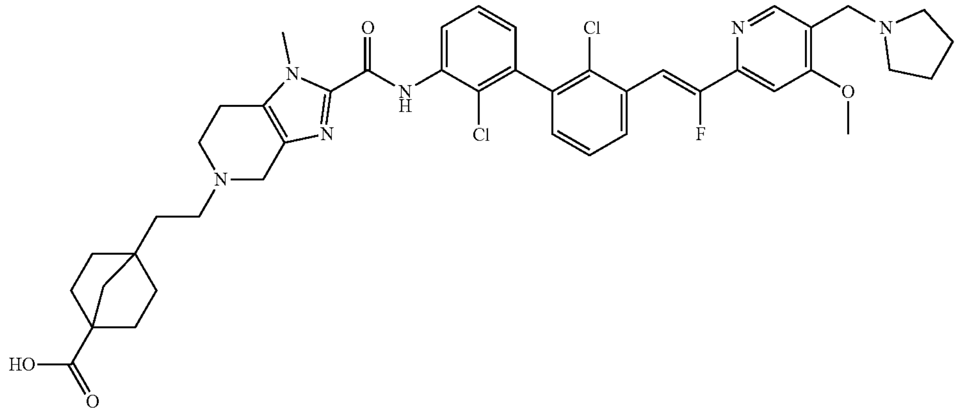

-continued
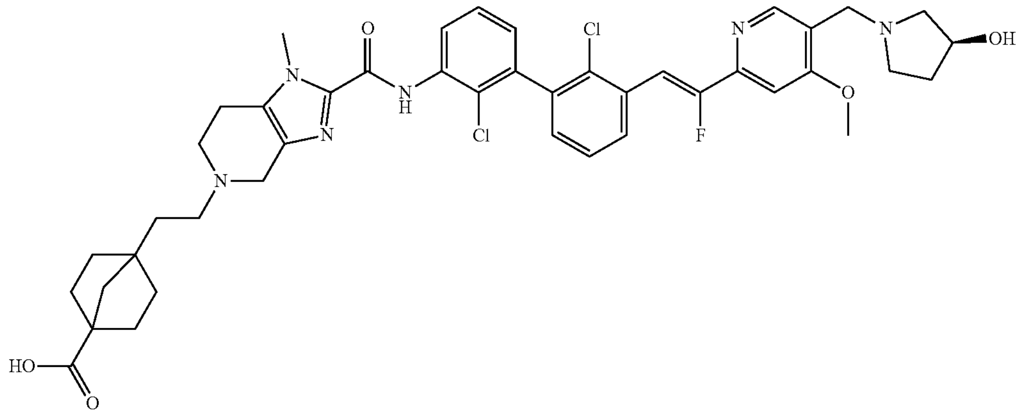
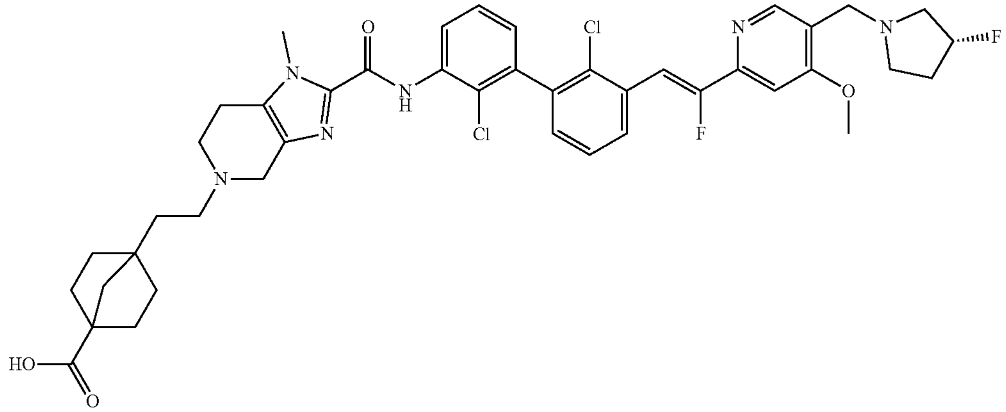
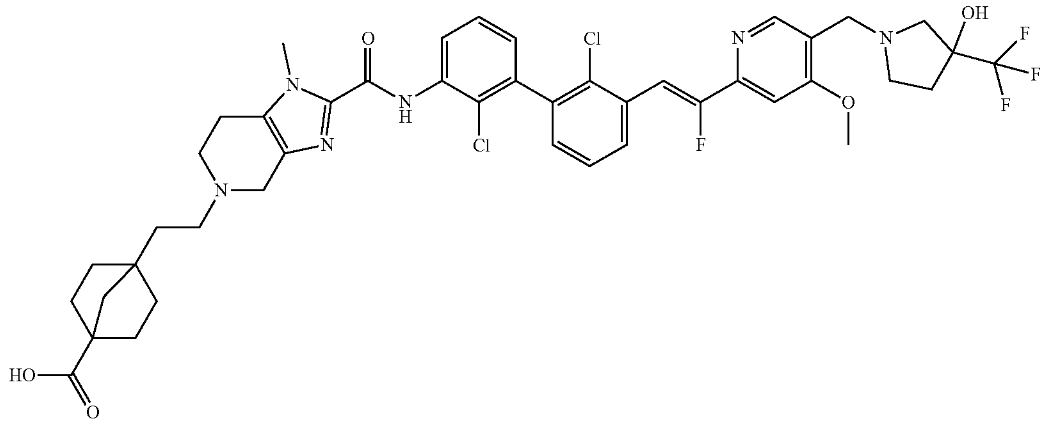
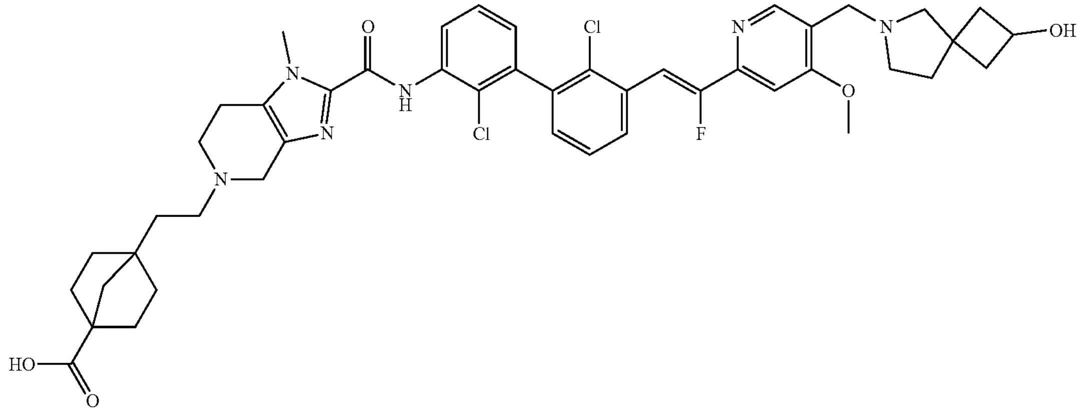

-continued
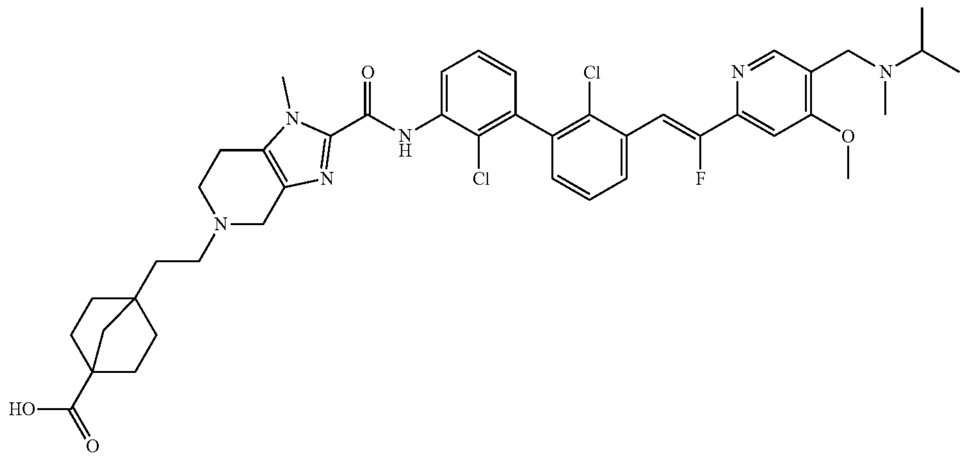
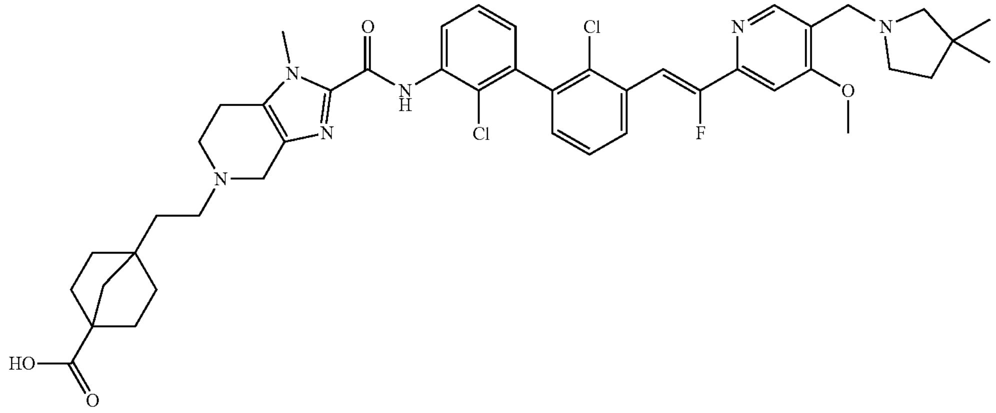
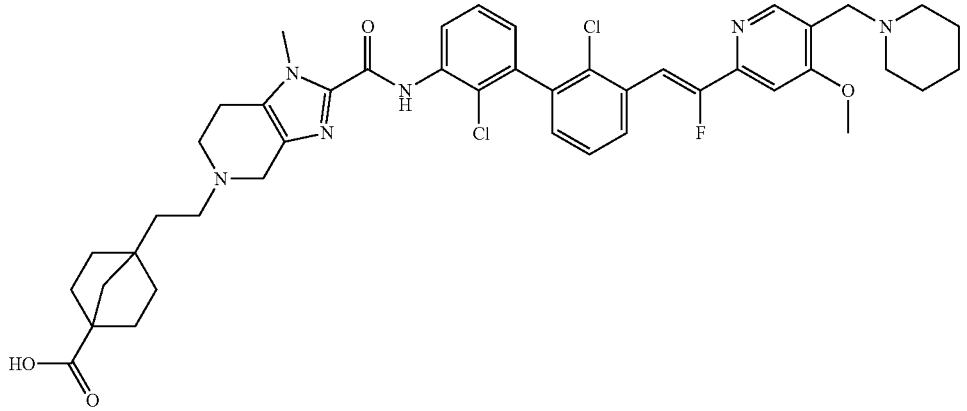
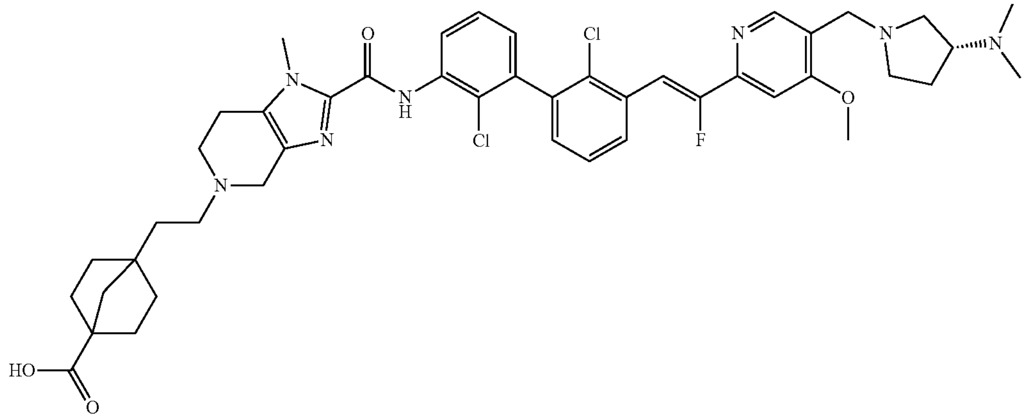

-continued
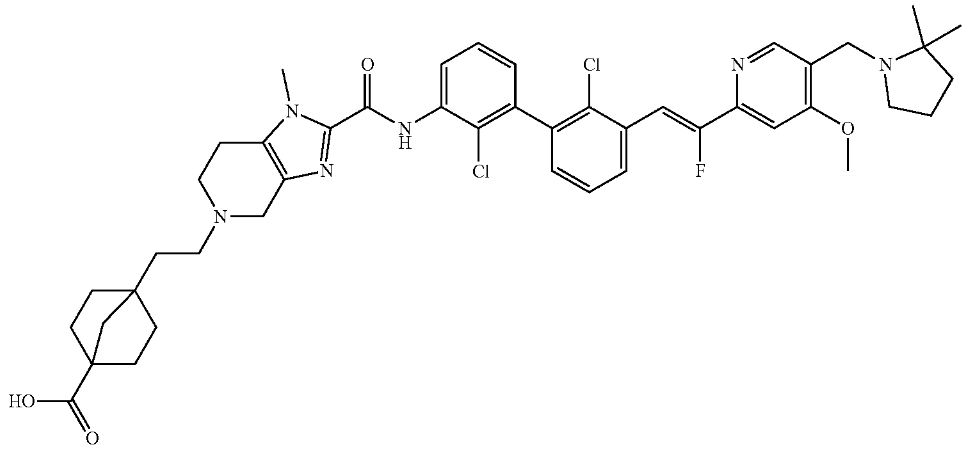
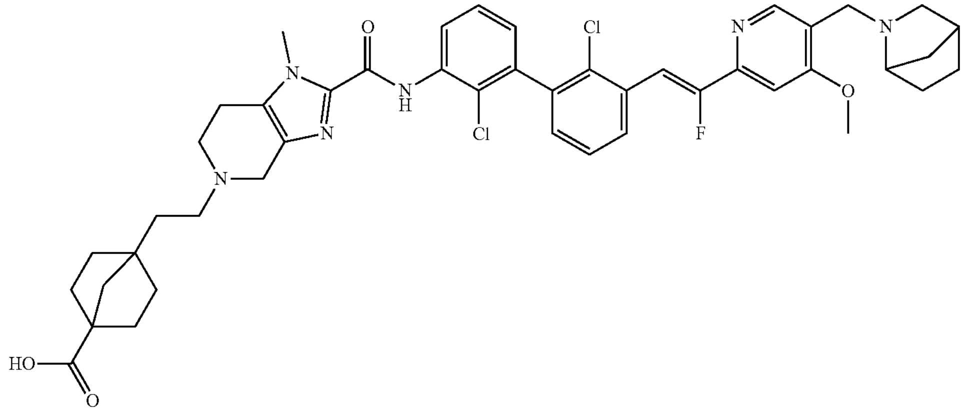
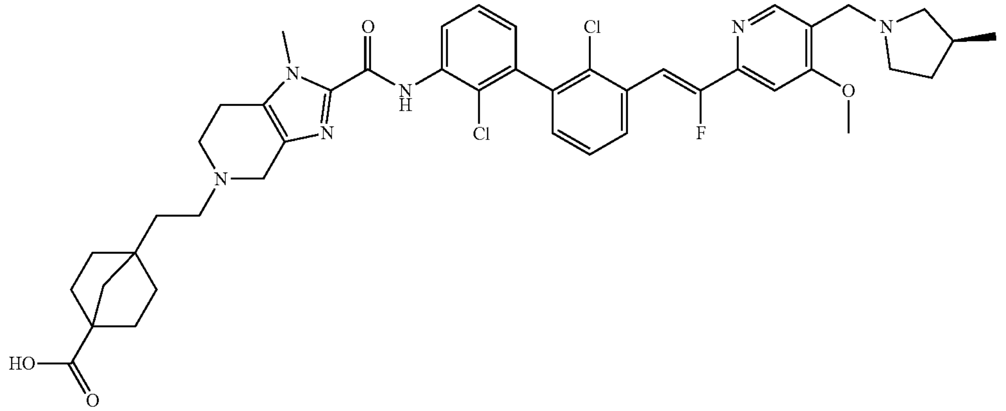
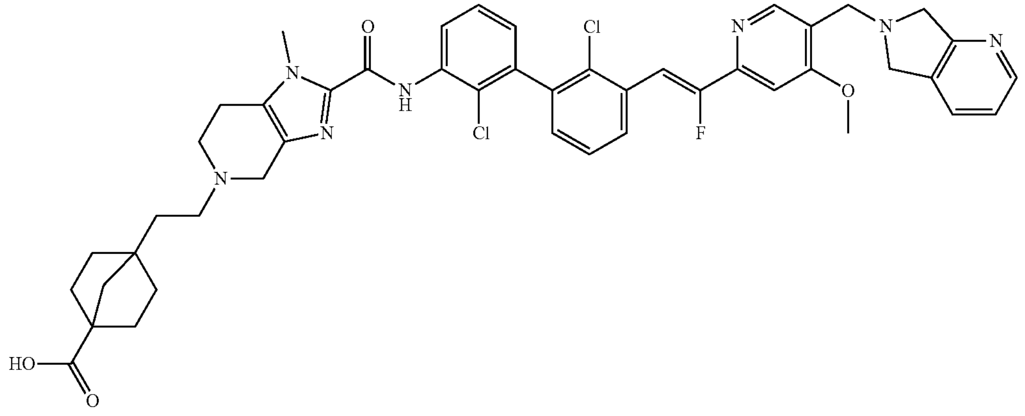

-continued
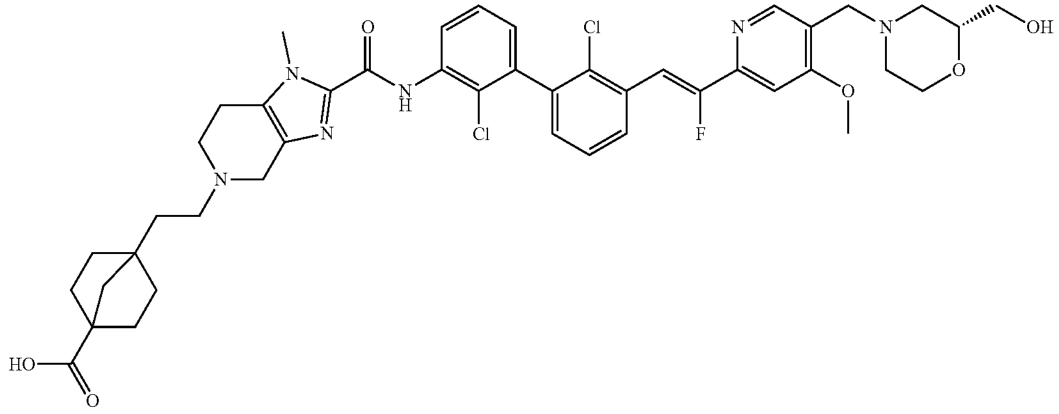
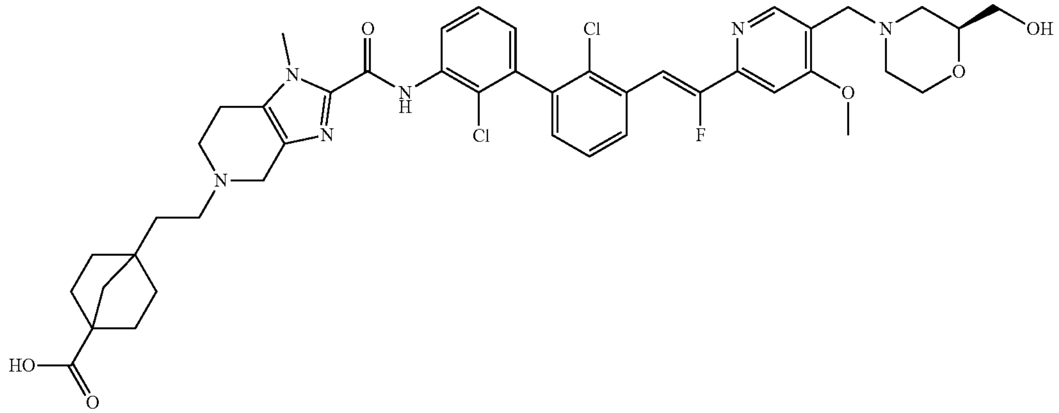
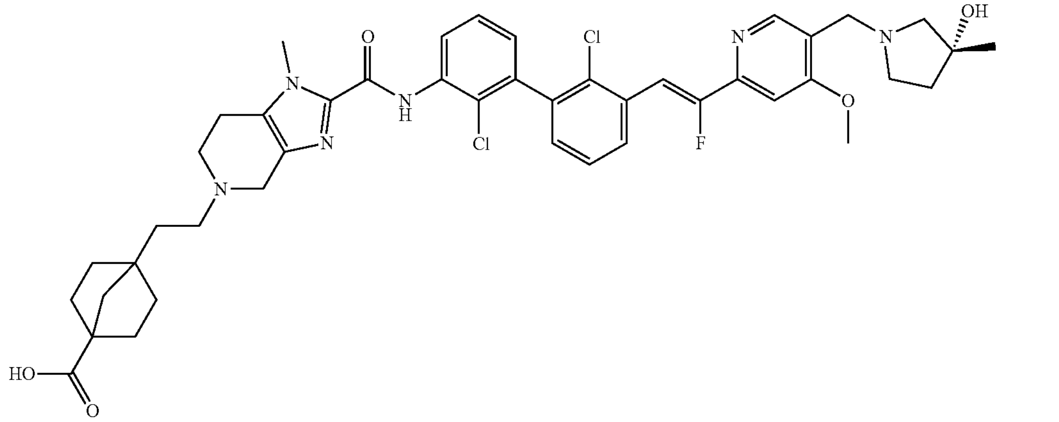
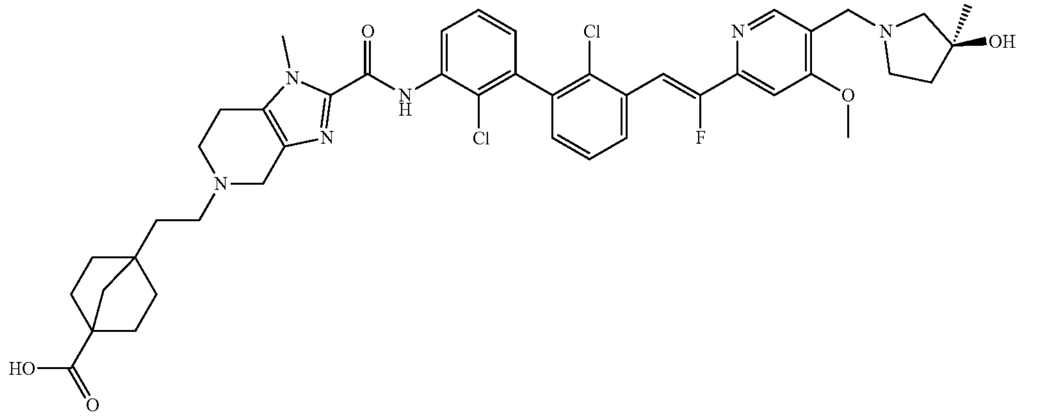

-continued
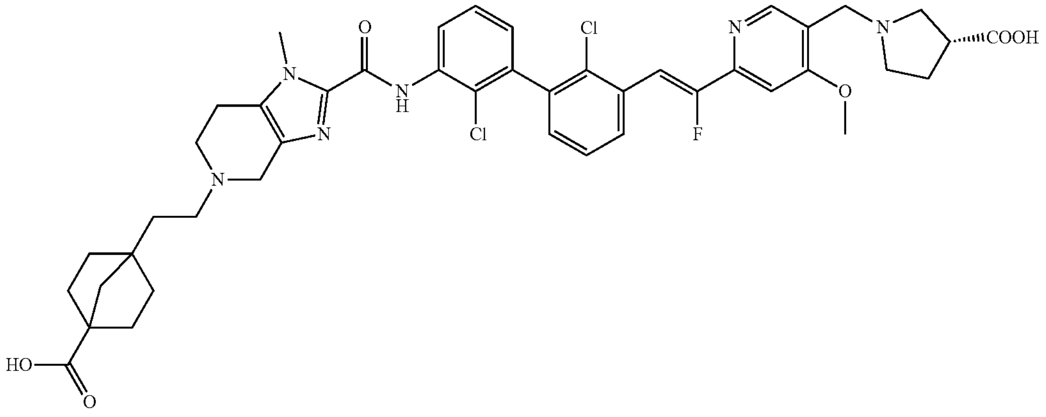
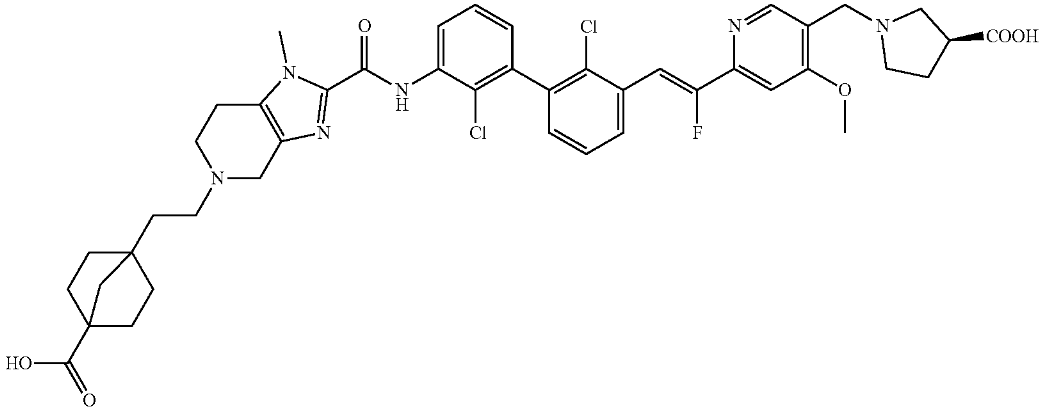
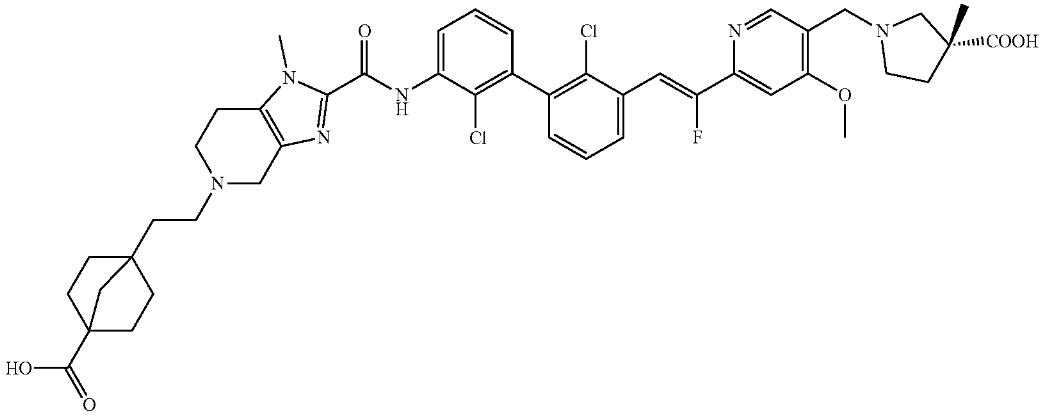
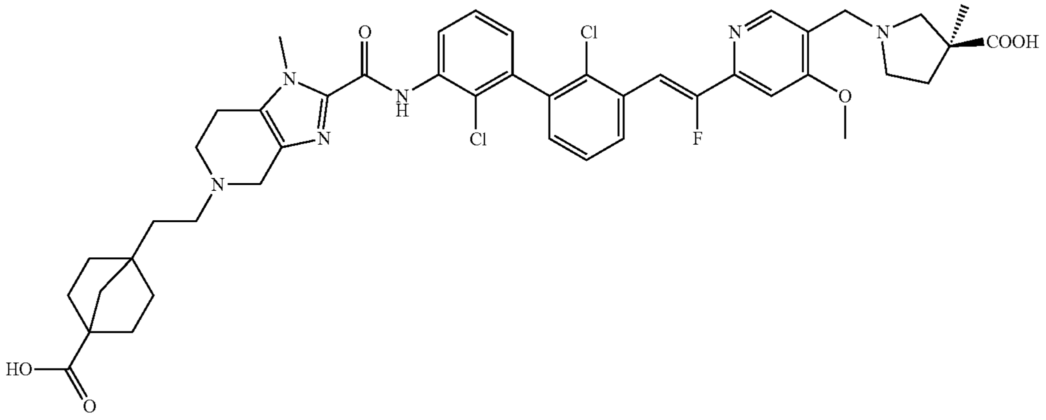
or

-continued

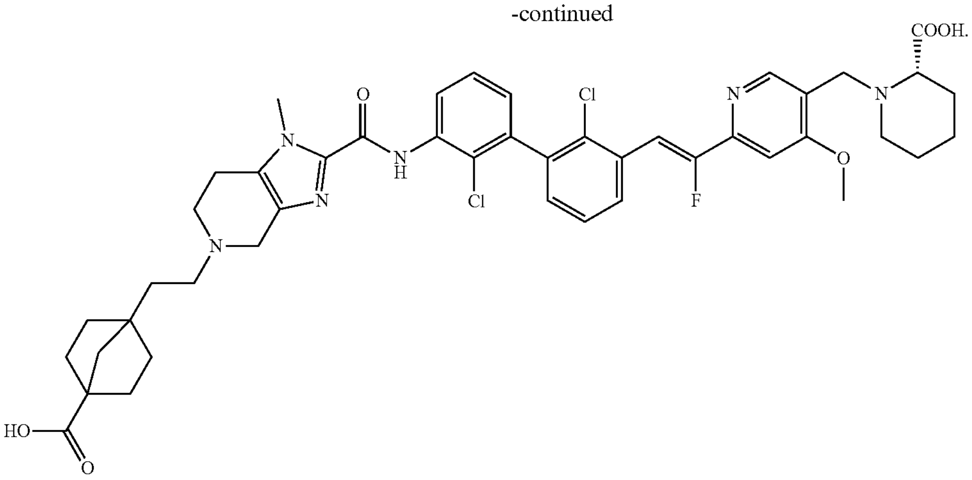

The second aspect of the present invention provides a process for preparing the compound of formula (I), the stereoisomer, prodrug or pharmaceutically acceptable salt thereof, including the following steps:

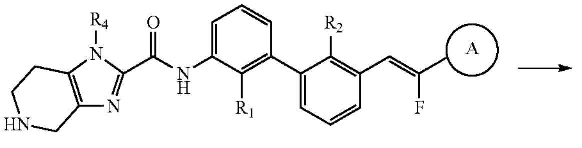

(I')

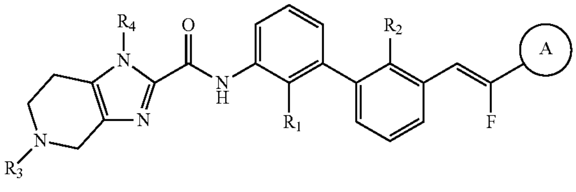

(I)

optionally, further reaction was carried out according to the different substituents to obtain corresponding compound of formula (I);

wherein, ring A, $R_1$, $R_2$, $R_3$ and $R_4$ are defined as those in the compound of formula (I).

The third aspect of the present invention provides a pharmaceutical composition, comprising the aforementioned compound of formula (I), the stereoisomer, prodrug or pharmaceutically acceptable salt thereof, and a pharmaceutically acceptable carrier.

The fourth aspect of the present invention provides a use of the aforementioned compound of formula (I), the stereoisomer, prodrug or pharmaceutically acceptable salt thereof in the preparation of a medicament for preventing and/or treating PD-1/PD-L1 signal pathway-mediated diseases.

In a preferred embodiment, the PD-1/PD-L1 signal pathway-mediated disease is cancer or tumor, immune-related disease and disorder, infectious disease and metabolic disease.

In a further preferred embodiment, the infectious disease is selected from bacterial infectious disease, viral infectious disease, or fungal infectious disease.

In a further preferred embodiment, the aforementioned cancer or tumor is selected from the group consisting of lymphoma (including but not limited to lymphocytic lymphoma, primary central nervous system lymphoma, T cell lymphoma, diffuse large B cell lymphoma, follicle center lymphoma, Hodgkin lymphoma, non-Hodgkin lymphoma or primary mediastinal large B cell lymphoma), sarcoma (including but not limited to Kaposi's sarcoma, fibrosarcoma, liposarcoma, chondrosarcoma, osteosarcoma, leiomyosarcoma, rhabdomyosarcoma, soft tissue sarcoma, angiosarcoma or lymphangiosarcoma), melanoma, glioblastoma, synovioma, meningioma, biliary tract tumor, thymic tumor, neuroma, seminoma, nephroblastoma, pleomorphic adenoma, hepatocellular papilloma, renal tubule adenoma, cystadenoma, papilloma, adenoma, leiomyoma, rhabdomyoma, hemangioma, lymphangioma, osteoma, chondroma, lipoma, fibroma, central nervous system tumor, rhachiophyma, brain stem glioma, pituitary adenoma, multiple myeloma, ovarian tumor, myelodysplastic syndrome or mesothelioma, prostate cancer, recurrent prostate cancer or prostate cancer having resistance to existing medicaments, thyroid cancer, parathyroid cancer, anal cancer, testicular cancer, urethral carcinoma, penile cancer, bladder cancer, ureteral cancer, uterine cancer, ovarian cancer, fallopian tube cancer, endometrial cancer, cervical cancer, vaginal cancer, vulvar cancer, adrenal cancer, Merkel cell carcinoma, embryonal carcinoma, chronic or acute leukemia (including but not limited to acute myeloid leukemia, chronic myeloid leukemia, acute lymphoblastic leukemia, chronic granulocytic leukemia and chronic lymphoblastic leukemia), bronchial carcinoma, esophageal cancer, nasopharyngeal carcinoma, hepatocellular carcinoma, renal cell carcinoma, small cell lung cancer, basal cell carcinoma, lung cancer, breast cancer, adenocarcinoma, papillary carcinoma, cystadenocarcinoma, squamous non-small cell lung cancer, non-squamous non-small cell lung cancer, rectal cancer, colon cancer, colorectal cancer, gastric cancer, pancreatic cancer, head and neck squamous cell carcinoma, head and neck cancer, gastrointestinal cancer, bone cancer, skin cancer, small intestine cancer, endocrine cancer, renal pelvic carcinoma, epidermoid carcinoma, abdominal wall carcinoma, renal cell carcinoma, transitional cell carcinoma, choriocarcinoma or metastatic tumor, especially metastatic tumor expressing PD-L1.

The immune-related disease and disorder is selected from the group consisting of rheumatic arthritis, renal failure, lupus erythematosus, asthma, psoriasis, ulcerative colitis, pancreatitis, allergy, fibrosis, anemia, fibromyalgia, Alzheimer's disease, congestive heart failure, stroke, aortic valve stenosis, arteriosclerosis, osteoporosis, Parkinson's disease, infection, Crohn's disease, ulcerative colitis, allergic contact dermatitis and eczema, systemic sclerosis or multiple sclerosis.

The communicable disease or infectious disease is selected from the group consisting of sepsis, liver infection, HIV, hepatitis A, hepatitis B, hepatitis C, hepatitis D, herpes virus, papillomavirus or influenza.

The metabolic disease is selected from the group consisting of diabetes, diabetic ketoacidosis, hyperglycemic hyperosmolar syndrome, hypoglycemia, gout, malnutrition, vitamin A deficiency, scurvy, vitamin D deficiency or osteoporosis.

The fifth aspect of the present invention provides a compound of formula (I), a stereoisomer, prodrug or pharmaceutically acceptable salt thereof for use as a medicament for preventing and/or treating PD-1/PD-L1 signal pathway-mediated cancer or tumor, immune-related disease and disorder, infectious disease, or metabolic disease. Preferably, the infectious disease includes but it not limited to communicable disease.

The present invention further provides a method for preventing and/or treating PD-1/PD-L1 signal pathway-mediated cancer or tumor, immune-related disease and disorder, infectious disease, or metabolic disease, comprising administering an effective amount of the compound of formula (I), the stereoisomer, prodrug or pharmaceutically acceptable salt thereof, or the pharmaceutical composition thereof to a patient in need thereof.

DETAILED DESCRIPTION OF THE INVENTION

After an extensive and intensive research, the inventors of the present invention, for the first time, developed a biphenyl fluorine double bond derivative of general formula (I). With a strong inhibitory effect on the interaction between PD-1 and PD-L1, the series of compounds of the present invention can be widely applied in the preparation of medicaments for preventing and/or treating cancer or tumor, immune-related disease and disorder, communicable disease, infectious disease or metabolic disease that is mediated by the PD-1/PD-L1 signal pathway, and are expected to be developed into a new generation of PD-1/PD-L1 inhibitors. The present invention is achieved on this basis.

Detailed description: Unless otherwise stated to the contrary or specifically noted, the following terms used in the specification and claims have the following meanings.

"Alkyl" refers to a straight or branched saturated aliphatic hydrocarbon group, preferably a straight or branched alkyl containing 1 to 10 carbon atoms or 1 to 6 carbon atoms or 1 to 4 carbon atoms, which includes, but is not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof and so on. "$C_{1-10}$ alkyl" refers to a straight or branched alkyl containing 1 to 10 carbon atoms; "$C_{1-8}$ alkyl" refers to a straight or branched alkyl containing 1 to 8 carbon atoms; "$C_{0-8}$ alkyl" refers to a straight or branched alkyl containing 0 to 8 carbon atoms; "$C_{1-4}$ alkyl" refers to a straight or branched alkyl containing 1 to 4 carbon atoms; "$C_{0-4}$ alkyl" refers to a straight or branched alkyl containing 0 to 4 carbon atoms; "$C_0$ alkyl" refers to that the number of carbon atom is 0.

Alkyl may be optionally substituted or unsubstituted, and when it is substituted, the substituent is preferably one or more (preferably, 1, 2, 3, or 4) of the groups independently selected from the group consisting of deuterium, halogen, cyano, nitro, azido, $C_{1-10}$ alkyl, $C_{1-10}$ alkoxy, $C_{2-10}$ alkenyl, $C_{2-10}$ alkynyl, $C_{1-10}$ haloalkyl, $C_{1-10}$ haloalkoxy, $C_{1-10}$ deuterioalkyl, $C_{1-10}$ deuterioalkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, =O, $-C_{0-8}-SF_5$, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$.

"Cycloalkyl" or "carbocycle" refers to a monocyclic or polycyclic cyclic hydrocarbon substituent that is saturated or partially unsaturated. The partially unsaturated cyclic hydrocarbon means a cyclic hydrocarbon that may contain one or more (preferably, 1, 2, or 3) double bonds, but none of rings has a fully conjugated π-electron system. The cycloalkyl includes monocyclic cycloalkyl and polycyclic cycloalkyl, preferably including a cycloalkyl containing 3 to 10 or 3 to 8 or 3 to 6 carbon atoms. For example, "$C_{3-10}$ cycloalkyl" means a cycloalkyl containing 3 to 10 carbon atoms, "$C_{3-8}$ cycloalkyl" means a cycloalkyl containing 3 to 8 carbon atoms, and "$C_{3-6}$ cycloalkyl" means a cycloalkyl containing 3 to 6 carbon atoms, wherein:

monocyclic cycloalkyl includes, but is not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl and the like;

and polycyclic cycloalkyl includes spiro, fused, and bridged cycloalkyls. "Spirocycloalkyl" refers to a polycyclic group in which a carbon atom (called spiro-atom) is shared among monocyclic rings, wherein those rings may contain one or more (preferably, 1, 2, or 3) double bonds, but none of them has a fully conjugated π-electron system. According to the number of the spiro-atoms shared among the rings, the spirocycloalkyl may be monospirocycloalkyl, bispirocycloalkyl or polyspirocycloalkyl, including but not limited to:

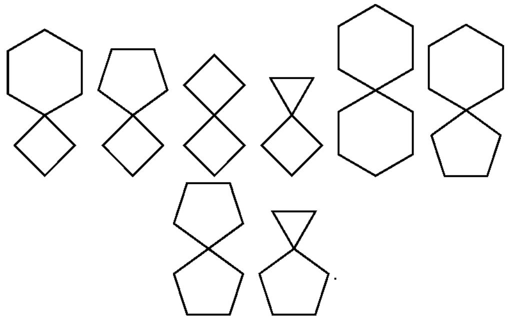

"Fused cycloalkyl" refers to an all-carbon polycyclic group in which each ring shares a pair of adjacent carbon atoms with the other rings in the system, wherein one or more of the rings may contain one or more (preferably, 1, 2, or 3) double bonds, but none of them has a fully conjugated π-electron system. According to the number of formed rings, the fused cycloalkyl may be bicyclic, tricyclic, tetracyclic or polycyclic, including but not limited to:

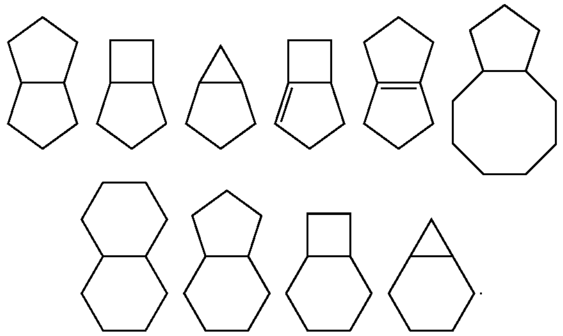

"Bridged cycloalkyl" refers to an all-carbon polycyclic group in which any two rings share two carbon atoms that are not directly connected to each other, wherein these rings may contain one or more (preferably, 1, 2, or 3) double bonds, but none of them has a fully conjugated π-electron system. According to the number of formed rings, the bridged cycloalkyl may be bicyclic, tricyclic, tetracyclic or polycyclic, including but not limited to:

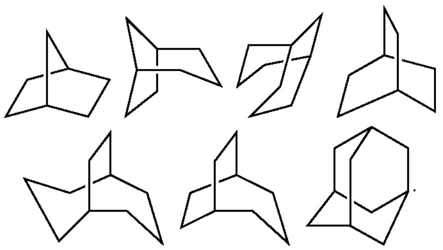

The cycloalkyl ring can be fused to an aryl, heteroaryl or heterocycloalkyl ring, wherein the ring attached to the parent structure is cycloalkyl, which includes, but is not limited to, indanyl, tetrahydronaphthyl, benzocycloheptyl, etc.

Cycloalkyl may be optionally substituted or unsubstituted, and when it is substituted, the substituent is preferably one or more (preferably, 1, 2, 3, or 4) of the groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-SF_5$, $-C_{0-8}-S(O)_rR_9$, $-C_{0-8}-O-R_{10}$, $-C_{0-8}-C(O)ORIO$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$.

"Heterocyclyl" or "heterocycle" refers to a monocyclic or polycyclic cyclic hydrocarbon substituent that is saturated or partially unsaturated. The partially unsaturated cyclic hydrocarbon means a cyclic hydrocarbon that may contain one or more (preferably, 1, 2, or 3) double bonds, but none of rings has a fully conjugated π-electron system. One or more (preferably 1, 2, 3 or 4) ring atoms in the heterocyclyl are selected from the group consisting of heteroatoms of nitrogen, oxygen, S(O)(=NH) or S(O), (wherein r is an integer of 0, 1, or 2), but excluding the ring moiety of —OO—, —OS— or —SS—, and the remaining ring atoms are carbon. The heterocyclyl preferably includes the one containing 3 to 10 or 3 to 8 or 3 to 6 ring atoms. For example, "3-6 membered heterocyclyl" refers to a ring group containing 3 to 6 ring atoms; "4-8 membered heterocyclyl" refers to a ring group containing 4 to 8 ring atoms; "5-8 membered heterocyclyl" refers to a ring group containing 5 to 8 ring atoms; "3-8 membered heterocyclyl" refers to a ring group containing 3 to 8 ring atoms; "4-10 membered heterocyclyl" refers to a ring group containing 4 to 10 ring atoms; "3-10 membered heterocyclyl" refers to a ring group containing a ring group containing 3 to 10 ring atoms.

Monocyclic heterocyclyl includes, but is not limited to pyrrolidinyl, piperidinyl, piperazinyl, morpholinyl, thiomorpholinyl, homopiperazinyl and the likes.

Polycyclic heterocyclyl includes spiro, fused, and bridged heterocyclyls. "Spiroheterocyclyl" refers to a polycyclic heterocyclyl that shares a carbon atom (called a spiro atom) between the monocyclic rings, wherein one or more (preferably, 1, 2, 3 or 4) of the ring atoms are heteroatoms selected from nitrogen, oxygen, S(O)(=NH) or S(O), (wherein r is an integer of 0, 1, 2), and the remaining ring atoms are carbon atoms. These groups may contain one or more (preferably, 1, 2, or 3) double bonds, but none of the rings have a fully conjugated π-electron system. The spiroheterocyclyl may be a monospiroheterocyclyl, a bispiroheterocyclyl or a polyspiroheterocyclyl according to the number of spiro atoms shared between the rings. Spiroheterocyclyl includes, but is not limited to:

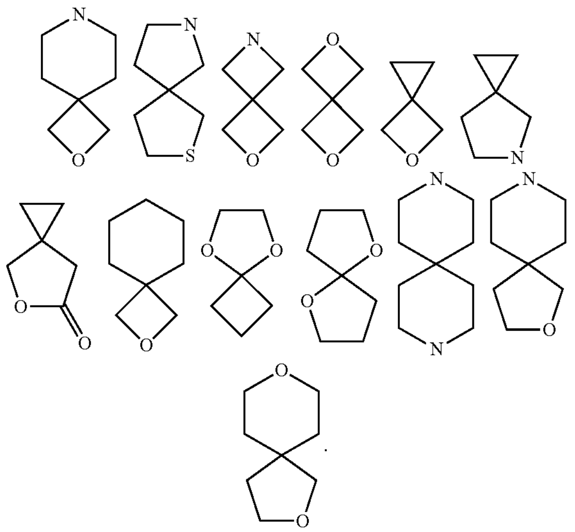

"Fused heterocyclyl" refers to a polycyclic heterocyclyl in which each ring shares an adjacent pair of carbon atoms with other rings in the system, wherein one or more (preferably, 1, 2, 3 or 4) of the rings may contain one or more (preferably, 1, 2 or 3) double bonds, but none of the rings have a fully conjugated π-electron system, wherein one or more (preferably, 1, 2, 3 or 4) of the ring atoms are heteroatoms selected from nitrogen, oxygen, S(O)(=NH) or S(O), (wherein r is an integer of 0, 1, 2), and the remaining ring atoms are carbon atoms. Depending on the number of rings, it may be bicyclic, tricyclic, tetracyclic or polycyclic, fused heterocyclyl includes, but is not limited to:

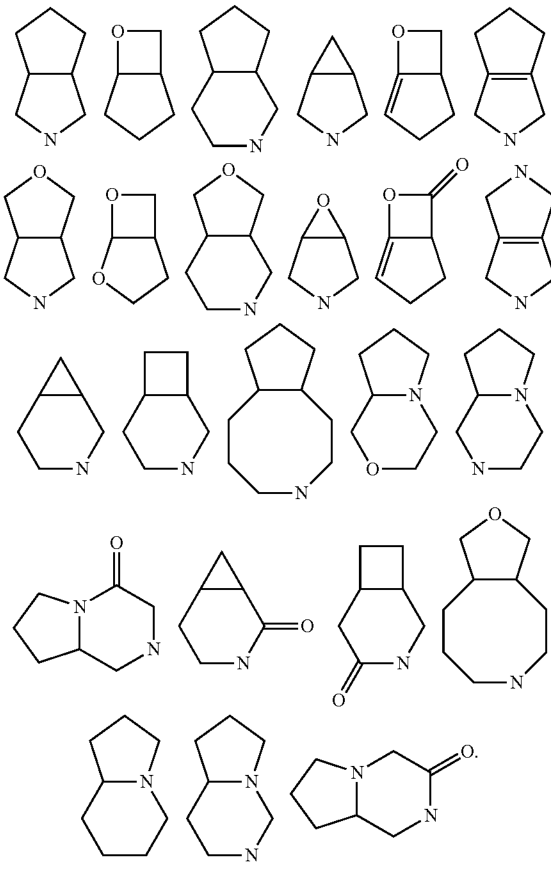

"Bridged heterocyclyl" refers to a polycyclic heterocyclyl in which any two rings share two carbon atoms that are not directly bonded, which may contain one or more (preferably, 1, 2 or 3) double bonds, but none of the rings have a fully conjugated pi-electron system, wherein one or more (preferably, 1, 2, 3 or 4) of the ring atoms are heteroatoms selected from nitrogen, oxygen, S(O)(=NH) or S(O)$_r$ (wherein r is an integer of 0, 1, 2), and the remaining ring atoms are carbon atoms. Depending on the number of rings, it may be bicyclic, tricyclic, tetracyclic or polycyclic, bridged heterocyclyl includes, but is not limited to:

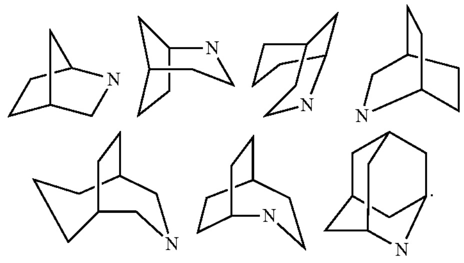

The ring of the heterocyclyl may be fused to a ring of aryl, heteroaryl or cycloalkyl wherein the ring attached to the parent structure is a heterocyclyl, includes, but is not limited to:

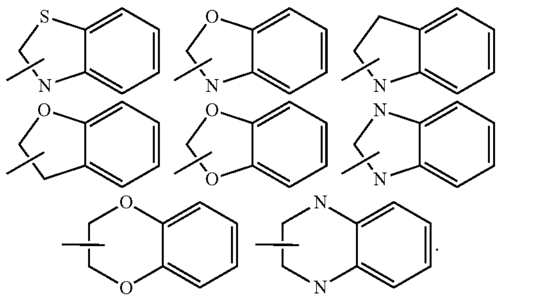

Heterocyclyl may be optionally substituted or unsubstituted, and when it is substituted, the substituent is preferably one or more (preferably, 1, 2, 3, or 4) of the groups independently selected from the group consisting of deuterium, halogen, cyano, nitro, azido, $C_{1-10}$ alkyl, $C_{1-10}$ alkoxy, $C_{2-10}$ alkenyl, $C_{2-10}$ alkynyl, $C_{1-10}$ haloalkyl, $C_{1-10}$ haloalkoxy, $C_{1-10}$ deuterioalkyl, $C_{1-10}$ deuterioalkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, =O, $-C_{0-8}-SF_5$, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$.

"Aryl" or "aromatic ring" refers to an all-carbon monocyclic or fused polycyclic (i.e., a ring that shares a pair of adjacent carbon atoms) group, and a polycyclic group having a conjugated π-electron system (i.e., a ring with adjacent pairs of carbon atoms), preferably an all-carbon aryl containing 5-10 or 5-8 carbons. For example, "$C_{5-10}$ aryl" refers to an all-carbon aryl containing 5-10 carbons, and "$C_{5-8}$ aryl" refers to an all-carbon aryl containing 5-8 carbons, including but not limited to phenyl and naphthyl. The aryl ring may be fused to a ring of heteroaryl, heterocyclyl or cycloalkyl, wherein the ring attached to the parent structure is an aryl ring, includes, but is not limited to:

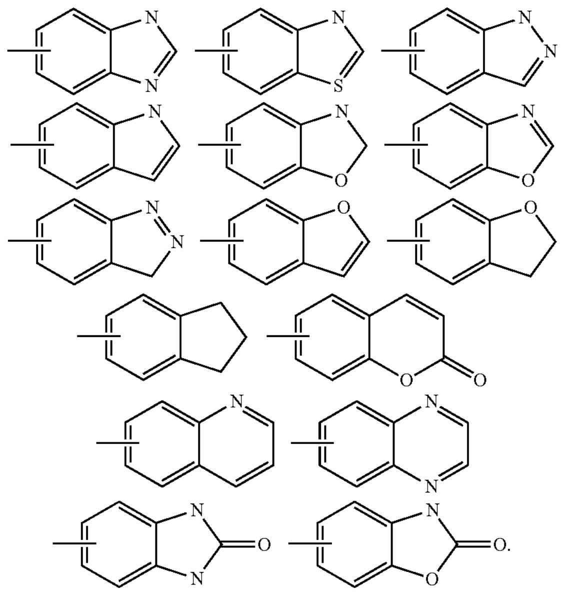

"Aryl" may be substituted or unsubstituted, and when it is substituted, the substituent is preferably one or more (preferably, 1, 2, 3, or 4) of the groups independently selected from the group consisting of deuterium, halogen, cyano, nitro, azido, $C_{1-10}$ alkyl, $C_{1-10}$ alkoxy, $C_{2-10}$ alkenyl, $C_{2-10}$ alkynyl, $C_{1-10}$ haloalkyl, $C_{1-10}$ haloalkoxy, $C_{1-10}$ deuterioalkyl, $C_{1-10}$ deuterioalkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, =O, $-C_{0-8}-SF_5$, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_2)-C(=NR_{13})R_{11}$, $-C_{0-8}-C(O)NR_{12}R_{13}$ and $-C_{0-8}-N(R_{12})-C(O)R_{11}$.

"Heteroaryl" refers to a heteroaromatic system containing one or more (preferably, 1, 2, 3 or 4) heteroatoms including a heteroatom selected from the group consisting of nitrogen, oxygen or S(O)r (wherein r is an integer of 0, 1, 2), preferably a heteroaromatic system containing 5-10 or 5-8 ring atoms. For example, 5-8 membered heteroaryl refers to a heteroaromatic system containing 5 to 8 ring atoms, and 5-10 membered heteroaryl refers to a heteroaromatic system containing 5 to 10 ring atoms, including but not limited to furyl, thiophenyl, pyridyl, pyrrolyl, N-alkylpyrrolyl, pyrimidinyl, pyrazinyl, imidazolyl, tetrazolyl group or the like. The heteroaryl ring may be fused to a ring of aryl, heterocyclyl or cycloalkyl wherein the ring attached to the parent structure is a heteroaryl ring, includes, but is not limited to:

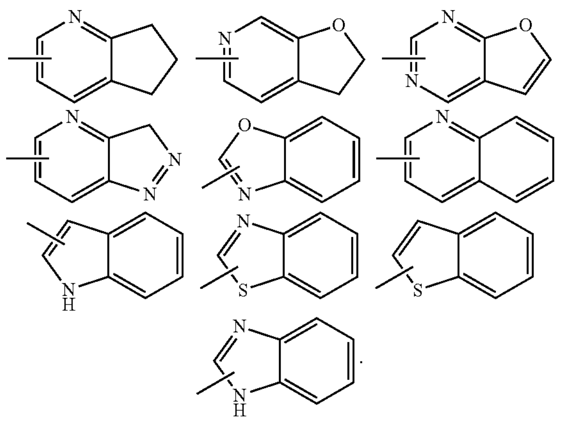

"Heteroaryl" may be optionally substituted or unsubstituted, and when it is substituted, the substituent is preferably one or more (preferably, 1, 2, 3, or 4) of the groups independently selected from the group consisting of deuterium, halogen, cyano, nitro, azido, $C_{1-10}$ alkyl, $C_{1-10}$ alkoxy, $C_{2-10}$ alkenyl, $C_{2-10}$ alkynyl, $C_{1-10}$ haloalkyl, $C_{1-10}$ haloalkoxy, $C_{1-10}$ deuterioalkyl, $C_{1-10}$ deuterioalkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, =O, $-C_{0-8}-SF_5$, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$.

"Alkenyl" refers to an alkyl group defined as above consisting of at least two carbon atoms and at least one carbon-carbon double bond, preferably a straight or branched alkenyl containing 2-10 or 2-4 carbons. For example, $C_{2-10}$ alkenyl refers to a straight or branched alkenyl containing 2 to 10 carbons. Alkenyl includes, but is not limited to vinyl, 1-propenyl, 2-propenyl, 1-, 2- or 3-butenyl, and the likes.

"Alkenyl" may be substituted or unsubstituted, and when it is substituted, the substituent is preferably one or more (preferably, 1, 2, 3, or 4) of the groups independently selected from the group consisting of deuterium, halogen, cyano, nitro, azido, $C_{1-10}$ alkyl, $C_{1-10}$ alkoxy, $C_{2-10}$ alkenyl, $C_{2-10}$ alkynyl, $C_{1-10}$ haloalkyl, $C_{1-10}$ haloalkoxy, $C_{1-10}$ deuterioalkyl, $C_{1-10}$ deuterioalkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, =O, $-C_{0-8}-SF_5$, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_2)-C(=NR_{13})R_{11}$, $-C_{0-8}-C(O)NR_{12}R_{13}$ and $-C_{0-8}-N(R_{12})-C(O)R_{11}$.

"Alkynyl" refers to an alkyl group defined as above consisting of at least two carbon atoms and at least one carbon-carbon double bond, preferably a straight or branched allkynyl containing 2-10 or 2-4 carbons. For example, $C_{2-10}$ allkynyl refers to a straight or branched allkynyl containing 2 to 10 carbons, and $C_{2-4}$ lkynyl refers to a straight or branched allkynyl containing 2 to 4 carbons. Alkynyl includes, but is not limited to ethynyl, 1-propynyl, 2-propynyl, 1-, 2- or 3-butynyl, and the likes.

"Alkynyl" may be substituted or unsubstituted, and when it is substituted, the substituent is preferably one or more (preferably, 1, 2, 3, or 4) of the groups independently selected from the group consisting of deuterium, halogen, cyano, nitro, azido, $C_{1-10}$ alkyl, $C_{1-10}$ alkoxy, $C_{2-10}$ alkenyl, $C_{2-10}$ alkynyl, $C_{1-10}$ haloalkyl, $C_{1-10}$ haloalkoxy, $C_{1-10}$ deuterioalkyl, $C_{1-10}$ deuterioalkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, =O, $-C_{0-8}-SF_5$, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$.

"Alkoxy" refers to —O-(alkyl), wherein alkyl is defined as above. For example, "$C_{1-10}$ alkoxy" refers to an alkyloxy containing 1 to 10 carbons, and $C_{1-4}$ alkoxy refers to an alkyloxy containing 1-4 carbons and includes, but is not limited to methoxy, ethoxy, propoxy, butoxy, and the likes.

"Alkoxy" may be optionally substituted or unsubstituted, and when it is substituted, the substituent is preferably one or more (preferably, 1, 2, 3, or 4) of the groups independently selected from the group consisting of deuterium, halogen, cyano, nitro, azido, $C_{1-10}$ alkyl, $C_{1-10}$ alkoxy, $C_{2-10}$ alkenyl, $C_{2-10}$ alkynyl, $C_{1-10}$ haloalkyl, $C_{1-10}$ haloalkoxy, $C_{1-10}$ deuterioalkyl, $C_{1-10}$ deuterioalkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, =O, =O, $-C_{0-8}-SF_5$, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$.

"Cycloalkyloxy" refers to —O-cycloalkyl, wherein the cycloalkyl is defined as above. For example, "$C_{3-10}$ cycloalkyloxy" refers to a cycloalkyloxy containing 3 to 10 carbon atoms, and "$C_{3-8}$ cycloalkyloxy" refers to a cycloalkyloxy containing 3 to 8 carbons. Cycloalkyloxy includes, but is not limited to, cyclopropyloxy, cyclobutyloxy, cyclopentyloxy, cyclohexyloxy and the likes.

"Cycloalkoxy" may be optionally substituted or unsubstituted, and when it is substituted, the substituent is preferably one or more (preferably, 1, 2, 3, or 4) of the groups independently selected from the group consisting of deuterium, halogen, cyano, nitro, azido, $C_{1-10}$ alkyl, $C_{1-10}$ alkoxy, $C_{2-10}$ alkenyl, $C_{2-10}$ alkynyl, $C_{1-10}$ haloalkyl, $C_{1-10}$ haloalkoxy, $C_{1-10}$ deuterioalkyl, $C_{1-10}$ deuterioalkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, =O, —$C_{0-8}$—$SF_5$, —$C_{0-8}$—$S(O)_rR_9$, —$C_{0-8}$—O—$R_{10}$, —$C_{0-8}$—C(O)$OR_{10}$, —$C_{0-8}$—C(O)$R_{11}$, —$C_{0-8}$—O—C(O)$R_{11}$, —$C_{0-8}$—$NR_{12}R_{13}$, —$C_{0-8}$—C(=$NR_{12}$)$R_{11}$, —$C_{0-8}$—N($R_{12}$)—C(=$NR_{13}$)$R_{11}$, —$C_{0-8}$—C(O)$NR_{12}R_{13}$ and —$C_{0-8}$—N($R_{12}$)—C(O)$R_{11}$.

"Heterocyclyloxy" refers to —O-heterocyclyl, wherein the heterocyclyl is defined as above. The heterocyclyloxy includes, but is not limited to, azacyclobutyloxy, oxacyclobutyloxy, azacyclopentyloxy, nitrogen, oxacyclohexyloxy, etc.

"Heterocyclyloxy" may be optionally substituted or unsubstituted, and when it is substituted, the substituent is preferably one or more (preferably, 1, 2, 3, or 4) of the groups independently selected from the group consisting of deuterium, halogen, cyano, nitro, azido, $C_{1-10}$ alkyl, $C_{1-10}$ alkoxy, $C_{2-10}$ alkenyl, $C_{2-10}$ alkynyl, $C_{1-10}$ haloalkyl, $C_{1-10}$ haloalkoxy, $C_{1-10}$ deuterioalkyl, $C_{1-10}$ deuterioalkoxy, $C_{3-10}$ cycloalkyl, $C_{3-10}$ cycloalkoxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, =O, —$C_{0-8}$—$SF_5$, —$C_{0-8}$—$S(O)_rR_9$, —$C_{0-8}$—O—$R_{10}$, —$C_{0-8}$—C(O)$OR_{10}$, —$C_{0-8}$—C(O)$R_{11}$, —$C_{0-8}$—O—C(O)$R_{11}$, —$C_{0-8}$—$NR_{12}R_{13}$, —$C_{0-8}$—C(=$NR_{12}$)$R_{11}$, —$C_{0-8}$—N($R_{12}$)—C(=$NR_{13}$)$R_{11}$, —$C_{0-8}$—C(O)$NR_{12}R_{13}$ and —$C_{0-8}$—N($R_{12}$)—C(O)$R_{11}$.

"$C_{1-10}$ alkanoyl" refers to a monovalent atomic group obtained by removing hydroxy from $C_{1-10}$ alkyl acid, is also generally referred to as "$C_{0-9}$—C(O)—", for example, "$C_1$—C(O)—" refers to acetyl; "$C_2$—C(O)—" refers to propionyl; "$C_3$—C(O)—" refers to butyryl or isobutyryl.

"$C_{1-4}$" means "$C_{1-4}$ alkyl", "$C_{0-4}$" means "$C_{0-4}$alkyl", "$C_{1-8}$" means $C_{1-8}$alkyl, "$C_{0-8}$" means $C_{0-8}$alkyl, and "$C_{1-10}$" means "$C_{1-10}$alkyl", defined as above.

"—$C_{0-8}$—$S(O)_rR_9$" means that the sulfur atom in —$S(O)_rR_9$ is bonded to $C_{0-8}$ alkyl, wherein $C_{0-8}$ is defined as above.

"—$C_{0-8}$—O—$R_{10}$" means that the oxygen atom in —O—$R_{10}$ is bonded to $C_{0-8}$ alkyl, wherein $C_{0-8}$ alkyl is defined as above.

"—$C_{0-8}$—C(O)$OR_{10}$" means that the carbonyl group in —C(O)$OR_{10}$ is bonded to $C_{0-8}$ alkyl, wherein $C_{0-8}$ alkyl is defined as above.

"—$C_{0-8}$—C(O)$R_{11}$" means that the carbonyl group in —C(O)$R_{11}$ is bonded to $C_{0-8}$ alkyl, wherein $C_{0-8}$ alkyl is defined as above.

"—$C_{0-8}$—O—C(O)$R_{11}$" means that the oxygen atom in —O—C(O)$R_{11}$ is bonded to $C_{0-8}$ alkyl, wherein $C_{0-8}$ alkyl is defined as above.

"—$C_{0-8}$—$NR_{12}R_{13}$" means that the nitrogen atom in —$NR_{12}R_{13}$ is bonded to $C_{0-8}$ alkyl, wherein $C_{0-8}$ alkyl is defined as above.

"—$C_{0-8}$—C(=$NR_{12}$)$R_{11}$" means that the nitrogen atom in —C(=$NR_{12}$)$R_{11}$ is bonded to $C_{0-8}$ alkyl, wherein $C_{0-8}$ alkyl is defined as above.

"—$C_{0-8}$—N($R_{12}$)—C(=$NR_{13}$)$R_{11}$" means that the nitrogen atom in —N($R_{12}$)—C(=$NR_{13}$)$R_{11}$, is bonded to $C_{0-8}$ alkyl, wherein $C_{0-8}$ alkyl is defined as above.

"—$C_{0-8}$—C(O)$NR_{12}R_{13}$" means that the carbonyl in —C(O)$NR_{12}R_{13}$ is bonded to $C_{0-8}$ alkyl, wherein $C_{0-8}$ alkyl is defined as above.

"—$C_{0-8}$—N($R_{12}$)—C(O)$R_{11}$" means that the nitrogen atom in —N($R_{12}$)—C(O)$R_{11}$ is bonded to $C_{0-8}$ alkyl, wherein $C_{0-8}$ alkyl is defined as above.

"$C_{1-10}$ haloalkyl" means a alkyl group having 1 to 10 carbon atoms, wherein any hydrogen atom on which is optionally substituted with F, Cl, Br or I, and includes, but is not limited to, difluoromethyl (—$CHF_2$), dichloromethyl (—$CHCl_2$), dibromomethyl (—$CHBr_2$), trifluoromethyl (—$CF_3$), trichloromethyl (—$CCl_3$), tribromomethyl (—$CBr_3$), and the likes.

"$C_{1-10}$ haloalkoxy" means an alkoxy group having 1 to 10 carbon atoms, wherein any hydrogen atom on which is optionally substituted with F, Cl, Br or I, and includes, but is not limited to difluoromethoxy, dichloromethoxy, dibromomethoxy, trifluoromethoxy, trichloromethoxy, tribromomethoxy, and the likes.

"$C_{1-10}$ deuterioalkyl" means an alkyl group having 1 to 10 carbon atoms, wherein any hydrogen atom on which is optionally substituted with F, Cl, Br or I, and includes, but is not limited to, monodeuteriomethyl (—$CH_2D$), dideuteriomethyl (—$CHD_2$), trideuteriomethyl (—$CD_3$), and the likes.

"$C_{1-10}$ deuterioalkoxy" means an alkoxy group having 1 to 10 carbon atoms, wherein any hydrogen atom on which is optionally substituted with F, Cl, Br or I, and includes, but is not limited to, monodeuterioethoxy, dideuteriomethoxy, trideuteriomethoxy, and the likes.

"Halogen" means F, Cl, Br or I. "$CH_2C_2$" means dichloromethane. "DCM" means dichloromethane. "MeOH" means methanol. "$Cs_2CO_3$" means cesium carbonate. "PE" means petroleum ether. "EA" means ethylamine. "DMF" means N,N-dimethylformamide. "THF" means tetrahydrofuran. "$SOCl_2$" means thionyl chloride. "EtOAc" means ethyl acetate. "NH4Cl" refers to ammonium chloride. "NaCl" means sodium chloride. "ACN" means acetonitrile. "DBU" means 1,8-diazabicycloundec-7-ene. "BOP" means Benzotriazole-1-yl-oxy-tris-(dimethylamino)-phosphonium hexafluorophosphate, i.e., Castro's Reagent. "NBS" means N-bromosuccinimide.

"Optional" or "optionally" means that the event or environment subsequently described may, but need not, occur, including where the event or environment occurs or does not occur, that is, including both substituted and unsubstituted situations. For example, "heterocyclyl optionally substituted by alkyl" means that an alkyl group may be, but is not necessarily, present, and the description includes the case where the heterocyclyl is substituted with an alkyl and the case where the heterocyclyl is not substituted with an alkyl.

The term "substituted" means that one or more "hydrogen atoms" in the group are each independently substituted by a corresponding number of substituents. It goes without saying that a substituent is only in its possible chemical position, which is consistent with the valence-bond theory of chemistry. Those skilled in the art will be able to determine (by experiments or theories) possible or impossible substitution without undue efforts. For example, it may be unstable that an amino group or a hydroxyl group having a free hydrogen is attached with a carbon atom having an unsaturated bond (such as an olefin).

"Stereoisomer" means an isomer produced due to a different spatial arrangement of atoms in the molecules, and can be classified into either cis-trans isomers and enantiomers, or enantiomers and diastereomers. Stereoisomers resulting from the rotation of a single bond are called conformational stereo-isomers, and sometimes also called rotamers. Stereoisomers induced by reasons such as bond lengths, bond angles, double bonds in molecules and rings are called configuration stereo-isomers, which are classified into two categories. Among them, isomers induced by the double bonds or single bonds of ring-forming carbon atoms that cannot rotate freely are called geometric isomers, also known as cis-trans isomers, which are divided into two configurations including Z and E. For example, cis-2-butene and trans-2-butene are a pair of geometric isomers. If the compound of the present invention contains a double bond, it can be understood as containing a E and/or Z form, unless otherwise specifically indicated. Stereoisomers with different optical activities due to the absence of anti-axial symmetry in the molecules are called optical isomers, which are classified into two configurations including R and S.

Unless otherwise specified, the "stereoisomer" in the present invention can be understood to include one or several of the above-mentioned enantiomers, configurational isomers and conformational isomers, preferably the S configuration.

"Pharmaceutically acceptable salt" in the present invention means pharmaceutically acceptable acid addition salts or alkali addition salts, including inorganic acid salts and organic acid salts, and these salts can be prepared by methods known in the art.

"Pharmaceutical composition" indicates a mixture comprising one or more of the compounds described herein, or a physiologically/pharmaceutically acceptable salt or prodrug thereof, and other chemical components, for example physiological/pharmaceutically acceptable carriers and excipients. The purpose of the pharmaceutical composition is to promote the administration to an organism, which facilitates the absorption of the active ingredient thereby exerting biological activities.

The present invention will be further described in detail below in conjunction with the embodiments which is not intended to limit the present invention. The present invention is also not limited to the contents of the embodiments.

The structure of the compound of the present invention is determined by nuclear magnetic resonance (NMR) or/and liquid chromatography-mass spectrometry (LC-MS). The NMR chemical shift (δ) is given in parts per million (ppm). The NMR determination is conducted by using a Bruker AVANCE-400 or AVANCE-500 nuclear magnetic resonance apparatus, with hexadeuterodimethyl sulfoxide (DMSO-$d_6$), tetradeuteromethanol ($CD_3OD$), deuterium oxide ($D_2O$) and deuterated chloroform ($CDCl_3$) as determination solvents, and tetramethylsilane (TMS) as an internal standard.

The measurement of LC-MS is performed by using an Agilent 6120 mass spectrometer. The measurement of HPLC is performed by using an Agilent 1200 DAD high pressure liquid chromatograph (Sunfire C18 150×4.6 mm column) and a Waters 2695-2996 high pressure liquid chromatograph (Gimini C18 150×4.6 mm column).

The thin layer chromatography silica gel plate is Yantai Yellow Sea HSGF254 or Qingdao GF254 silica gel plate. The specification of TLC is 0.15 mm-0.20 mm, and the specification for thin layer chromatography separation and purification is 0.4 mm-0.5 mm. 200-300 mesh silica gel (Yantai Huanghai silica gel) as a carrier is generally used in column chromatography.

The starting materials in the examples of the present invention are known and commercially available or can be synthesized according to methods known in the art.

Unless otherwise stated, all reactions of the present invention are carried out under continuous magnetic stirring in a dry nitrogen or argon atmosphere, the solvent is a dry solvent, and the unit of the reaction temperature is degrees Celsius (° C.).

PREPARATION OF INTERMEDIATES

Intermediate A1: Preparation of (Z)-2-(2-(2-chloro-3-(methoxymethoxy)phenyl)-1-fluorovinyl)-4,4,5,5-tetramethyl-1,3,2-dioxaborolane

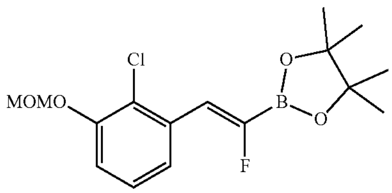

Step 1: Synthesis of 2-chloro-3-(methoxymethoxy)benzaldehyde

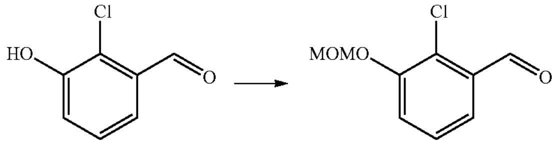

2-chloro-3-hydroxybenzaldehyde (10.0 g, 64.10 mmol) was dissolved in acetonitrile (80 mL), to which N,N-diisopropylethylenediamine (16.5 g, 128.20 mmol) and bromomethoxy-methane (17.9 g, 128.20 mmol) were then added. A tube was sealed and heated to 80° C. to react overnight. After cooling, the reaction mixture was poured into water (150 mL), then extracted with ethyl acetate (100 mL*2), and dried over anhydrous sodium sulfate. After concentrating, column chromatographic separation [eluent:petroleum ether=100%-ethyl acetate=10%] was conducted to obtain 2-chloro-3-(methoxymethoxy)benzaldehyde (12.7 g, yield: 100%).

$^1$H NMR (400 MHz, Chloroform-d) δ 10.45 (d, J=0.8 Hz, 1H), 7.52 (dd, J=7.7, 1.6 Hz, 1H), 7.35 (dd, J=8.2, 1.6 Hz, 1H), 7.25 (td, J=7.9, 0.8 Hz, 1H), 5.22 (s, 2H), 3.47 (s, 3H).

Step 2: Synthesis of 2-chloro-1-(2,2-dichlorovinyl)-3-(methoxymethoxy)benzene

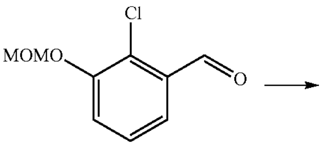

-continued

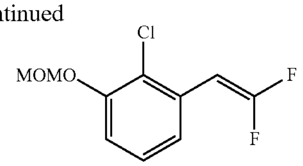

2-Chloro-3-(methoxymethoxy)benzaldehyde (18.2 g, 91.0 mmol) was dissolved in N, N-dimethylformamide (182 mL) (i.e., 0.5M aldehyde solution), to which triphenylphosphine (28.6 g, 109.2 mmol) was then added. The mixture was heated to 100° C. and then added dropwise with a solution of sodium difluoroacetate (20.8 g, 136.5 mmol, 2 M) in N,N-dimethylformamide. The reaction mixture was continuously stirred for 1 hour at 100° C., poured into water (250 mL), and then extracted with petroleum ether (300 mL*2). The organic phase was washed sequentially with water (100 mL) and saturated saline water (100 mL), dried over anhydrous sodium sulfate, and dried. Then, column chromatographic separation [eluent:petroleum ether] was conducted to obtain 2-chloro-1-(2,2-difluoro vinyl)-3-(methoxymethoxy)benzene (13.3 g, yield: 62%).

$^1$H NMR (400 MHz, Chloroform-d) δ 7.24-7.14 (m, 2H), 7.08 (dd, J=6.8, 3.0 Hz, 1H), 5.72 (dd, J=25.4, 3.9 Hz, 1H), 5.25 (s, 2H), 3.52 (s, 3H).

$^{19}$F NMR (377 MHz, Chloroform-d) 6-81.31 (d, J=24.9 Hz), −82.22 (d, J=25.0 Hz).

Step 3: Synthesis of (Z)-2-(2-(2-chloro-3-(methoxymethoxy)phenyl)-1-fluorovinyl)-4,4,5,5-tetramethyl-1,3,2-dioxaborolane

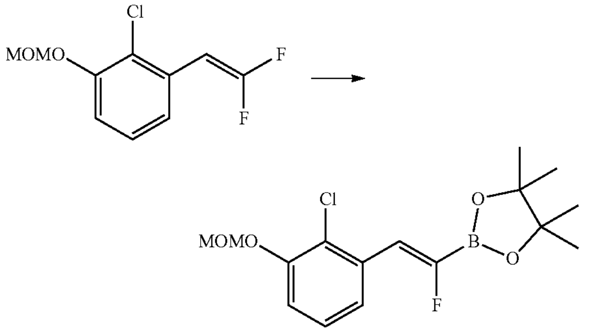

2-chloro-1-(2,2-difluorovinyl)-3-(methoxymethoxy)benzene (4.6 g, 19.65 mmol) was dissolved in tetrahydrofuran (150 mL), to which bis(pinacolato)diboron (6.0 g, 23.59 mmol), cuprous chloride (20 mg, 0.196 mmol), tricyclohexylphosphine (110 mg, 0.393 mmol) and potassium acetate (5.8 g, 58.97 mmol) were then added. The reaction mixture was stirred for 16 hours at 40° C., poured to water (100 mL), then extracted with ethyl acetate (100 mL*2), dried over anhydrous sodium sulfate, and concentrated. Then, column chromatographic separation [eluent:petroleum ether=100%-ethyl acetate=10%] was conducted to obtain (Z)-2-(2-(2-chloro-3-(methoxymethoxy)phenyl)-1-fluorovinyl)-4,4,5,5-tetramethyl-1,3,2-dioxa borolane (3.7 g, yield: 55%).

$^1$H NMR (400 MHz, Chloroform-d) δ 7.66 (dd, J=7.8, 1.5 Hz, 1H), 7.22 (t, J=8.0 Hz, 1H), 7.14 (dd, J=8.3, 1.5 Hz, 1H), 6.87 (d, J=45.4 Hz, 1H), 5.27 (s, 2H), 3.54 (s, 3H), 1.37 (s, 12H).

$^{19}$F NMR (377 MHz, Chloroform-d) 6-122.01.

Intermediate A2 can be prepared by referring to the preparation method for intermediate A1:

| Intermediate No. | Structural formula | Compound name | ESI-MS: [M + H]$^+$ |
|---|---|---|---|
| A2 | 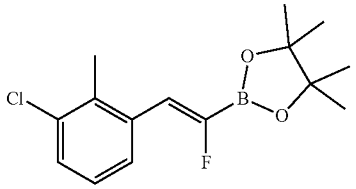 [SMILES: Cc1c(Cl)cccc1/C=C(\F)B1OC(C)(C)C(C)(C)O1] | (Z)-2-(2-(3-chloro-2-methylphenyl)-1-fluorovinyl )-4,4,5,5-tetramethyl-1,3,2-dioxaborolane | NA |

Intermediate B: Preparation of methyl 4-(2-oxoethyl)bicyclo[2.2.1]heptane-1-carboxylate

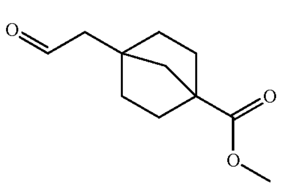

Step 1: Synthesis of 4-(methoxycarbonyl)bicyclo[2.2.1]heptane-1-carboxylic acid

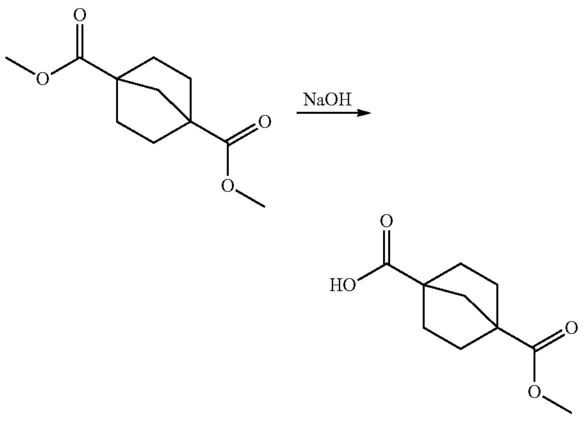

Tetrahydrofuran (180 mL) was added to a single-mouth flask filled with dimethylbicyclo[2.2.1]heptane-1,4-dicarboxylate (5.6 g, 26.4 mmol), to which a solution of sodium hydroxide (1.06 g, 26.4 mmol) in methanol (11 mL) was added dropwise by using a constant-pressure dropping funnel. The reaction mixture was stirred at room temperature overnight. The reaction mixture was carefully concentrated to spin-dry the solvent. The solid was washed with petroleum ether and then filtered, and the filter cake was dissolved in water (50 mL). The water solution was acidified to pH=4 with 2M hydrochloric acid and then extracted with ethyl acetate. The organic phase was washed with water and saturated sodium chloride, dried over anhydrous sodium sulfate, filtered, and concentrated to obtain 4-(methoxycarbonyl)bicyclo[2.2.1]heptane-1-carboxylic acid (4.17 g, yield: 80%).

Step 2: Synthesis of methyl 4-(hydroxymethyl)bicyclo[2.2.1]heptane-1-carboxylate

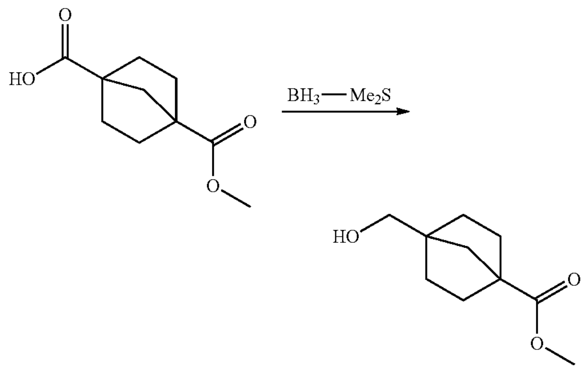

In an ice bath, dry tetrahydrofuran (100 mL) was added to a single-mouth flask filled with 4-(methoxycarbonyl)bicyclo[2.2.1]heptane-1-carboxylic acid (4.17 g, 21.03 mmol), to which a borane dimethyl sulfide complex (2.7 mL, 27.35 mmol, 10.0 M) was added dropwise by using a syringe. After dropwise addition, the mixture was stirred overnight at room temperature. Methanol (10 mL) was dropped to the reaction mixture, which was refluxed for 4 hours and then quenched. Ethyl acetate/water was used for extraction. The organic phase was washed with water and saturated sodium chloride, dried over anhydrous sodium sulfate, filtered, and concentrated. Then, column chromatography (petroleum ether/ethyl acetate=3:2) was conducted to obtain methyl 4-(hydroxymethyl)bicyclo[2.2.1]heptane-1-carboxylate (3.53 g, yield: 90%).

$^1$H NMR (400 MHz, Chloroform-d) δ 3.70 (s, 2H), 3.67 (s, 3H), 2.06-1.93 (m, 2H), 1.73-1.62 (m, 4H), 1.58-1.54 (m, 2H), 1.43-1.34 (m, 2H).

Step 3: Synthesis of methyl 4-formylbicyclo[2.2.1]heptane-1-carboxylate

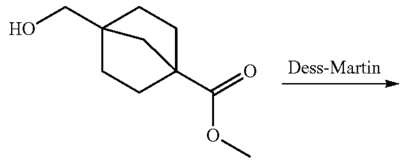

-continued

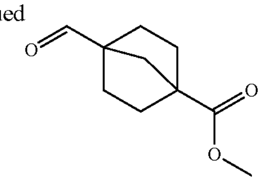

Dichloromethane (180 mL) was added to a single-mouth flask filled with methyl 4-(hydroxymethyl)bicyclo[2.2.1]heptane-1-carboxylate (4.75 g, 25.7 mmol) and dissolved. A Dess-Martin reagent (13.1 g, 30.9 mmol) was added to a resulting solution. The reaction mixture was stirred at room temperature, and the reaction was detected by TLC until the starting materials disappeared. Diatomite was used for filtration. The filtrate was concentrated and then subjected to column chromatography (petroleum ether/ethyl acetate=5:1) to obtain methyl 4-formylbicyclo[2.2.1]heptane-1-carboxylate (3.38 g, yield: 72%).

$^1$H NMR (400 MHz, Chloroform-d) δ 9.81 (s, 1H), 3.70 (s, 3H), 2.13-2.00 (m, 4H), 1.86-1.82 (m, 2H), 1.79-1.68 (m, 2H), 1.60-1.52 (m, 2H).

Step 4: Synthesis of methyl (E/Z)-4-(2-methoxyvinyl)bicyclo[2.2.1]heptane-1-carboxylate

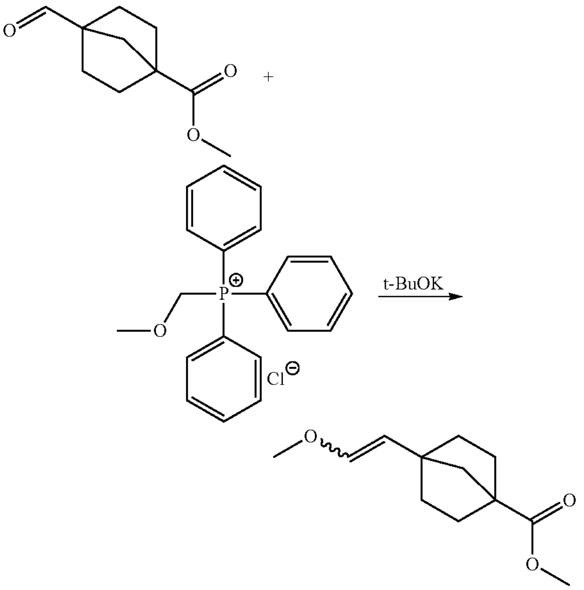

In a nitrogen atmosphere, potassium tert-butoxide (10 mL, 1.0 M) was added drop wise to a suspension of (methoxymethyl) triphenylphosphorus chloride (3.4 g, 9.87 mmol) in dry tetrahydrofuran (45 mL). After dropwise addition, the mixture was stirred for half an hour at room temperature. A solution of methyl 4-formylbicyclo[2.2.1]heptane-1-carboxylate (1.2 g, 6.58 mmol) in tetrahydrofuran (12 mL) was added dropwise to the reaction mixture. After dropwise addition, the mixture was stirred for 3 hours at room temperature. A saturated ammonium chloride solution was added for quenching. Ethyl acetate/water was used for extraction. The organic phase was washed with water and saturated sodium chloride, dried over anhydrous sodium sulfate, filtered, and concentrated. The n, column chromatography (petroleum ether/ethyl acetate=9:1) was conducted to obtain methyl (E/Z)-4-(2-methoxyvinyl)bicyclo[2.2.1]heptane-1-carboxylate (0.74 g, containing little triphenylphosphine).

Step 5: Synthesis of methyl 4-(2-oxoethyl)bicyclo[2.2.1]heptane-1-carboxylate

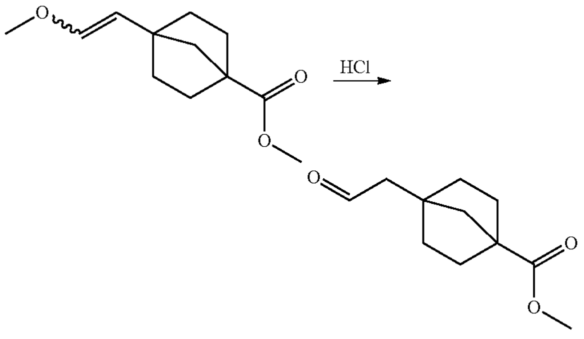

1M HCl (47 mL) was added to a solution of methyl (E/Z)-4-(2-methoxyvinyl)bicyclo [2.2.1]heptane-1-carboxylate (1.0 g, 4.7 mmol) in tetrahydrofuran (30 mL). The reaction mixture was stirred for 2 hours at room temperature, alkalified with saturated sodium bicarbonate, and then extracted with ethyl acetate. The organic phase was washed with water and saturated sodium chloride, dried over anhydrous sodium sulfate, filtered, and concentrated. Then, column chromatography (petroleum ether/ethyl acetate=3:1) was conducted to obtain methyl 4-(2-oxoethyl)bicyclo[2.2.1]heptane-1-carboxylate (0.85 g).

$^1$H NMR (400 MHz, Chloroform-d) δ 9.80 (t, J=2.7 Hz, 1H), 3.68 (s, 3H), 2.60 (d, J=2.6 Hz, 2H), 2.06-1.95 (m, 2H), 1.69-1.55 (m, 8H).

Intermediate C: Preparation of 5-(tert-butyl) 2-methyl 1-methyl-1,4,6,7-tetrahydro-5H-imidazo[4,5-c]pyridine-2,5-dicarboxylate

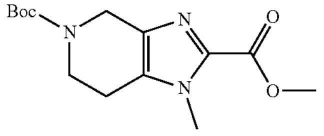 [SMILES: COC(=O)c1nc2c(n1C)CCN(C(=O)OC(C)(C)C)C2]

Step 1: Synthesis of N-methyl-3-nitropyridin-4-amine

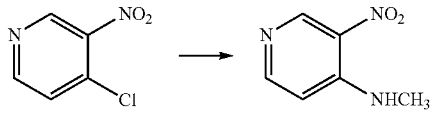 [SMILES: O=[N+]([O-])c1cnccc1Cl ; CNc1ccncc1[N+](=O)[O-]]

4-Chloro-3-nitropyridine (25.0 g, 158.22 mmol) was dissolved in dichloromethane (200 mL), to which methylamine water solution (40%, 78 mL) was added dropwise in an ice bath. The reaction mixture was stirred for 3 hours at room temperature to separate an organic phase. The aqueous phase was extracted with dichloromethane (200 mL*3). The organic phases were combined, dried over anhydrous sodium sulfate, and concentrated to obtain N-methyl-3-nitropyridin-4-amine (24 g, yield: 96%). ESI-MS: 154 $[M+H]^+$.

Step 2: Synthesis of $N^4$-methylpyridin-3,4-diamine

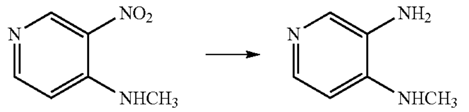

N-methyl-3-nitropyridin-4-amine (23.7 g) was dissolved in methanol (600 mL), to which wet powder of palladium carbon (10% Pd, 4.0 g) was then added. The reaction mixture was stirred overnight at room temperature in the presence of hydrogen. The palladium carbon was removed by filtering. The filtrate was concentrated to obtain $N^4$-methylpyridin-3,4-diamine (crude product). ESI-MS: 124 $[M+H]^+$.

Step 3: Synthesis of 1-methyl-1H-imidazo[4,5-c]pyridine

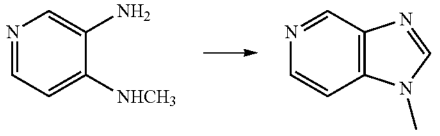

$N^4$-methylpyridin-3,4-diamine (crude product) was dissolved in 98% formic acid (150 mL), and heated to 100° C. to react for 48 hours. The reaction mixture was concentrated, to which dichloromethane (200 mL) was then added. The pH of the reaction mixture was adjusted to 8-10 by using 10% sodium hydroxide solution. The aqueous phase was extracted with dichloromethane:methanol=10:1. The organic phase were combined, dried over anhydrous sodium sulfate, and concentrated. Then, column chromatographic separation [eluent: dichloromethane (100%)-methanol (10%)] was conducted to obtain 1-methyl-1H-imidazo[4,5-c]pyridine (16 g). ESI-MS: 134 $[M+H]^+$.

Step 4: Synthesis of 5-(2-(4-methoxyphenyl)-2-oxoethyl)-1-methyl-1H-imidazo[4,5-c]pyridin-5-bromide positive ion

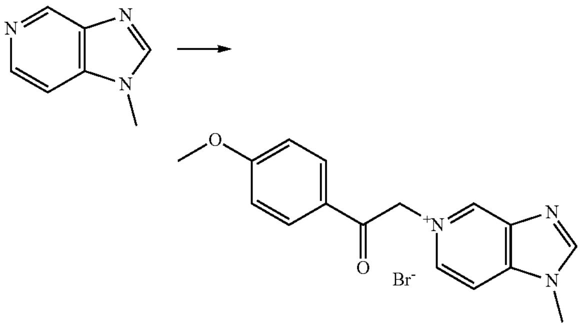

1-methyl-1H-imidazo[4,5-c]pyridine (29.7 g, 223.30 mmol) was dissolved in acetone (400 mL), to which a solution of 2-bromo-1-(4-methoxyphenyl)ethane-1-ketone (56 g, 24 5.63 mmol) in acetone (300 mL) was added dropwise. The reaction mixture was stirred for 3 hours at room temperature and filtered. The filter cake was dried to obtain 5-(2-(4-methoxyphenyl)-2-oxoethyl)-1-methyl-1H-imidazo[4,5-c]pyridin-5-bromide positive ion (78.5 g, yield: 97%). ESI-MS: 282 $[M+H]^+$.

Step 5: Synthesis of 1-(4-methoxyphenyl)-2-(1-methyl-1,4,6,7-tetrahydro-5H-imidazo[4,5-c]pyridin-5-yl)ethane-1-ol

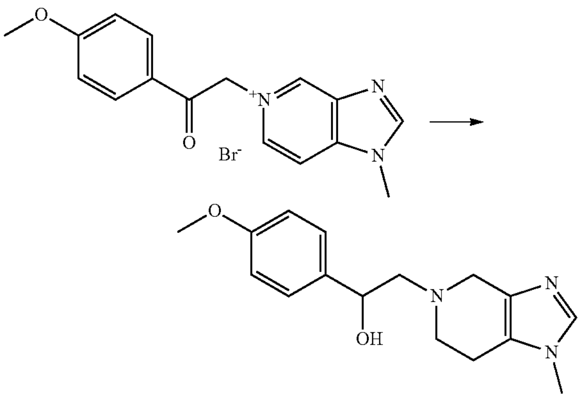

5-(2-(4-methoxyphenyl)-2-oxoethyl)-1-methyl-1H-imidazo[4,5-c]pyridin-5-bromide positive ion (73.5 g, 203.60 mmol) was dissolved in methanol (600 mL), to which sodium borohydride (23.2 g, 610.80 mmol) was added portionwise slowly in an ice bath. The reaction mixture was stirred overnight at room temperature. After the reaction mixture was concentrated, water and ethyl acetate were added. The organic phase was dried over anhydrous sodium sulfate, and concentrated to obtain 1-(4-methoxyphenyl)-2-(1-methyl-1,4,6,7-tetrahydro-5H-imidazo[4,5-c]pyridin-5-yl)ethane-1-ol (66 g of crude product). ESI-MS: 288 $[M+H]^+$.

Step 6: Synthesis of tert-butyl 1-methyl-1,4,6,7-tetrahydro-5H-imidazo[4,5-c]pyridin-5-carboxylate

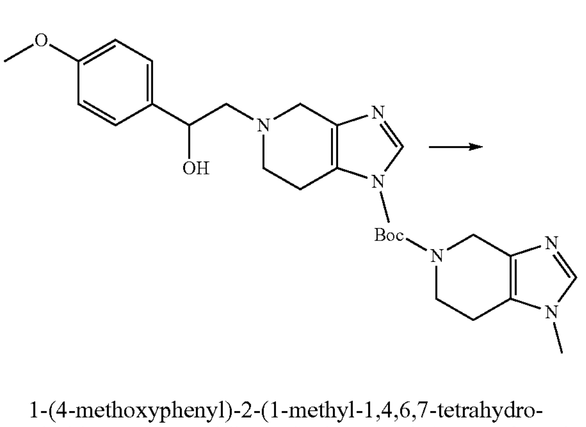

1-(4-methoxyphenyl)-2-(1-methyl-1,4,6,7-tetrahydro-5H-imidazo[4,5-c]pyridin-5-yl)ethane-1-ol (55 g of crude product) was dissolved in ethanol (150 mL), to which concentrated hydrochloric acid (100 mL) was then added. The reaction mixture was stirred overnight at 110° C. After concentrating, water and ethyl acetate were added to separate the organic phase. Acetone (150 mL) was added to the aqueous phase, the pH of which was adjusted to 8-9 with potassium carbonate. The di-tert-butyldicarbonate (41.8 g) was added dropwise. The reaction mixture was stirred overnight at room temperature. The acetone was spinned to dryness. Ethyl acetate was used for extraction. The organic phase was dried over anhydrous sodium sulfate, and concentrated. Then, column chromatographic separation [eluent: dichloromethane (100%-methanol (6%))] was conducted to obtain tert-butyl 1-methyl-1,4,6,7-tetrahydro-5H-imidazo[4,5-c]pyridine-5-carboxylate (28 g). ESI-MS: 238 $[M+H]^+$.

$^1H$ NMR (400 MHz, Chloroform-d) δ 7.27 (s, 1H), 4.38 (s, 2H), 3.67 (d, J=6.1 Hz, 2H), 3.46 (s, 3H), 2.53 (t, J=5.8 Hz, 2H), 1.40 (s, 9H).

Step 7: Synthesis of 5-(tert-butyl) 2-methyl 1-methyl-1,4,6,7-tetrahydro-5H-imidazo[4,5-c]pyridine-2,5-dicarboxylate

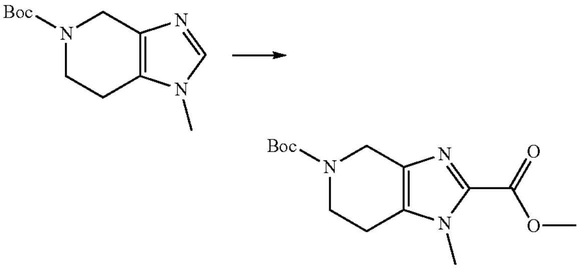

Tert-butyl 1-methyl-1,4,6,7-tetrahydro-5H-imidazo[4,5-c]pyridine-5-carboxylate (3.5 g, 14.77 mmol) was dissolved in anhydrous tetrahydrofuran (40 mL), to which n-butyllithium (7 mL, 17.72 mmol) was added dropwise at −78° C. After dropwise addition, the react ion mixture was stirred for 10 min at −78° C. Then, the reaction mixture was rapidly added dropwise to methylchlorofonmate (1.7 mL, 22.15 mmol) in anhydrous tetrahydrofuran (40 mL). The mixture was stirred for another 30 min at −78° C., poured into water, and extracted with ethyl acetate. The organic phase was dried over anhydrous sodium sulfat e and concentrated. Then, column chromatographic separation [eluent: dichloromethane (100%)-methanol (6%)] was conducted to obtain 5-(tert-butyl) 2-methyl 1-methyl-1,4,6,7-tetra hydro-5H-imidazo[4,5-c]pyridine-2,5-dicarboxylate (2.6 g, yield: 60%). ESI-MS: 296 $[M+H]^+$.

Intermediate D1: Preparation of tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate

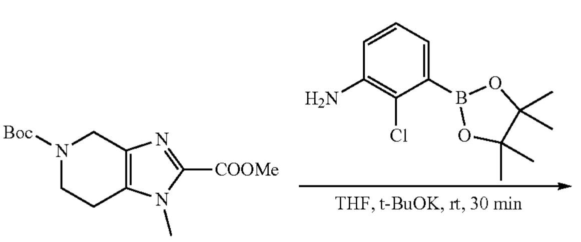

-continued

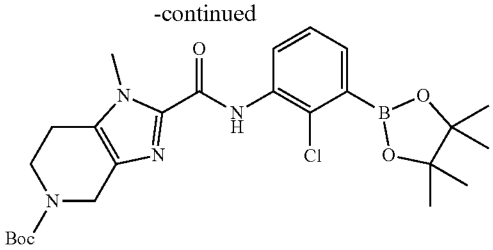

2-Chloro-3-(4,4,5,5-tetramethyl-1,3,2-dioxaborolan-2-yl) phenylamine (500 mg, 1.98 mmol) was dissolved in anhydrous tetrahydrofuran (20 mL), to which 5-(tert-butyl) 2-methyl 1-methyl-1,4,6,7-tetrahydro-5H-imidazo[4,5-c] pyridine-2,5-dicarboxylate (700 mg, 2.37 mmol) was then added. The reaction mixture was stirred for 10 min at room temperature. A solution of 1M potassium tert-butoxide in tetrahydrofuran (4 mL, 3.95 mmol) was added dropwise. The mixture was stirred for half an hour, then diluted with water, and extracted with ethyl acetate. The organic phase was dried and concentrated to obtain a crude product. The crude product was pulped by using a solution of PE:EA=50: 1, filtered and dried to obtain tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c] pyridine-5-carboxylate (540 mg). ESI-MS: 517 $[M+H]^+$.

Intermediates D2-D3 can be Prepared by Referring to the Preparation Method for Intermediate D1

| Intermediate No. | Structural Formula | Compound name | ESI-MS: $[M + H]^+$ |
|---|---|---|---|
| D2 | 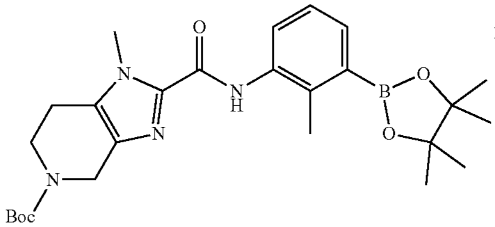 | tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo [4,5-c]pyridine-5-carboxylate | 497.3 |
| D3 | 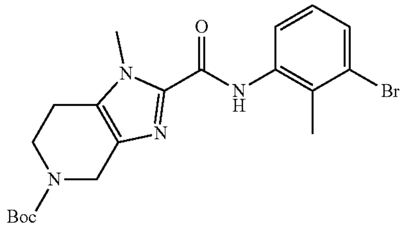 [SMILES: Cc1c(Br)cccc1NC(=O)c1nc2c(n1C)CCN(C(=O)OC(C)(C)C)C2] | tert-butyl 2-((3-bromo-2-methylphenyl) carbamoyl)-1-methyl-1,4,6,7-tetrahydro-5H-imidazo[4,5-c] pyridine-5-carboxylate | 449.2 |

PREPARATION OF SPECIFIC EXAMPLES

Example 1: Preparation of (Z)-4-(2-(2-((3'-(2-fluoro-2-(5-isopropyl-1-methyl-4,5,6,7-tetrahydro-1H-imidazo[4,5-c]pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl) bicyclo[2.2.1]heptane-1-carboxylic acid

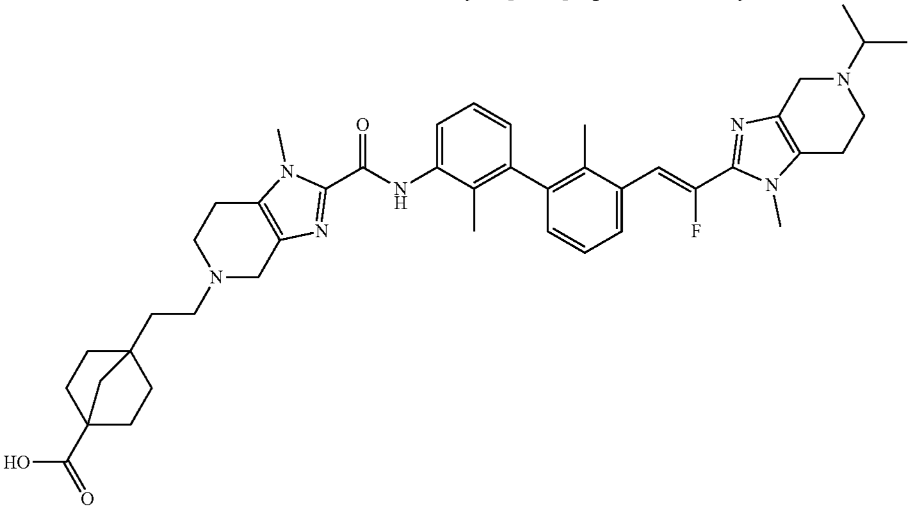

Step 1: Synthesis of tert-butyl 2-bromo-1-methyl-1,4,6,7-tetrahydro-5H-imidazo[4,5-c]pyridine-5-carboxylate

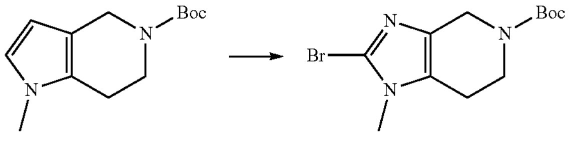 [SMILES: Cn1ccc2c1CCN(C(=O)OC(C)(C)C)C2 ; Cn1c(Br)nc2c1CCN(C(=O)OC(C)(C)C)C2]

Tert-butyl 1-methyl-1,4,6,7-tetrahydro-5H-imidazo[4,5-c]pyridine-5-carboxylate (2.3 g, 9.7 mmol) was dissolved in acetonitrile (40 mL), to which NBS (1.9 g, 10.67 mmol) was then added. The reaction mixture was stirred for 2 hours at room temperature. After concentrating, column chromatography [eluent:petroleum ether-petroleum ether/ethyl acetate (2:1)] was conducted to obtain tert-butyl 2-bromo-1-methyl-1,4,6,7-tetrahydro-5H-imidazo[4,5-c]pyridine-5-carboxylate (1.89 g, yield: 61.85%). MS m/z (ESI): 318.0 $[M+H]^+$.

Step 2: Synthesis of tert-butyl (Z)-2-(2-(3-chloro-2-methylphenyl)-1-fluorovinyl)-1-meth yl-1,4,6,7-tetrahydro-5H-imidazo[4,5-c]pyridine-5-carboxylate

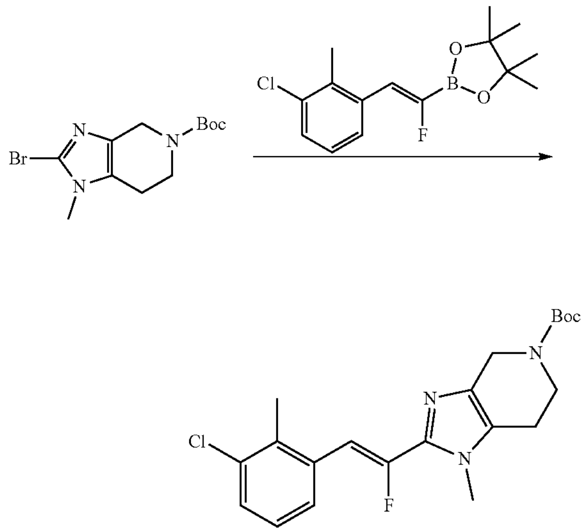

Tert-butyl 2-bromo-1-methyl-1,4,6,7-tetrahydro-5H-imidazo[4,5-c]pyridine-5-carboxylate (1.89 g, 6.0 mmol) was dissolved in tetrahydrofuran/water (20 mL/20 mL), to which (Z)-2-(2-(3-chloro-2-methylphenyl)-1-fluorovinyl)-4,4,5,5-tetramethyl-1,3,2-dioxaborolan (2.0 g, 6.75 mmol), (2-di-tert-butyl-phosphino-2',4',6'-triisopropyl-1,1'-biphenyl)(2'-amino-1,1'-biphenyl-2-yl)palladium methanesulfonate (II) (tBuXPhos Pd G3) (536 mg, 0.675 mmol) and potassium phosphate (4.3 g, 20.25 mmol) were then added. The reaction mixture was stirred overnight at 40° C. After concentrating, column chromatography [eluent:petroleum ether-petroleum ether/ethyl acetate (2:1)] was conducted to obtain tert-butyl (Z)-2-(2-(3-chloro-2-methylphenyl)-1-fluorovinyl)-1-methyl-1,4,6,7-tetrahydro-5H-imidazo[4,5-c]pyridine-5-carboxylate (0.8 g, yield: 32.84%). ESI-MS 406.2 $[M+H]^+$.

Step 3: Synthesis of (Z)-2-(2-(3-chloro-2-methylphenyl)-1-fluorovinyl)-1-methyl-4,5,6,7-tetrahydro-1H-imidazo[4,5-c]pyridine

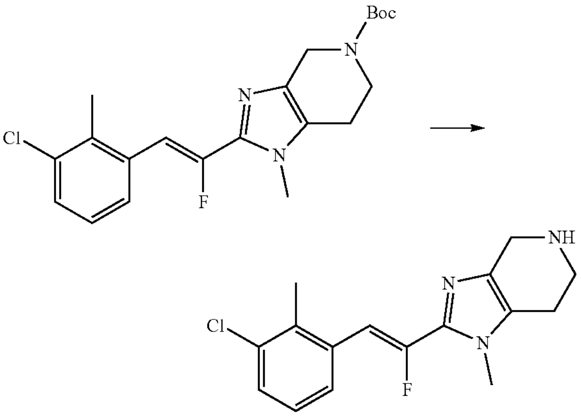

Tert-butyl (Z)-2-(2-(3-chloro-2-methylphenyl)-1-fluorovinyl)-1-methyl-1,4,6,7-tetrahydro-5H-imidazo[4,5-c]pyridine-5-carboxylate (250 mg, 0.612 mmol) was dissolved in dioxane hydrochloride solution (2 mL). The reaction mixture was stirred for 2 hours at room temperature, and concentrated to obtain (Z)-2-(2-(3-chloro-2-methylphenyl)-1-fluorovinyl)-1-methyl-4,5,6,7-tetrahydro-1H-imidazo[4,5-c]pyridine (180 mg, yield: 96%). ESI-MS 306.0 $[M+H]^+$.

Step 4: Synthesis of (Z)-2-(2-(3-chloro-2-methylphenyl)-1-fluorovinyl)-5-isopropyl-1-methyl-4,5,6,7-tetrahydro-1H-imidazo[4,5-c]pyridine

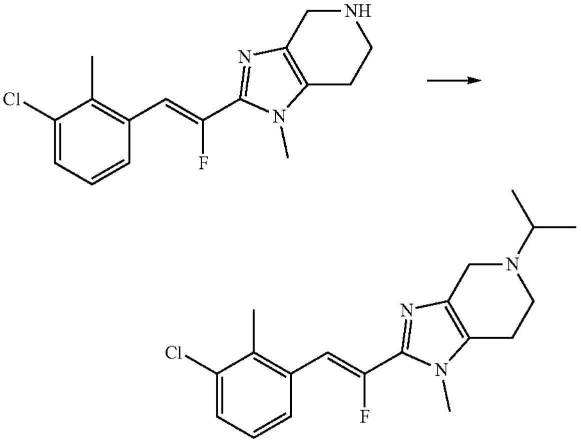

(Z)-2-(2-(3-chloro-2-methylphenyl)-1-fluorovinyl)-1-methyl-4,5,6,7-tetrahydro-1H-imidazo[4,5-c]pyridine (180 mg, 0.59 mmol) was dissolved in dichloromethane (5 mL), to which acetone (0.5 mL) and triethylamine (60 mg, 0.59 mmol) were then added. The mixture was well mixed, and then sodium triacetoxyborohydride (250 mg, 1.18 mmol) was added. The reaction mixture was stirred for 3 hours at room temperature. After concentrating, column chromatography [eluent:petroleum ether-petroleum ether/ethyl acetate (2:1)] was condcuted to obtain (Z)-2-(2-(3-chloro-2-methylphenyl)-1-fluorovinyl)-5-isopropyl-1-methyl-4,5,6,7-tetrahydro-1H-imidazo[4,5-c]pyridine (162 mg, yield: 79%). ESI-MS 348.0 [M+H]$^+$.

Step 5: Synthesis of (Z)-2-(1-fluoro-2-(2-methyl-3-(4,4,5,5-tetramethyl-1,3,2-dioxaborolan-2-yl)phenyl)vinyl)-5-isopropyl-1-methyl-4,5,6,7-tetrahydro-1H-imidazo[4,5-c]pyridine

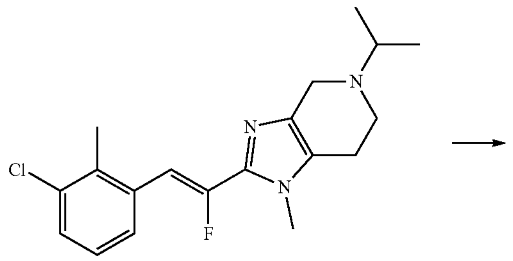

-continued

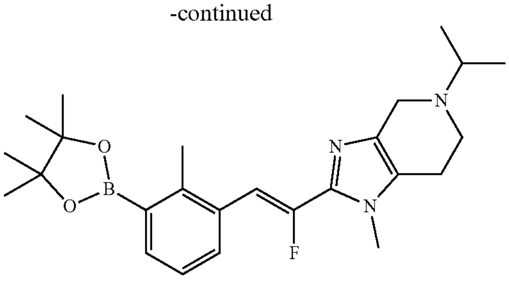

(Z)-2-(2-(3-chloro-2-methylphenyl)-1-fluorovinyl)-5-isopropyl-1-methyl-4,5,6,7-tetrahydro-1H-imidazo[4,5-c]pyridine (162 mg, 0.46 mmol) was dissolved in dioxane (2 mL), to which bis(pinacolato)diboron (140 mg, 0.55 mmol), potassium acetate (135 mg, 1.38 mmol), tris(dibenzylideneacetone)dipalladium (63 mg, 0.069 mmol) and tricyclohexylphosphine (32 mg, 0.115 mmol) were then added. The reaction mixture was stirred overnight at 90° C. After concentrating, reversed-phase column chromatography [eluent: water-water/acetonitrile (20:80)] was conducted to obtain (Z)-2-(1-fluoro-2-(2-methyl-3-(4,4,5,5-tetra methyl-1,3,2-dioxaborolan-2-yl)phenyl)vinyl)-5-isopropyl-1-methyl-4,5,6,7-tetrahydro-1H-imidazo[4,5-c]pyridine (50 mg, yield: 25%). ESI-MS 440.2 [M+H]$^+$.

Step 6: Synthesis of (Z)—N-(3'-(2-fluoro-2-(5-isopropyl-1-methyl-4,5,6,7-tetrahydro-1H-imidazo[4,5-c]pyridin-2-yl)vinyl)-2,2'-dimethyl-[1,1'-biphenyl]-3-yl)-1-methyl-4,5,6,7-tetrahydro-1H-imidazo[4,5-c]pyridine-2-formamide

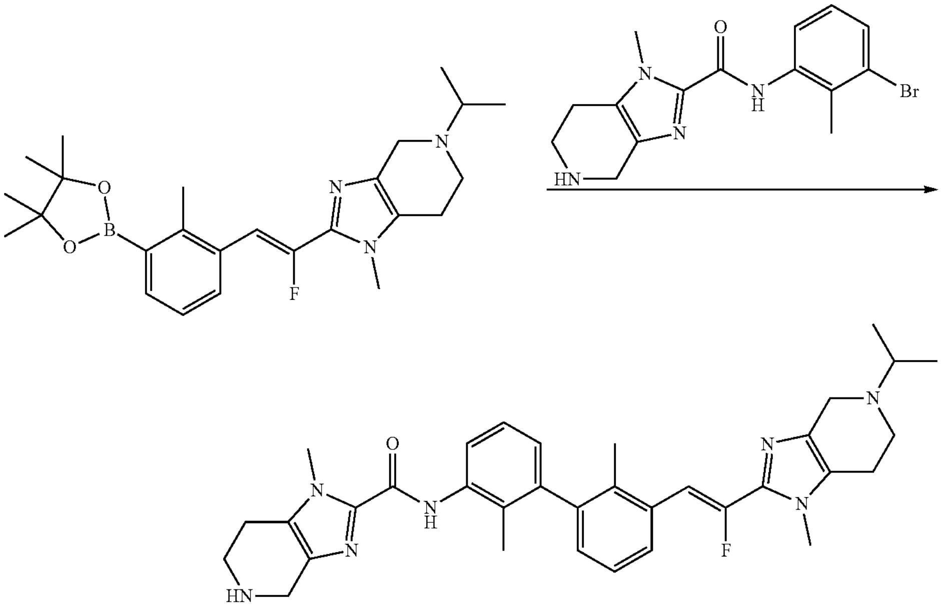

(Z)-2-(1-fluoro-2-(2-methyl-3-(4,4,5,5-tetramethyl-1,3,2-dioxaborolan-2-yl)phenyl)vinyl)-5-isopropyl-1-methyl-4,5,6,7-tetrahydro-1H-imidazo[4,5-c]pyridine (50 mg, 0.11 mmol) was dissolved in dioxane/water (2 mL/0.5 mL), to which N-(3-bromo-2-methylphenyl)-1-methyl-4,5,6,7-tetrahydro-1H-imidazo[4,5-c]pyridin-2-formamide (40 mg, 0.11 mmol), potassium carbonate (46 mg, 0.33 mmol) and [1,1'-bis(diphenylphosphine)ferrocene]palladium dichloride (8 mg, 0.011 mmol) were then added. The reaction mixture was stirred for 3 hours at 100° C. After concentrating, column chromatography [eluent: ethyl acetate-ethyl acetate/methanol (1:1)] was conducted to obtain (Z)—N-(3'-(2-fluoro-2-(5-isopropyl-1-methyl-4,5,6,7-tetrahydro-1H-imidazo[4,5-c]pyridin-2-yl)vinyl)-2,2'-dimethyl-[1,1'-biphenyl]-3-yl)-1-methyl-4,5,6,7-tetrahydro-1H-imidazo[4,5-c]pyridine-2-formamide (35 mg, yield: 55%). ESI-MS 582.4 [M+H]$^+$.

Step 7: Synthesis of methyl (Z)-4-(2-(2-((3'-(2-fluoro-2-(5-isopropyl-1-methyl-4,5,6,7-tetrahydro-1H-imidazo[4,5-c]pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate

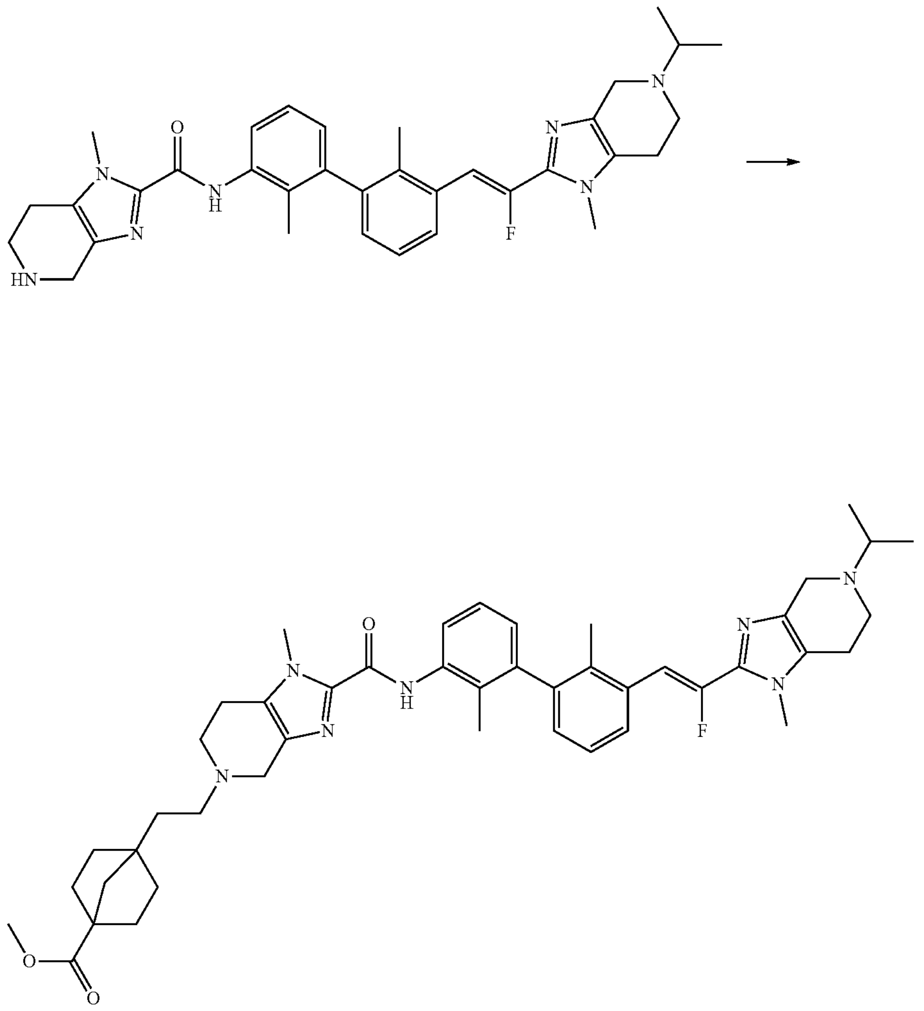

(Z)—N-(3'-(2-fluoro-2-(5-isopropyl-1-methyl-4,5,6,7-tetrahydro-1H-imidazo[4,5-c]pyridin-2-yl)vinyl)-2,2'-dimethyl-[1,1'-biphenyl]-3-yl)-1-methyl-4,5,6,7-tetrahydro-1H-imidazo[4,5-c]pyridine-2-formamide (35 mg, 0.06 mmol) was dissolved in dichloromethane (5 mL), to which methyl 4-(2-oxoethyl)bicyclo[2.2.1]heptane-1-carboxylate (18 mg, 0.09 mmol) was then added. The mixture was well mixed, and then sodium triacetoxyborohydride (25 mg, 0.12 mmol) was then added. The reaction mixture was stirred for 2 hours at room temperature. After concentration, the reversed-phase column chromatography [eluent: water-water/acetonitrile (70:30)] was conducted to obtain methyl (Z)-4-(2-(2-((3'-(2-fluoro-2-(5-isopropyl-1-methyl-4,5,6,7-tetrahydro-1H-imidazo[4,5-c]pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (30 mg, yield: 65.6%). ESI-MS 381.9 $[M/2+H]^+$.

Step 8: Synthesis of (Z)-4-(2-(2-((3'-(2-fluoro-2-(5-isopropyl-1-methyl-4,5,6,7-tetrahydro-1H-imidazo[4,5-c]pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

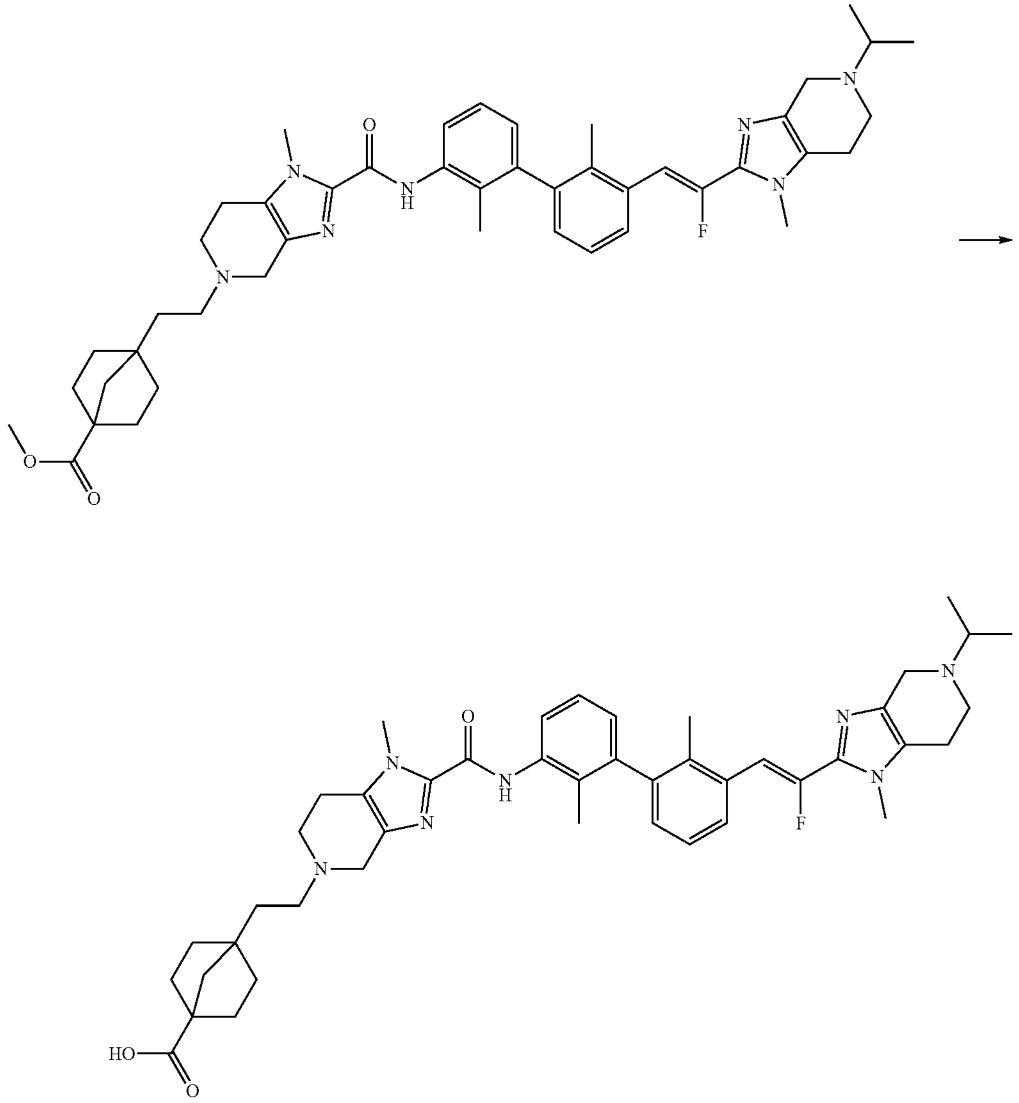

Methyl (Z)-4-(2-(2-((3'-(2-fluoro-2-(5-isopropyl-1-methyl-4,5,6,7-tetrahydro-1H-imidazo[4,5-c]pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (30 mg, 0.039 mmol) was dissolved in methanol/water/tetrahydrofuran (1 mL/1 mL/1 mL), to which lithium hydroxide monohydrate (8 mg, 0.197 mmol) was then added. The reaction mixture was stirred for 2 hours at room temperature. Then, reversed-phase column chromatographic separation [eluent: 0.500 formic acid in water-0.5% formic acid in water/acetonitrile (80:20)] was conducted to obtain (Z)-4-(2-(2-((3'-(2-fluoro-2-(5-isopropyl-1-methyl-4,5,6,7-tetrahydro-11H-imidazo[4,5-c]pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid (3.9 mg, yield: 13.37%). ESI-MS 748.4 $[M+H]^+$.

$^1H$ NMR (400 MHz, DMSO-$d_6$) δ 9.71 (s, 1H), 7.68 (dd, J=7.9, 2.9 Hz, 2H), 7.29 (dt, J=16.2, 7.7 Hz, 2H), 7.05 (d, J=7.4 Hz, 1H), 6.95 (d, J=7.4 Hz, 1H), 6.64 (d, J=38.9 Hz, 1H), 3.86 (s, 3H), 3.64 (d, J=2.8 Hz, 3H), 3.42 (d, J=8.9 Hz, 4H), 2.92 (p, J=6.6 Hz, 1H), 2.75 (q, J=5.0, 4.4 Hz, 4H), 2.69-2.57 (m, 4H), 2.55 (d, J=7.0 Hz, 2H), 2.02 (s, 3H), 1.94 (s, 3H), 1.85 (d, J=13.9 Hz, 2H), 1.72 (t, J=7.8 Hz, 2H), 1.43 (t, J=30.1 Hz, 8H), 1.05 (d, J=6.5 Hz, 6H).

$^{19}F$ NMR (377 MHz, DMSO-$d_6$) δ −117.66.

Examples 2-15 can be prepared by selecting corresponding starting materials according to complete or partial synthesis method of Example 1.

| Example No. | Compound structure and name | MS: m/z [M + H]$^+$ |
|---|---|---|
| 2 | 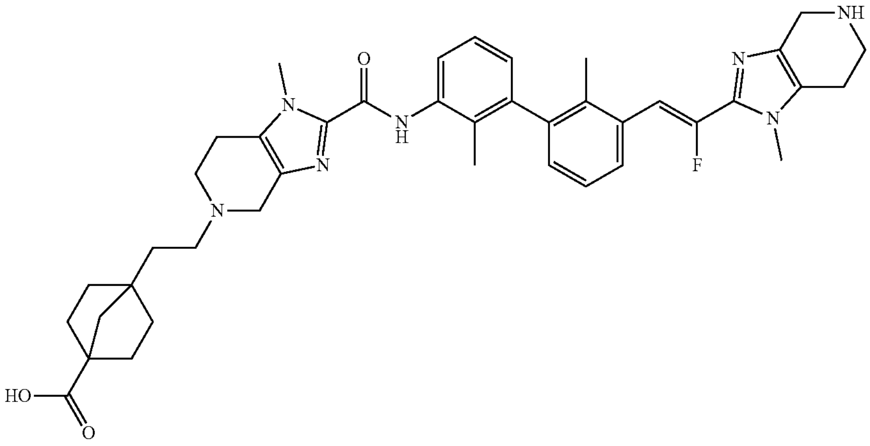 [SMILES: Cc1c(/C=C(\F)c2nc3c(n2C)CCNC3)cccc1-c1cccc(NC(=O)c2nc3c(n2C)CCN(CCC24CCC(C(=O)O)(CC2)C4)C3)c1C] (Z)-4-(2-(2-((3'-(2-fluoro-2-(1-methyl-4,5,6,7-tetrahydro-1H-imidazo [4,5-c]pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl) ethyl)bicyclo[2.2.1]heptane-1-carboxylic acid | 706.4 |
| 3 | 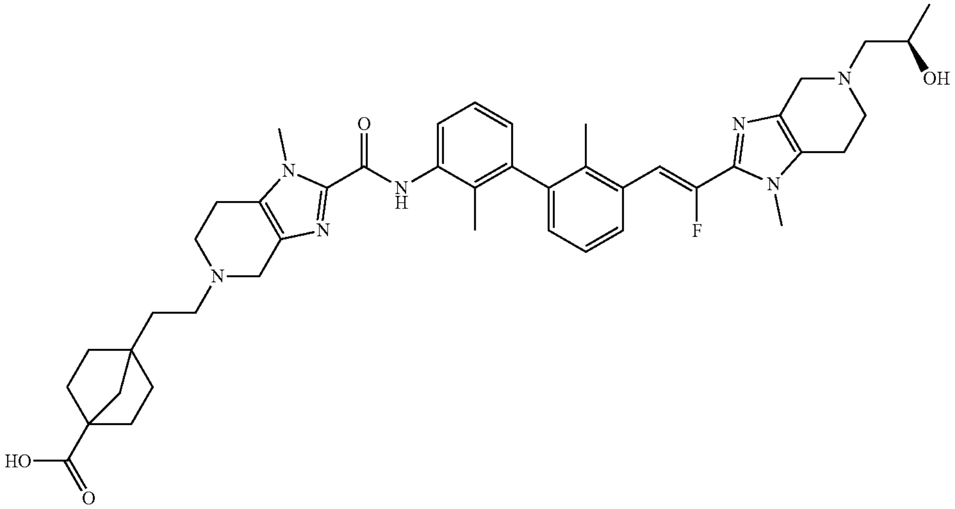 [SMILES: Cc1c(/C=C(\F)c2nc3c(n2C)CCN(C[C@@H](C)O)C3)cccc1-c1cccc(NC(=O)c2nc3c(n2C)CCN(CCC24CCC(C(=O)O)(CC2)C4)C3)c1C] (R,Z)-4-(2-(2-((3'-(2-fluoro-2-(5-(2-hydroxypropyl)-1-methyl-4,5,6,7-tetrahydro-1H-imidazo[4,5-c]pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 764.4 |

-continued

| Example No. | Compound structure and name | MS: m/z [M + H]+ |
|---|---|---|
| 4 | 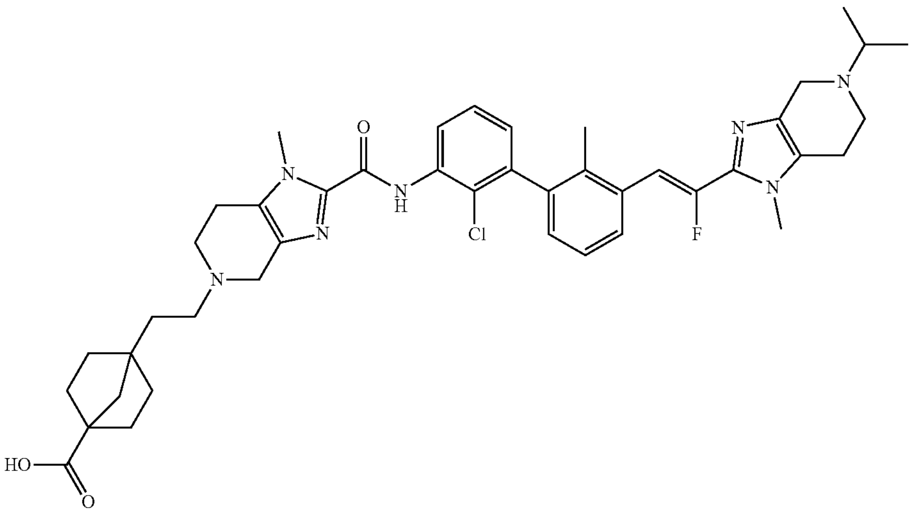 [SMILES: Cc1c(/C=C(\F)c2nc3c(n2C)CCN(C(C)C)C3)cccc1-c1cccc(NC(=O)c2nc3c(n2C)CCN(CCC24CCC(C(=O)O)(CC2)C4)C3)c1Cl] (Z)-4-(2-(2-((2-chloro-3'-(2-fluoro-2-(5-isopropyl-1-methyl-4,5,6,7-tetrahydro-1H-imidazo[4,5-c]pyridin-2-yl)vinyl)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 768.4 |
| 5 | 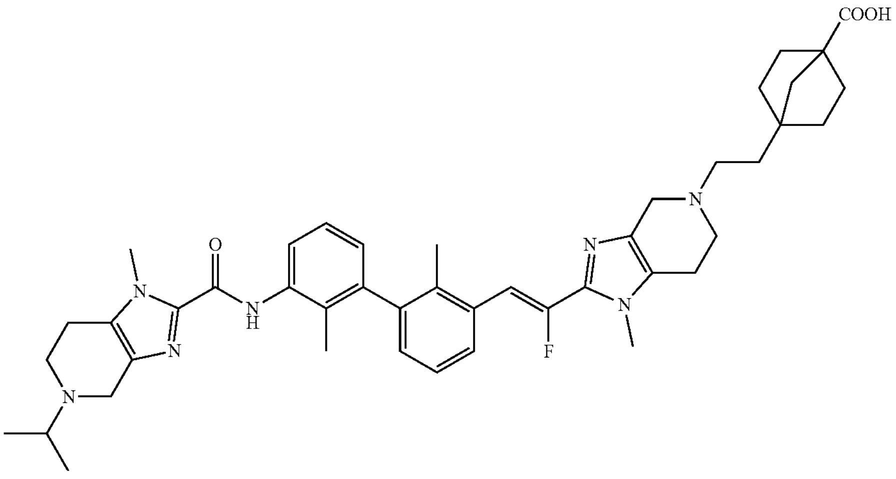 [SMILES: Cc1c(/C=C(\F)c2nc3c(n2C)CCN(CCC24CCC(C(=O)O)(CC2)C4)C3)cccc1-c1cccc(NC(=O)c2nc3c(n2C)CCN(C(C)C)C3)c1C] (Z)-4-(2-(2-(1-fluoro-2-(3'-(5-isopropyl-1-methyl-4,5,6,7-tetrahydro-1H-imidazo[4,5-c]pyridine-2-carboxamido)-2,2'-dimethyl-[1,1'-biphenyl]-3-yl)vinyl)-1-methyl-1,4,6,7-tetrahydro-5H-imidazo[4,5-c]pyridin-5-yl)ethyl)bicyclo[2.2.1]heptane-1-carboxylic acid | 748.4 |

-continued

| Example No. | Compound structure and name | MS: m/z $[M + H]^+$ |
|---|---|---|
| 6 | 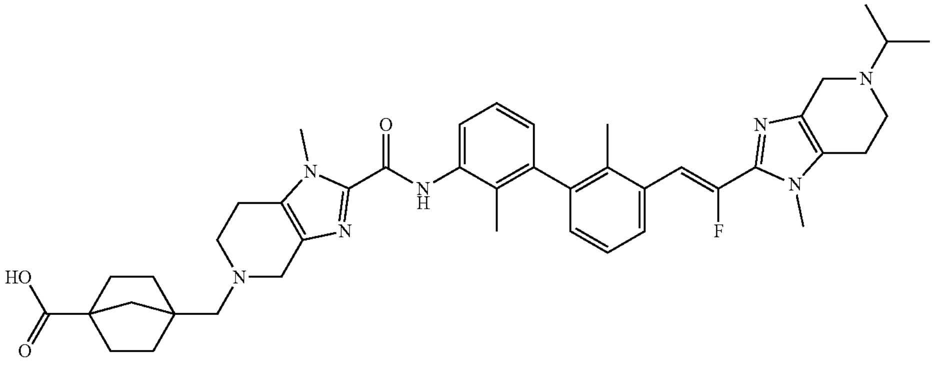 [SMILES: Cc1c(/C=C(\F)c2nc3c(n2C)CCN(C(C)C)C3)cccc1-c1cccc(NC(=O)c2nc3c(n2C)CCN(CC24CCC(C(=O)O)(CC2)C4)C3)c1C] (Z)-4-((2-((3'-(2-fluoro-2-(5-isopropyl-1-methyl-4,5,6,7-tetrahydro-1H-imidazo[4,5-c]pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid | 734.4 |
| 7 | 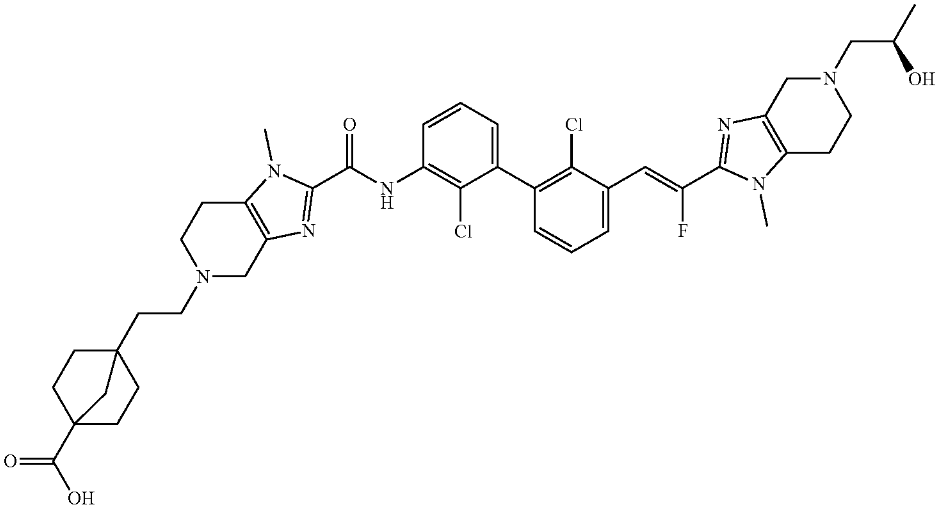 [SMILES: C[C@@H](O)CN1CCc2c(nc(/C(F)=C/c3cccc(-c4cccc(NC(=O)c5nc6c(n5C)CCN(CCC57CCC(C(=O)O)(CC5)C7)C6)c4Cl)c3Cl)n2C)C1] (R,Z)-4-(2-(2-((2,2'-dichloro-3'-(2-fluoro-2-(5-(2-hydroxypropyl)-1-methyl-4,5,6,7-tetrahydro-1H-imidazo[4,5-c]pyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 402.9 $[M/2 + H]^+$ |

-continued

| Example No. | Compound structure and name | MS: m/z [M + H]$^+$ |
| --- | --- | --- |
| 8 | 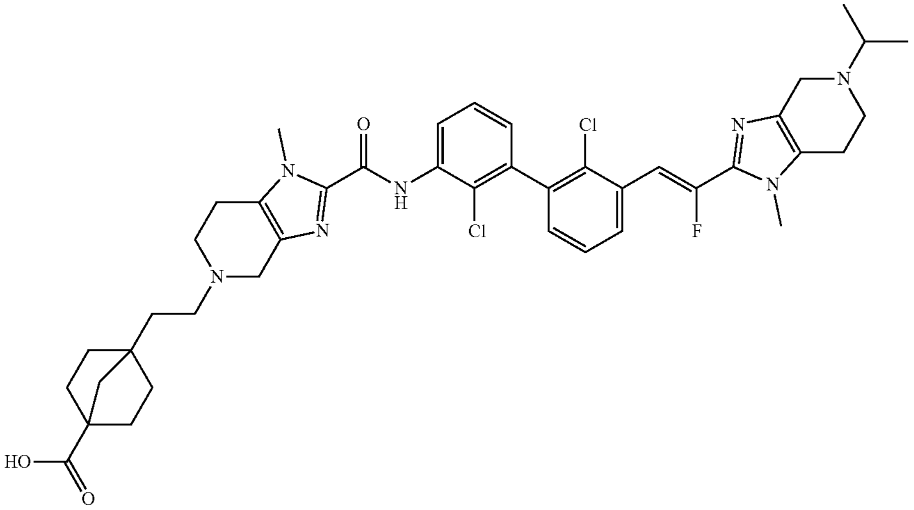 [SMILES: CC(C)N1CCc2c(nc(/C(F)=C/c3cccc(-c4cccc(NC(=O)c5nc6c(n5C)CCN(CCC57CCC(C(=O)O)(CC5)C7)C6)c4Cl)c3Cl)n2C)C1] (Z)-4-(2-(2-((2,2'-dichloro-3'-(2-fluoro-2-(5-isopropyl-1-methyl-4,5,6,7-tetrahydro-1H-imidazo[4,5-c]pyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 394.9 [M/2 + H]$^+$ |
| 9 | 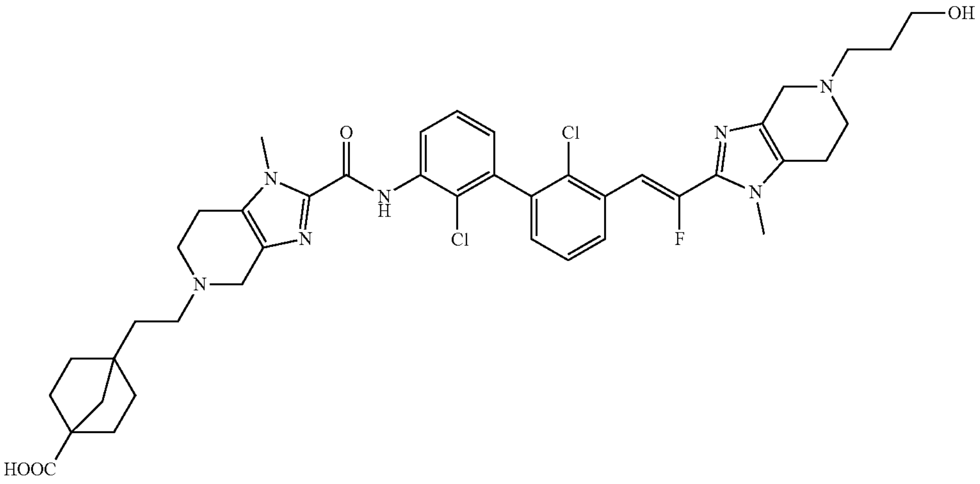 [SMILES: Cn1c(C(=O)Nc2cccc(-c3cccc(/C=C(\F)c4nc5c(n4C)CCN(CCCO)C5)c3Cl)c2Cl)nc2c1CCN(CCC13CCC(C(=O)O)(CC1)C3)C2] (Z)-4-(2-(2-((2,2'-dichloro-3'-(2-fluoro-2-(5-(3-hydroxypropyl)-1-methyl-4,5,6,7-tetrahydro-1H-imidazo[4,5-c]pyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 805 |

-continued

| Example No. | Compound structure and name | MS: m/z $[M + H]^+$ |
|---|---|---|
| 10 | 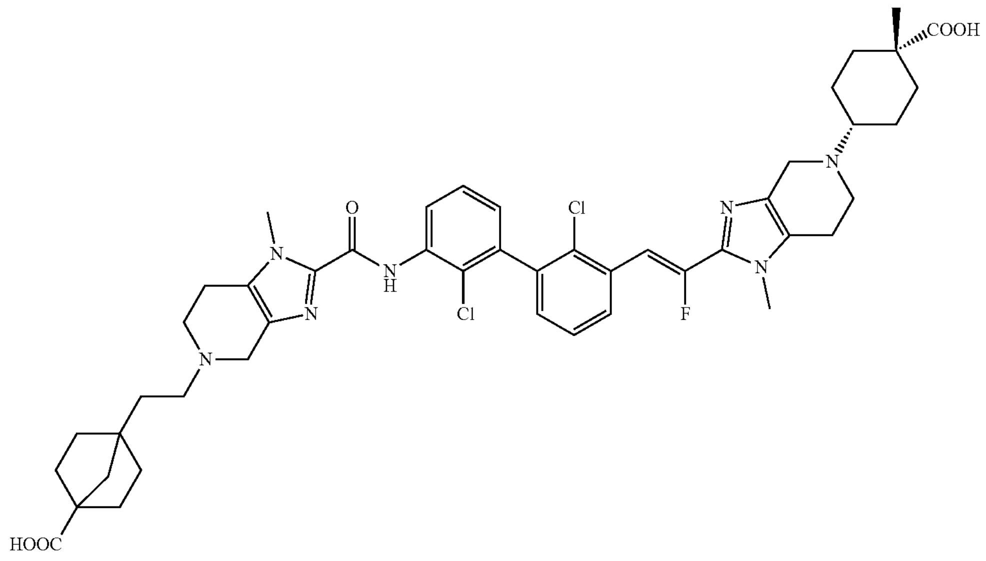 [SMILES: Cn1c(C(=O)Nc2cccc(-c3cccc(/C=C(\F)c4nc5c(n4C)CCN([C@H]4CC[C@@](C)(C(=O)O)CC4)C5)c3Cl)c2Cl)nc2c1CCN(CCC13CCC(C(=O)O)(CC1)C3)C2]<br>4-(2-(2-((3'-((Z)-2-(5-((1s,4s)-4-carboxy-4-methylcyclohexyl)-1-methyl-4,5,6,7-tetrahydro-1H-imidazo[4,5-c]pyridin-2-yl)-2-fluorovinyl)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 887 |
| 11 | 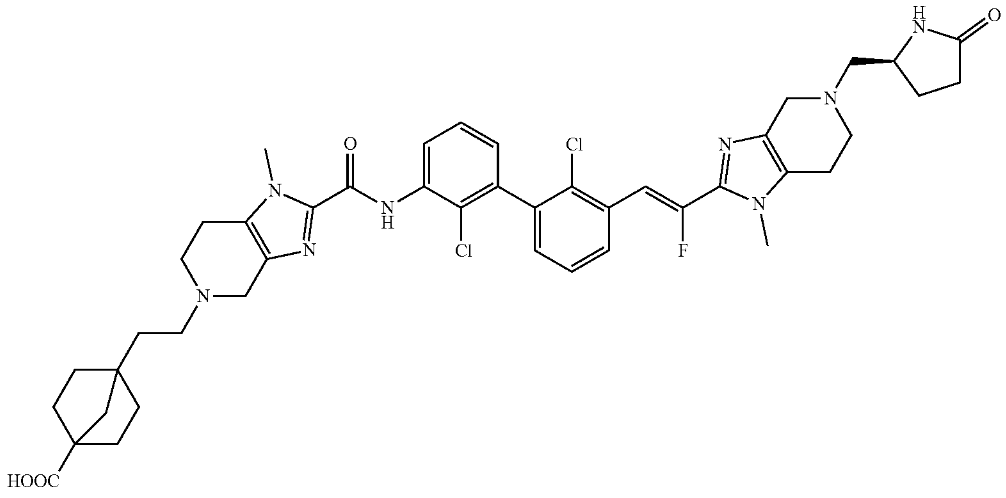 [SMILES: Cn1c(C(=O)Nc2cccc(-c3cccc(/C=C(\F)c4nc5c(n4C)CCN(C[C@@H]4CCC(=O)N4)C5)c3Cl)c2Cl)nc2c1CCN(CCC13CCC(C(=O)O)(CC1)C3)C2]<br>(S,Z)-4-(2-(2-((2,2'-dichloro-3'-(2-fluoro-2-(1-methyl-5-((5-oxopyrrolidin-2-yl)methyl)-4,5,6,7-tetrahydro-1H-imidazo[4,5-c]pyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 843 |

-continued

| Example No. | Compound structure and name | MS: m/z $[M + H]^+$ |
|---|---|---|
| 12 | 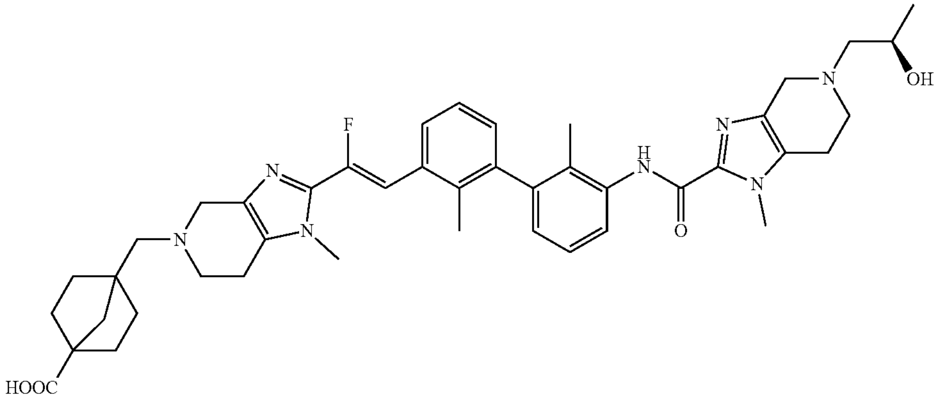 [SMILES: Cc1c(/C=C(\F)c2nc3c(n2C)CCN(CC24CCC(C(=O)O)(CC2)C4)C3)cccc1-c1cccc(NC(=O)c2nc3c(n2C)CCN(C[C@@H](C)O)C3)c1C] (R,Z)-4-((2-(1-fluoro-2-(3'-(5-(2-hydroxypropyl)-1-methyl-4,5,6,7-tetrahydro-1H-imidazo[4,5-c]pyridine-2-carboxamido)-2,2'-dimethyl-[1,1'-biphenyl]-3-yl)vinyl)-1-methyl-1,4,6,7-tetrahydro-5H-imidazo [4,5-c]pyridin-5-yl)methyl)bicyclo[2.2.1]heptane-1-carboxylic acid | 750 |
| 13 | 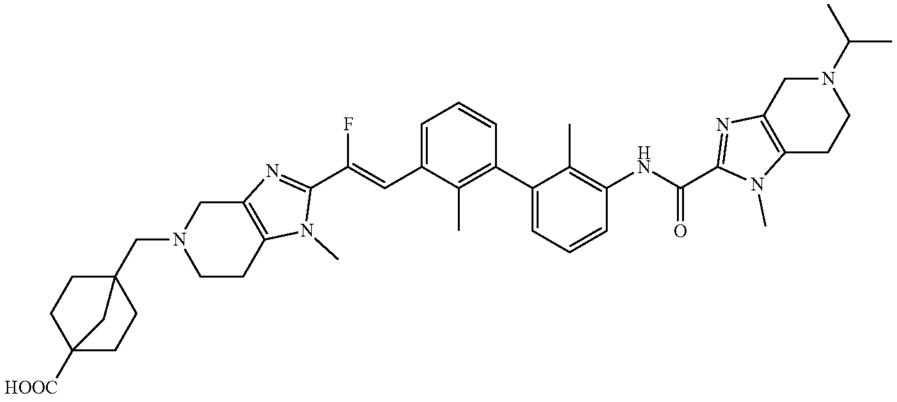 [SMILES: Cc1c(/C=C(\F)c2nc3c(n2C)CCN(CC24CCC(C(=O)O)(CC2)C4)C3)cccc1-c1cccc(NC(=O)c2nc3c(n2C)CCN(C(C)C)C3)c1C] (Z)-4-((2-(1-fluoro-2-(3'-(5-isopropyl-1-methyl-4,5,6,7-tetrahydro-1H-imidazo[4,5-c]pyridine-2-carboxamido)-2,2'-dimethyl-[1,1'-biphenyl]-3-yl)vinyl)-1-methyl-1,4,6,7-tetrahydro-5H-imidazo[4,5-c] pyridin-5-yl)methyl)bicyclo[2.2.1]heptane-1-carboxylic acid | 734 |
| 14 | 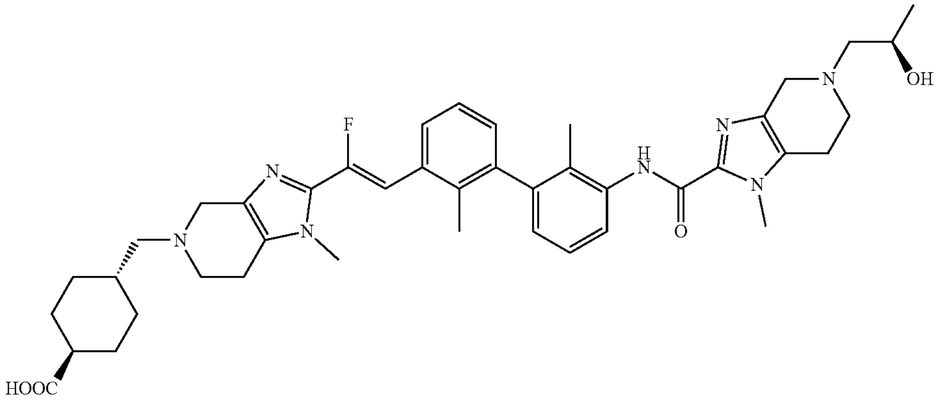 [SMILES: Cc1c(/C=C(\F)c2nc3c(n2C)CCN(C[C@H]2CC[C@H](C(=O)O)CC2)C3)cccc1-c1cccc(NC(=O)c2nc3c(n2C)CCN(C[C@@H](C)O)C3)c1C] (1R,4R)-4-((2-((Z)-1-fluoro-2-(3'-(5-((R)-2-hydroxypropyl)-1-methyl-4,5,6,7-tetrahydro-1H-imidazo[4,5-c]pyridine-2-carboxamido)-2,2'-dimethyl-[1,1'-biphenyl]-3-yl)vinyl)-1-methyl-1,4,6,7-tetrahydro-5H-imidazo[4,5-c]pyridin-5-yl)methyl)cyclohexane-1-carboxylic acid | 738 |

-continued

| Example No. | Compound structure and name | MS: m/z [M + H]+ |
|---|---|---|
| 15 | 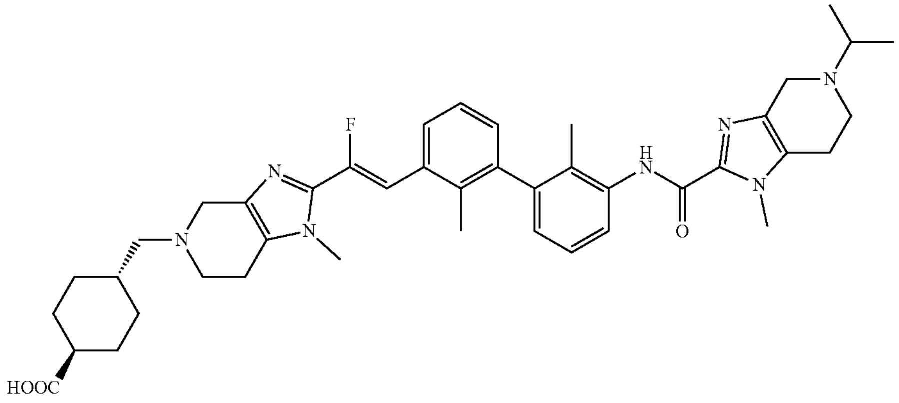 [SMILES: Cc1c(/C=C(\F)c2nc3c(n2C)CCN(C[C@H]2CC[C@H](C(=O)O)CC2)C3)cccc1-c1cccc(NC(=O)c2nc3c(n2C)CCN(C(C)C)C3)c1C]<br>(1R,4R)-4-((2-((Z)-1-fluoro-2-(3'-(5-isopropyl-1-methyl-4,5,6,7-tetrahydro-1H-imidazo[4,5-c]pyridine-2-carboxamido)-2,2'-dimethyl-[1,1'-biphenyl]-3-yl)vinyl)-1-methyl-1,4,6,7-tetrahydro-5H-imidazo[4,5-c]pyridin-5-yl)methyl)cyclohexane-1-carboxylic acid | 722 |

The magnetic resonance imaging data of the compound prepared from the above examples was as follows:

| Example No. | $^1$H NMR/$^{19}$F NMR |
|---|---|
| 2 | $^1$H NMR (400 MHz, DMSO-d$_6$) δ 9.70 (s, 1H), 7.68 (dd, J = 8.0, 3.1 Hz, 2H), 7.34 − 7.23 (m, 2H), 7.05 (dd, J = 7.6, 1.3 Hz, 1H), 6.95 (dd, J = 7.6, 1.3 Hz, 1H), 6.65 (d, J = 38.8 Hz, 1H), 3.86 (s, 3H), 3.64 (d, J = 2.6 Hz, 4H), 3.41 (s, 4H), 2.98 (t, J = 5.7 Hz, 2H), 2.75 (t, J = 5.7 Hz, 2H), 2.67 − 2.62 (m, 2H), 2.56 (t, J = 6.2 Hz, 3H), 2.02 (s, 3H), 1.94 (s, 3H), 1.85 (d, J = 12.3 Hz, 2H), 1.72 (t, J = 7.8 Hz, 2H), 1.51 (d, J = 11.2 Hz, 4H), 1.44 (s, 2H), 1.38 (d, J = 11.2 Hz, 2H). $^{19}$F NMR (377 MHz, DMSO-d$_6$) δ −117.35 (d, J = 3.8 Hz). |
| 3 | $^1$H NMR (400 MHz, DMSO-d$_6$) δ 9.71 (s, 1H), 7.71 − 7.65 (m, 2H), 7.05 (dd, J = 7.6, 1.3 Hz, 1H), 6.95 (dd, 7 = 7.6, 1.3 Hz, 1H), 6.64 (d, J = 38.8 Hz, 1H), 3.89 − 3.80 (m, 4H), 3.65 (d, J = 2.8 Hz, 3H), 3.42 (d, J = 9.9 Hz, 4H), 2.78 (dt, J = 19.1, 5.7 Hz, 4H), 2.64 (q, J = 5.7 Hz, 4H), 2.55 (d, J = 7.8 Hz, 2H), 2.48 − 2.44 (m, 1H), 2.38 (dd, J = 12.4, 5.5 Hz, 1H), 2.02 (s, 3H), 1.94 (s, 3H), 1.89 − 1.81 (m, 2H), 1.72 (t, J = 7.7 Hz, 2H), 1.57 − 1.48 (m, 4H), 1.44 (s, 2H), 1.38 (d, J = 11.4 Hz, 2H), 1.07 (d, J = 6.1 Hz, 3H). $^{19}$F NMR (377 MHz, DMSO-d$_6$) δ −117.60. |
| 4 | $^1$H NMR (400 MHz, DMSO-d$_6$) δ 9.90 (s, 1H), 7.71 (d, J = 7.8 Hz, 1H), 7.45 (t, J = 7.9 Hz, 1H), 7.34 (t, J = 7.7 Hz, 1H), 6.64 (d, J = 38.7 Hz, 1H), 3.90 (s, 3H), 3.64 (d, J = 2.8 Hz, 3H), 3.42 (d, J = 10.9 Hz, 4H), 2.97 − 2.89 (m, 1H), 2.76 (q, J = 5.3 Hz, 4H), 2.67 (d, J = 5.4 Hz, 2H), 2.60 (d, J = 5.6 Hz, 2H), 2.54 (d, J = 7.5 Hz, 2H), 2.06 (s, 3H), 1.84 (d, J = 11.7 Hz, 2H), 1.72 (t, J = 7.8 Hz, 2H), 1.50 (d, J = 11.8 Hz, 4H), 1.43 (s, 2H), 1.37 (d, J = 11.2 Hz, 2H), 1.05 (d, J = 6.5 Hz, 6H). $^{19}$F NMR (377 MHz, DMSO-d$_6$) δ −117.51. |
| 5 | $^1$H NMR (400 MHz, DMSO-d$_6$) δ 9.68 (s, 1H), 7.69 (dd, J = 16.3, 7.8 Hz, 2H), 7.29 (dt, J = 15.5, 7.6 Hz, 2H), 7.05 (d, J = 7.5 Hz, 1H), 6.94 (d, J = 7.5 Hz, 1H), 6.65 (d, J = 38.8 Hz, 1H), 3.86 (s, 3H), 3.64 (d, J = 2.8 Hz, 3H), 3.47 (s, 2H), 3.36 (s, 2H), 2.97 − 2.90 (m, 1H), 2.77 (t, J = 5.6 Hz, 2H), 2.73 (t, J = 5.4 Hz, 2H), 2.63 (d, J = 5.5 Hz, 4H), 2.54 (s, 2H), 2.03 (s, 3H), 1.94 (s, 3H), 1.90 − 1.85 (m, 2H), 1.71 (t, J = 7.9 Hz, 2H), 1.49 (d, J = 9.4 Hz, 4H), 1.38 (d, J = 24.2 Hz, 4H), 1.05 (d, J = 6.4 Hz, 6H). $^{19}$F NMR (377 MHz, DMSO-d$_6$) δ −117.58. |
| 6 | $^1$H NMR (400 MHz, DMSO-d$_6$) δ 9.71 (s, 1H), 7.68 (dd, J = 8.1, 1.4 Hz, 2H), 7.29 (dt, J = 17.1, 7.7 Hz, 2H), 7.05 (dd, J = 7.6, 1.3 Hz, 1H), 6.95 (dd, J = 7.6, 1.3 Hz, 1H), 6.64 (d, J = 38.8 Hz, 1H), 3.87 (s, 3H), 3.64 (d, J = 2.8 Hz, 3H), 3.49 (s, 2H), 3.45 (s, 2H), 2.98 − 2.88 (m, 1H), 2.79 (dt, J = 11.8, 5.6 Hz, 4H), 2.69 − 2.57 (m, 6H), 2.02 (s, 3H), 1.94 (s, 3H), 1.91 − 1.80 (m, 2H), 1.70 − 1.59 (m, 2H), 1.58 − 1.50 (m, 2H), 1.47 (s, 2H), 1.33 (d, J = 8.6 Hz, 2H), 1.06 (d, J = 6.5 Hz, 6H). $^{19}$F NMR (377 MHz, DMSO-d$_6$) δ −117.71. |
| 7 | $^1$H NMR (400 MHz, DMSO-d$_6$) δ 9.89 (s, 1H), 8.37 (dd, J = 8.3, 1.6 Hz, 1H), 8.31 (s, 1H), 7.94 (dd, J = 7.9, 1.5 Hz, 1H), 7.49 (dt, J = 13.9, 7.9 Hz, 2H), 7.31 (dd, J = 7.6, 1.6 Hz, 1H), 7.13 (dd, J = 7.6, 1.6 Hz, 1H), 6.85 (d, J = 38.5 Hz, 1H), 3.90 (s, 3H), 3.83 (q, J = 6.1 Hz, 1H), 3.67 (d, J = 3.1 Hz, 3H), 3.42 (d, J = 12.1 Hz, 4H), 2.77 (dd, J = 18.8, 5.6 Hz, 4H), 2.72 − 2.60 (m, 4H), 2.55 (s, 1H), 2.47 − 2.28 (m, 3H), 1.84 (d, J = 12.2 Hz, 2H), 1.72 (t, J = 7.7 Hz, 2H), 1.44 (t, J = 31.1 Hz, 8H), 1.06 (d, J = 6.1 Hz, 3H). |
| 8 | $^1$H NMR (400 MHz, DMSO-d$_6$) δ 9.91 − 9.64 (m, 1H), 8.41 − 8.27 (m, 1H), 7.94 (dd, J = 7.9, 1.6 Hz, 1H), 7.49 (dt, J = 13.3, 7.7 Hz, 2H), 7.30 (dd, J = 7.6, 1.6 Hz, 1H), 7.13 (dd, J = 7.6, 1.6 Hz, 1H), 6.84 (d, J = 38.5 Hz, 1H), 3.90 (s, 3H), |

-continued

| Example No. | $^{1}$H NMR/$^{19}$F NMR |
|---|---|
| | 3.65 (dd, J = 8.1, 3.1 Hz, 3H), 3.42 (d, J = 11.4 Hz, 4H), 2.92 (d, J = 6.4 Hz, 1H), 2.75 (d, J = 5.7 Hz, 4H), 2.68 - 2.57 (m, 4H), 1.86 (s, 3H), 1.72 (t, J = 7.8 Hz, 2H), 1.61 - 1.30 (m, 11H), 1.05 (d, J = 6.6 Hz, 6H). |

Example 16: Preparation of (Z)-4-(2-(2-((2,2'-dichloro-3'-(2-fluoro-2-(5-(((2-hydroxyethyl)amino)methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid

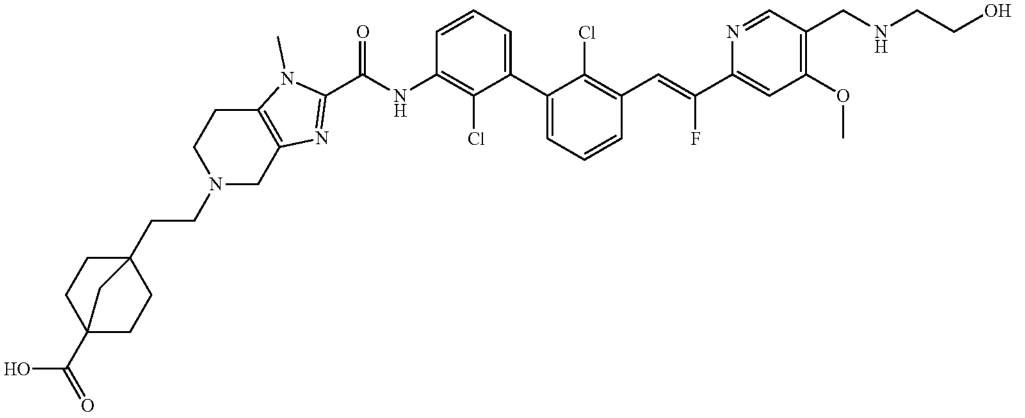 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNCCO]

Step 1: Synthesis of (Z)-(6-(2-(2-chloro-3-(methoxymethoxy)phenyl)-1-fluorovinyl)-4-methoxypyridin-3-yl)methanol

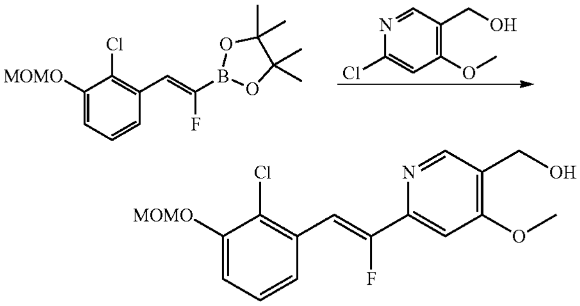

(Z)-2-(2-(2-chloro-3-(methoxymethoxy)phenyl)-1-fluorovinyl)-4,4,5,5-tetramethyl-1,3,2-dioxaborolan (7.78 g, 22.7 mmol) was dissolved in tetrahydrofuran/water (100 mL/50 mL), to which (6-chloro-4-methoxypyridin-3-yl) methanol (3.0 g, 17.3 mmol), potassium phosphate (11 g, 51.9 mmol) and (2-ditert-butylphosphino-2',4',6'-triisopropyl-1,1'-biphenyl)(2'-amino-1,1'-biphenyl-2-yl) palladium (II) methanesulfonate (tBuXPhos Pd G3) (686 mg, 0.865 mmol) were then added. The reaction mixture was stirred overnight at 40° C. After concentrating, column chromatographic separation [eluent:petroleum ether-petroleum ether/ethyl acetate/dichloromethane (40/40/20)] was conducted to obtain (Z)-(6-(2-(2-chloro-3-(methoxymethoxy)phenyl)-1-fluorovinyl)-4-methoxypyridin-3-yl)methanol (5.0 g, yield: 81.8%). M S m/z (ESI): 354.3 [M+H]$^+$.

Step 2: Synthesis of (Z)-6-(2-(2-chloro-3-(methoxymethoxy)phenyl)-1-fluorovinyl)-4-methoxynicotine aldehyde

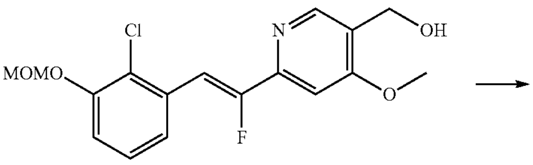

-continued

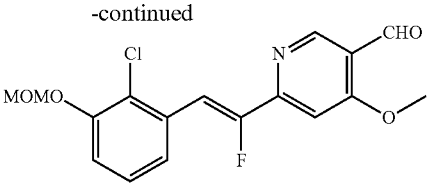

(Z)-(6-(2-(2-chloro-3-(methoxymethoxy)phenyl)-1-fluorovinyl)-4-methoxypyridin-3-yl)methanol (5.0 g, 14.1 mmol) was dissolved in ethyl acetate (400 mL), to which 2-iodoacylbenzoic acid (19.7 g, 70.5 mmol) was then added. The reaction mixture was stirred for 5 hours at 90° C. After cooling, the mixture was filtered and concentrated to obtain (Z)-6-(2-(2-chloro-3-(methoxymethoxy)phenyl)-1-fluorovinyl)-4-methoxynicotine aldehyde (5.0 g, yield: 100%). MS m/z (ESI): 352.1 [M+H]$^+$.

Step 3: Synthesis of (Z)-6-(2-(2-chloro-3-hydroxyphenyl)-1-fluorovinyl)-4-methoxynicotine aldehyde

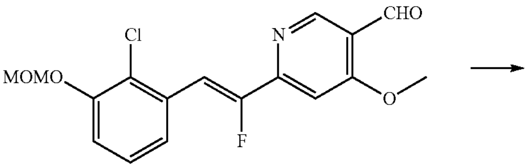

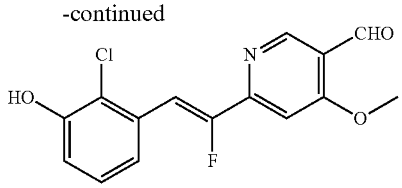

(Z)-6-(2-(2-chloro-3-(methoxymethoxy)phenyl)-1-fluorovinyl)-4-methoxynicotine aldehyde (5.0 g, 14.21 mmol) was dissolved in tetrahydrofuran (40 mL), to which 4M aqueous hydrochloric acid (40 mL) was then added. The reaction mixture was stirred for 2 hours at 50° C. The pH of the mixture was adjusted to 7 by using saturated aqueous sodium bicarbonate. The solution was extracted with ethyl acetate (100 mL*3). The organic phase was washed with water and saturated sodium chloride, dried over anhydrous sodium sulfate, filtered and concentrated to obtain (Z)-6-(2-(2-chloro-3-hydroxyphenyl)-1-fluorovinyl)-4-methoxynicotine aldehyde (4.4 g, yield: 100%). MS m/z (ESI): 308.2 [M+H]$^+$.

Step 4: Synthesis of (Z)-2-chloro-3-(2-fluoro-2-(5-formyl-4-methoxypyridin-2-yl)vinyl)phenyl trifluoromethanesulfonic acid

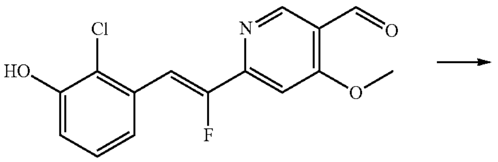

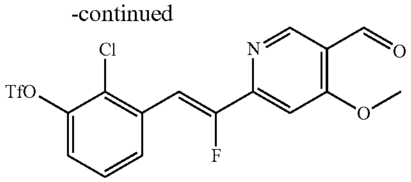

(Z)-6-(2-(2-chloro-3-hydroxyphenyl)-1-fluorovinyl)-4-methoxynicotine aldehyde (4.4 g, 14.3 mmol) was dissolved in dichloromethane (100 mL), to which triethylamine (4.33 g, 42.9 mmol), and trifluoromethanesulfonic anhydride (4.0 g, 14.3 mmol) were then added. The reaction mixture was stirred for 1 hour at room temperature. The reaction mixture was poured into saturated aqueous sodium bicarbonate, and extracted with dichloromethane (50 mL*3). The organic phase was washed with water and saturated sodium chloride, dried over anhydrous sodium sulfate and concentrated. Then, column chromatographic separation [eluent:petroleum ether-petroleum ether/ethyl acetate (80/20)] was conducted to obtain (Z)-2-chloro-3-(2-fluoro-2-(5-formyl-4-methoxypyridin-2-yl)vinyl)phenyl trifluoromethanesulfonic acid (4.0 g, yield: 36%). MS m/z (ESI): 440.0 [M+H]$^+$.

Step 5: Synthesis of methyl (Z)-4-(2-(2-((2,2'-dichloro-3'-(2-fluoro-2-(5-formyl-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate

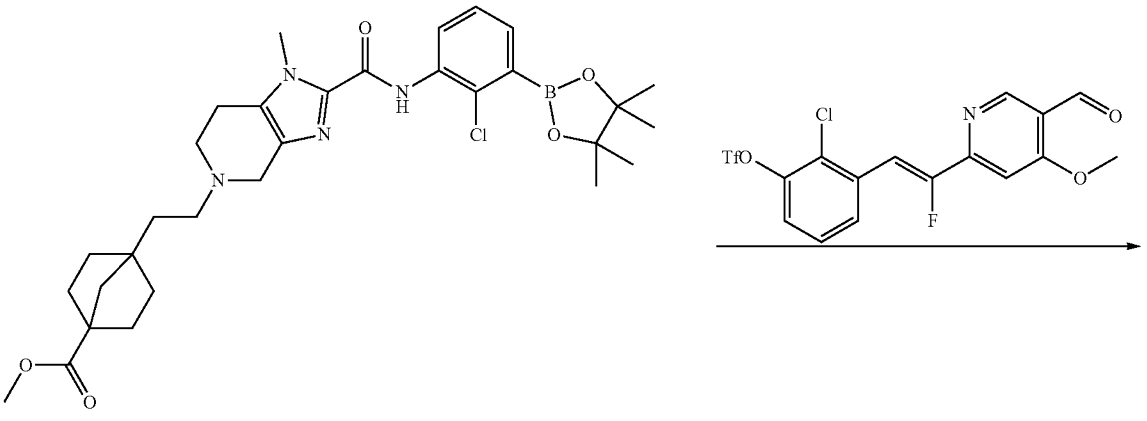

-continued

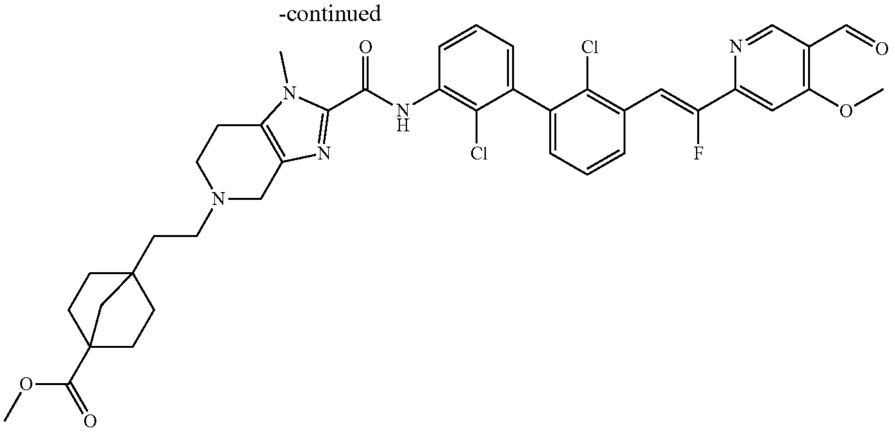

Methyl 4-(2-(2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridin-5-yl)ethyl)bicyclo[2.2.1]heptane-1-carboxylate (6.2 g, 10.3 mmol) was dissolved in tetrahydrofuran/water (100 mL/100 mL), to which (Z)-2-chloro-3-(2-fluoro-2-(5-formyl-4-methoxypyridin-2-yl)vinyl)phenyl trifluoromethanesulfonic acid (4.0 g, 9.1 mmol), potassium phosphate (5.8 g, 27.3 mmol) and chloro(2-dicyclohexyl phosphonyl-2',4',6'-triisopropyl-1,1'-biphenyl)[2-(2'-amino-1,1'-biphenyl)]palladium(II) (XPhos Pd G2) (715 mg, 0.91 mmol) were then added. The reaction mixture was stirred overnight at 85° C. under the protection of nitrogen. After concentrating, column chromatographic separation [eluent: dichloromethane-dichloromethane/methanol (93:7)] was conducted to obtain methyl (Z)-4-(2-(2-((2,2'-dichloro-3'-(2-fluoro-2-(5-formyl-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (4.8 g, yield: 70%). ESI-MS 760.2 $[M+H]^+$.

Step 6: Synthesis of methyl (Z)-4-(2-(2-((2,2'-dichloro-3'-(2-fluoro-2-(5-(((2-hydroxyethyl)amino)methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate

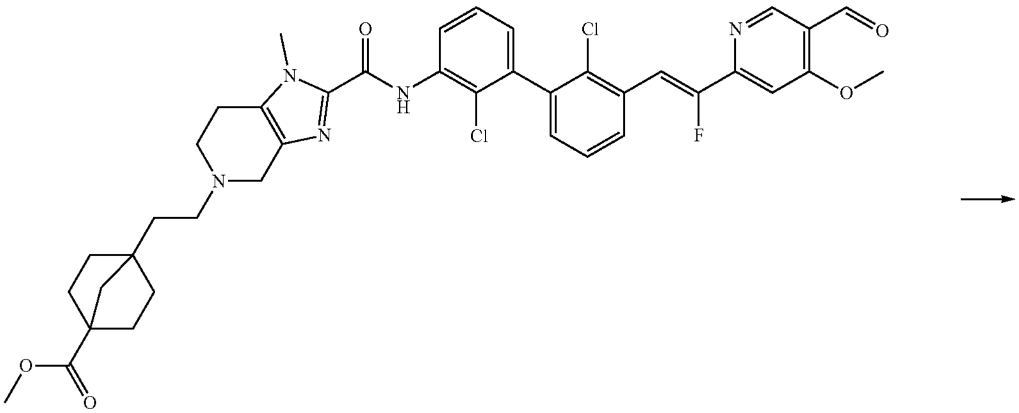

-continued

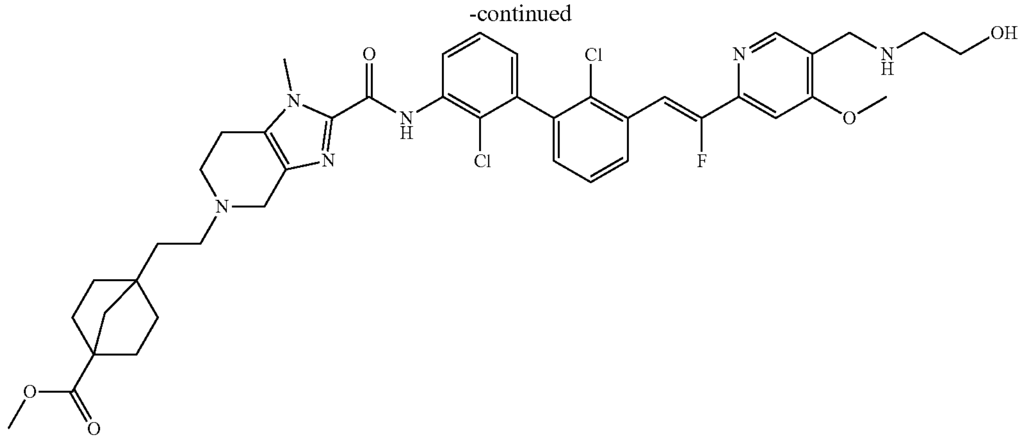

Methyl (Z)-4-(2-(2-((2,2'-dichloro-3'-(2-fluoro-2-(5-formyl-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate (50 mg, 0.066 mmol) was dissolved in a solution of N,N-dimethylformamide/acetic acid (2.0 mL/0.4 mL), to which ethanol amine (20 mg, 0.33 mmol) was then added. The mixture was stirred for 0.5 hour at room temperature, added with sodium cyanoborohydride (21 mg, 0.33 mmol), and then continuously stirred for 1 hour. Water and dichloromethane were added for delamination. The organic phase was dried over anhydrous sodium sulfate and concentrated to obtain a crude product, namely, methyl (Z)-4-(2-(2-((2,2'-dichloro-3'-(2-fluoro-2-(5-(((2-hydroxyethyl)amino)methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylate, which was directly used in the next step. ESI-MS 806.8 $[M+H]^+$.

Step 7: Synthesis of (Z)-4-(2-(2-((2,2'-dichloro-3'-(2-fluoro-2-(5-(((2-hydroxyethyl)amino) methyl)-4-methoxypyridin-2-yl)vinyl)-[1,1'-biphenyl]-3-yl) carbamoyl)-1-methyl-1,4,6,7-tetrahydro-5H-imidazo [4,5-c]pyridin-5-yl)ethyl)bicyclo[2.2.1]heptane-1-carboxylic acid

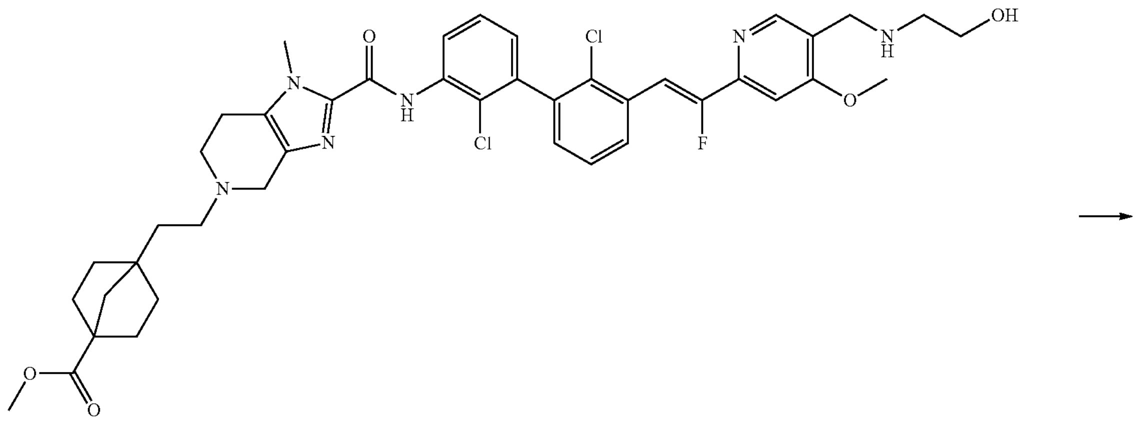

-continued

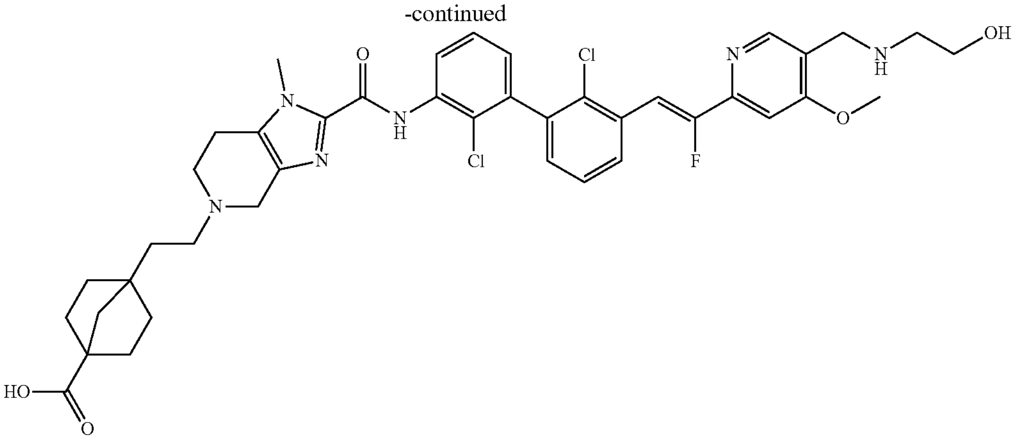

Methyl (Z)-4-(2-(2-((2,2'-dichloro-3'-(2-fluoro-2-(5-(((2-hydroxyethyl)amino)methyl)-4-m ethoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo [2.2.1]heptane-1-carboxylate (crude product from the previous step) was dissolved in methanol/water/tetrahydrofuran (1 mL/1 mL/1 mL), to which lithium hydroxide monohydrate (21 mg, 0.5 mmol) was then added. The mixture was stirred for 2 hours at room temperature. Then, high performance liquid chromatography was conducted to obtain (Z)-4-(2-(2-((2,2'-dichloro-3'-(2-fluoro-2-(5-(((2-hydroxyethyl)amino) methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid (11.1 mg, two-step yield: 21.24%). ESI-MS 791.4 $[M+H]^+$.

$^1H$ NMR (400 MHz, DMSO-$d_6$) δ 9.89 (s, 1H), 8.49 (s, 1H), 8.37 (dd, J=8.2, 1.5 Hz, 1H), 8.01 (dd, J=8.0, 1.6 Hz, 1H), 7.59-7.46 (m, 3H), 7.40-7.32 (m, 2H), 7.15 (dd, J=7.6, 1.6 Hz, 1H), 4.76 (s, 1H), 3.99 (s, 3H), 3.91 (d, J=7.4 Hz, 5H), 3.55 (s, 2H), 3.42 (s, 3H), 2.75 (d, J=5.8 Hz, 2H), 2.67 (dd, J=4.1, 2.1 Hz, 2H), 2.56 (s, 2H), 1.84 (d, J=13.1 Hz, 2H), 1.72 (t, J 7.8 Hz, 2H), 1.50 (d, J=10.7 Hz, 4H), 1.43 (s, 2H), 1.38 (d, J=11.4 Hz, 2H).

$^{19}F$ NMR (377 MHz, DMSO-$d_6$) δ −120.74.

Example 17-79 can be prepared by selecting corresponding starting materials according to complete or partial synthesis method of Example 16.

| Example No. | Compound structure and name | MS: m/z $[M + H]^+$ |
| --- | --- | --- |
| 17 | 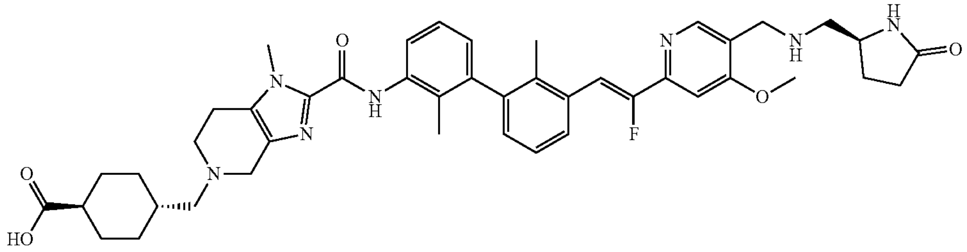 [SMILES: COc1cc(/C(F)=C/c2cccc(-c3cccc(NC(=O)c4nc5c(n4C)CCN(C[C@H]4CC[C@H](C(=O)O)CC4)C5)c3C)c2C)ncc1CNC[C@@H]1CCC(=O)N1] (1R,4R)-4-((2-((3'-((Z)-2-fluoro-2-(4-methoxy-5-(((((S)-5-oxopyrrolidin-2-yl)methyl)amino)methyl)pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 778.5 |

-continued

| Example No. | Compound structure and name | MS: m/z [M + H]+ |
| --- | --- | --- |
| 18 | 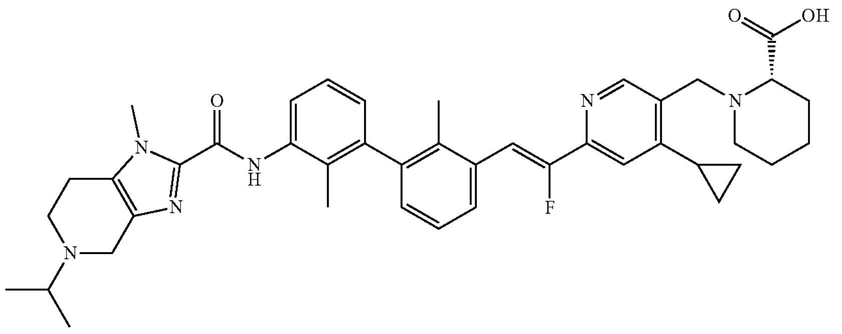 [SMILES: Cc1c(/C=C(\F)c2cc(C3CC3)c(CN3CCCC[C@H]3C(=O)O)cn2)cccc1-c1cccc(NC(=O)c2nc3c(n2C)CCN(C(C)C)C3)c1C] (S,Z)-1-((4-cyclopropyl-6-(1-fluoro-2-(3'-(5-isopropyl-1-methyl-4,5,6,7-tetrahydro-1H-imidazo[4,5-c]pyridine-2-carboxamido)-2,2'-dimethyl-[1,1'-biphenyl]-3-yl)vinyl)pyridin-3-yl)methyl)piperidine-2-carboxylic acid | 705.2 |
| 19 | 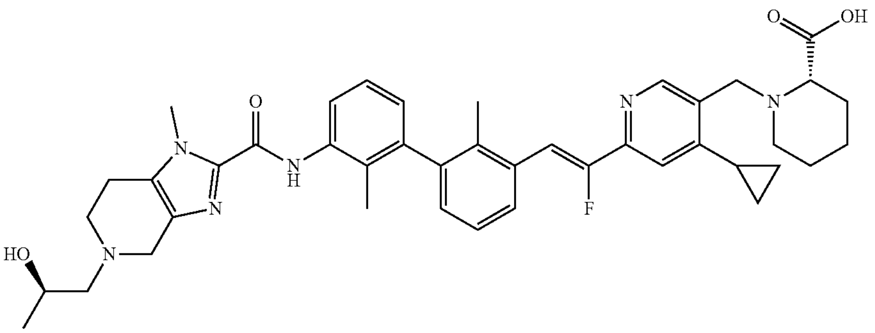 [SMILES: Cc1c(/C=C(\F)c2cc(C3CC3)c(CN3CCCC[C@H]3C(=O)O)cn2)cccc1-c1cccc(NC(=O)c2nc3c(n2C)CCN(C[C@@H](C)O)C3)c1C] (S)-1-((4-cyclopropyl-6-((Z)-1-fluoro-2-(3'-(5-((R)-2-hydroxypropyl)-1-methyl-4,5,6,7-tetrahydro-1H-imidazo[4,5-c]pyridine-2-carboxamido)-2,2'-dimethyl-[1,1'-biphenyl]-3-yl)vinyl)pyridin-3-yl)methyl) | 361.3 [M/2 + H]+ |
| 20 | 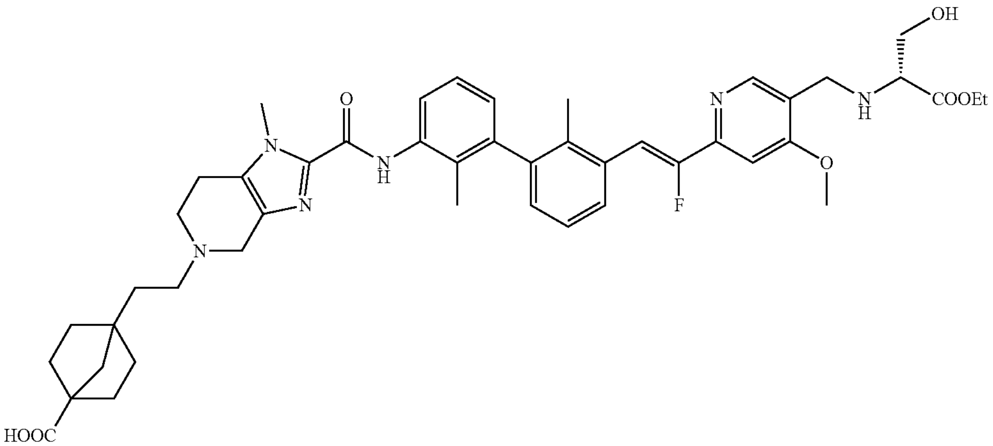 [SMILES: CCOC(=O)[C@@H](CO)NCc1cnc(/C(F)=C/c2cccc(-c3cccc(NC(=O)c4nc5c(n4C)CCN(CCC46CCC(C(=O)O)(CC4)C6)C5)c3C)c2C)cc1OC] (R, Z)-4-(2-(2-((3'-(2-(5-(((1-ethoxy-3-hydroxy-1-oxopropan-2-yl) amino)methyl)-4-methoxypyridin-2-yl)-2-fluorovinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 823 |

-continued

| Example No. | Compound structure and name | MS: m/z $[M + H]^+$ |
|---|---|---|
| 21 | 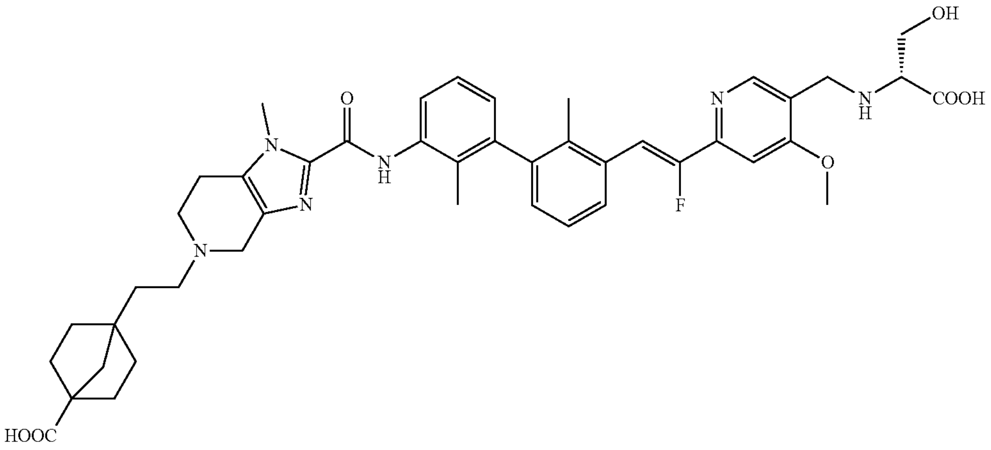 [SMILES: COc1cc(/C(F)=C/c2cccc(-c3cccc(NC(=O)c4nc5c(n4C)CCN(CCC46CCC(C(=O)O)(CC4)C6)C5)c3C)c2C)ncc1CN[C@H](CO)C(=O)O] (R,Z)-4-(2-(2-((3'-(2-(5-(((1-carboxy-2-hydroxyethyl)amino)methyl)-4-methoxypyridin-2-yl)-2-fluorovinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 795 |
| 22 | 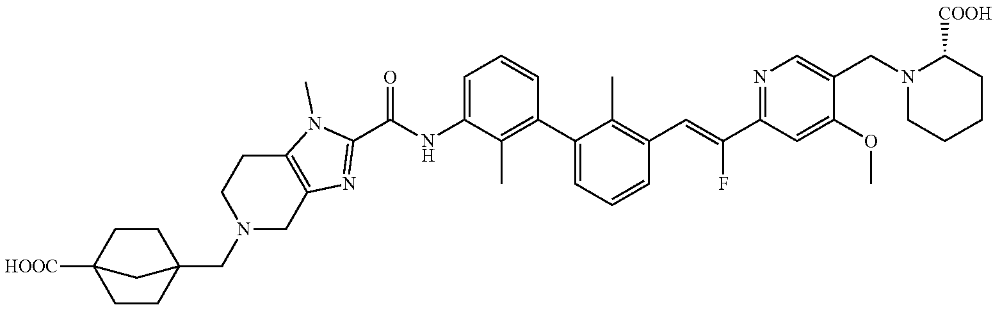 [SMILES: COc1cc(/C(F)=C/c2cccc(-c3cccc(NC(=O)c4nc5c(n4C)CCN(CC46CCC(C(=O)O)(CC4)C6)C5)c3C)c2C)ncc1CN1CCCC[C@H]1C(=O)O] (S,Z)-1-((6-(2-(3'-(5-((4-carboxybicyclo[2.2.1]heptan-1-yl)methyl)-1-methyl-4,5,6,7-tetrahydro-1H-imidazo[4,5-c]pyridine-2-carboxamido)-2,2'-dimethyl-[1,1'-biphenyl]-3-yl)-1-fluorovinyl)-4-methoxypyridin-3-yl)methyl)piperidine-2-carboxylic acid | 805 |
| 23 | 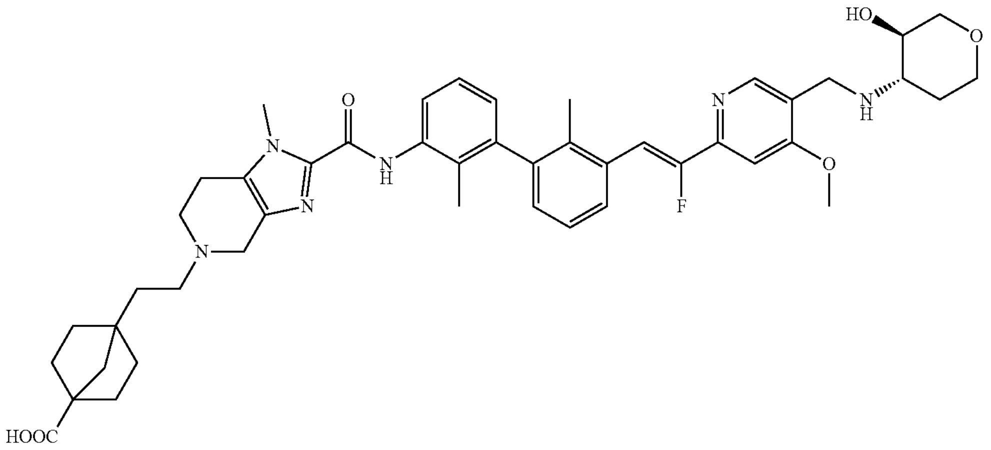 [SMILES: COc1cc(/C(F)=C/c2cccc(-c3cccc(NC(=O)c4nc5c(n4C)CCN(CCC46CCC(C(=O)O)(CC4)C6)C5)c3C)c2C)ncc1CN[C@H]1CCOC[C@@H]1O] 4-(2-(2-((3'-((Z)-2-fluoro-2-(5-((((3R,4S)-3-hydroxytetrahydro-2H-pyran-4-yl)amino)methyl)-4-methoxypyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 807 |

-continued

| Example No. | Compound structure and name | MS: m/z [M + H]+ |
|---|---|---|
| 24 | 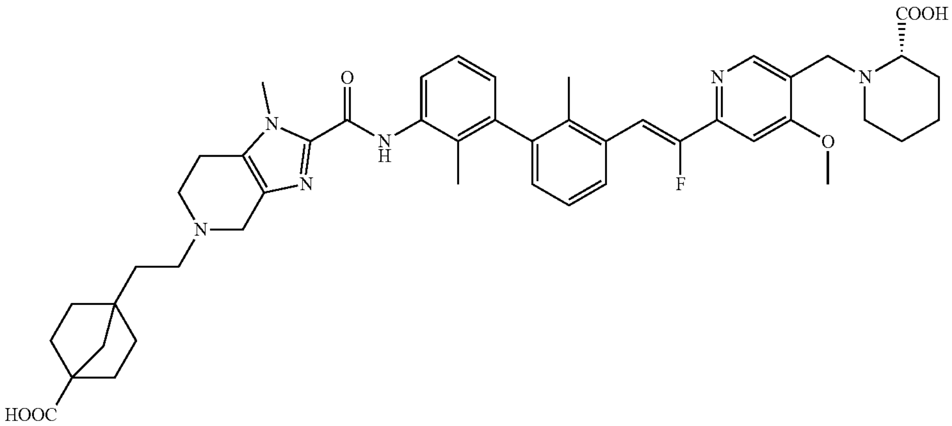 [SMILES: COc1cc(/C(F)=C/c2cccc(-c3cccc(NC(=O)c4nc5c(n4C)CCN(CCC46CCC(C(=O)O)(CC4)C6)C5)c3C)c2C)ncc1CN1CCCC[C@H]1C(=O)O] (S,Z)-1-((6-(2-(3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dimethyl-[1,1'-biphenyl]-3-yl)-1-fluorovinyl)-4-methoxypyridin-3-yl)methyl)piperidine-2-carboxylic acid | 819 |
| 25 | 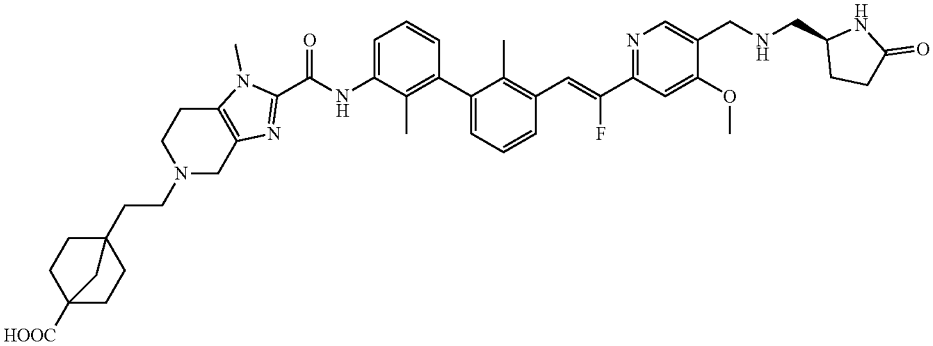 [SMILES: COc1cc(/C(F)=C/c2cccc(-c3cccc(NC(=O)c4nc5c(n4C)CCN(CCC46CCC(C(=O)O)(CC4)C6)C5)c3C)c2C)ncc1CNC[C@@H]1CCC(=O)N1] (S,Z)-4-(2-(2-((3'-(2-fluoro-2-(4-methoxy-5-((((5-oxopyrrolidin-2-yl) methyl)amino)methyl)pyridin-2-yl)vinyl)-2,2'-dimethyl-[1,1'-biphenyl]-3-yl)carbamoyl)-1-methyl-1,4,6,7-tetrahydro-5H-imidazo [4,5-c]pyridin-5-yl)ethyl)bicyclo[2.2.1]heptane-1-carboxylic acid | 804 |
| 26 | 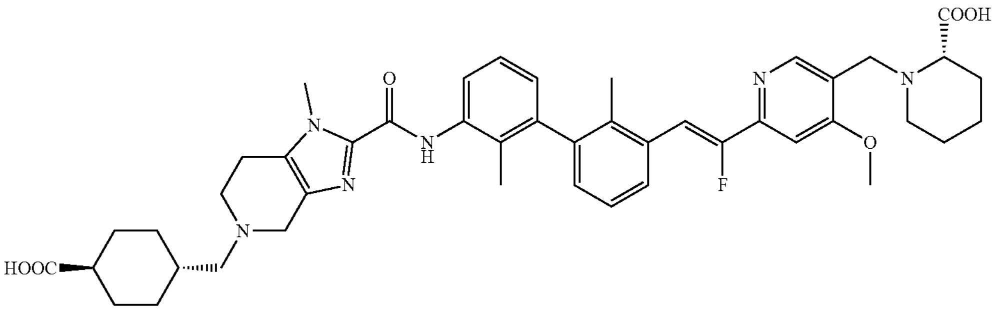 [SMILES: COc1cc(/C(F)=C/c2cccc(-c3cccc(NC(=O)c4nc5c(n4C)CCN(C[C@H]4CC[C@H](C(=O)O)CC4)C5)c3C)c2C)ncc1CN1CCCC[C@H]1C(=O)O] (S)-1-((6-((Z)-2-(3'-(5-(((1r,4r)-4-carboxycyclohexyl)methyl)-1-methyl-4,5,6,7-tetrahydro-1H-imidazo[4,5-c]pyridine-2-carboxamido)-2,2'-dimethyl-[1,1'-biphenyl]-3-yl)-1-fluorovinyl)-4-methoxypyridin-3-yl)methyl)piperidine-2-carboxylic acid | 793 |

-continued

| Example No. | Compound structure and name | MS: m/z [M + H]$^+$ |
|---|---|---|
| 27 | 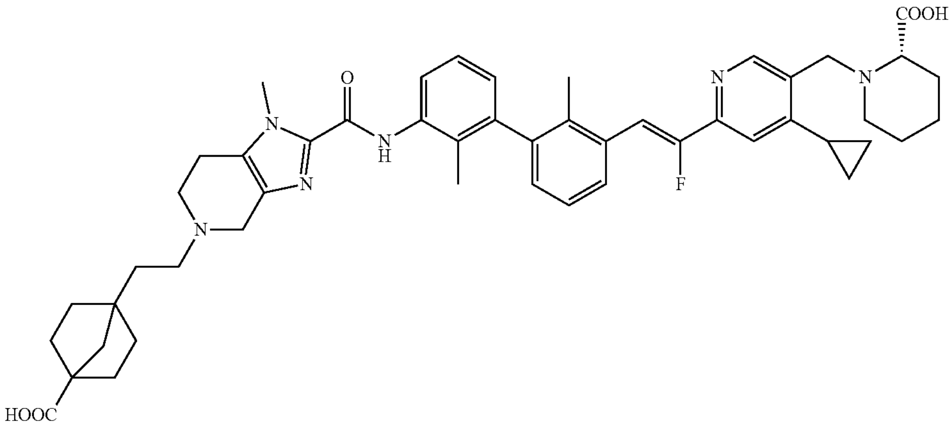 [SMILES: Cc1c(/C=C(\F)c2cc(C3CC3)c(CN3CCCC[C@H]3C(=O)O)cn2)cccc1-c1cccc(NC(=O)c2nc3c(n2C)CCN(CCC24CCC(C(=O)O)(CC2)C4)C3)c1C] (S,Z)-1-((6-(2-(3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dimethyl-[1,1'-biphenyl]-3-yl)-1-fluorovinyl)-4-cyclopropylpyridin-3-yl)methyl)piperidine-2-carboxylic acid | 829 |
| 28 | 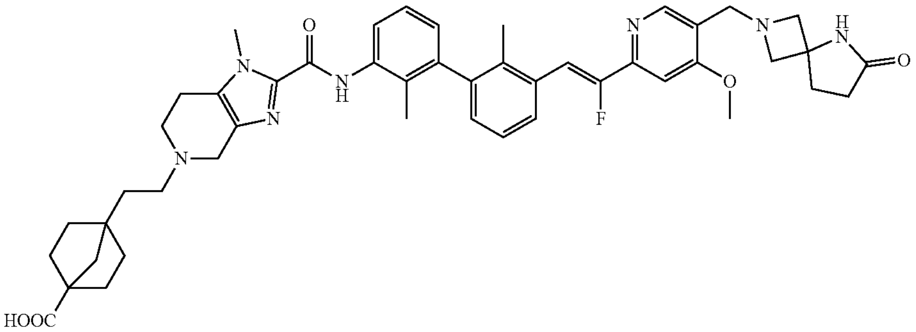 [SMILES: COc1cc(/C(F)=C/c2cccc(-c3cccc(NC(=O)c4nc5c(n4C)CCN(CCC46CCC(C(=O)O)(CC4)C6)C5)c3C)c2C)ncc1CN1CC2(CCC(=O)N2)C1] (Z)-4-(2-(2-((3'-(2-fluoro-2-(4-methoxy-5-((6-oxo-2,5-diazaspiro[3.4]octan-2-yl)methyl)pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 816 |
| 29 | 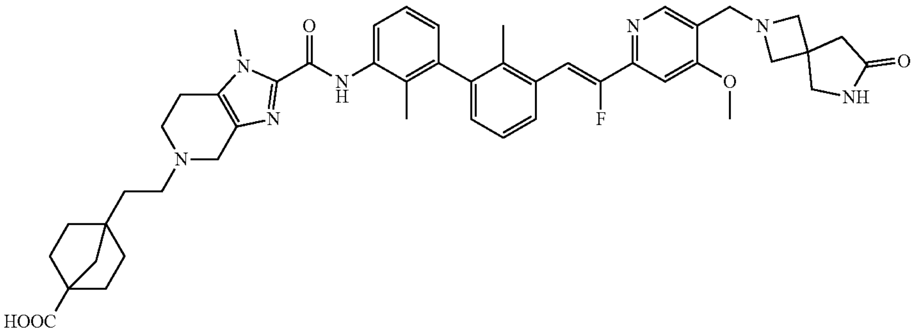 [SMILES: COc1cc(/C(F)=C/c2cccc(-c3cccc(NC(=O)c4nc5c(n4C)CCN(CCC46CCC(C(=O)O)(CC4)C6)C5)c3C)c2C)ncc1CN1CC2(CNC(=O)C2)C1] (Z)-4-(2-(2-((3'-(2-fluoro-2-(4-methoxy-5-((7-oxo-2,6-diazaspiro[3.4]octan-2-yl)methyl)pyridin-2-yl)vinyl)-2,2'-dimethyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 816 |

-continued

| Example No. | Compound structure and name | MS: m/z $[M + H]^+$ |
| --- | --- | --- |
| 30 | 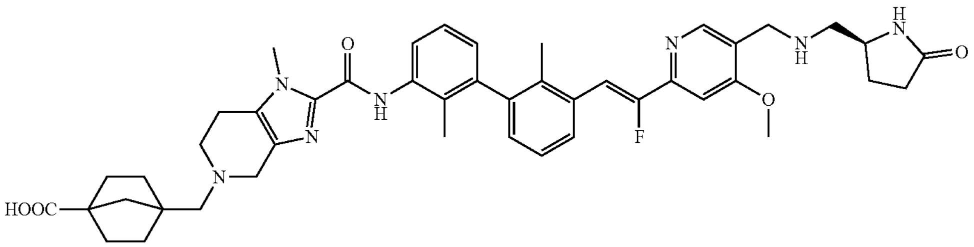 [SMILES: COc1cc(/C(F)=C/c2cccc(-c3cccc(NC(=O)c4nc5c(n4C)CCN(CC46CCC(C(=O)O)(CC4)C6)C5)c3C)c2C)ncc1CNC[C@@H]1CCC(=O)N1] (S',Z)-4-((2-((3'-(2-fluoro-2-(4-methoxy-5-((((5-oxopyrrolidin-2-yl) methyl)amino)methyl)pyridin-2-yl)vinyl)-2,2'-dimethyl-[1,1'-biphenyl]-3-yl)carbamoyl)-1-methyl-1,4,6,7-tetrahydro-5H-imidazo[4,5-c] pyridin-5-yl)methyl)bicyclo[2.2. 1]heptane-1-carboxylic acid | 790 |
| 31 | 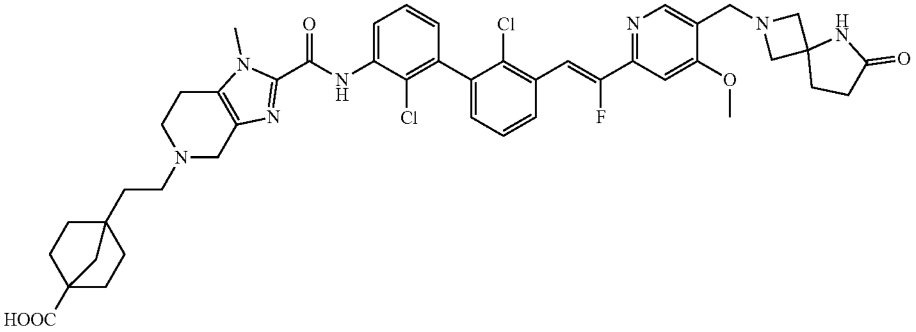 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC2(CCC(=O)N2)C1] (Z)-4-(2-(2-((2,2'-dichloro-3'-(2-fluoro-2-(4-methoxy-5-((6-oxo-2,5-diazaspiro[3 4]octan-2-yl)methyl)pyridin-2-yl)vinyl)-[1,1'-biphenyl]-3-yl)carbamoyl)-1-methyl-1,4,6,7-tetrahydro-5H-imidazo[4,5-c] pyridin-5-yl)ethyl)bicyclo[2.2.1]heptane-1-carboxylic acid | 856 |
| 32 | 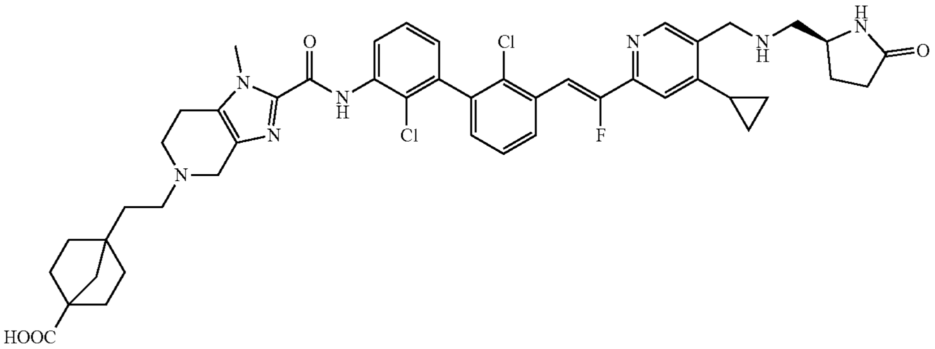 [SMILES: Cn1c(C(=O)Nc2cccc(-c3cccc(/C=C(\F)c4cc(C5CC5)c(CNC[C@@H]5CCC(=O)N5)cn4)c3Cl)c2Cl)nc2c1CCN(CCC13CCC(C(=O)O)(CC1)C3)C2] (S,Z)-4-(2-(2-((2,2'-dichloro-3'-(2-(4-cyclopropyl-5-((((5-oxopyrrolidin-2-yl)methyl)amino)methyl)pyridin-2-yl)-2-fluorovinyl)-[1,1'-biphenyl]-3-yl)carbamoyl)-1-methyl-1,4,6,7-tetrahydro-5H-imidazo [4,5-c]pyridin-5-yl)ethyl)bicyclo[2.2.1]heptane-1-carboxylic acid | 854 |

-continued

| Example No. | Compound structure and name | MS: m/z $[M + H]^+$ |
|---|---|---|
| 33 | 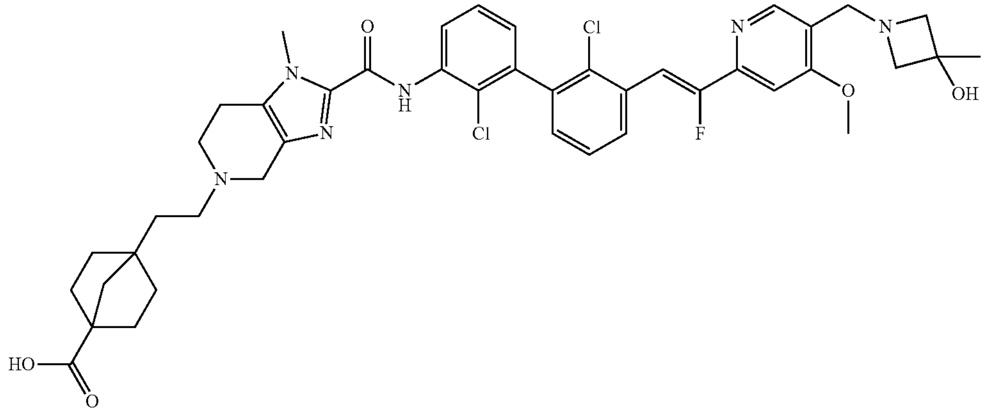 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC(C)(O)C1] (Z)-4-(2-(2-((2,2'-dichloro-3'-(2-fluoro-2-(5-((3-hydroxy-3-methylazetidin-1-yl)methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 817.4 |
| 34 | 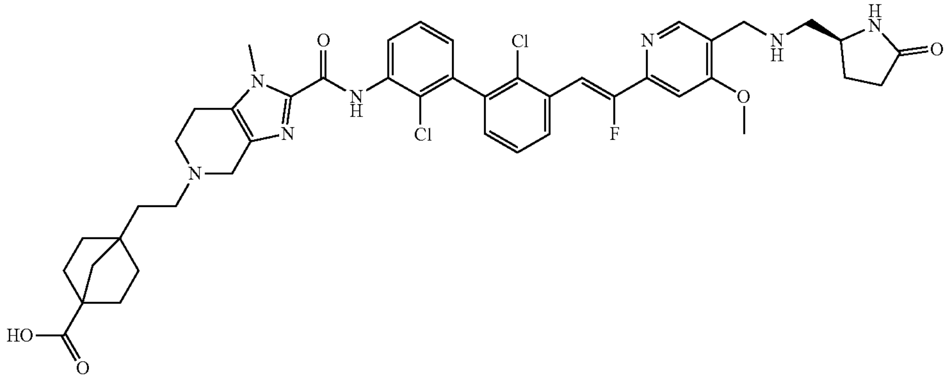 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNC[C@@H]1CCC(=O)N1] (S,Z)-4-(2-(2-((2,2'-dichloro-3'-(2-fluoro-2-(4-methoxy-5-((((5-oxopyrrolidin-2-yl)methyl)amino)methyl)pyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 844.4 |

-continued

| Example No. | Compound structure and name | MS: m/z $[M + H]^+$ |
| --- | --- | --- |
| 35 | 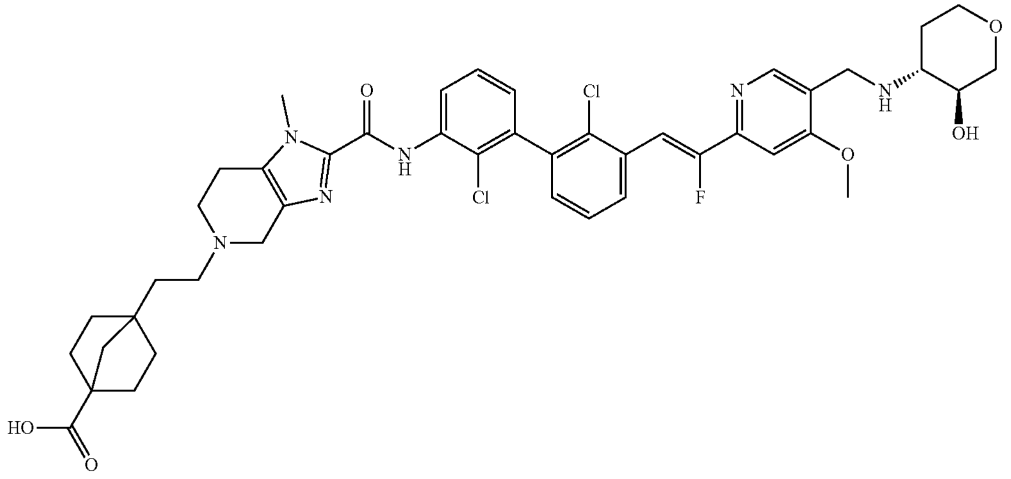 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN[C@@H]1CCOC[C@H]1O] 4-(2-(2-((2,2'-dichloro-3'-((Z)-2-fluoro-2-(5-((((3S,4R)-3-hydroxytetrahydro-2H-pyran-4-yl)amino)methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 847.4 |
| 36 | 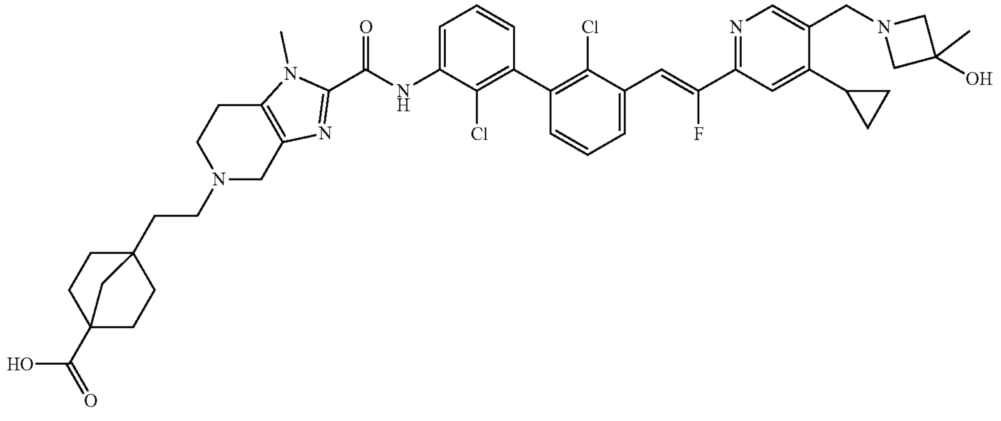 [SMILES: Cn1c(C(=O)Nc2cccc(-c3cccc(/C=C(\F)c4cc(C5CC5)c(CN5CC(C)(O)C5)cn4)c3Cl)c2Cl)nc2c1CCN(CCC13CCC(C(=O)O)(CC1)C3)C2] (Z)-4-(2-(2-((2,2'-dichloro-3'-(2-(4-cyclopropyl-5-((3-hydroxy-3-methylazetidin-1-yl)methyl)pyridin-2-yl)-2-fluorovinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 827.4 |

-continued

| Example No. | Compound structure and name | MS: m/z [M + H]+ |
|---|---|---|
| 37 | 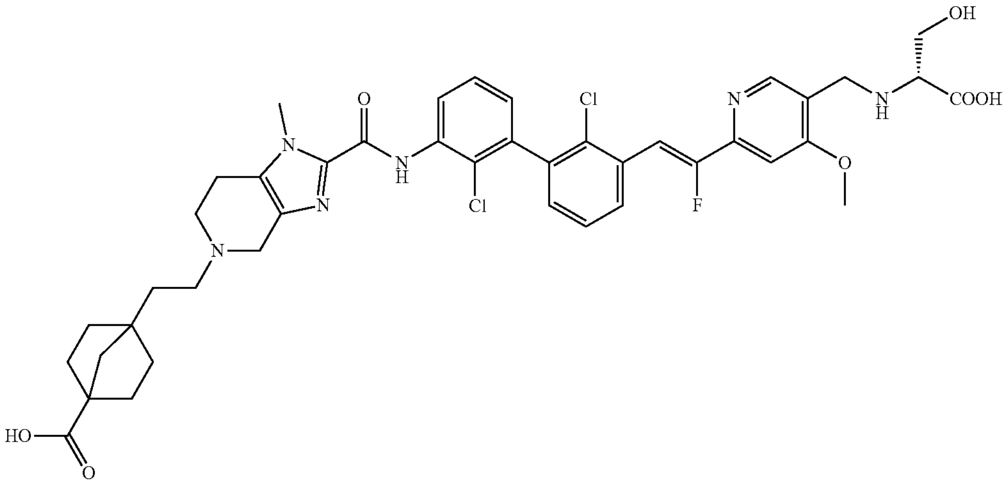 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN[C@H](CO)C(=O)O] (R,Z)-4-(2-(2-((3'-(2-(5-(((1-carboxy-2-hydroxyethyl)amino)methyl)-4-methoxypyridin-2-yl)-2-fluorovinyl)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 418.3 [M/2+H]+ |
| 38 | 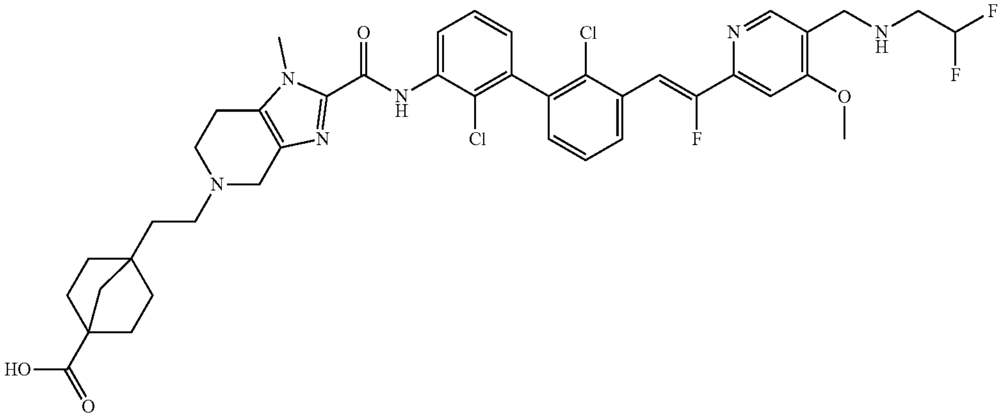 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNCC(F)F] (Z)-4-(2-(2-((2,2'-dichloro-3'-(2-(5-(((2,2-difluoroethyl)amino)methyl)-4-methoxypyridin-2-yl)-2-fluorovinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 811.3 |

-continued

| Example No. | Compound structure and name | MS: m/z $[M + H]^+$ |
|---|---|---|
| 39 | 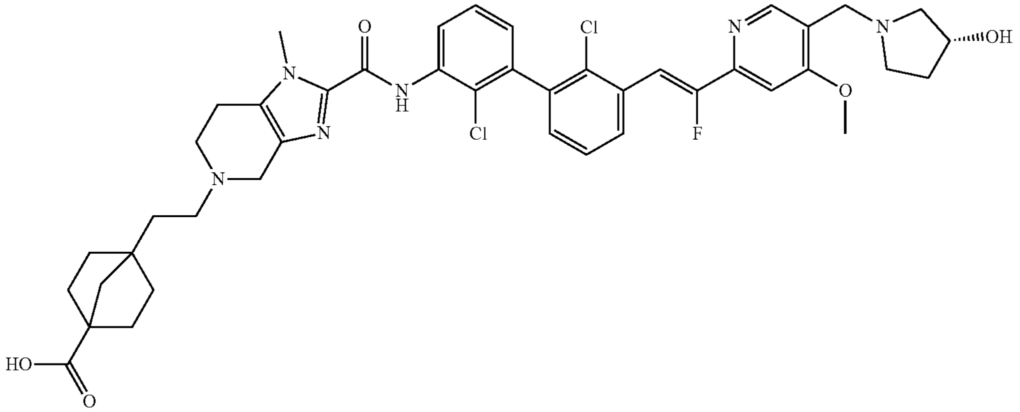 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@@H](O)C1] (R,Z)-4-(2-(2-((2,2'-dichloro-3'-(2-fluoro-2-(5-((3-hydroxypyrrolidin-1-yl)methyl)-4-methoxypyridin-2-yl)vinyl)-[1,1'-biphenyl]-3-yl) carbamoyl)-1-methyl-1,4,6,7-tetrahydro-5H-imidazo[4,5-c]pyridin-5-yl)ethyl)bicyclo[2.2.1]heptane-1-carboxylic acid | 817.4 |
| 40 | 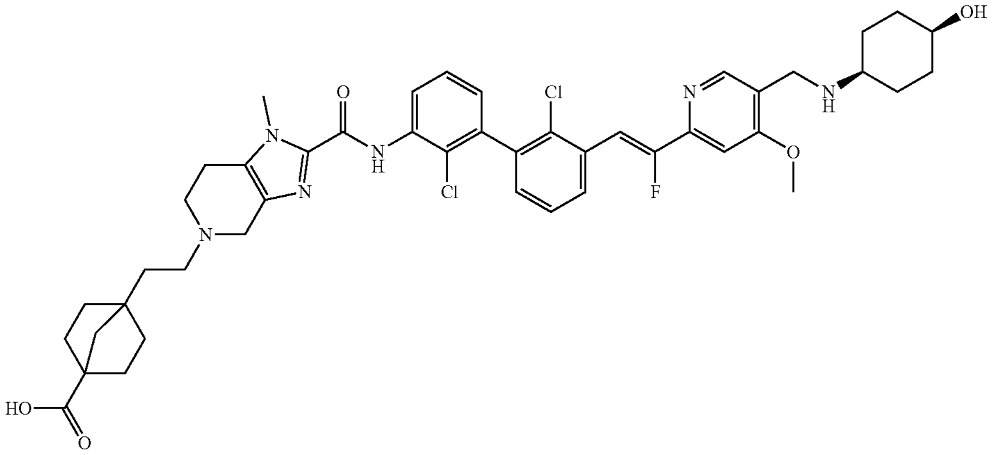 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN[C@H]1CC[C@@H](O)CC1] 4-(2-(2-((2,2'-dichloro-3'-((Z)-2-fluoro-2-(5-((((1S,4S)-4-hydroxycyclohexyl) amino)methyl)-4-methoxypyridin-2-yl)vinyl)-[1,1'-biphenyl]-3-yl)carbamoyl)-1-methyl-1,4,6,7-tetrahydro-5H-imidazo[4,5-c] pyridin-5-yl)ethyl)bicyclo[2.2.1]heptane-1-carboxylic acid | 845.4 |

-continued

| Example No. | Compound structure and name | MS: m/z [M + H]+ |
|---|---|---|
| 41 | 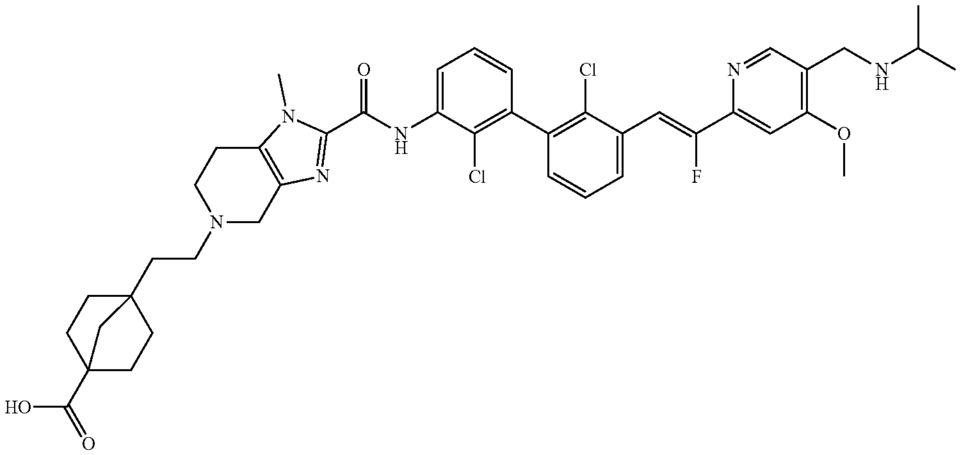 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNC(C)C] (Z)-4-(2-(2-((2,2'-dichloro-3'-(2-fluoro-2-(5-((isopropylamino) methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl) bicyclo[2.2.1]heptane-1-carboxylic acid | 789.4 |
| 42 | 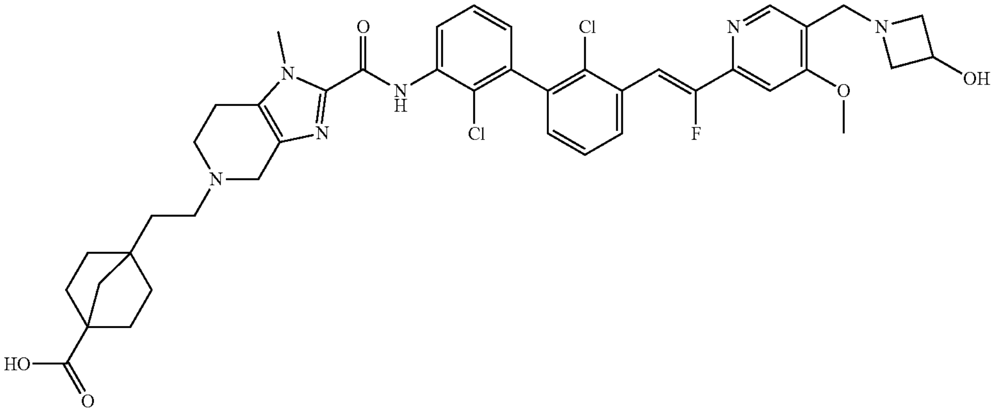 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC(O)C1] (Z)-4-(2-(2-((2,2'-dichloro-3'-(2-fluoro-2-(5-((3-hydroxyazetidin-1-yl)methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl) ethyl)bicyclo[2.2.1]heptane-1-carboxylic acid | 803.3 |
| 43 | 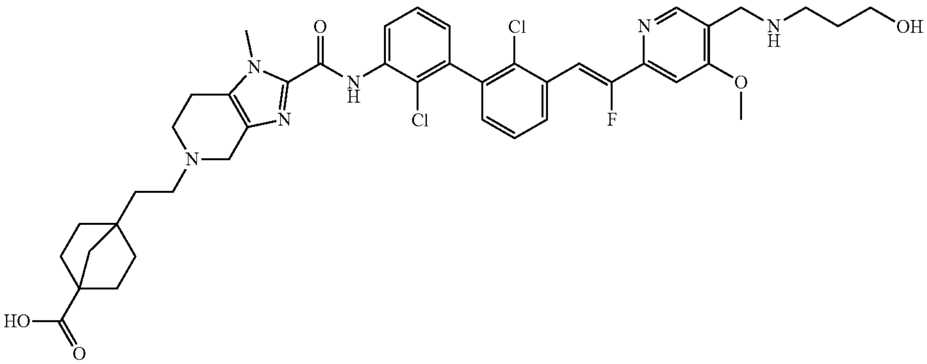 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNCCCO] (Z)-4-(2-(2-((2,2'-dichloro-3'-(2-fluoro-2-(5-(((3-hydroxypropyl) amino)methyl)-4-methoxypyridin-2-yl)vinyl)-[1,1'-biphenyl]-3-yl) carbamoyl)-1-methyl-1,4,6,7-tetrahydro-5H-imidazo[4,5-c]pyridin-5-yl) ethyl)bicyclo[2.2.1]heptane-1-carboxylic acid | 805.3 |

-continued

| Example No. | Compound structure and name | MS: m/z [M + H]+ |
|---|---|---|
| 44 | 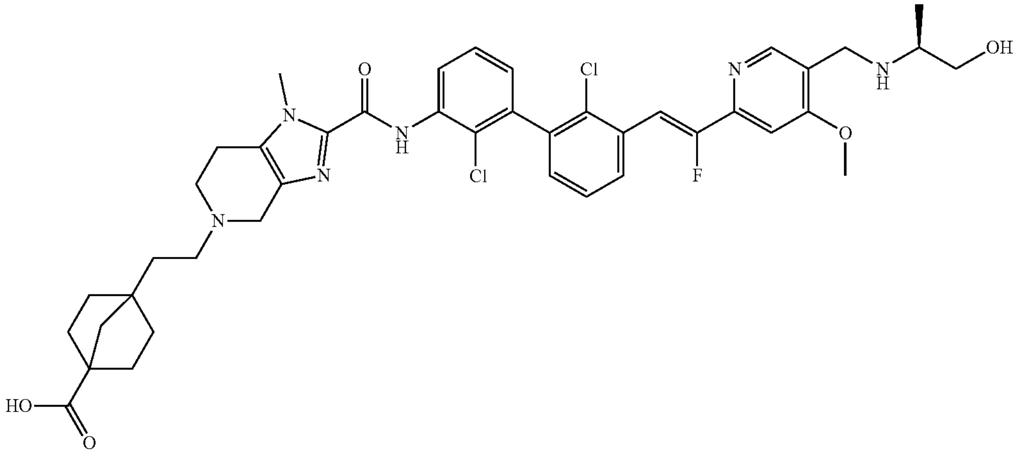 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN[C@@H](C)CO] (S,Z)-4-(2-(2-((2,2'-dichloro-3'-(2-fluoro-2-(5-(((1-hydroxypropan-2-yl)amino)methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 805.3 |
| 45 | 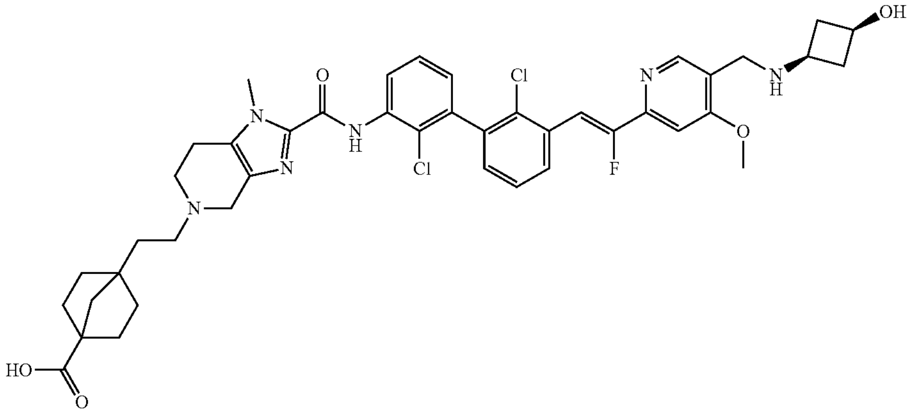 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN[C@H]1C[C@@H](O)C1] 4-(2-(2-((2,2'-dichloro-3'-((Z)-2-fluoro-2-(5-((((1S,3S)-3-hydroxycyclobutyl)amino)methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 817.4 |
| 46 | 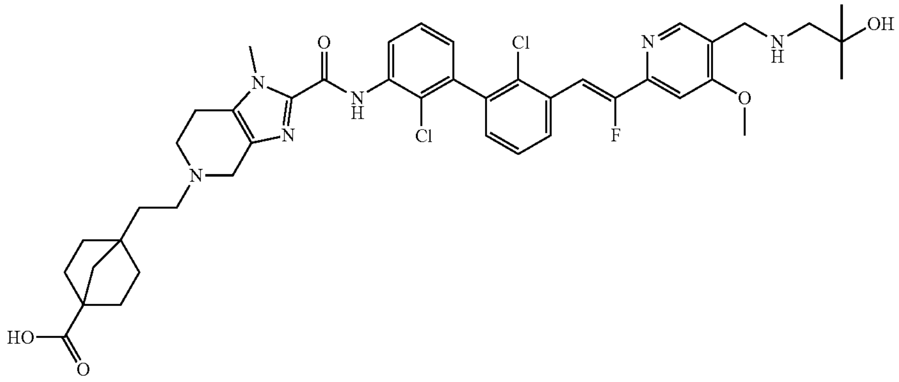 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNCC(C)(C)O] (Z)-4-(2-(2-((2,2'-dichloro-3'-(2-fluoro-2-(5-(((2-hydroxy-2-methylpropyl)amino)methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 819.3 |

-continued

| Example No. | Compound structure and name | MS: m/z [M + H]+ |
| --- | --- | --- |
| 47 | 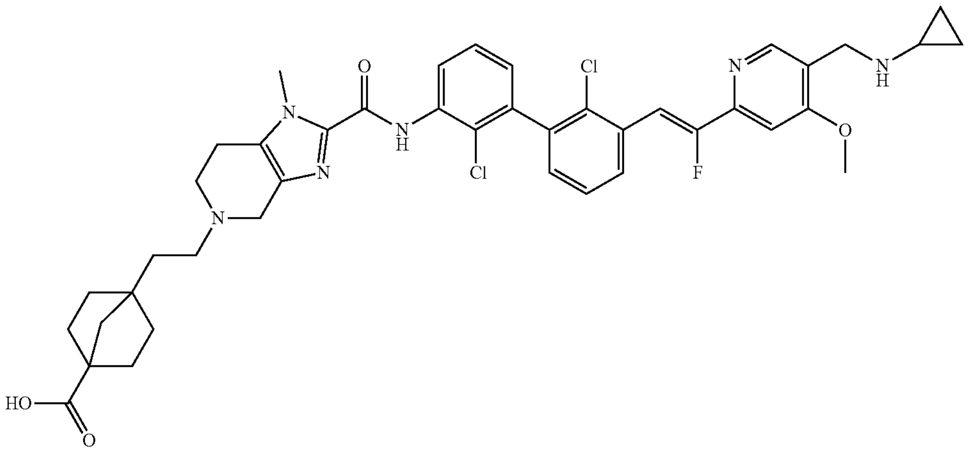 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNC1CC1] (Z)-4-(2-(2-((2,2'-dichloro-3'-(2-(5-((cyclopropylamino)methyl)-4-methoxypyridin-2-yl)-2-fluorovinyl)-[1,1'-biphenyl]-3-yl)carbamoyl)-1-methyl-1,4,6,7-tetrahydro-5H-imidazo[4,5-c]pyridin-5-yl)ethyl) bicyclo[2.2. l]heptane-1-carboxylic acid | 787.4 |
| 48 | 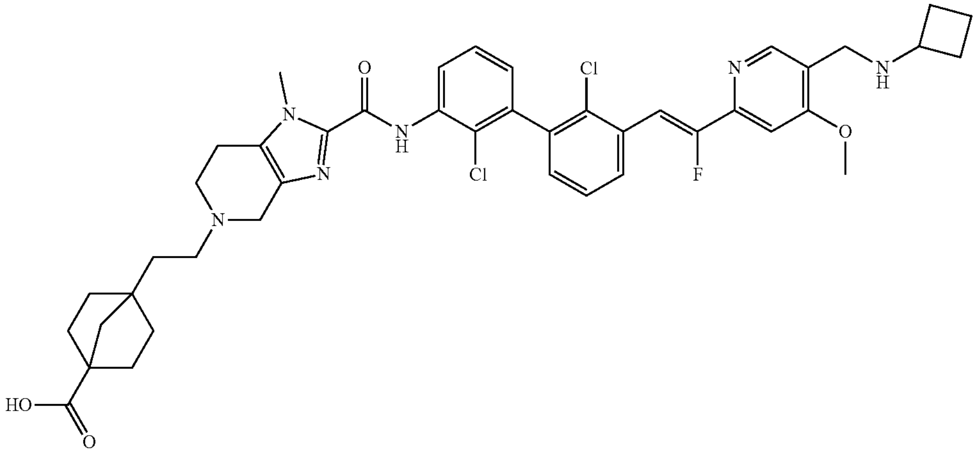 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNC1CCC1] (Z)-4-(2-(2-((2,2'-dichloro-3'-(2-(5-((cyclobutylamino)methyl)-4-methoxypyridin-2-yl)-2-fluorovinyl)-[1,1'-biphenyl]-3-yl)carbamoyl)-1-methyl-1,4,6,7-tetrahydro-5H-imidazo[4,5-c]pyridin-5-yl)ethyl) bicyclo[2.2.1]heptane-1-carboxylic acid | 801.4 |

-continued

| Example No. | Compound structure and name | MS: m/z $[M + H]^+$ |
|---|---|---|
| 49 | 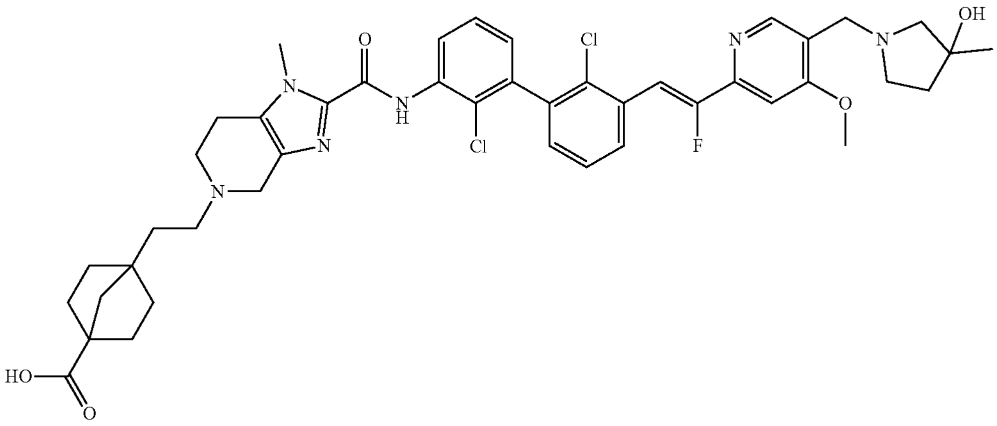 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCC(C)(O)C1] (Z)-4-(2-(2-((2,2'-dichloro-3'-(2-fluoro-2-(5-((3-hydroxy-3-methylpyrrolidin-1-yl)methyl)-4-methoxypyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 831.4 |
| 50 | 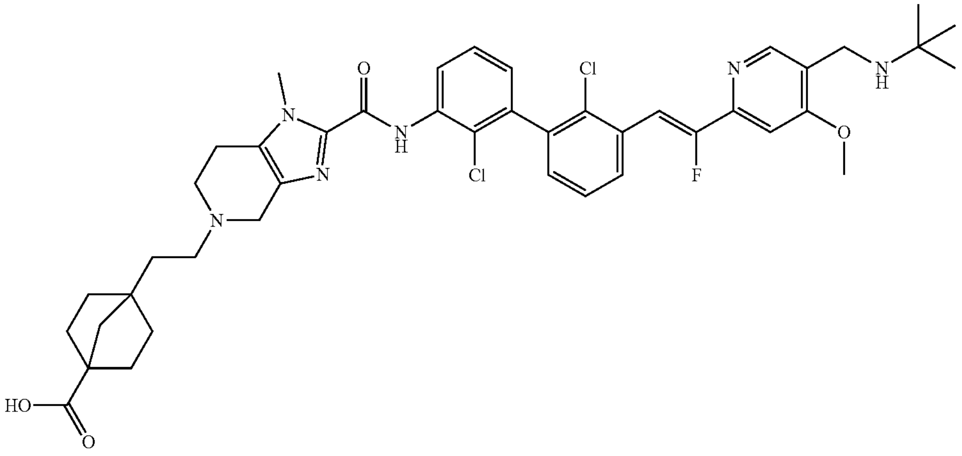 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNC(C)(C)C] (Z)-4-(2-(2-((3'-(2-(5-((tert-butylamino)methyl)-4-methoxypyridin-2-yl)-2-fluorovinyl)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 804.4 |

-continued

| Example No. | Compound structure and name | MS: m/z $[M + H]^+$ |
|---|---|---|
| 51 | 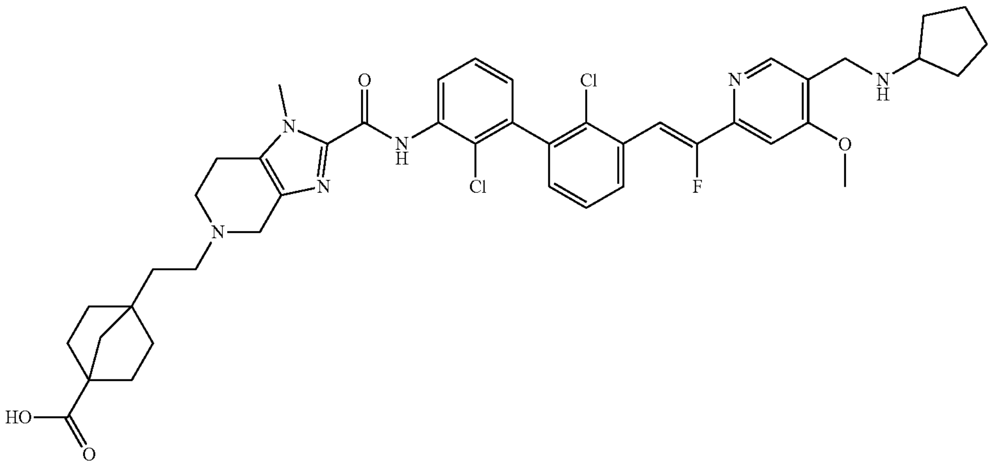 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNC1CCCC1] (Z)-4-(2-(2-((2,2'-dichloro-3'-(2-(5-((cyclopentylamino)methyl)-4-methoxypyridin-2-yl)-2-fluorovinyl)-[1,1'-biphenyl]-3-yl)carbamoyl)-1-methyl-1,4,6,7-tetrahydro-5H-imidazo[4,5-c]pyridin-5-yl)ethyl) bicyclor[2.2.1]heptane-1-carboxylic acid | 815.3 |
| 52 | 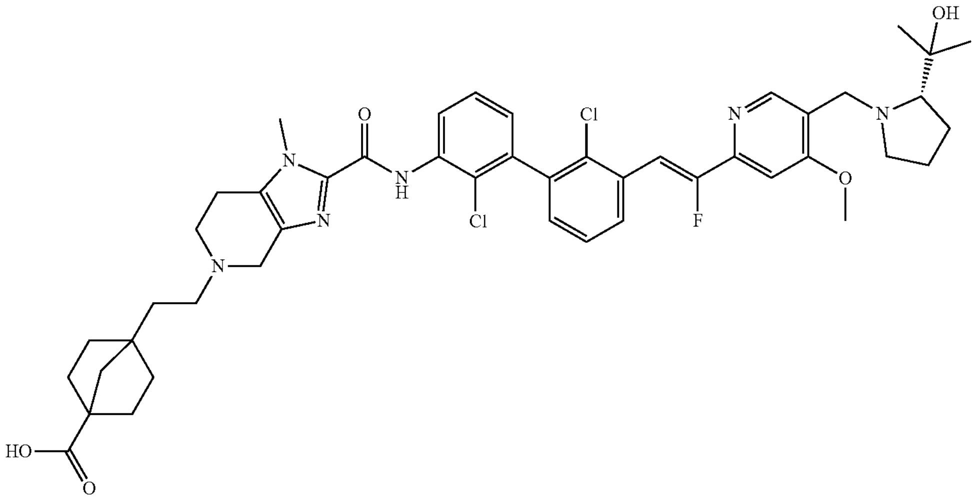 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCC[C@H]1C(C)(C)O] (S,Z)-4-(2-(2-((2,2'-dichloro-3'-(2-fluoro-2-(5-((2-(2-hydroxypropan-2-yl)pyrrolidin-1-yl)methyl)-4-methoxypyridin-2-yl)vinyl)-[1,1'-biphenyl]-3-yl)carbamoyl)-1-methyl-1,4,6,7-tetrahydro-5H-imidazo [4,5-c]pyridin-5-yl)ethyl)bicyclo[2.2.1]heptane-1-carboxylic acid | 859.4 |

-continued

| Example No. | Compound structure and name | MS: m/z [M + H]+ |
| --- | --- | --- |
| 53 | 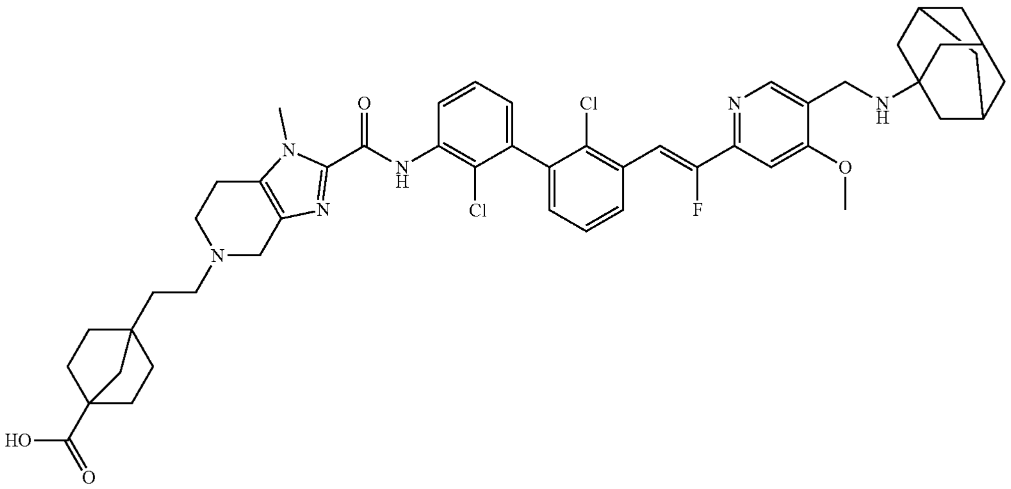 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CNC12CC3CC(CC(C3)C1)C2] (Z)-4-(2-(2-((3'-(2-(5-((adamantan-1-ylamino)methyl)-4-methoxypyridin-2-yl)-2-fluorovinyl)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 885.3 |
| 54 | 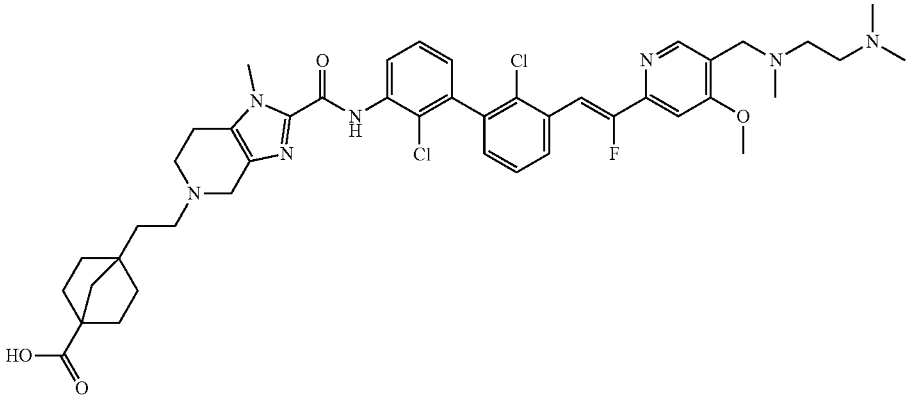 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN(C)CCN(C)C] (Z)-4-(2-(2-((2,2'-dichloro-3'-(2-(5-(((2-(dimethylamino)ethyl)(methyl)amino)methyl)-4-methoxypyridin-2-yl)-2-fluorovinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 832.4 |

-continued

| Example No. | Compound structure and name | MS: m/z [M + H]+ |
|---|---|---|
| 55 | 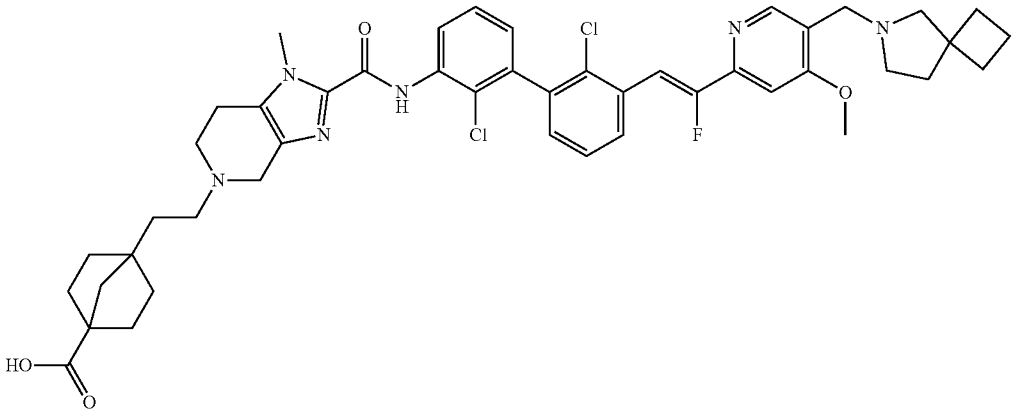 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCC2(CCC2)C1] (Z)-4-(2-(2-((3'-(2-(5-((6-azaspiro[3.4]octan-6-yl)methyl)-4-methoxypyridin-2-yl)-2-fluorovinyl)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 841.3 |
| 56 | 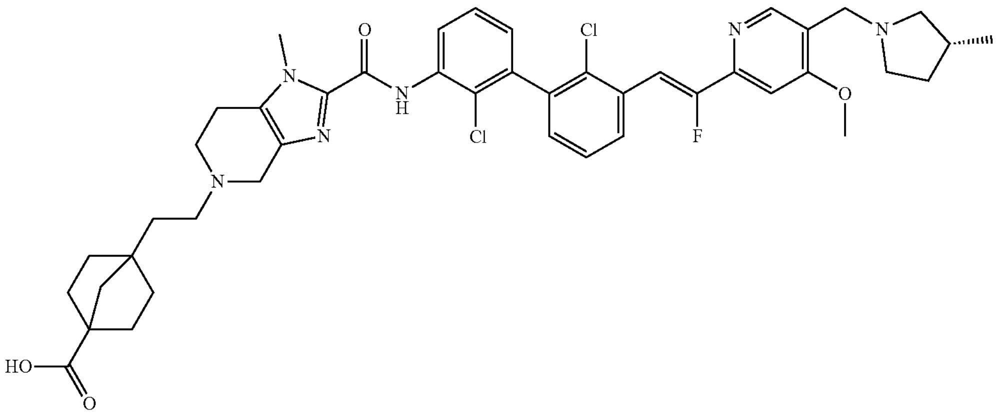 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@@H](C)C1] (R,Z)-4-(2-(2-((2,2'-dichloro-3'-(2-fluoro-2-(4-methoxy-5-((3-methylpyrrolidin-1-yl)methyl)pyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 815.4 |
| 57 | 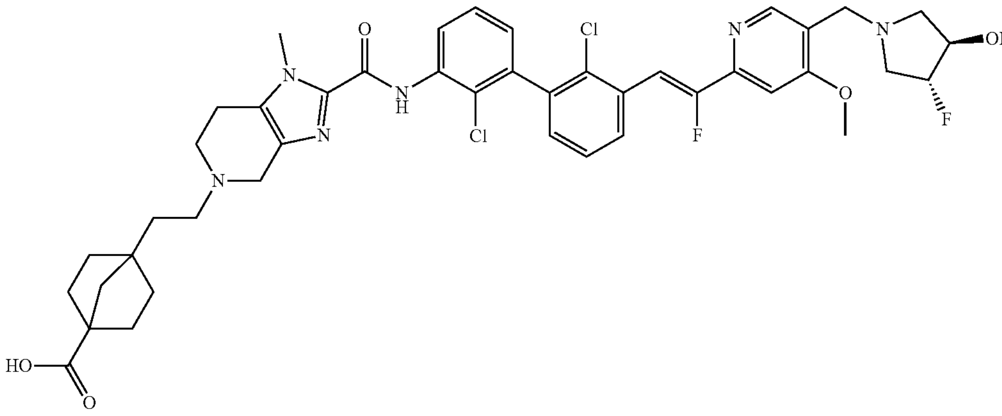 4-(2-(2-((2,2'-dichloro-3'-((Z)-2-fluoro-2-(5-(((3R,4R)-3-fluoro-4-hydroxypyrrolidin-1-yl)methyl)-4-methoxypyridin-2-yl)vinyl)-[1,1-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid | 418.3 [M/2 + H]+ |

-continued

| Example No. | Compound structure and name | MS: m/z $[M + H]^+$ |
|---|---|---|
| 58 | 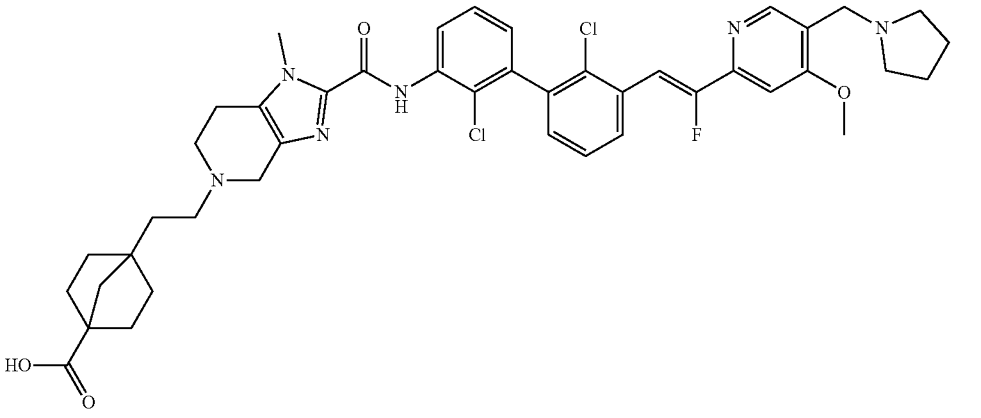 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCCC1]<br>(Z)-4-(2-(2-((2,2'-dichloro-3'-(2-fluoro-2-(4-methoxy-5-(pyrrolidin-1-ylmethyl)pyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl) bicyclo[2.2.1]heptane-1-carboxvlic acid | 801.3 |
| 59 | 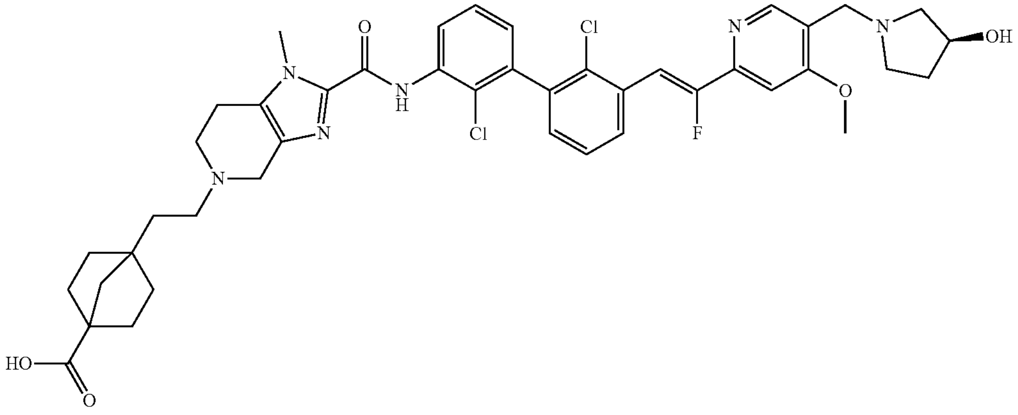 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@H](O)C1]<br>(S,Z)-4-(2-(2-((2,2'-dichloro-3'-(2-fluoro-2-(5-((3-hydroxypyrrolidin-1-yl)methyl)-4-methoxypyridin-2-yl)vinyl)-[1,1'-biphenyl]-3-yl) carbamoyl)-1-methyl-1,4,6,7-tetrahydro-5H-imidazo[4,5-c]pyridin-5-yl) ethyl)bicyclo[2.2.1]heptane-1-carboxylic acid | 817.4 |
| 60 | 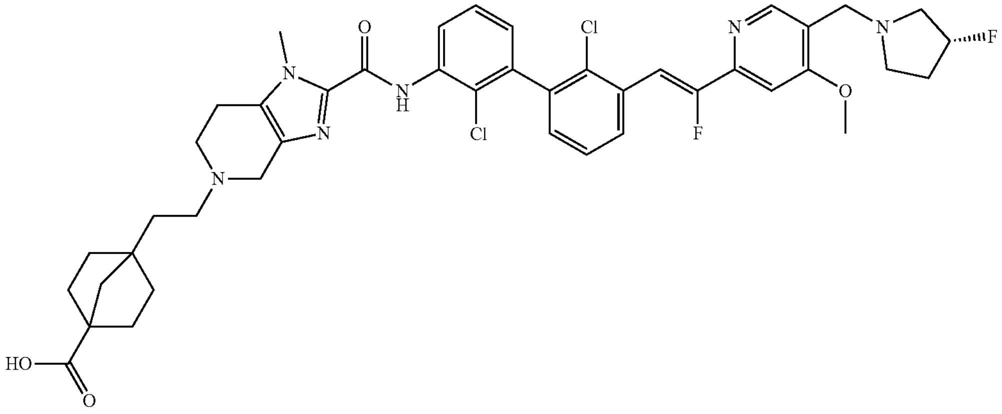 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@@H](F)C1]<br>(R,Z)-4-(2-(2-((2,2'-dichloro-3'-(2-fluoro-2-(5-((3-fluoropyrrolidin-1-yl)methyl)-4-methoxypyridin-2-yl)vinyl)-[1,1'-biphenyl]-3-yl) carbamoyl)-1-methyl-1,4,6,7-tetrahydro-5H-imidazo[4,5-c]pyridin-5-yl) ethyl)bicyclo[2.2.1]heptane-1-carboxylic acid | 819.4 |

-continued

| Example No. | Compound structure and name | MS: m/z [M + H]+ |
| --- | --- | --- |
| 61 | 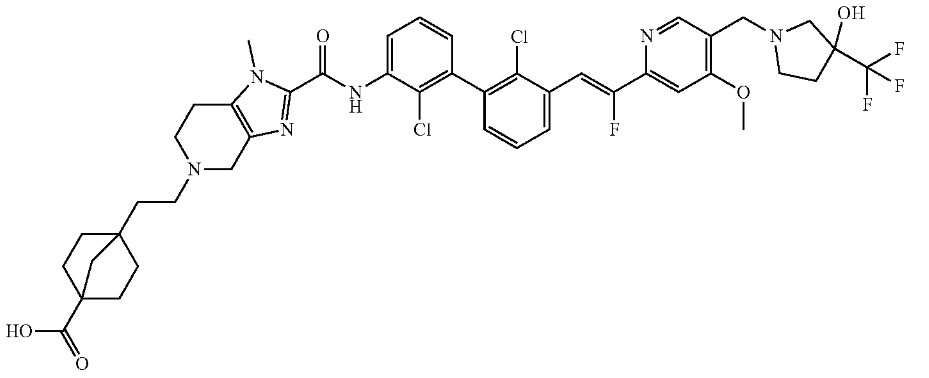 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCC(O)(C(F)(F)F)C1] (Z)-4-(2-(2-((2,2'-dichloro-3'-(2-fluoro-2-(5-((3-hydroxy-3-(trifluoromethyl) pyrrolidin-1-yl)methyl)-4-methoxypyridin-2-yl)vinyl)-[1,1'-biphenyl]-3-yl)carbamoyl)-1-methyl-1,4,6,7-tetrahydro-5H-imidazo [4,5-c]pyridin-5-yl)ethyl)bicyclo[2.2.1]heptane-1-carboxylic acid | 885.4 |
| 62 | 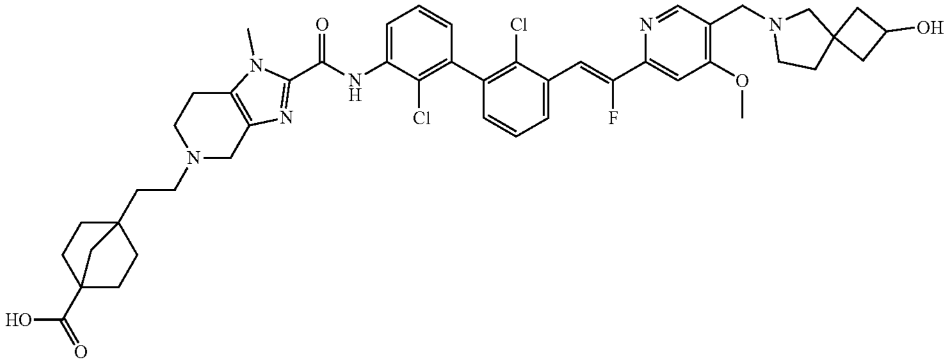 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCC2(CC(O)C2)C1] (Z)-4-(2-(2-((2,2'-dichloro-3'-(2-fluoro-2-(5-((2-hydroxy-6-azaspiro [3.4]octan-6-yl)methyl)-4-methoxypyridin-2-yl)vinyl)-[1,1'-biphenyl]-3-yl)carbamoyl)-1-methyl-1,4,6,7-tetrahydro-5H-imidazo[4,5-c] pyridin-5-yl)ethyl)bicyclo[2.2.1]heptane-1-carboxylic acid | 857.4 |
| 63 | 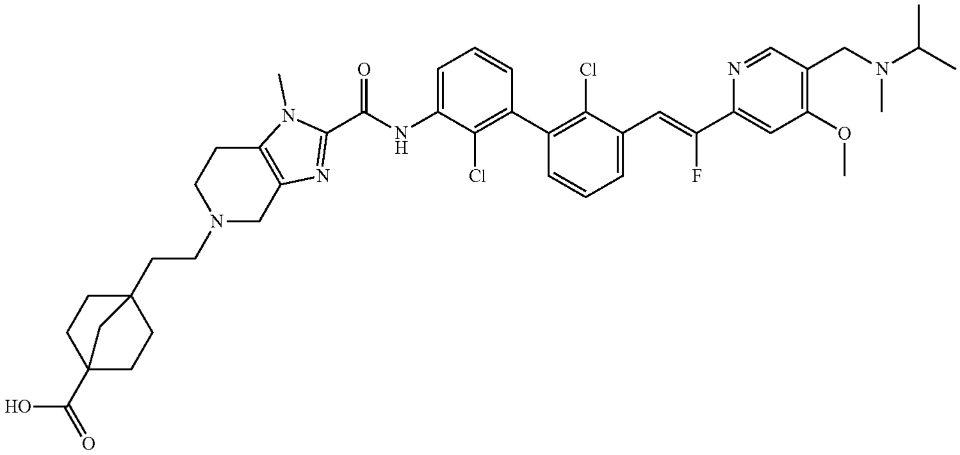 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN(C)C(C)C] (Z)-4-(2-(2-((2,2'-dichloro-3'-(2-fluoro-2-(5-((isopropyl(methyl)amino) methyl)-4-methoxypyridin-2-yl)vinyl)-[1,1'-biphenyl]-3-yl) carbamoyl)-1-methyl-1,4,6,7-tetrahydro-5H-imidazo[4,5-c]pyridin-5-yl) ethyl)bicyclo[2.2.1]heptane-1-carboxylic acid | 803.3 |

-continued

| Example No. | Compound structure and name | MS: m/z [M + H]+ |
|---|---|---|
| 64 | 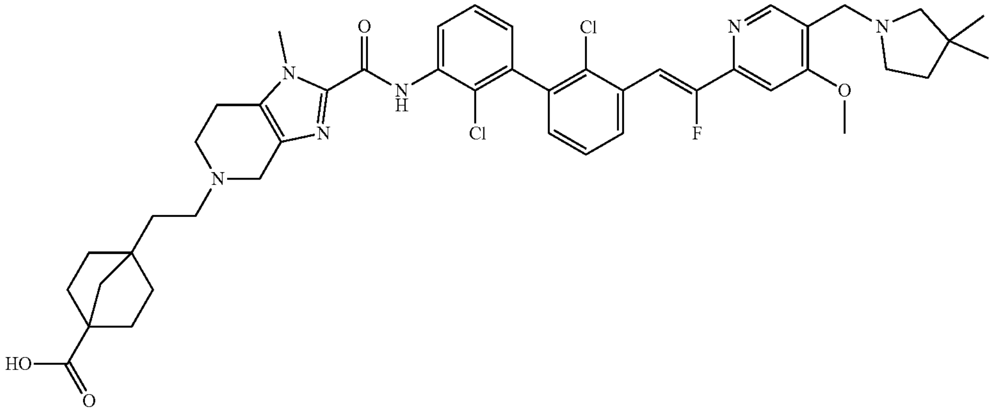 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCC(C)(C)C1] (Z)-4-(2-(2-((2,2'-dichloro-3'-(2-(5-((3,3-dimethylpyrrolidin-1-yl) methyl)-4-methoxypyridin-2-yl)-2-fluorovinyl)-[1,1'-biphenyl]-3-yl) carbamoyl)-1-methyl-1,4,6,7-tetrahydro-5H-imidazo[4,5-c]pyridin-5-yl)ethyl)bicyclo[2.2.1]heptane-1-carboxylic acid | 829.3 |
| 65 | 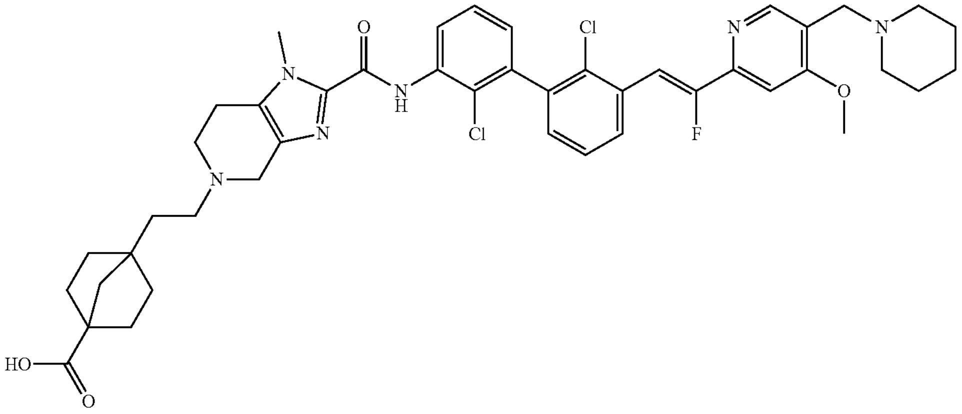 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCCCC1] (Z)-4-(2-(2-((2,2'-dichloro-3'-(2-fluoro-2-(4-methoxy-5-(piperidin-1-ylmethyl)pyridin-2-yl)vinyl)-[1,1'-biphenyl]-3-yl)carbamoyl)-1-methyl-1,4,6,7-tetrahydro-5H-imidazo[4,5-c]pyridin-5-yl)ethyl) bicyclo[2.2.1]heptane-1-carboxylic acid | 815.4 |
| 66 | 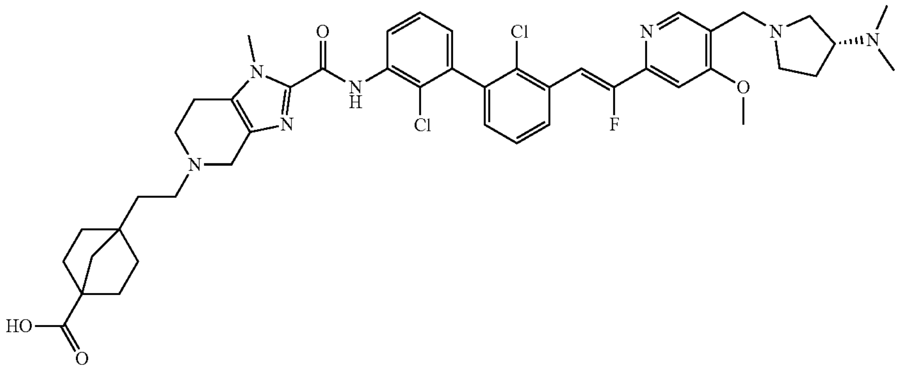 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@@H](N(C)C)C1] (R,Z)-4-(2-(2-((2,2'-dichloro-3'-(2-(5-((3-(dimethylamino)pyrrolidin-1-yl)methyl)-4-methoxypyridin-2-yl)-2-fluorovinyl)-[1,1'-biphenyl]-3-yl)carbamoyl)-1-methyl-1,4,6,7-tetrahydro-5H-imidazo[4,5-c] pyridin-5-yl)ethyl)bicyclo[2.2.1]heptane-1-carboxylic acid | 844.4 |

-continued

| Example No. | Compound structure and name | MS: m/z [M + H]$^+$ |
|---|---|---|
| 67 | 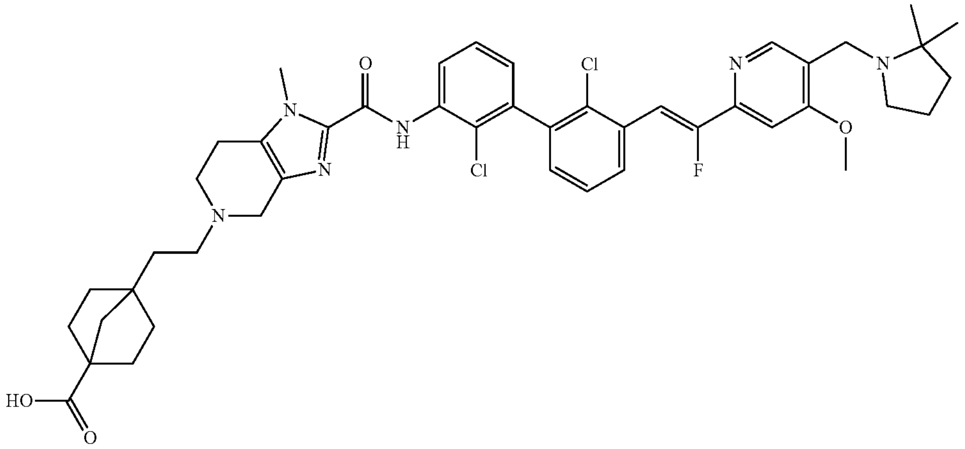 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCCC1(C)C] (Z)-4-(2-(2-((2,2'-dichloro-3'-(2-(5-((2,2-dimethylpyrrolidin-1-yl) methyl)-4-methoxypyridin-2-yl)-2-fluorovinyl)-[1,1'-biphenyl]-3-yl) carbamoyl)-1-methyl-1,4,6,7-tetrahydro-5H-imidazo[4,5-c]pyridin-5-yl)ethyl)bicyclo[2.2.1]heptane-1-carboxylic acid | 829.4 |
| 68 | 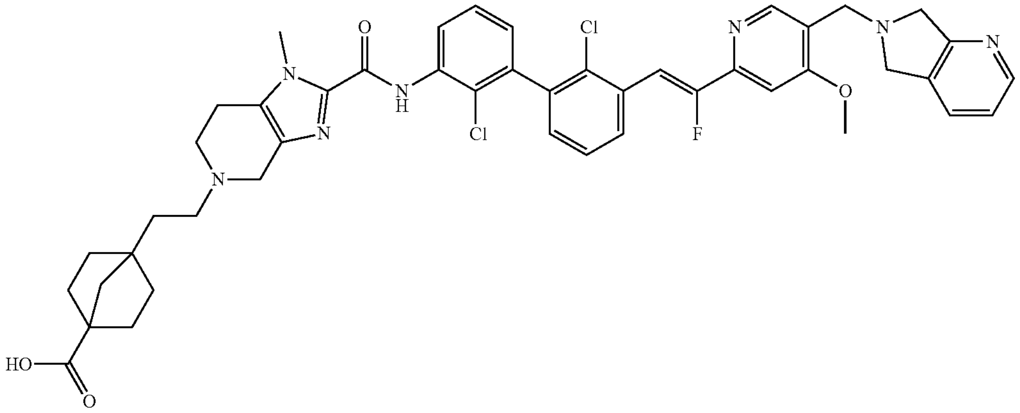 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1Cc2cccnc2C1] (Z)-4-(2-(2-((2,2'-dichloro-3'-(2-(5-((5,7-dihydro-6H-pyrrolo[3,4-b] pyridin-6-yl)methyl)-4-methoxypyridin-2-yl)-2-fluorovinyl)-[1,1'-biphenyl]-3-yl)carbamoyl)-1-methyl-1,4,6,7-tetrahydro-5H-imidazo [4,5-c]pyridin-5-yl)ethyl)bicyclo[2.2.1]heptane-1-carboxylic acid | 850.4 |
| 69 | 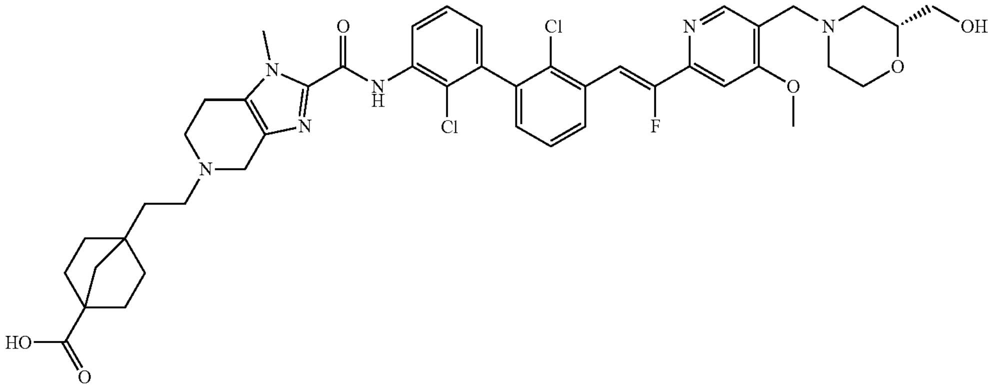 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCO[C@@H](CO)C1] (R,Z)-4-(2-(2-((2,2'-dichloro-3'-(2-fluoro-2-(5-((2-(hydroxymethyl) morpholino)methyl)-4-methoxypyridin-2-yl)vinyl)-[1,1'-biphenyl]-3-yl)carbamoyl)-1-methyl-1,4,6,7-tetrahydro-5H-imidazo[4,5-c] pyridin-5-yl)ethyl)bicyclo[2.2.1]heptane-1-carboxylic acid | 847.4 |

-continued

| Example No. | Compound structure and name | MS: m/z [M + H]+ |
|---|---|---|
| 70 | 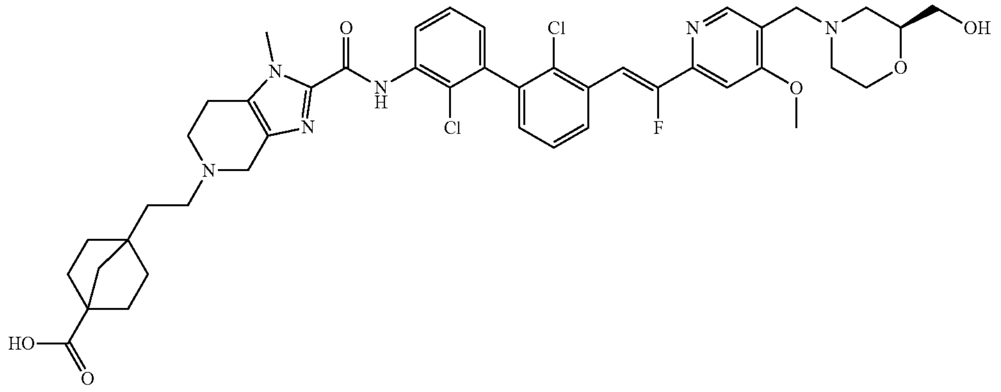 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCO[C@H](CO)C1] (S,Z)-4-(2-(2-((2,2'-dichloro-3'-(2-fluoro-2-(5-((2-(hydroxymethyl) morpholino)methyl)-4-methoxypyridin-2-yl)vinyl)-[1,1'-biphenyl]-3-yl)carbamoyl)-1-methyl-1,4,6,7-tetrahydro-5H-imidazo[4,5-c] pyridin-5-yl)ethyl)bicyclo[2.2.1]heptane-1-carboxylic acid | 847.4 |
| 71 | 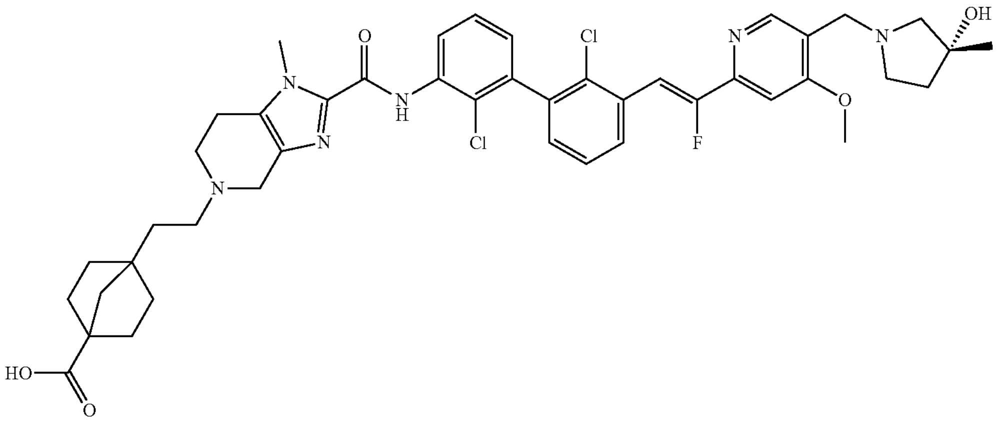 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@@](C)(O)C1] (R,Z)-4-(2-(2-((2,2'-dichloro-3'-(2-fluoro-2-(5-((3-hydroxy-3-methylpyrrolidin-1-yl)methyl)-4-methoxypyridin-2-yl)vinyl)-[1,1'-biphenyl]-3-yl)carbamoyl)-1-methyl-1,4,6,7-tetrahydro-5H-imidazo[4,5-c] pyiidin-5-yl)ethyl)bicyclo[2.2.1]heptane-1-carboxylic acid | 831.4 |
| 72 | 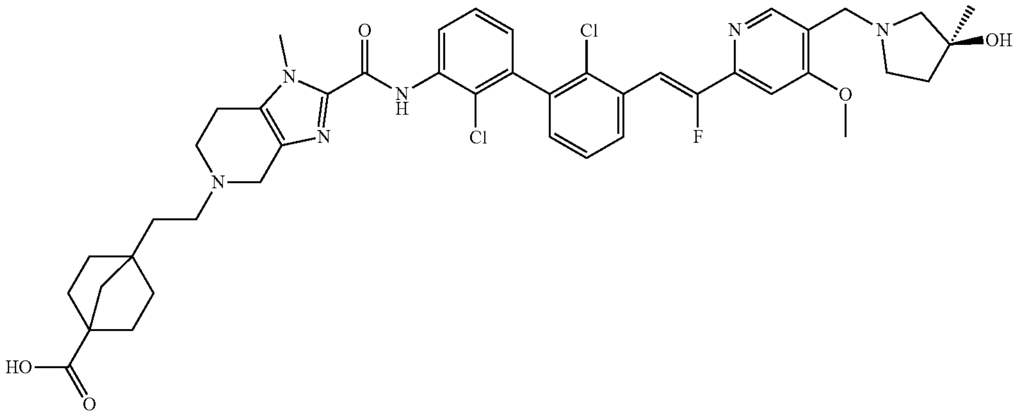 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@](C)(O)C1] (S,Z)-4-(2-(2-((2,2'-dichloro-3'-(2-fluoro-2-(5-((3-hydroxy-3-methylyrrolidin-1-yl)methyl)-4-methoxypyridin-2-yl)vinyl)-[1,1'-biphenyl]-3-yl)carbamoyl)-1-methyl-1,4,6,7-tetrahydro-5H-imidazo[4,5-c] pyridin-5-yl)ethyl)bicyclo[2.2.1]heptane-1-carboxylic acid | 831.4 |

-continued

| Example No. | Compound structure and name | MS: m/z [M + H]+ |
|---|---|---|
| 73 | 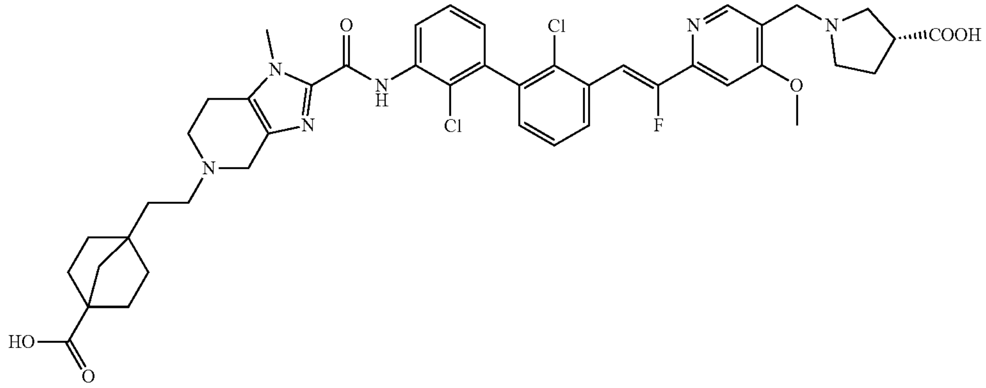 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@@H](C(=O)O)C1] (R,Z)-1-((6-(2-(3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)-1-fluorovinyl)-4-methoxypyridin-3-yl)methyl)pyrrolidine-3-carboxylic acid | 845.4 |
| 74 | 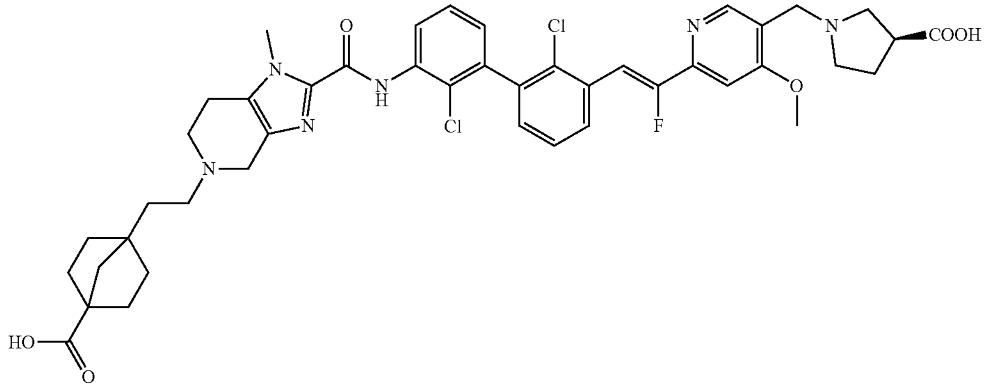 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@H](C(=O)O)C1] (S,Z)-1-((6-(2-(3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)-1-fluorovinyl)-4-methoxypyridin-3-yl)methyl)pyrrolidine-3-carboxylic acid | 845.4 |
| 75 | 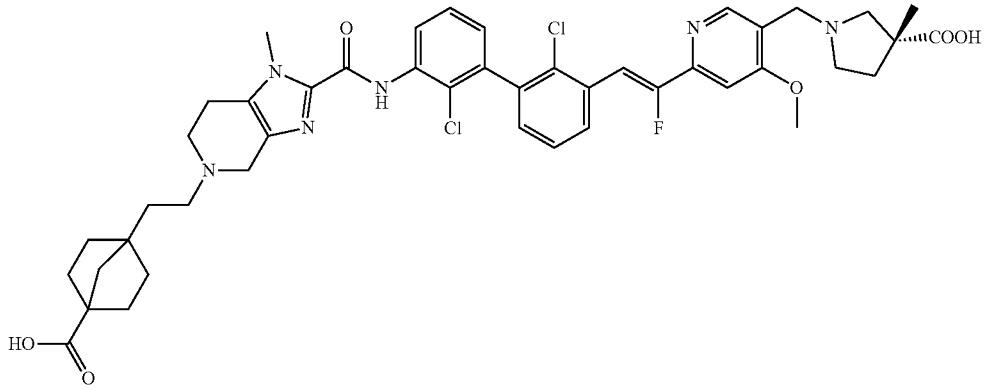 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@@](C)(C(=O)O)C1] (R,Z)-1-((6-(2-(3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)-1-fluorovinyl)-4-methoxypyridin-3-yl)methyl)-3-methylpyrrolidine-3-carboxylic acid | 859.4 |

-continued

| Example No. | Compound structure and name | MS: m/z [M + H]+ |
|---|---|---|
| 76 | 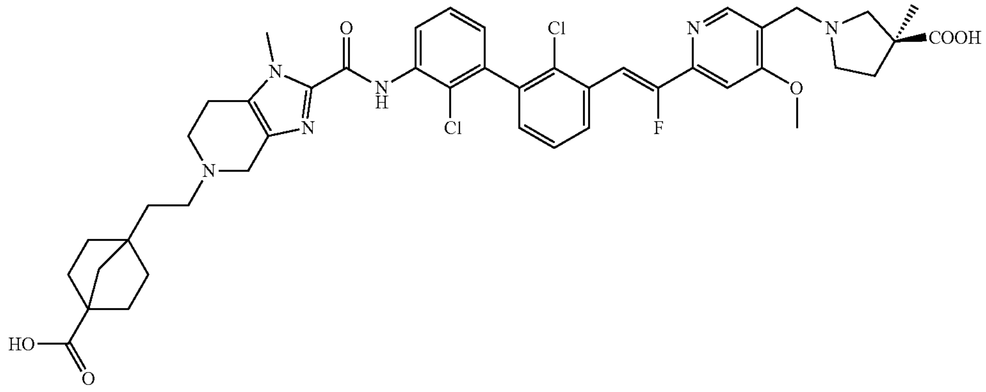 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@](C)(C(=O)O)C1] (S,Z)-1-((6-(2-(3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)-1-fluorovinyl)-4-methoxypyridin-3-yl)methyl)-3-methylpyrrolidine-3-carboxylic acid | 859.4 |
| 77 | 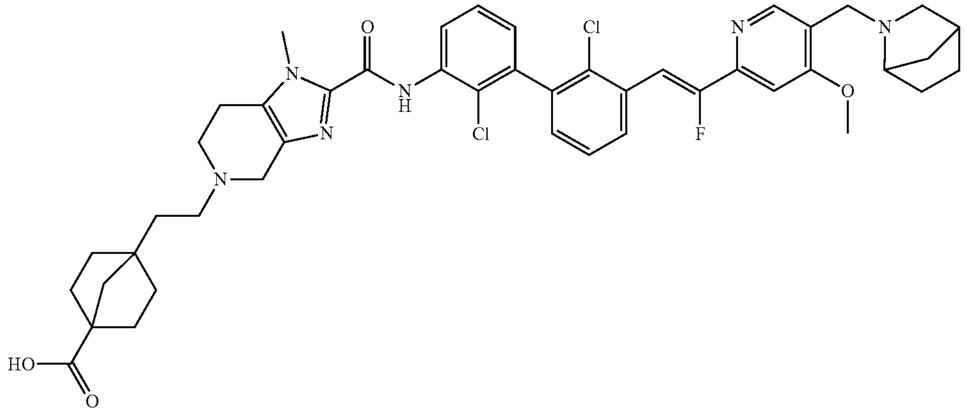 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC2CCC1C2] (Z)-4-(2-(2-((3'-(2-(5-((2-azabicyclo[2.2.1]heptan-2-yl)methyl )-4-methoxypyridin-2-yl)-2-fluorovinyl)-2,2'-dichloro-[1,1'-biphenyl]-3-yl) carbamoyl)-1-methyl-1,4,6,7-tetrahydro-5H-imidazo[4,5-c]pyridin-5-yl)ethyl)bicyclo[2.2.1]heptane-1-carboxylic acid | 827.4 |
| 78 | 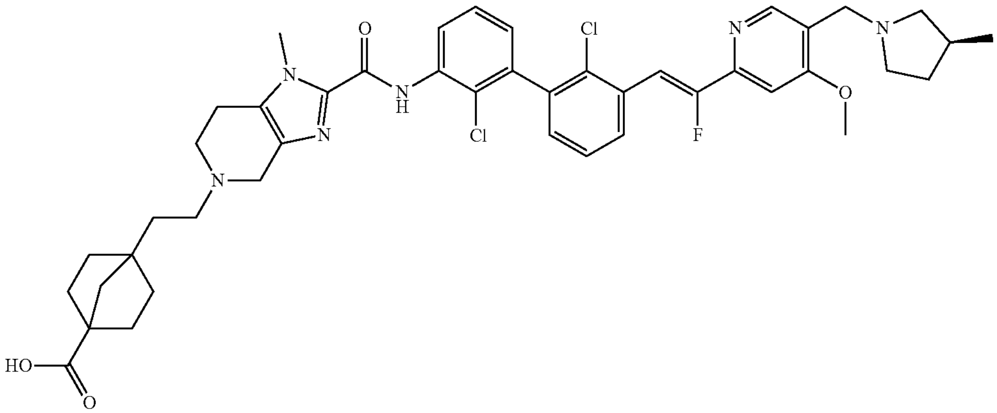 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CC[C@H](C)C1] (S,Z)-4-(2-(2-((2,2'-dichloro-3'-(2-fluoro-2-(4-methoxy-5-((3-methylpyrrolidin-1-yl)methyl)pyridin-2-yl)vinyl)-[1,1'-biphenyl]-3-yl) carbamoyl)-1-methyl-1,4,6,7-tetrahydro-5H-imidazo[4,5-c]pyridin-5-yl) ethyl)bicyclo[2.2.1]heptane-1-carboxylie acid | 815.4 |

-continued

| Example No. | Compound structure and name | MS: m/z [M + H]+ |
|---|---|---|
| 79 | 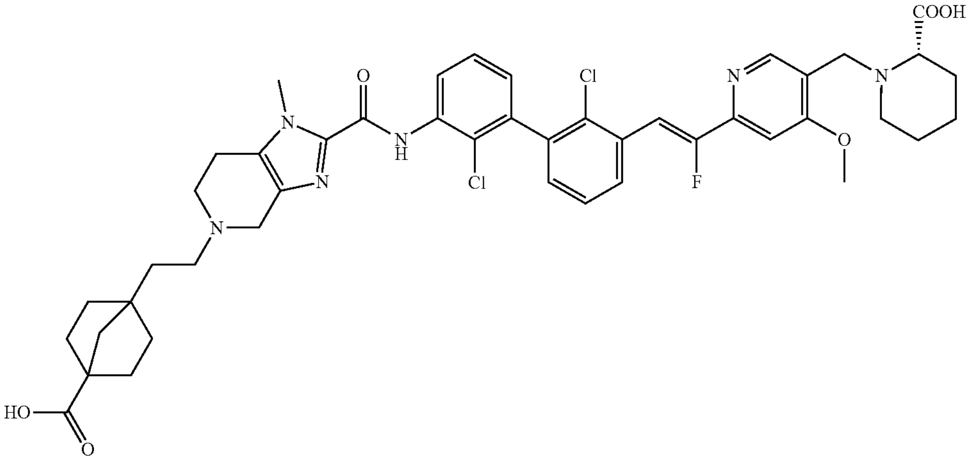 [SMILES: COc1cc(/C(F)=C/c2cccc(-c3cccc(NC(=O)c4nc5c(n4C)CCN(CCC46CCC(C(=O)O)(CC4)C6)C5)c3Cl)c2Cl)ncc1CN1CCCC[C@H]1C(=O)O] (S,Z)-1-((6-(2-(3'-(5-(2-(4-carboxybicyclo[2.2.1]heptan-1-yl)ethyl)-1-methyl-4,5,6,7-tetrahydro-1H-imidazo[4,5-c]pyridine-2-carboxamido)-2,2'-dichloro-[1,1'-biphenyl]-3-yl)-1-fluorovinyl)-4-methoxypyridin-3-yl)methyl)piperidine-2-carboxylic acid | 860 |

The magnetic resonance imaging data of the compound prepared from the above example was as follows:

| Example No. | $^1$H NMR/$^{19}$F NMR |
|---|---|
| 17 | $^1$H NMR (400 MHz, DMSO-$d_6$) δ 9.71 (s, 1H), 8.45 (s, 1H), 7.78 - 7.61 (m, 3H), 7.41 - 7.23 (m, 4H), 7.08 (d, J = 7.5 Hz, 1H), 6.96 (d, J = 7.5 Hz, 1H), 3.95 (s, 3H), 3.87 (s, 3H), 3.73 (d, J = 3.4 Hz, 2H), 3.60 (s, 4H), 3.38 (s, 2H), 2.79 - 2.59 (m, 4H), 2.32 (d, J = 7.3 Hz, 2H), 2.13 - 2.04 (m, 6H), 1.95 (s, 3H), 1.88 (d, J = 12.8 Hz, 2H), 1.81 (d, J = 13.0 Hz, 2H), 1.71 - 1.61 (m, 1H), 1.54 (s, 1H), 1.30 (q, J = 13.0 Hz, 2H), 0.88 (q, J = 12.1 Hz, 2H). $^{19}$F NMR (377 MHz, DMSO-$d_6$) δ -123.37. |
| 18 | $^1$H NMR (400 MHz, DMSO-$d_6$) δ 9.68 (s, 1H), 8.43 (s, 1H), 7.72 (d, J = 7.9 Hz, 2H), 7.38 - 7.19 (m, 3H), 7.16 - 7.03 (m, 2H), 6.96 (d, J = 7.4 Hz, 1H), 4.00 (dd, J = 13.5, 1.7 Hz, 1H), 3.87 (s, 3H), 3.64 (d, J = 13.4 Hz, 1H), 3.48 (s, 2H), 3.18 (d, J = 5.7 Hz, 1H), 2.97 - 2.84 (m, 2H), 2.78 (t, J = 5.6 Hz, 2H), 2.70 - 2.58 (m, 2H), 2.48 - 2.39 (m, 2H), 2.30 - 2.21 (m, 1H), 2.06 (s, 3H), 1.95 (s, 3H), 1.76 (d, J = 5.7 Hz, 2H), 1.55 - 1.33 (m, 4H), 1.06 (d, J = 6.5 Hz, 8H), 0.91 (q, J = 5.0, 4.5 Hz, 1H), 0.77 (dt, J = 9.5, 4.6 Hz, 1H). $^{19}$F NMR (377 MHz, DMSO-$d_6$) δ -123.67. |
| 19 | $^1$H NMR (400 MHz, DMSO-$d_6$) δ 9.71 (s, 1H), 8.43 (s, 1H), 7.71 (t, J = 8.7 Hz, 2H), 7.38 - 7.20 (m, 3H), 7.14 - 7.03 (m, 2H), 6.97 (dd, J = 7.6, 1.3 Hz, 1H), 4.35 (s, 1H), 4.01 (dd, J = 13.6, 1.8 Hz, 1H), 3.88 (s, 4H), 3.49 (s, 2H), 3.17 (d, J = 5.5 Hz, 1H), 2.93 - 2.78 (m, 3H), 2.67 (d, J = 5.8 Hz, 2H), 2.43 (ddd, J = 17.9, 13.4, 6.2 Hz, 3H), 2.30 - 2.20 (m, 1H), 2.06 (s, 3H), 1.95 (s, 3H), 1.76 (d, J = 5.8 Hz, 2H), 1.54 - 1.35 (m, 4H), 1.14 - 1.03 (m, 5H), 0.91 (dt, J = 9.3, 4.4 Hz, 1H), 0.77 (dt, J = 9.2, 4.4 Hz, 1H). $^{19}$F NMR (377 MHz, DMSO-$d_6$) δ -123.66. |
| 33 | $^1$H NMR (400 MHz, DMSO-$d_6$) δ 9.82 (s, 1H), 8.36 - 8.26 (m, 2H), 8.10 (s, 1H), 7.94 (dd, J = 8.0, 1.6 Hz, 1H), 7.51 - 7.35 (m, 3H), 7.28 (dd, J = 7.6, 1.6 Hz, 1H), 7.24 (s, 1H), 7.08 (dd, J = 7.5, 1.5 Hz, 1H), 5.07 (s, 1H), 3.89 (s, 3H), 3.83 (s, 3H), 3.53 (s, 2H), 3.35 (s, 1H), 3.17 (s, 1H), 3.15 (d, J = 1.9 Hz, 1H), 2.87 (d, J = 6.7 Hz, 4H), 2.68 (d, J = 5.5 Hz, 2H), 2.63 - 2.56 (m, 2H), 2.47 (d, J = 1.5 Hz, 1H), 1.86 - 1.72 (m, 2H), 1.65 (t, J = 7.8 Hz, 2H), 1.45 (q, J = 10.6, 7.9 Hz, 4H), 1.36 (s, 2H), 1.28 (s, 5H). $^{19}$F NMR (377 MHz, DMSO-$d_6$) δ -120.70. |
| 34 | $^1$H NMR (400 MHz, DMSO-$d_6$) δ 9.82 (s, 1H), 8.41 (s, 1H), 8.31 (d, J = 8.0 Hz, 1H), 8.14 (s, 1H), 7.94 (d, J = 7.9 Hz, 1H), 7.57 (s, 1H), 7.52 - 7.37 (m, 3H), 7.32 - 7.24 (m, 2H), 7.08 (d, J = 7.7 Hz, 1H), 3.90 (s, 3H), 3.83 (s, 3H), 3.67 (d, J = 3.4 Hz, 2H), 3.55 (d, J = 6.8 Hz, 1H), 3.34 (s, 3H), 2.69 (t, J = 5.7 Hz, 2H), 2.63 - 2.59 (m, 3H), 2.26 (q, J = 2.3, 1.9 Hz, 1H), 2.08 - 1.93 (m, 4H), 1.82 - 1.76 (m, 2H), 1.69 - 1.58 (m, 3H), 1.46 (d, J = 11.6 Hz, 4H), 1.37 (s, 2H), 1.31 (d, J = 10.8 Hz, 2H). $^{19}$F NMR (377 MHz, DMSO-$d_6$) δ -120.67. |
| 35 | $^1$H NMR (400 MHz, DMSO-$d_6$) δ 9.89 (s, 1H), 8.49 (s, 1H), 8.37 (d, J = 8.0 Hz, 1H), 8.22 (s, 1H), 8.01 (d, J = 7.8 Hz, 1H), 7.59 - 7.42 (m, 3H), 7.37 - 7.29 (m, 2H), 7.15 (d, J = 7.2 Hz, 1H), 4.93 (s, 1H), 3.97 (s, 3H), 3.90 (s, 3H), 3.84 - 3.68 (m, 4H), 3.42 (s, 2H), 2.94 (d, J = 10.5 Hz, 2H), 2.76 (t, J = 5.7 Hz, 2H), 2.67 (d, J = 4.6 Hz, 2H), 2.41 - 2.32 (m, 2H), 1.90 (dq, J = 37.4, 10.2, 7.0 Hz, 4H), 1.72 |

-continued

| Example No. | $^{1}$H NMR/$^{19}$F NMR |
|---|---|
| | (t, J = 7.7 Hz, 2H), 1.52 (h, J = 4.4 Hz, 4H), 1.43 (s, 2H), 1.38 (d, J = 10.6 Hz, 2H), 1.25 (dt, J = 16.3, 5.2 Hz, 2H). $^{19}$F NMR (377 MHz, DMSO-$d_6$) δ −120.67. |
| 36 | $^{1}$H NMR (400 MHz, DMSO-$d_6$) δ 9.89 (s, 1H), 8.44 (s, 1H), 8.37 (dd, J = 8.4, 1.5 Hz, 1H), 7.98 (dd, J = 7.9, 1.6 Hz, 1H), 7.57 − 7.39 (m, 3H), 7.34 (dd, J = 7.6, 1.5 Hz, 1H), 7.18 − 7.11 (m, 2H), 5.19 (s, 1H), 3.90 (s, 3H), 3.81 (s, 2H), 3.43 (s, 2H), 3.23 (d, J = 6.4 Hz, 2H), 2.99 (d, J = 6.4 Hz, 2H), 2.77 (s, 2H), 2.68 (d, J = 5.3 Hz, 2H), 2.55 (dd, J = 10.8, 4.4 Hz, 2H), 2.27 − 2.20 (m, 1H), 1.92 − 1.80 (m, 2H), 1.73 (t, J = 7.8 Hz, 2H), 1.52 (q, J = 10.2, 7.4 Hz, 4H), 1.43 (s, 2H), 1.37 (s, 5H), 1.14 − 1.07 (m, 2H), 0.88 − 0.79 (m, 2H). $^{19}$F NMR (377 MHz, DMSO-$d_6$) δ −120.95. |
| 37 | $^{1}$H NMR (400 MHz, DMSO-$d_6$) δ 9.89 (s, 1H), 8.49 (s, 1H), 8.37 (dd, J = 8.3, 1.5 Hz, 1H), 8.01 (dd, J = 7.9, 1.6 Hz, 1H), 7.62 − 7.43 (m, 3H), 7.40 − 7.29 (m, 2H), 7.15 (dd, J = 7.6, 1.6 Hz, 1H), 3.98 (s, 3H), 3.94 (s, 1H), 3.89 (d, J = 5.1 Hz, 4H), 3.63 (dd, J = 13.8, 5.2 Hz, 2H), 3.42 (s, 2H), 3.19 (d, J = 5.2 Hz, 2H), 2.75 (d, J = 5.6 Hz, 2H), 2.70 − 2.62 (m, 2H), 2.58 − 2.53 (m, 1H), 1.84 (dd, J = 12.9, 3.6 Hz, 2H), 1.72 (t, J = 7.8 Hz, 2H), 1.59 − 1.30 (m, 8H). $^{19}$F NMR (377 MHz, DMSO-$d_6$) δ −120.73 |
| 38 | $^{1}$H NMR (400 MHz, DMSO-$d_6$) δ 9.89 (s, 1H), 8.46 (s, 1H), 8.37 (dd, J = 8.3, 1.5 Hz, 1H), 8.00 (dd, J = 7.9, 1.6 Hz, 1H), 7.62 − 7.42 (m, 3H), 7.40 − 7.26 (m, 2H), 7.15 (dd, J = 7.6, 1.6 Hz, 1H), 6.03 (tt, J = 56.4, 4.3 Hz, 1H), 3.96 (s, 3H), 3.90 (s, 3H), 3.78 (s, 2H), 3.41 (d, J = 24.3 Hz, 3H), 2.94 − 2.83 (m, 2H), 2.80 (d, J = 21.6 Hz, 2H), 2.67 (s, 2H), 1.91 − 1.78 (m, 2H), 1.73 (t, J = 7.9 Hz, 2H), 1.50 (d, J = 10.1 Hz, 4H), 1.43 (s, 2H), 1.37 (d, J = 11.0 Hz, 2H). $^{19}$F NMR (377 MHz, DMSO-$d_6$) δ −120.55, −120.67. |
| 39 | $^{1}$H NMR (400 MHz, DMSO-$d_6$) δ 9.89 (s, 1H), 8.45 (s, 1H), 8.37 (dd, J = 8.3, 1.5 Hz, 1H), 8.01 (dd, J = 7.9, 1.6 Hz, 1H), 7.59 − 7.44 (m, 3H), 7.37 − 7.29 (m, 2H), 7.15 (dd, J = 7.6, 1.6 Hz, 1H), 4.72 (s, 1H), 4.20 (s, 1H), 3.96 (s, 3H), 3.90 (s, 3H), 3.66 (s, 1H), 3.43 (s, 3H), 2.76 (s, 2H), 2.71 − 2.62 (m, 3H), 2.54 (t, J = 8.0 Hz, 3H), 2.41 (s, 1H), 2.00 (dd, J = 13.3, 6.9 Hz, 1H), 1.90 − 1.79 (m, 2H), 1.72 (t, J = 7.8 Hz, 2H), 1.53 (d, J = 8.0 Hz, 5H), 1.43 (s, 2H), 1.37 (d, J = 11.4 Hz, 2H). $^{19}$F NMR (377 MHz, DMSO-$d_6$) δ −120.74. |
| 40 | $^{1}$H NMR (400 MHz, DMSO-$d_6$) δ 9.89 (s, 1H), 8.49 (s, 1H), 8.37 (dd, J = 8.2, 1.6 Hz, 1H), 8.01 (dd, J = 7.9, 1.6 Hz, 1H), 7.59 − 7.43 (m, 3H), 7.38 − 7.30 (m, 2H), 7.15 (dd, J = 7.6, 1.6 Hz, 1H), 4.31 (s, 1H), 3.97 (s, 3H), 3.90 (s, 3H), 3.80 (s, 1H), 3.64 (s, 1H), 3.41 (s, 3H), 2.75 (t, J = 5.7 Hz, 2H), 2.71 − 2.63 (m, 2H), 2.54 (d, J = 7.7 Hz, 2H), 2.48 − 2.42 (m, 1H), 1.92 − 1.79 (m, 2H), 1.72 (t, J = 7.7 Hz, 2H), 1.52 (dd, J = 14.4, 8.0 Hz, 10H), 1.41 (d, J = 16.5 Hz, 6H). $^{19}$F NMR (377 MHz, DMSO-$d_6$) δ −120.66. |
| 41 | $^{1}$H NMR (400 MHz, DMSO-$d_6$) δ 9.89 (s, 1H), 8.48 (s, 1H), 8.37 (dd, J = 8.3, 1.5 Hz, 1H), 8.00 (dd, J = 7.9, 1.6 Hz, 1H), 7.59 − 7.43 (m, 3H), 7.37 − 7.30 (m, 2H), 7.14 (dd, J = 7.6, 1.6 Hz, 1H), 3.97 (s, 3H), 3.89 (s, 3H), 3.75 (s, 2H), 3.41 (s, 2H), 2.94 (d, J = 29.8 Hz, 1H), 2.75 (t, J = 5.6 Hz, 2H), 2.69 − 2.63 (m, 2H), 2.56 − 2.52 (m, 2H), 1.92 − 1.80 (m, 2H), 1.72 (t, J = 7.8 Hz, 2H), 1.58 − 1.46 (m, 4H), 1.43 (s, 2H), 1.37 (d, J = 11.7 Hz, 2H), 1.03 (d, J = 6.2 Hz, 6H). $^{19}$F NMR (377 MHz, DMSO-$d_6$) δ −120.65. |
| 42 | $^{1}$H NMR (400 MHz, DMSO-$d_6$) δ 9.89 (s, 1H), 8.37 (dd, J = 8.4, 1.4 Hz, 2H), 8.00 (dd, J = 7.9, 1.6 Hz, 1H), 7.60 − 7.43 (m, 3H), 7.38 − 7.28 (m, 2H), 7.15 (dd, J = 7.6, 1.6 Hz, 1H), 5.31 (s, 1H), 4.18 (s, 1H), 3.96 (s, 3H), 3.90 (s, 3H), 3.64 − 3.51 (m, 4H), 3.42 (s, 2H), 2.83 (t, J = 6.8 Hz, 2H), 2.75 (d, J = 5.6 Hz, 2H), 2.66 (t, J = 5.4 Hz, 2H), 2.55 (d, J = 7.2 Hz, 2H), 1.94 − 1.79 (m, 2H), 1.72 (t, J = 7.8 Hz, 2H), 1.52 (h, J = 4.1 Hz, 4H), 1.43 (s, 2H), 1.37 (d, J = 11.4 Hz, 2H). $^{19}$F NMR (377 MHz, DMSO-$d_6$) δ −120.71. |
| 43 | $^{1}$H NMR (400 MHz, DMSO-$d_6$) δ 9.89 (s, 1H), 8.45 (s, 1H), 8.37 (dd, J = 8.3, 1.6 Hz, 1H), 8.01 (dd, J = 7.9, 1.6 Hz, 1H), 7.59 − 7.42 (m, 3H), 7.40 − 7.29 (m, 2H), 7.15 (dd, J = 7.6, 1.6 Hz, 1H), 3.97 (s, 3H), 3.90 (s, 3H), 3.74 (s, 2H), 3.46 (s, 2H), 3.41 (s, 2H), 2.75 (t, J = 5.7 Hz, 2H), 2.68 − 2.64 (m, 2H), 2.60 (t, J = 6.9 Hz, 2H), 2.54 (d, J = 7.7 Hz, 2H), 1.84 (dd, J = 12.5, 3.8 Hz, 2H), 1.72 (t, J = 7.8 Hz, 2H), 1.60 (q, J = 6.6 Hz, 2H), 1.52 (q, J = 10.5, 7.7 Hz, 4H), 1.43 (s, 2H), 1.37 (d, J = 11.2 Hz, 2H). $^{19}$F NMR (377 MHz, DMSO-$d_6$) δ −120.67. |
| 44 | $^{1}$H NMR (400 MHz, DMSO-$d_6$) δ 9.89 (s, 1H), 8.48 (s, 1H), 8.38 (dd, J = 8.3, 1.6 Hz, 1H), 8.01 (dd, J = 7.9, 1.6 Hz, 1H), 7.59 − 7.42 (m, 3H), 7.38 − 7.30 (m, 2H), 7.15 (dd, J = 7.6, 1.6 Hz, 1H), 3.97 (s, 3H), 3.90 (s, 3H), 3.86 − 3.71 (m, 2H), 3.41 (s, 2H), 3.25 (d, J = 4.0 Hz, 2H), 2.75 (d, J = 5.6 Hz, 2H), 2.67 (d, J = 6.0 Hz, 2H), 2.63 − 2.57 (m, 1H), 2.56 − 2.52 (m, 2H), 1.92 − 1.80 (m, 2H), 1.72 (t, J = 7.8 Hz, 2H), 1.58 − 1.47 (m, 4H), 1.44 (s, 2H), 1.37 (t, J = 6.3 Hz, 2H), 0.96 (d, J = 6.3 Hz, 3H). $^{19}$F NMR (377 MHz, DMSO-$d_6$) δ −120.66. |
| 45 | $^{1}$H NMR (400 MHz, DMSO-$d_6$) δ 9.89 (s, 1H), 8.42 (s, 1H), 8.37 (dd, J = 8.2, 1.5 Hz, 1H), 8.01 (dd, J = 7.9, 1.6 Hz, 1H), 7.59 − 7.41 (m, 3H), 7.37 − 7.27 (m, 2H), 7.15 (dd, J = 7.6, 1.6 Hz, 1H), 4.88 (s, 1H), 3.97 (s, 3H), 3.90 (s, 3H), 3.72 (t, J = 7.4 Hz, 1H), 3.63 (s, 2H), 3.41 (s, 2H), 2.75 (t, J = 5.7 Hz, 2H), 2.66 (t, J = 6.5 Hz, 3H), 2.54 (d, J = 7.3 Hz, 2H), 2.39 (dh, J = 11.4, 3.1 Hz, 2H), 1.91 − 1.78 (m, 2H), 1.72 (t, J = 7.8 Hz, 2H), 1.52 (pd, J = 7.3, 6.6, 2.5 Hz, 6H), 1.43 (s, 2H), 1.37 (d, J = 11.6 Hz, 2H). $^{19}$F NMR (377 MHz, DMSO-$d_6$) δ −120.64. |
| 46 | $^{1}$H NMR (400 MHz, DMSO-$d_6$) δ 9.89 (s, 1H), 8.47 (s, 1H), 8.37 (dd, J = 8.3, 1.6 Hz, 1H), 8.00 (dd, J = 7.9, 1.6 Hz, 1H), 7.59 − 7.41 (m, 3H), 7.40 − 7.30 (m, 2H), 7.15 (dd, J = 7.6, 1.6 Hz, 1H), 3.96 (s, 3H), 3.89 (s, 3H), 3.77 (s, 2H), 3.41 (s, 2H), 2.75 (t, J = 5.7 Hz, 2H), 2.66 (d, J = 5.3 Hz, 2H), 2.56 − 2.51 (m, 2H), 2.40 (s, 2H), 1.90 − 1.78 (m, 2H), 1.72 (t, J = 7.8 Hz, 2H), 1.57 − 1.46 (m, 4H), 1.43 (s, 2H), 1.37 (d, J = 11.3 Hz, 2H), 1.09 (s, 6H). $^{19}$F NMR (377 MHz, DMSO-$d_6$) δ −120.68. |
| 47 | $^{1}$H NMR (400 MHz, DMSO-$d_6$) δ 9.89 (s, 1H), 8.43 (s, 1H), 8.38 (dd, J = 8.3, 1.5 Hz, 1H), 8.01 (dd, J = 7.9, 1.6 Hz, 1H), |

-continued

| Example No. | $^1$H NMR/$^{19}$F NMR |
|---|---|
| | 7.58 – 7.42 (m, 3H), 7.35 (dd, J = 7.6, 1.6 Hz, 1H), 7.31 (s, 1H), 7.15 (dd, J = 7.6, 1.6 Hz, 1H), 3.97 (s, 3H), 3.90 (s, 3H), 3.75 (s, 2H), 3.41 (s, 2H), 2.75 (t, J = 5.7 Hz, 2H), 2.67 (d, J = 5.5 Hz, 2H), 2.54 (d, J = 7.4 Hz, 2H), 2.03 (td, J = 6.8, 3.5 Hz, 1H), 1.84 (d, J = 12.8 Hz, 2H), 1.72 (t, J = 7.8 Hz, 2H), 1.50 (d, J = 10.6 Hz, 4H), 1.43 (s, 2H), 1.37 (d, J = 11.3 Hz, 2H), 0.40 – 0.34 (m, 2H), 0.24 (dd, J = 3.7, 2.4 Hz, 2H). $^{19}$F NMR (377 MHz, DMSO-$d_6$) δ −120.63. |
| 48 | $^1$H NMR (400 MHz, DMSO-$d_6$) δ 9.89 (s, 1H), 8.42 (s, 1H), 8.38 (dd, J = 8.3, 1.5 Hz, 1H), 8.01 (dd, J = 7.9, 1.6 Hz, 1H), 7.58 – 7.43 (m, 3H), 7.35 (dd, J = 7.6, 1.5 Hz, 1H), 7.29 (s, 1H), 7.15 (dd, J = 7.6, 1.5 Hz, 1H), 3.96 (s, 3H), 3.90 (s, 3H), 3.62 (s, 2H), 3.41 (s, 2H), 3.15 (q, J = 7.6 Hz, 2H), 2.74 (d, J = 5.7 Hz, 2H), 2.66 (t, J = 5.2 Hz, 2H), 2.54 (d, J = 7.4 Hz, 2H), 2.06 – 2.04 (m, 1H), 1.90 – 1.80 (m, 2H), 1.72 (t, J = 7.7 Hz, 2H), 1.69 – 1.58 (m, 3H), 1.52 (h, J = 6.0, 4.7 Hz, 5H), 1.43 (s, 2H), 1.37 (d, J = 11.4 Hz, 2H). $^{19}$F NMR (377 MHz, DMSO-$d_6$) δ −120.61. |
| 49 | $^1$H NMR (400 MHz, DMSO-$d_6$) δ 9.89 (s, 1H), 8.46 (s, 1H), 8.38 (dd, J = 8.3, 1.5 Hz, 1H), 8.01 (dd, J = 7.9, 1.6 Hz, 1H), 7.60 – 7.43 (m, 3H), 7.35 (dd, J = 7.6, 1.6 Hz, 1H), 7.31 (s, 1H), 7.15 (dd, J = 7.6, 1.6 Hz, 1H), 4.52 (s, 1H), 3.96 (s, 3H), 3.90 (s, 3H), 3.61 (d, J = 3.7 Hz, 2H), 3.41 (s, 2H), 2.75 (t, J = 5.7 Hz, 2H), 2.70 – 2.62 (m, 3H), 2.55 (td, J = 7.3, 6.8, 4.0 Hz, 2H), 2.48 – 2.43 (m, 2H), 1.91 – 1.82 (m, 2H), 1.76 – 1.67 (m, 4H), 1.59 – 1.48 (m, 4H), 1.43 (s, 2H), 1.37 (d, J = 11.5 Hz, 2H), 1.23 (s, 3H). $^{19}$F NMR (377 MHz, DMSO-$d_6$) δ −120.72. |
| 50 | $^1$H NMR (400 MHz, DMSO-$d_6$) δ 9.89 (s, 1H), 8.53 (s, 1H), 8.38 (dd, J = 8.4, 1.5 Hz, 1H), 8.01 (dd, J = 7.9, 1.6 Hz, 1H), 7.60 – 7.43 (m, 3H), 7.37 – 7.30 (m, 2H), 7.15 (dd, J = 7.6, 1.6 Hz, 1H), 3.98 (s, 3H), 3.90 (s, 3H), 3.80 (s, 2H), 3.41 (s, 2H), 2.75 (t, J = 5.7 Hz, 2H), 2.67 (d, J = 5.3 Hz, 2H), 2.54 (d, J = 7.6 Hz, 2H), 1.84 (dd, J = 12.6, 3.5 Hz, 2H), 1.72 (t, J = 7.8 Hz, 2H), 1.59 – 1.47 (m, 4H), 1.43 (s, 2H), 1.37 (d, J = 11.7 Hz, 2H), 1.17 (s, 9H). $^{19}$F NMR (377 MHz, DMSO-$d_6$) δ −120.58. |
| 51 | $^1$H NMR (400 MHz, DMSO-$d_6$) δ 9.89 (s, 1H), 8.46 (s, 1H), 8.38 (dd, J = 8.2, 1.5 Hz, 1H), 8.01 (dd, J = 7.9, 1.6 Hz, 1H), 7.58 – 7.42 (m, 3H), 7.35 (dd, J = 7.6, 1.6 Hz, 1H), 7.30 (s, 1H), 7.15 (dd, J = 7.6, 1.6 Hz, 1H), 3.96 (s, 3H), 3.90 (s, 3H), 3.69 (s, 2H), 3.41 (s, 2H), 2.98 (t, J = 6.2 Hz, 1H), 2.74 (d, J = 5.5 Hz, 2H), 2.69 – 2.62 (m, 2H), 2.54 (d, J = 7.1 Hz, 2H), 1.91 – 1.79 (m, 2H), 1.70 (ddd, J = 12.0, 8.0, 4.7 Hz, 4H), 1.62 (tt, J = 5.1, 2.7 Hz, 2H), 1.55 – 1.41 (m, 8H), 1.35 (tt, J = 11.7, 6.5 Hz, 4H). $^{19}$F NMR (377 MHz, DMSO-$d_6$) δ −120.63. |
| 52 | $^1$H NMR (400 MHz, DMSO-$d_6$) δ 11.94 (s, 1H), 9.89 (s, 1H), 8.62 (s, 1H), 8.38 (dd, J = 8.3, 1.5 Hz, 1H), 8.01 (dd, J = 7.9, 1.6 Hz, 1H), 7.59 – 7.44 (m, 3H), 7.35 (dd, J = 7.6, 1.5 Hz, 1H), 7.30 (s, 1H), 7.15 (dd, J = 7.6, 1.5 Hz, 1H), 4.19 (d, J = 15.1 Hz, 1H), 4.00 (s, 1H), 3.95 (s, 3H), 3.90 (s, 3H), 3.59 (d, J = 15.1 Hz, 1H), 3.41 (s, 2H), 2.87 (q, J = 4.7, 4.1 Hz, 1H), 2.74 (d, J = 5.5 Hz, 2H), 2.65 (dt, J = 8.9, 4.7 Hz, 3H), 2.54 (d, J = 7.5 Hz, 2H), 2.24 (q, J = 7.8 Hz, 1H), 1.91 – 1.70 (m, 5H), 1.61 (t, J = 5.4 Hz, 3H), 1.52 (d, J = 6.2 Hz, 4H), 1.43 (s, 2H), 1.37 (d, J = 11.4 Hz, 2H), 1.08 (d, J = 7.3 Hz, 6H). $^{19}$F NMR (377 MHz, DMSO-$d_6$) δ −120.72. |
| 53 | $^1$H NMR (400 MHz, DMSO-$d_6$) δ 9.89 (s, 1H), 8.52 (s, 1H), 8.38 (dd, J = 8.3, 1.5 Hz, 1H), 8.01 (dd, J = 7.9, 1.6 Hz, 1H), 7.59 – 7.43 (m, 3H), 7.34 (dd, J = 7.6, 1.5 Hz, 1H), 7.28 (s, 1H), 7.15 (dd, J = 7.6, 1.5 Hz, 1H), 3.96 (s, 3H), 3.90 (s, 3H), 3.71 (s, 2H), 3.41 (s, 2H), 2.74 (d, J = 5.6 Hz, 2H), 2.66 (t, J = 5.7 Hz, 2H), 2.54 (d, J = 7.2 Hz, 2H), 2.02 (s, 3H), 1.86 (d, J = 4.3 Hz, 2H), 1.72 (t, J = 7.8 Hz, 2H), 1.61 (t, J = 6.9 Hz, 12H), 1.52 (td, J = 13.1, 12.2, 5.0 Hz, 5H), 1.43 (s, 2H), 1.37 (d, J = 11.3 Hz, 2H), 1.24 (s, 1H). $^{19}$F NMR (377 MHz, DMSO-$d_6$) δ −120.52. |
| 54 | $^1$H NMR (400 MHz, DMSO-$d_6$) δ 9.89 (s, 1H), 8.43 (s, 1H), 8.38 (dd, J = 8.3, 1.5 Hz, 1H), 8.01 (dd, J = 7.9, 1.5 Hz, 1H), 7.60 – 7.43 (m, 3H), 7.37 – 7.30 (m, 2H), 7.15 (dd, J = 7.6, 1.5 Hz, 1H), 3.95 (s, 3H), 3.90 (s, 3H), 3.52 (s, 2H), 3.41 (s, 2H), 2.74 (d, J = 5.5 Hz, 2H), 2.66 (t, J = 4.8 Hz, 2H), 2.54 (d, J = 7.4 Hz, 2H), 2.45 (dd, J = 8.4, 5.8 Hz, 2H), 2.36 (dd, J = 7.6, 5.2 Hz, 2H), 2.17 (s, 3H), 2.12 (s, 6H), 1.91 – 1.81 (m, 2H), 1.72 (t, J = 7.8 Hz, 2H), 1.50 (d, J = 10.7 Hz, 4H), 1.43 (s, 2H), 1.37 (d, J = 11.5 Hz, 2H). $^{19}$F NMR (377 MHz, DMSO-$d_6$) δ −120.69. |
| 55 | $^1$H NMR (400 MHz, DMSO-$d_6$) δ 9.89 (s, 1H), 8.43 (s, 1H), 8.38 (dd, J = 8.3, 1.5 Hz, 1H), 8.01 (dd, J = 7.9, 1.6 Hz, 1H), 7.60 – 7.43 (m, 3H), 7.35 (dd, J = 7.6, 1.6 Hz, 1H), 7.31 (s, 1H), 7.15 (dd, J = 7.7, 1.5 Hz, 1H), 3.96 (s, 3H), 3.90 (s, 3H), 3.59 (s, 2H), 3.41 (s, 2H), 2.75 (t, J = 5.5 Hz, 2H), 2.67 (d, J = 5.3 Hz, 2H), 2.55 (s, 2H), 2.53 (d, J = 6.8 Hz, 2H), 1.99 – 1.69 (m, 13H), 1.52 (q, J = 10.1, 7.8 Hz, 4H), 1.43 (s, 2H), 1.37 (d, J = 11.1 Hz, 2H). $^{19}$F NMR (377 MHz, DMSO-$d_6$) δ −120.71. |
| 56 | $^1$H NMR (400 MHz, DMSO-$d_6$) δ 9.89 (s, 1H), 8.43 (s, 1H), 8.38 (dd, J = 8.3, 1.5 Hz, 1H), 8.01 (dd, J = 7.9, 1.6 Hz, 1H), 7.61 – 7.42 (m, 3H), 7.35 (dd, J = 7.6, 1.6 Hz, 1H), 7.31 (s, 1H), 7.15 (dd, J = 7.6, 1.6 Hz, 1H), 3.96 (s, 3H), 3.90 (s, 3H), 3.65 – 3.54 (m, 2H), 3.41 (s, 2H), 2.78 – 2.64 (m, 5H), 2.57 (dt, J = 14.0, 5.3 Hz, 4H), 2.16 (dt, J = 9.3, 6.7 Hz, 1H), 2.04 (dd, J = 8.7, 6.6 Hz, 1H), 1.98 – 1.90 (m, 1H), 1.90 – 1.82 (m, 2H), 1.72 (t, J = 7.8 Hz, 2H), 1.50 (d, J = 10.8 Hz, 4H), 1.43 (s, 2H), 1.37 (d, J = 11.6 Hz, 2H), 1.26 (ddd, J = 12.5, 6.3, 2.5 Hz, 1H), 0.97 (d, J = 6.7 Hz, 3H). $^{19}$F NMR (377 MHz, DMSO-$d_6$) δ −120.71. |
| 57 | $^1$H NMR (400 MHz, DMSO-$d_6$) δ 9.89 (s, 1H), 8.43 (s, 1H), 8.38 (dd, J = 8.3, 1.5 Hz, 1H), 8.01 (dd, J = 7.9, 1.6 Hz, 1H), 7.58 – 7.44 (m, 3H), 7.39 – 7.31 (m, 2H), 7.15 (dd, J = 7.5, 1.6 Hz, 1H), 5.30 (s, 1H), 4.91 – 4.71 (m, 1H), 4.15 (dt, J = 23.8, 5.7 Hz, 1H), 3.97 (s, 3H), 3.90 (s, 3H), 3.64 (d, J = 8.9 Hz, 2H), 3.41 (s, 2H), 3.08 – 3.04 (m, 1H), 2.87 – 2.74 (m, 4H), 2.67 (d, J = 5.3 Hz, 2H), 2.57 – 2.52 (m, 2H), 2.22 (dd, J = 9.6, 5.5 Hz, 1H), 1.90 – 1.83 (m, 2H), 1.72 (t, J = 7.7 Hz, 2H), 1.55 – 1.49 (m, 4H), 1.43 (s, 2H), 1.38 (d, J = 11.1 Hz, 2H). $^{19}$F NMR (377 MHz, DMSO-$d_6$) δ −120.73, −176.58. |

| Example No. | $^1$H NMR/$^{19}$F NMR |
|---|---|
| 58 | $^1$H NMR (400 MHz, DMSO-$d_6$) δ 9.89 (s, 1H), 8.43 (s, 1H), 8.38 (dd, J = 8.3, 1.6 Hz, 1H), 8.01 (dd, J = 7.9, 1.7 Hz, 1H), 7.60 − 7.42 (m, 3H), 7.39 − 7.29 (m, 2H), 7.15 (dd, J = 7.6, 1.6 Hz, 1H), 3.96 (s, 3H), 3.90 (s, 3H), 3.61 (s, 2H), 3.41 (s, 2H), 2.74 (d, J = 5.6 Hz, 2H), 2.67 (d, J = 5.1 Hz, 2H), 2.54 (d, J = 7.5 Hz, 2H), 2.48 − 2.44 (m, 4H), 1.84 (d, J = 11.9 Hz, 2H), 1.75 − 1.66 (m, 6H), 1.58 − 1.48 (m, 4H), 1.43 (s, 2H), 1.38 (d, J = 11.2 Hz, 2H). $^{19}$F NMR (377 MHz, DMSO-$d_6$) δ −120.69. |
| 59 | $^1$H NMR (400 MHz, DMSO-$d_6$) δ 11.95 (s, 1H), 9.89 (s, 1H), 8.44 (s, 1H), 8.38 (dd, J = 8.3, 1.5 Hz, 1H), 8.01 (dd, J = 7.8, 1.6 Hz, 1H), 7.61 − 7.41 (m, 3H), 7.41 − 7.30 (m, 2H), 7.15 (dd, J = 7.6, 1.6 Hz, 1H), 4.66 (d, J = 4.6 Hz, 1H), 4.18 (s, 1H), 3.96 (s, 3H), 3.90 (s, 3H), 3.68 − 3.54 (m, 2H), 3.41 (s, 2H), 2.89 (s, 1H), 2.79 − 2.58 (m, 6H), 2.54 (d, J = 7.6 Hz, 2H), 2.48 − 2.34 (m, 2H), 1.99 (dd, J = 13.2, 6.8 Hz, 1H), 1.84 (d, J = 12.6 Hz, 2H), 1.72 (t, J = 7.8 Hz, 2H), 1.56 − 1.50 (m, 4H), 1.43 (s, 2H), 1.37 (d, J = 10.6 Hz, 2H). $^{19}$F NMR (377 MHz, DMSO-$d_6$) δ −120.70. |
| 60 | $^1$H NMR (400 MHz, DMSO-$d_6$) δ 11.95 (s, 1H), 9.89 (s, 1H), 8.44 (s, 1H), 8.38 (dd, J = 8.2, 1.5 Hz, 1H), 8.01 (dd, J = 7.9, 1.6 Hz, 1H), 7.59 − 7.44 (m, 3H), 7.40 − 7.30 (m, 2H), 7.15 (dd, J = 7.6, 1.6 Hz, 1H), 5.19 (ddd, J = 56.0, 6.6, 4.9 Hz, 1H), 3.97 (s, 3H), 3.90 (s, 3H), 3.66 (s, 2H), 3.41 (s, 2H), 2.82 − 2.60 (m, 7H), 2.54 (d, J = 7.4 Hz, 2H), 2.37 (p, J = 9.5, 8.7 Hz, 1H), 2.13 (ddd, J = 28.0, 14.0, 7.5 Hz, 1H), 1.88 (td, J = 13.8, 8.5 Hz, 3H), 1.72 (t, J = 7.8 Hz, 2H), 1.57 − 1.47 (m, 4H), 1.43 (s, 2H), 1.38 (d, J = 11.3 Hz, 2H). $^{19}$F NMR (377 MHz, DMSO-$d_6$) δ −120.73, −166.68. |
| 61 | $^1$H NMR (400 MHz, DMSO-$d_6$) δ 11.95 (s, 1H), 9.89 (s, 1H), 8.45 (s, 1H), 8.38 (dd, J = 8.3, 1.5 Hz, 1H), 8.01 (dd, J = 8.0, 1.5 Hz, 1H), 7.61 − 7.45 (m, 3H), 7.43 − 7.30 (m, 2H), 7.15 (dd, J = 7.7, 1.5 Hz, 1H), 6.17 (s, 1H), 3.97 (s, 3H), 3.90 (s, 3H), 3.72 − 3.61 (m, 2H), 3.41 (s, 2H), 2.83 (d, J = 10.5 Hz, 1H), 2.80 − 2.71 (m, 3H), 2.71 − 2.52 (m, 6H), 2.10 (dt, J = 13.9, 7.1 Hz, 1H), 1.84 (dt, J = 12.0, 5.9 Hz, 3H), 1.72 (t, J = 7.7 Hz, 2H), 1.58 − 1.48 (m, 4H), 1.43 (s, 2H), 1.37 (d, J = 11.2 Hz, 2H). $^{19}$F NMR (377 MHz, DMSO-$d_6$) δ −79.96, −120.77. |
| 62 | $^1$H NMR (400 MHz, Chloroform-d) δ 9.83 (s, 1H), 8.50 (dd, J = 8.4, 1.6 Hz, 1H), 8.44 (s, 1H), 8.00 (dd, J = 7.9, 1.6 Hz, 1H), 7.57 (dd, J = 38.6, 1.9 Hz, 1H), 7.36 (q, J = 7.8 Hz, 2H), 7.22 − 7.12 (m, 2H), 7.02 (d, J = 7.6 Hz, 1H), 4.16 (dq, J = 29.5, 7.2 Hz, 1H), 3.92 (d, J = 2.6 Hz, 6H), 3.79 (dd, J = 11.3, 2.9 Hz, 2H), 3.55 (s, 10H), 2.84 (q, J = 7.0 Hz, 4H), 2.77 − 2.55 (m, 6H), 2.44 − 2.24 (m, 2H), 2.00 − 1.85 (m, 6H), 1.79 (t, J = 8.1 Hz, 2H), 1.55 (dd, J = 23.2, 8.8 Hz, 4H), 1.43 − 1.31 (m, 2H). $^{19}$F NMR (377 MHz, Chloroform-d) δ −121.92. |
| 63 | $^1$H NMR (400 MHz, DMSO-$d_6$) δ 11.92 (s, 1H), 9.89 (s, 1H), 8.44 (s, 1H), 8.38 (dd, 7 = 8.3, 1.5 Hz, 1H), 8.01 (dd, 7 = 7.9, 1.6 Hz, 1H), 7.59 − 7.44 (m, 3H), 7.39 − 7.29 (m, 2H), 7.15 (dd, J = 7.6, 1.5 Hz, 1H), 3.95 (s, 3H), 3.90 (s, 3H), 3.51 (s, 2H), 3.41 (s, 2H), 2.87 − 2.82 (m, 1H), 2.74 (d, J = 5.7 Hz, 2H), 2.67 (d, J = 5.2 Hz, 2H), 2.54 (d, J = 7.5 Hz, 2H), 2.10 (s, 3H), 1.84 (d, J = 10.2 Hz, 2H), 1.72 (t, J = 7.7 Hz, 2H), 1.50 (d, J = 10.6 Hz, 4H), 1.43 (s, 2H), 1.37 (d, J = 11.1 Hz, 2H), 1.02 (d, J = 6.6 Hz, 6H). $^{19}$F NMR (377 MHz, DMSO-$d_6$) δ −120.66. |
| 64 | $^1$H NMR (400 MHz, DMSO-$d_6$) δ 9.82 (s, 1H), 8.38 (s, 1H), 8.30 (d, J = 8.3 Hz, 1H), 8.22 (s, 0H), 7.94 (d, J = 7.9 Hz, 1H), 7.52 − 7.36 (m, 3H), 7.32 − 7.20 (m, 2H), 7.08 (d, J = 7.6 Hz, 1H), 3.89 (s, 3H), 3.83 (s, 3H), 3.53 (s, 2H), 2.68 (d, J = 5.6 Hz, 2H), 2.60 (d, J = 5.6 Hz, 2H), 2.53 (t, J = 7.0 Hz, 2H), 2.48 (s, 2H), 2.22 (s, 2H), 1.85 − 1.74 (m, 2H), 1.65 (t, J = 7.7 Hz, 2H), 1.45 (q, J = 7.1, 6.0 Hz, 6H), 1.36 (s, 2H), 1.31 (d, J = 11.3 Hz, 2H), 0.98 (s, 6H). $^{19}$F NMR (377 MHz, DMSO-$d_6$) δ −120.67. |
| 65 | $^1$H NMR (400 MHz, DMSO-$d_6$) δ 9.89 (s, 1H), 8.42 (s, 1H), 8.38 (dd, J = 8.3, 1.5 Hz, 1H), 8.01 (dd, J = 7.9, 1.6 Hz, 1H), 7.59 − 7.42 (m, 3H), 7.35 (dd, J = 7.6, 1.6 Hz, 1H), 7.31 (s, 1H), 7.15 (dd, J = 7.6, 1.5 Hz, 1H), 3.95 (s, 3H), 3.90 (s, 3H), 3.47 (s, 2H), 3.41 (s, 2H), 2.75 (t, J = 5.6 Hz, 2H), 2.70 − 2.64 (m, 2H), 2.54 (d, J = 7.1 Hz, 2H), 2.35 (d, J = 5.5 Hz, 4H), 1.91 − 1.81 (m, 2H), 1.72 (t, J = 7.8 Hz, 2H), 1.51 (h, J = 5.5, 5.0 Hz, 8H), 1.43 (s, 2H), 1.38 (q, J = 5.8, 5.2 Hz, 4H). $^{19}$F NMR (377 MHz, DMSO-$d_6$) δ −120.75. |
| 66 | $^1$H NMR (400 MHz, DMSO-$d_6$) δ 9.89 (s, 1H), 8.42 (s, 1H), 8.38 (dd, J = 8.3, 1.5 Hz, 1H), 8.01 (dd, J = 7.9, 1.5 Hz, 1H), 7.60 − 7.42 (m, 3H), 7.39 − 7.30 (m, 2H), 7.15 (dd, J = 7.7, 1.5 Hz, 1H), 3.96 (s, 3H), 3.90 (s, 3H), 3.65 − 3.55 (m, 2H), 3.41 (s, 2H), 2.74 (d, J = 5.5 Hz, 2H), 2.71 − 2.63 (m, 4H), 2.62 − 2.53 (m, 2H), 2.29 (d, J = 2.1 Hz, 1H), 1.93 − 1.81 (m, 3H), 1.72 (t, J = 7.8 Hz, 2H), 1.62 − 1.56 (m, 1H), 1.55 − 1.47 (m, 4H), 1.43 (s, 2H), 1.37 (d, J = 11.2 Hz, 2H). $^{19}$F NMR (377 MHz, DMSO-$d_6$) δ −120.71. |
| 67 | $^1$H NMR (400 MHz, DMSO-$d_6$) δ 9.89 (s, 1H), 8.42 (s, 1H), 8.38 (dd, J = 8.3, 1.5 Hz, 1H), 8.01 (dd, J = 7.9, 1.6 Hz, 1H), 7.59 − 7.42 (m, 3H), 7.35 (dd, J = 7.6, 1.6 Hz, 1H), 7.29 (s, 1H), 7.15 (dd, J = 7.6, 1.6 Hz, 1H), 3.95 (s, 3H), 3.90 (s, 3H), 3.53 (s, 2H), 3.41 (s, 2H), 2.75 (t, J = 5.7 Hz, 2H), 2.69 − 2.63 (m, 2H), 2.60 (t, J = 6.8 Hz, 2H), 2.54 (d, J = 7.5 Hz, 2H), 1.92 − 1.82 (m, 2H), 1.72 (t, J = 7.8 Hz, 2H), 1.64 (dtd, J = 11.8, 5.8, 3.2 Hz, 4H), 1.52 (q, J = 10.6, 7.7 Hz, 4H), 1.43 (s, 2H), 1.37 (d, J = 11.5 Hz, 2H), 1.05 (s, 6H). $^{19}$F NMR (377 MHz, DMSO-$d_6$) δ −120.66. |
| 68 | $^1$H NMR (400 MHz, DMSO-$d_6$) δ 11.94 (s, 1H), 9.88 (s, 1H), 8.42 − 8.33 (m, 2H), 8.27 (dd, J = 4.0, 1.6 Hz, 1H), 8.00 (dd, J = 7.9, 1.6 Hz, 1H), 7.90 (dt, J = 8.5, 1.3 Hz, 1H), 7.61 − 7.45 (m, 4H), 7.40 − 7.32 (m, 3H), 7.14 (dd, J = 7.5, 1.6 Hz, 1H), 6.82 (dd, J = 8.5, 4.0 Hz, 1H), 5.50 (s, 2H), 4.03 (s, 3H), 3.89 (s, 3H), 3.41 (s, 2H), 2.74 (d, J = 5.7 Hz, 2H), 2.66 (d, J = 5.0 Hz, 2H), 2.55 (s, 2H), 1.84 (d, J = 12.9 Hz, 2H), 1.72 (t, J = 7.8 Hz, 2H), 1.50 (d, J = 10.4 Hz, 4H), 1.43 (s, 2H), 1.37 (d, J = 11.0 Hz, 2H). $^{19}$F NMR (377 MHz, DMSO-$d_6$) δ −120.87. |
| 69 | $^1$H NMR (400 MHz, DMSO-$d_6$) δ 9.89 (s, 1H), 8.45 (s, 1H), 8.38 (dd, J = 8.3, 1.5 Hz, 1H), 8.01 (dd, J = 8.0, 1.6 Hz, |

-continued

| Example No. | $^{1}$H NMR/$^{19}$F NMR |
|---|---|
| | 1H), 7.59 – 7.44 (m, 3H), 7.38 – 7.31 (m, 2H), 7.15 (dd, J = 7.6, 1.5 Hz, 1H), 4.60 (s, 1H), 3.96 (s, 3H), 3.90 (s, 3H), 3.75 (d, J = 11.0 Hz, 1H), 3.58 – 3.47 (m, 3H), 3.39 (d, J = 13.9 Hz, 4H), 2.82 – 2.73 (m, 3H), 2.70 – 2.62 (m, 3H), 2.59 – 2.52 (m, 2H), 2.15 – 2.05 (m, 1H), 1.89 – 1.79 (m, 3H), 1.72 (t, J = 7.8 Hz, 2H), 1.56 – 1.46 (m, 4H), 1.43 (s, 2H), 1.40 – 1.33 (m, 2H). $^{19}$F NMR (377 MHz, DMSO-$d_6$) δ −120.80. |
| 70 | $^{1}$H NMR (400 MHz, DMSO-$d_6$) δ 9.89 (s, 1H), 8.45 (s, 1H), 8.38 (dd, J = 8.3, 1.6 Hz, 1H), 8.01 (dd, J = 7.9, 1.6 Hz, 1H), 7.60 – 7.44 (m, 3H), 7.39 – 7.31 (m, 2H), 7.15 (dd, J = 7.6, 1.6 Hz, 1H), 4.60 (s, 1H), 3.96 (s, 3H), 3.90 (s, 3H), 3.75 (d, J = 10.9 Hz, 1H), 3.54 – 3.47 (m, 3H), 3.39 (d, J = 11.5 Hz, 4H), 2.81 – 2.71 (m, 3H), 2.69 – 2.61 (m, 3H), 2.54 (d, J = 7.4 Hz, 2H), 2.18 – 2.06 (m, 1H), 1.84 (d, J = 11.0 Hz, 2H), 1.72 (t, J = 7.7 Hz, 2H), 1.55 – 1.48 (m, 4H), 1.43 (s, 2H), 1.38 (d, J = 15.4 Hz, 2H). $^{19}$F NMR (377 MHz, DMSO-$d_6$) δ −120.81. |
| 71 | $^{1}$H NMR (400 MHz, DMSO-$d_6$) δ 11.95 (s, 1H), 9.89 (s, 1H), 8.46 (s, 1H), 8.38 (dd, J = 8.4, 1.5 Hz, 1H), 8.01 (dd, J = 7.8, 1.6 Hz, 1H), 7.58 – 7.43 (m, 3H), 7.39 – 7.29 (m, 2H), 7.15 (dd, J = 7.6, 1.5 Hz, 1H), 4.51 (s, 1H), 3.96 (s, 3H), 3.90 (s, 3H), 3.61 (d, J = 3.7 Hz, 2H), 3.41 (s, 2H), 2.75 (t, J = 5.7 Hz, 2H), 2.70 – 2.63 (m, 3H), 2.56 – 2.52 (m, 2H), 2.48 – 2.42 (m, 2H), 1.91 – 1.81 (m, 2H), 1.76 – 1.67 (m, 4H), 1.52 (q, J = 10.9, 7.9 Hz, 4H), 1.43 (s, 2H), 1.37 (d, J = 11.4 Hz, 2H), 1.23 (s, 3H). $^{19}$F NMR (377 MHz, DMSO-$d_6$) δ −120.72. |
| 72 | $^{1}$H NMR (400 MHz, DMSO-$d_6$) δ 11.94 (s, 1H), 9.89 (s, 1H), 8.46 (s, 1H), 8.38 (dd, J = 8.2, 1.5 Hz, 1H), 8.01 (dd, J = 7.9, 1.5 Hz, 1H), 7.61 – 7.42 (m, 3H), 7.41 – 7.27 (m, 2H), 7.15 (dd, J = 7.7, 1.5 Hz, 1H), 4.52 (s, 1H), 3.96 (s, 3H), 3.90 (s, 3H), 3.66 – 3.56 (m, 2H), 3.41 (s, 2H), 2.75 (d, J = 5.7 Hz, 2H), 2.67 (d, J = 6.3 Hz, 3H), 2.58 – 2.53 (m, 2H), 2.47 (d, J = 6.3 Hz, 2H), 1.84 (d, J = 11.9 Hz, 2H), 1.71 (dt, J = 12.5, 6.1 Hz, 4H), 1.50 (d, J = 10.5 Hz, 4H), 1.43 (s, 2H), 1.38 (d, J = 11.0 Hz, 2H), 1.23 (s, 3H). $^{19}$F NMR (377 MHz, DMSO-$d_6$) δ −120.72. |
| 73 | $^{1}$H NMR (400 MHz, DMSO-$d_6$) δ 9.89 (s, 1H), 8.43 (s, 1H), 8.38 (dd, J = 8.2, 1.6 Hz, 1H), 8.01 (dd, J = 7.9, 1.6 Hz, 1H), 7.58 – 7.43 (m, 3H), 7.40 – 7.30 (m, 2H), 7.15 (dd, J = 7.6, 1.6 Hz, 1H), 3.96 (s, 3H), 3.90 (s, 3H), 3.63 (d, J = 9.3 Hz, 2H), 2.93 (t, J = 7.6 Hz, 2H), 2.81 – 2.63 (m, 7H), 2.57 – 2.54 (m, 2H), 2.02 – 1.92 (m, 2H), 1.89 – 1.82 (m, 2H), 1.72 (t, J = 7.8 Hz, 2H), 1.52 (q, J = 10.4, 7.7 Hz, 4H), 1.43 (s, 2H), 1.38 (d, J = 11.2 Hz, 2H). $^{19}$F NMR (377 MHz, DMSO-$d_6$) δ −120.72. |
| 74 | $^{1}$H NMR (400 MHz, DMSO-$d_6$) δ 9.89 (s, 1H), 8.43 (s, 1H), 8.38 (dd, J = 8.3, 1.5 Hz, 1H), 8.01 (dd, J = 7.8, 1.6 Hz, 1H), 7.58 – 7.43 (m, 3H), 7.39 – 7.30 (m, 2H), 7.15 (dd, J = 7.6, 1.6 Hz, 1H), 3.96 (s, 3H), 3.90 (s, 3H), 3.62 (d, J = 9.4 Hz, 2H), 2.97 – 2.89 (m, 2H), 2.79 – 2.63 (m, 7H), 2.55 (t, J = 3.6 Hz, 2H), 1.95 (td, J = 7.7, 4.5 Hz, 2H), 1.89 – 1.81 (m, 2H), 1.72 (t, J = 7.7 Hz, 2H), 1.52 (q, J = 10.3, 7.5 Hz, 4H), 1.43 (s, 2H), 1.38 (d, J = 11.3 Hz, 2H). $^{19}$F NMR (377 MHz, DMSO-$d_6$) δ −120.67. |
| 75 | $^{1}$H NMR (400 MHz, DMSO-$d_6$) δ 9.89 (s, 1H), 8.44 (s, 1H), 8.38 (dd, J = 8.3, 1.6 Hz, 1H), 8.01 (dd, J = 7.9, 1.6 Hz, 1H), 7.60 – 7.42 (m, 3H), 7.39 – 7.28 (m, 2H), 7.15 (dd, J = 7.6, 1.5 Hz, 1H), 3.96 (s, 3H), 3.90 (s, 3H), 3.63 (d, J = 4.6 Hz, 2H), 3.43 – 3.41 (m, 2H), 2.94 (d, J = 9.2 Hz, 2H), 2.76 (s, 2H), 2.69 – 2.52 (m, 5H), 2.39 – 2.18 (m, 3H), 1.91 – 1.80 (m, 2H), 1.72 (s, 2H), 1.61 – 1.48 (m, 5H), 1.43 (s, 2H), 1.38 (d, J = 11.6 Hz, 2H), 1.24 (s, 3H). $^{19}$F NMR (377 MHz, DMSO-$d_6$) δ −120.73. |
| 76 | $^{1}$H NMR (400 MHz, DMSO-$d_6$) δ 9.89 (s, 1H), 8.44 (s, 1H), 8.38 (dd, J = 8.3, 1.5 Hz, 1H), 8.01 (dd, J = 7.8, 1.6 Hz, 1H), 7.60 – 7.43 (m, 3H), 7.39 – 7.30 (m, 2H), 7.15 (dd, J = 7.6, 1.5 Hz, 1H), 3.96 (s, 3H), 3.90 (s, 3H), 3.63 (d, J = 4.7 Hz, 2H), 3.41 (s, 2H), 2.93 (d, J = 9.2 Hz, 2H), 2.75 (d, J = 5.7 Hz, 2H), 2.69 – 2.59 (m, 4H), 2.54 (d, J = 6.8 Hz, 1H), 2.35 – 2.22 (m, 3H), 1.91 – 1.81 (m, 2H), 1.72 (t, J = 7.8 Hz, 2H), 1.53 (q, J = 10.8, 8.6 Hz, 5H), 1.43 (s, 2H), 1.38 (d, J = 11.6 Hz, 2H), 1.24 (s, 3H). $^{19}$F NMR (377 MHz, DMSO-$d_6$) δ −120.73. |
| 77 | $^{1}$H NMR (400 MHz, DMSO-$d_6$) δ 9.89 (s, 1H), 8.47 (s, 1H), 8.38 (dd, J = 8.3, 1.5 Hz, 1H), 8.00 (dd, J = 7.9, 1.6 Hz, 1H), 7.60 – 7.42 (m, 3H), 7.35 (dd, J = 7.6, 1.6 Hz, 1H), 7.29 (s, 1H), 7.15 (dd, J = 7.6, 1.6 Hz, 1H), 3.95 (s, 3H), 3.90 (s, 3H), 3.69 – 3.54 (m, 2H), 3.41 (s, 2H), 3.16 (s, 1H), 2.78 – 2.63 (m, 5H), 2.54 (d, J = 7.3 Hz, 2H), 2.32 (dd, J = 4.1, 2.0 Hz, 1H), 2.21 (d, J = 8.7 Hz, 1H), 1.91 – 1.82 (m, 2H), 1.77 – 1.68 (m, 3H), 1.65 – 1.58 (m, 1H), 1.50 (d, J = 11.1 Hz, 5H), 1.45 – 1.34 (m, 5H), 1.30 – 1.19 (m, 2H). |
| 78 | $^{1}$H NMR (400 MHz, DMSO-$d_6$) δ 9.89 (s, 1H), 8.43 (s, 1H), 8.38 (dd, J = 8.2, 1.7 Hz, 1H), 8.01 (dd, J = 7.9, 1.8 Hz, 1H), 7.58 – 7.43 (m, 3H), 7.39 – 7.28 (m, 2H), 7.15 (dd, J = 7.6, 1.7 Hz, 1H), 3.95 (d, J = 5.9 Hz, 3H), 3.90 (d, J = 2.1 Hz, 3H), 3.59 (t, J = 4.5 Hz, 2H), 3.41 (s, 2H), 2.71 (dq, J = 26.7, 5.8 Hz, 5H), 2.57 (ddd, J = 17.2, 8.6, 4.2 Hz, 3H), 2.20 – 2.11 (m, 1H), 2.04 (dd, J = 8.8, 6.5 Hz, 1H), 1.93 (dd, J = 9.1, 5.0 Hz, 1H), 1.84 (d, J = 11.9 Hz, 2H), 1.72 (t, J = 7.8 Hz, 2H), 1.50 (d, J = 12.2 Hz, 4H), 1.43 (s, 2H), 1.37 (d, J = 11.4 Hz, 2H), 1.28 – 1.23 (m, 1H), 0.98 (dd, J = 6.8, 2.1 Hz, 3H). |

Biological Test Evaluation

I. PD1-PDL1 HTRF Binding Activity Test

The effect of compounds of the examples of the present invention on the interaction between PD-1 and PD-L1 was determined by the PD-1/PD-L1 binding assay kit from Cisbio (#64ICP01PEG or 64ICP01PEH). The detailed experimental process was as follows:

1. Pre-diluted compound solution, 4 μL of Tag1-PD-L1 and 4 μL of Tag2-PD1 were added to each well of a 384-well plate;
2. After the mixture was incubated at room temperature for 15 min, 5 μL of anti-Tag1-Eu3+ antibody and 5 μL of anti-Tag2-XL665 antibody were then added;
3. After incubated for 2 hrs at room temperature or overnight at 4° C., plates were read on Envision of Pelkin Elmer; and readings at 665 nm and 620 nm were recorded, and the ratio of the two readings was taken as a reading for each well;

4. The reading of each well after compound treatment was compared with the reading of DMSO treated wells to obtain the percent inhibition of the compound;
5. $IC_{50}$ values of compounds and positive compounds of the examples of the present invention were determined by non-linear regression analysis of percent inhibition at different compound concentrations. The specific experimental results were shown in Table 1.

II. Jurkat Reporter Gene Cellular Assay

The effect of compounds of the examples of the present invention and positive compounds on the interaction between PD-1 and PD-L1 expressed on cell surfaces, and the related influence on T cell functions, were determined by a Jurkat reporter gene cellular assay.

Briefly, the reporter gene plasmid of NF-κB-luc and the plasmid of human PD-1 were transfected into Jurkat cells to establish a stably transfected cell line capable of stably expressing both PD-1 and NF-κB-Luc reporter genes; the expression level of PD-1 on the cell surface was confirmed by flow cytometry; and the expression of the reporter gene was confirmed via the response of the reporter gene stimulated by OKT-3 and Raiji cells.

In addition, the plasmid of human PD-L1 was transfected into Raji cells to obtain a cell line capable of stably expressing PD-L1. Jurkat/NF-κB-luc/PD1 cells and Raji-PD-L1 cells were then cocultured and stimulated with OKT-3. On this basis, the compounds were added, and the enhancement of the signal pathway of T cell activation by the inhibitory effect of the compounds on the interaction between PD-1 and PD-L1 was evaluated by readings of reporter gene responses. The specific experimental process was as follows:

1. 30 μL of compound or antibody solution was added to each well of a white 96-well plate (corning, 3610) at different diluted concentrations, and 10 μL of OKT3 (Biolegend, 317326) was then added (the final concentration of OKT3: 1 μg/mL);
2. 20 μL of Raji-PD-L1 cell suspension was added to each well with $5*10^4$ cells for each well, and was incubated in an incubator for 20 min;
3. 20 μL of Jurkat/NF-Kb-luc/PD-1 cell suspension was added to each well with $5*10^4$ cells for each well, and well mixed, and 6 hrs later, Bright-glo (Promega, E2620) was applied and plates were read on Envision;
4. The reading of each well treated with the compound was compared with the reading of each well treated with DMSO to obtain the activation fold of the compound;
5. $EC_{50}$ values of compounds and positive compounds of the examples of the present invention were determined by non-linear regression analysis of activation folds at different compound concentrations. The specific experimental results were shown in Table 1:

TABLE 1

| Biological test results | | | | | |
|---|---|---|---|---|---|
| Example No. | PD1-PDL1 HTRF Binding Activity $IC_{50}$/nM | Cell Activity $EC_{50}$/nM | Example No. | PD1-PDL1 HTRF Binding Activity $IC_{50}$/nM | Cell Activity $EC_{50}$/nM |
| 1 | 0.688 | 257.8 | 41 | 0.2491 | 86.7 |
| 2 | NT | 244.4 | 42 | NT | 118.5 |
| 3 | NT | 95.2 | 43 | NT | 137.4 |
| 4 | NT | 289.4 | 44 | NT | 105.3 |
| 5 | NT | 719.3 | 45 | NT | 113.6 |
| 6 | NT | 973.1 | 46 | NT | 152.0 |
| 7 | 0.4187 | 62.2 | 47 | NT | 146.6 |
| 8 | 0.5161 | 97.5 | 48 | NT | 80.6 |
| 9 | NT | NT | 49 | 0.232 | 46.2 |
| 10 | NT | NT | 50 | 0.7307 | 54.0 |
| 11 | NT | NT | 51 | NT | 90.1 |
| 12 | NT | NT | 52 | NT | 115.6 |
| 13 | NT | NT | 53 | NT | 1035 |
| 14 | NT | NT | 54 | NT | 250.5 |
| 15 | NT | NT | 55 | NT | 148.7 |
| 16 | 0.1907 | 133.0 | 56 | NT | 61.4 |
| 17 | 0.3313 | 464.4 | 57 | NT | 72.0 |
| 18 | NT | 249.1 | 58 | 0.1927 | 44.1 |
| 19 | NT | 192.1 | 59 | 0.2987 | 47.5 |
| 20 | NT | NT | 60 | NT | 133.7 |
| 21 | NT | NT | 61 | NT | 522.3 |
| 22 | NT | NT | 62 | NT | 117.0 |
| 23 | NT | NT | 63 | NT | 158.9 |
| 24 | NT | NT | 64 | NT | 113.1 |
| 25 | NT | NT | 65 | NT | 137.0 |
| 26 | NT | NT | 66 | NT | 347.1 |
| 27 | NT | NT | 67 | NT | 54.1 |
| 28 | NT | NT | 68 | NT | 953.9 |
| 29 | NT | NT | 69 | NT | 116.0 |
| 30 | NT | NT | 70 | NT | 127.7 |
| 31 | NT | NT | 71 | NT | 42.1 |
| 32 | NT | NT | 72 | NT | 115.8 |
| 33 | 0.4887 | 85.8 | 73 | 0.1856 | 50.6 |
| 34 | 0.3517 | 80.4 | 74 | NT | 136.3 |
| 35 | 0.6379 | 93.1 | 75 | 0.1846 | 54.4 |
| 36 | 0.3063 | 3129 | 76 | NT | 98.1 |
| 37 | 0.2023 | 177.8 | 77 | NT | 54.4 |
| 38 | 0.3321 | 977.1 | 78 | NT | 56.5 |
| 39 | 0.2378 | 64.7 | 79 | NT | NT |
| 40 | 0.3096 | 178.6 | | | |

Note

"NT", i.e., "Not Tested", means that the compound was not tested.

The bioactivity data of the compounds of the specific examples indicates that the series of compounds of the present invention have a strong inhibitory effect on the interaction between PD-1 and PD-L1, and moreover, such an inhibitory effect can enhance or recover the activation of T cells at the cellular level.

III. Pharmacokinetic Assay in Mice

1. Purpose of Study

The purpose of this study was to study the pharmacokinetic behaviors of some compounds of the present invention, and administration routes were: per oral administration (PO) to ICR mice at a dose of 10 mg/kg.

2. Testing Scheme 2.1 Tested Drug

The compounds used in this test came from the compounds of the specific examples of the present invention.

2.2 Tested Animal

ICR mice, male, N=3, with the original source of Shanghai Sippr-BK Laboratory Animal Co. Ltd.

2.3 Preparation and Administration of Drug

The compounds were weighed, and dissolved in a solvent of 0.5% SDS+0.5% CMCNa. The mixture solutions were mixed well by shaking and ultrasonic treatment to obtain colorless clear solutions. The solutions were orally administered to nine mice after an overnight fast. The dosage of administration was 10 mg/kg.

2.4 Sampling

1) With about 90 μL/time point, blood was drawn from the submaxillary vein, and heparin sodium was added for anticoagulation. The blood samples were placed onto the ice, and were centrifuged (centrifugation conditions: 8000 r/min, 6 min, 2-8° C.) within 1 hr to obtain plasmas.

2) The time points for blood sampling were at 0 hr, 0.25 hr, 0.5 hr, 1 hr, 2 hrs, 4 hrs, 6 hrs, 8 hrs and 24 hrs after administration. The samples were stored in a refrigerator at −20° C.

3) 40 μL of plasma sample was added to 160 μL of cold acetonitrile containing an internal standard, and the mixture solution was vortexed for 3 min and centrifuged at 11,000 r/min for 5 min.

4) 100 μL of supernate was taken and added to 100 μL of water, and 5 μL of the sample was taken and analyzed by LC/MS/MS.

Only the original compounds were analyzed for the compounds from the examples of the present invention and the reference compound from Example 158 of WO2020011209A1; and both the original compounds and possible products of ester hydrolysis, namely Example 217, were analyzed for the reference compound from Example 216 of WO2020011209A1. Experimental results can be found in Table 2.

TABLE 2

PK Results for Per Oral Administration (PO) of 10 mg/kg of Compounds to Mice

| Compound No. | Detected compound | $C_{max}$ (ng/mL) | $T_{max}$ (h) | $AUC_{last}$ (hr*ng/mL) | $T_{1/2}$ (h) | MRT (h) |
|---|---|---|---|---|---|---|
| Example 1 | Example 1 | 323 | 4 | 2490 | 5.2 | 8.3 |
| Example 49 | Example 49 | 1007 | 2 | 15058 | 4 | 7.4 |
| Example 58 | Example 58 | 173 | 6 | 1949 | 5 | 9.6 |
| Example 73 | Example 73 | 442 | 0.5 | 590 | 1.1 | 2 |
| Example 75 | Example 75 | 806 | 1.8 | 2648 | 1.8 | 2.9 |
| WO2020011209A1 Example 158 | WO2020011209A1 Example 158 | 20 | NA | NA | NA | NA |
| WO2020011209A1 Example 216 | WO2020011209A1 Example 217 | 712 | 1 | 2160 | 1 | 0.4 |

Note

1. Example 216 of WO2020011209A1 was absorbed into the bodies of the mice by oral administration, and rapidly became corresponding acids (Example 217) via ester hydrolysis. The detection result of each index in Example 216 was below the detection limit (i.e., "NA"), or without a result.

2. Experiments proved that Example 216 of WO2020011209A1 was the prodrug compound of Example 217.

All documents mentioned in the present application are hereby incorporated by reference in their entirety, just as each document is cited separately as a reference. In addition, it should be understood that various modifications and changes may be made by those skilled in the art after reading the above teachings of the present invention and these equivalent forms also fall within the scope defined by the claims appended hereto.

The invention claimed is:

1. A compound of formula (I), a stereoisomer, prodrug or pharmaceutically acceptable salt thereof:

(I)

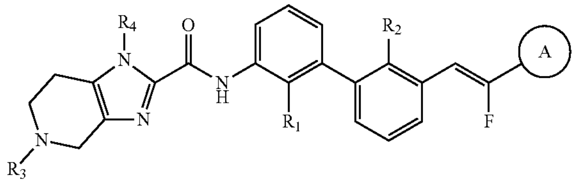

wherein, ring A is selected from the following groups:

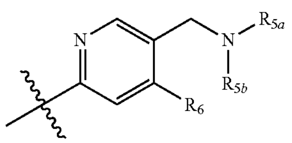
or
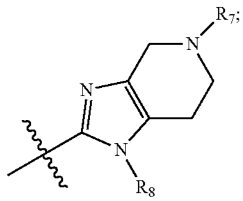

$R_1$ and $R_2$ are each independently selected from the group consisting of hydrogen, deuterium, halogen, cyano, hydroxy, carboxyl, $C_{1-10}$ alkyl, $C_{3-10}$ cycloalkyl and $C_{1-10}$ alkoxy, above groups are optionally further substituted by one or more substituents selected from the group consisting of deuterium, halogen, cyano, cyclopropyl, hydroxy and $C_{1-4}$ alkoxy;

$R_3$ is selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$, above groups are optionally more further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$;

$R_4$ is selected from the group consisting of hydrogen, deuterium, hydroxy, $C_{1-10}$ alkyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, cyano, cyclopropyl, hydroxy and $C_{1-4}$ alkoxy;

$R_{5a}$ and $R_{5b}$ are each independently selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl and 5-10 membered heteroaryl, or $R_{5a}$ and $R_{5b}$, together with the nitrogen atom directly attached thereto, form 4-10 membered heterocyclyl, or, the formed 4-10 membered heterocyclyl is further fused to $C_{5-10}$ aryl or 5-10 membered heteroaryl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$, above groups are optionally more further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_{11}$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$;

$R_6$ is selected from the group consisting of hydrogen, deuterium, halogen, cyano, hydroxy, carboxyl, $C_{1-10}$ alkyl, $C_{3-10}$ cycloalkyl and $C_{1-10}$ alkoxy, above groups are optionally further substituted by one or more substituents selected from the group consisting of deuterium, halogen, cyano, cyclopropyl, hydroxy and $C_{1-4}$ alkoxy;

$R_7$ is selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_{11}$, $-C_{0-8}-O-C(O)R_1$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$, above groups are optionally more further substituted by one or more substituents selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-10}$ cycloalkyl, 3-10 membered heterocyclyl, $C_{5-10}$ aryl, 5-10 membered heteroaryl, =O, $-C_{0-8}-S(O)_rR_9$, $-C_{0-8}-O-R_{10}$, $-C_{0-8}-C(O)OR_{10}$, $-C_{0-8}-C(O)R_1$, $-C_{0-8}-O-C(O)R_1$, $-C_{0-8}-NR_{12}R_{13}$, $-C_{0-8}-C(=NR_{12})R_{11}$, $-C_{0-8}-N(R_{12})-C(=NR_{13})R_{11}$, $-C_{0-8}-C(O)NR_{12}R_{13}$ and $-C_{0-8}-N(R_{12})-C(O)R_{11}$;

$R_8$ is selected from the group consisting of hydrogen, deuterium, hydroxy, $C_{1-10}$ alkyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, cyano, cyclopropyl, hydroxy and $C_{1-4}$ alkoxy;

each $R_9$ is independently selected from the group consisting of hydrogen, deuterium, hydroxy, $C_{1-10}$ alkyl, $C_{2-10}$ alkenyl, $C_{3-10}$ cycloalkyl, 3-10 membered heterocyclyl, $C_{5-10}$ aryl, 5-10 membered heteroaryl and $-NR_{12}R_{13}$, above groups are optionally further substituted by one or more substituents selected from the group consisting of deuterium, halogen, hydroxy, oxo, cyano, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $-NR_{12}R_{13}$;

each $R_{10}$ is independently selected from the group consisting of hydrogen, deuterium, $C_{1-10}$ alkyl, $C_{2-10}$ alkenyl, $C_{3-10}$ cycloalkyl, 3-10 membered heterocyclyl, $C_{5-10}$ aryl and 5-10 membered heteroaryl, above groups are optionally further substituted by one or more substituents selected from the group consisting of deuterium, halogen, hydroxy, oxo, cyano, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $-NR_{12}R_{13}$;

each $R_{11}$ is independently selected from the group consisting of hydrogen, deuterium, hydroxy, $C_{1-10}$ alkyl, $C_{1-10}$ alkoxy, $C_{2-10}$ alkenyl, $C_{2-10}$ alkynyl, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $-NR_{12}R_{13}$, above groups are optionally further substituted by one or more substituents selected from the group consisting of deuterium, halogen, hydroxy, cyano, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy and $-NR_{12}R_{13}$;

each of $R_{12}$ and $R_{13}$ is independently selected from the group consisting of hydrogen, deuterium, hydroxy, $C_{1-10}$ alkyl, $C_{2-10}$ alkenyl, $C_{2-10}$ alkynyl, $C_{3-10}$ cycloalkyl, 3-10 membered heterocyclyl, $C_{5-10}$ aryl, 5-10 membered heteroaryl, sulfonyl, methanesulfonyl, isopropylsulfonyl, cyclopropylsulfonyl, p-toluenesulfonyl, amino, $C_{1-10}$ monoalkylamino, di($C_{1-10}$ alkyl)amino and $C_{1-10}$ alkanoyl, above groups are optionally further substituted by one or more substituents selected from the group consisting of deuterium, halogen, hydroxy, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, $C_{1-10}$ monoalkylamino, di($C_{1-10}$ alkyl) amino and $C_{1-10}$ alkanoyl;

or $R_{12}$ and $R_{13}$, together with the nitrogen atom directly attached thereto, form 4-10 membered heterocyclyl, above group is optionally further substituted by one or more substituents selected from the group consisting of deuterium, halogen, hydroxy, $C_{1-10}$ alkyl, $C_{1-10}$ alkoxy, $C_{3-10}$ cycloalkyl, $C_{3-10}$ cycloalkyloxy, 3-10 membered heterocyclyl, 3-10 membered heterocyclyloxy, $C_{5-10}$ aryl, $C_{5-10}$ aryloxy, 5-10 membered heteroaryl, 5-10 membered heteroaryloxy, amino, $C_{1-10}$ monoalkylamino, di($C_{1-10}$ alkyl)amino and $C_{1-10}$ alkanoyl;

each r is independently 0, 1 or 2.

2. The compound of formula (I), the stereoisomer, prodrug or pharmaceutically acceptable salt thereof according to claim 1, wherein, $R_1$ and $R_2$ are each independently selected from the group consisting of hydrogen, deuterium, halogen, cyano, hydroxy, carboxyl, $C_{1-4}$ alkyl, $C_{3-6}$ cycloalkyl and $C_{1-4}$ alkoxy, above groups are optionally further substituted by one or more substituents selected from the group consisting of deuterium, halogen, cyano, cyclopropyl, hydroxy and $C_{1-4}$ alkoxy;

$R_3$ is selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, =O, $—C_{0-4}—S(O)_rR_9$, $—C_{0-4}—O—R_{10}$, $—C_{0-4}—C(O)OR_{10}$, $—C_{0-4}—C(O)R_{11}$, $—C_{0-4}—O—C(O)R_{11}$, $—C_{0-4}—NR_{12}R_{13}$, $—C_{0-4}—C(=NR_{12})R_{11}$, $—C_{0-4}—N(R_{12})—C(=NR_{13})R_{11}$, $—C_{0-4}—C(O)NR_{12}R_{13}$ and $—C_{0-4}—N(R_{12})—C(O)R_{11}$, above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, $—C_{0-4}—S(O)_rR_9$, $—C_{0-4}—O—R_{10}$, $—C_{0-4}—C(O)OR_{10}$, $—C_{0-4}—C(O)R_{11}$, $—C_{0-4}—O—C(O)R_{11}$, $—C_{0-4}—NR_{12}R_{13}$, $—C_{0-4}—C(=NR_{12})R_{11}$, $—C_{0-4}—N(R_{12})—C(=NR_{13})R_{11}$, $—C_{0-4}—C(O)NR_{12}R_{13}$ and $—C_{0-4}—N(R_{12})—C(O)R_{11}$;

$R_4$ is selected from the group consisting of hydrogen, deuterium, hydroxy, $C_{1-4}$ alkyl, $C_{3-6}$ cycloalkyl, 3-6 membered heterocyclyl, $C_{5-8}$ aryl and 5-8 membered heteroaryl, above groups are optionally further substituted by one or more substituents selected from the group consisting of deuterium, halogen, cyano, cyclopropyl, hydroxy and $C_{1-4}$ alkoxy; and $R_{5a}$ and $R_{5b}$ are each independently selected from the group consisting of hydrogen, deuterium, hydroxy, $C_{1-4}$ alkyl, $C_{2-4}$ alkenyl, $C_{2-4}$ alkynyl, $C_{3-10}$ cycloalkyl, 3-10 membered heterocyclyl, $C_{5-8}$ aryl and 5-8 membered heteroaryl, or $R_{5a}$ and $R_{5b}$, together with the nitrogen atom directly attached thereto, form 4-8 membered heterocyclyl, or, the formed 4-8 membered heterocyclyl is fused to $C_{5-8}$ aryl or 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, =O, $—C_{0-4}—S(O)_rR_9$, $—C_{0-4}—O—R_{10}$, $—C_{0-4}—C(O)OR_{10}$, $—C_{0-4}—C(O)R_{11}$, $—C_{0-4}—O—C(O)R_{11}$, $—C_{0-4}—NR_{12}R_{13}$, $—C_{0-4}—C(=NR_{12})R_{11}$, $—C_{0-4}—N(R_{12})—C(=NR_{13})R_{11}$, $—C_{0-4}—C(O)NR_{12}R_{13}$ and $—C_{0-4}—N(R_{12})—C(O)R_{11}$, above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, $—C_{0-4}—S(O)_rR_9$, $—C_{0-4}—O—R_{10}$, $—C_{0-4}—C(O)OR_{10}$, $—C_{0-4}—C(O)R_{11}$, $—C_{0-4}—O—C(O)R_{11}$, $—C_{0-4}—NR_{12}R_{13}$, $—C_{0-4}—C(=NR_{12})R_{11}$, $—C_{0-4}—N(R_{12})—C(=NR_{13})R_{11}$, $—C_{0-4}—C(O)NR_{12}R_{13}$ and $—C_{0-4}—N(R_{12})—C(O)R_{11}$.

3. The compound of formula (I), the stereoisomer, prodrug or pharmaceutically acceptable salt thereof according to claim 1, wherein, the compound of formula (I) is a compound with the structure shown as formula (IIa):

(IIa)

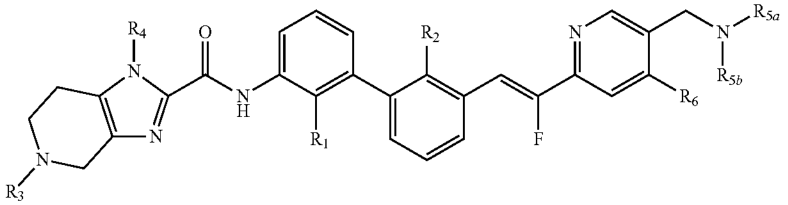

wherein, $R_1$ and $R_2$ are each independently selected from the group consisting of hydrogen, deuterium, halogen, cyano, hydroxy, carboxyl, $C_{1-4}$ alkyl, $C_{3-6}$ cycloalkyl and $C_{1-4}$ alkoxy;

$R_3$ is selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are optionally further substituted by one or more substituents selected from the group consisting of deuterium, halogen, cyano, $C_{1-4}$ alkyl, $C_{3-8}$ cycloalkyl, 3-8 membered heterocyclyl, $C_{5-8}$ aryl, 5-8 membered heteroaryl, =O, $—S(O)_rR_9$, $—O—R_{10}$, $—C(O)OR_{10}$, $—C(O)R_{11}$, $—O—C(O)R_{11}$, $—NR_{12}R_{13}$, $—C(=NR_{12})R_{11}$, $—N(R_{12})—C(=NR_{13})R_{11}$, $—C(O)NR_{12}R_{13}$ and $—N(R_{12})—C(O)R_{11}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, —NR$_{12}$R$_{13}$, —C(=NR$_{12}$)R$_1$, —N(R$_{12}$)—C(=NR$_{13}$)R$_{11}$, —C(O)NR$_{12}$R$_{13}$ and —N(R$_{12}$)—C(O)R$_{11}$;

$R_4$ is selected from the group consisting of hydrogen, deuterium, hydroxy, methyl, ethyl, isopropyl, difluoromethyl, dideuteriomethyl, trifluoromethyl, trideuteriomethyl, cyclopropyl and cyclobutyl;

$R_{5a}$ is hydrogen or $C_{1-4}$ alkyl, $R_{5b}$ is selected from the group consisting of hydrogen, deuterium, hydroxy, $C_{1-4}$ alkyl, $C_{2-4}$ alkenyl, $C_{2-4}$ alkynyl, $C_{3-10}$ cycloalkyl, 3-10 membered heterocyclyl, $C_{5-8}$ aryl and 5-8 membered heteroaryl, or $R_{5a}$ and $R_{5b}$, together with the nitrogen atom directly attached thereto, form 4-8 membered heterocyclyl, or, $R_{5a}$ and $R_{5b}$, together with the nitrogen atom directly attached thereto, form the following group:

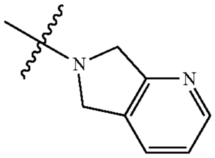

or

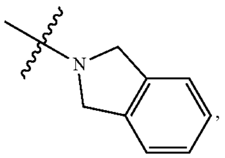

, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$ and —NR$_{12}$R$_{13}$, above groups are optionally more further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$ and —NR$_{12}$R$_{13}$; and $R_6$ is selected from the group consisting of hydrogen, deuterium, halogen, cyano, hydroxy, carboxyl, methyl, ethyl, isopropyl, difluoromethyl, dideuteriomethyl, trifluoromethyl, trideuteriomethyl, cyclopropyl, cyclobutyl, methoxy, ethyoxy and isopropoxy.

4. The compound of formula (I), the stereoisomer, prodrug or pharmaceutically acceptable salt thereof according to claim 1, wherein, the compound of formula (I) is a compound with the structure shown as formula (IIb):

(IIb)

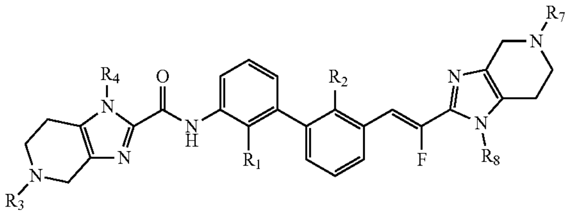

wherein, $R_1$ and $R_2$ are each independently selected from the group consisting of hydrogen, deuterium, halogen, cyano, hydroxy, carboxyl, $C_{1-4}$ alkyl, $C_{3-6}$ cycloalkyl and $C_{1-4}$ alkoxy;

$R_3$ is selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are optionally further substituted by one or more substituents selected from the group consisting of deuterium, halogen, cyano, $C_{1-4}$ alkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, —NR$_{12}$R$_{13}$, —C(=NR$_{12}$)R$_{11}$, —N(R$_{12}$)—C(=NR$_{13}$)R$_{11}$, —C(O)NR$_{12}$R$_{13}$ and —N(R$_{12}$)—C(O)R$_{11}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, —NR$_{12}$R$_{13}$, —C(=NR$_{12}$)R$_{11}$, —N(R$_{12}$)—C(=NR$_{13}$)R$_{11}$, —C(O)NR$_{12}$R$_{13}$ and —N(R$_{12}$)—C(O)R$_{11}$;

$R_4$ is selected from the group consisting of hydrogen, deuterium, hydroxy, methyl, ethyl, isopropyl, difluoromethyl, dideuteriomethyl, trifluoromethyl, trideuteriomethyl, cyclopropyl and cyclobutyl;

$R_7$ is selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are optionally further substituted by one or more substituents selected from the group consisting of deuterium, halogen, cyano, $C_{1-4}$ alkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, —NR$_{12}$R$_{13}$, —C(=NR$_{12}$)R$_{11}$, —N(R$_{12}$)—C(=NR$_{13}$)R$_{11}$, —C(O)NR$_{12}$R$_{13}$ and —N(R$_{12}$)—C(O)R$_{11}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —S(O)$_r$R$_9$, —O—R$_{10}$, —C(O)OR$_{10}$, —C(O)R$_{11}$, —O—C(O)R$_{11}$, —NR$_{12}$R$_{13}$, —C(=NR$_{12}$)R$_{11}$, —N(R$_{12}$)—C(=NR$_{13}$)R$_{11}$, —C(O)NR$_{12}$R$_{13}$ and —N(R$_{12}$)—C(O)R$_{11}$; and $R_8$ is selected from the group consisting of hydrogen, deuterium, hydroxy, methyl, ethyl, isopropyl, difluoromethyl, dideuteriomethyl, trifluoromethyl, trideuteriomethyl, cyclopropyl and cyclobutyl.

5. The compound of formula (I), the stereoisomer, prodrug or pharmaceutically acceptable salt thereof according to claim 1, wherein, $R_1$ and $R_2$ are each independently selected from the group consisting of hydrogen, deuterium, fluorine, chlorine, methyl, and cyclopropyl;

$R_3$ is selected from the group consisting of hydrogen, deuterium, $C_{1-4}$ alkyl, $C_{3-8}$ cycloalkyl and 3-8 membered heterocyclyl, above groups are optionally further substituted by one or more substituents selected from the group consisting of deuterium, halogen, cyano, $C_{1-4}$ alkyl, $C_{3-8}$ cycloalkyl, 3-8 membered heterocyclyl, =O, —O—R$_{10}$, —C(O)OR$_{10}$, —C(O)R$_{11}$ and —O—C(O)R$_{11}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, =O, —O—R$_{10}$, —C(O)OR$_{10}$, —C(O)R$_{11}$, and —O—C(O)R$_{11}$; and $R_4$ is selected from the group consisting of hydrogen, deuterium, methyl, difluoromethyl, dideuteriomethyl, trifluoromethyl, trideuteriomethyl, and cyclopropyl.

6. The compound of formula (I), the stereoisomer, prodrug or pharmaceutically acceptable salt thereof according to claim 3, wherein, $R_{5a}$ is hydrogen or methyl, $R_{5b}$ is selected from the group consisting of hydrogen, deuterium, $C_{1-4}$ alkyl, $C_{3-10}$ cycloalkyl and 3-10 membered heterocyclyl, or $R_{5a}$ and $R_{5b}$, together with the nitrogen atom directly attached thereto, form 4-8 membered nitrogen-containing heterocyclyl, or $R_{5a}$ and $R_{5b}$, together with the nitrogen atom directly attached thereto, form the following group:

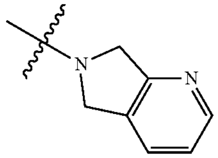

or

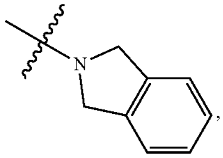

, above groups are optionally further substituted by one or more substituents selected from the group consisting of deuterium, halogen, cyano, $C_{1-4}$ alkyl, $C_{3-8}$ cycloalkyl, 3-8 membered heterocyclyl, =O, —O—$R_{10}$, —C(O)O$R_{10}$, —C(O)$R_{11}$, —O—C(O)$R_{11}$ and —N$R_{12}R_{13}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, =O, —O—$R_{10}$, —C(O)O$R_{10}$, —C(O)$R_{11}$, —O—C(O)$R_{11}$ and —N$R_{12}R_{13}$; and $R_6$ is selected from the group consisting of hydrogen, deuterium, methyl, difluoromethyl, dideuteriomethyl, trifluoromethyl, trideuteriomethyl, cyclopropyl, methoxy, and ethyoxy.

7. The compound of formula (I), the stereoisomer, prodrug or pharmaceutically acceptable salt thereof according to claim 4, wherein, $R_7$ is selected from the group consisting of hydrogen, deuterium, $C_{1-4}$ alkyl, $C_{3-8}$ cycloalkyl and 3-8 membered heterocyclyl, above groups are optionally further substituted by one or more substituents selected from the group consisting of deuterium, halogen, cyano, $C_{1-4}$ alkyl, $C_{3-8}$ cycloalkyl, 3-8 membered heterocyclyl, =O, —O—$R_{10}$, —C(O)O$R_{10}$, —C(O)$R_{11}$ and —O—C(O)$R_{11}$, above groups are optionally more further substituted by one or more substituents selected from the group consisting of deuterium, halogen, cyano, $C_{1-4}$ alkyl, $C_{1-4}$ haloalkyl, $C_{1-4}$ deuterioalkyl, $C_{3-8}$ cycloalkyl, 3-8 membered heterocyclyl, =O, —O—$R_{10}$, —C(O)O$R_{10}$, —C(O)$R_{11}$ and —O—C(O)$R_{11}$; and $R_8$ is selected from the group consisting of hydrogen, deuterium, methyl, difluoromethyl, dideuteriomethyl, trifluoromethyl, trideuteriomethyl, and cyclopropyl wherein, $R_{10}$ and $R_{11}$ are defined as in claim 4.

8. The compound of formula (I), the stereoisomer, prodrug or pharmaceutically acceptable salt thereof according to claim 3, wherein, each $R_9$ is independently selected from the group consisting of hydrogen, deuterium, hydroxy, $C_{1-4}$ alkyl, $C_{2-4}$ alkenyl, $C_{3-6}$ cycloalkyl, 3-6 membered heterocyclyl, $C_{5-8}$ aryl, 5-8 membered heteroaryl and —N$R_{12}R_{13}$, above groups are optionally further substituted by one or more substituents selected from the group consisting of deuterium, halogen, hydroxy, oxo, cyano, $C_{1-4}$ alkyl, $C_{1-4}$ alkoxy, $C_{3-6}$ cycloalkyl, $C_{3-6}$ cycloalkyloxy, 3-8 membered heterocyclyl, 3-8 membered heterocyclyloxy, $C_{5-8}$ aryl, $C_{5-8}$ aryloxy, 5-8 membered heteroaryl, 5-8 membered heteroaryloxy and —N$R_{12}R_{13}$;

each $R_{10}$ is independently selected from the group consisting of hydrogen, deuterium, $C_{1-4}$ alkyl, $C_{2-4}$ alkenyl, $C_{3-4}$ cycloalkyl, 3-6 membered heterocyclyl, $C_{5-8}$ aryl and 5-8 membered heteroaryl, above groups are optionally further substituted by one or more substituents selected from the group consisting of deuterium, halogen, hydroxy, oxo, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —N$R_{12}R_{13}$;

each $R_{11}$ is independently selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —N$R_{12}R_{13}$, above groups are optionally further substituted by one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy and —N$R_{12}R_{13}$;

each of $R_{12}$ and $R_{13}$ is independently selected from the group consisting of hydrogen, deuterium, hydroxy, $C_{1-4}$ alkyl, $C_{2-4}$ alkenyl, $C_{2-4}$ alkynyl, $C_{3-6}$ cycloalkyl, 3-6 membered heterocyclyl, $C_{5-8}$ aryl, 5-8 membered heteroaryl, sulfonyl, methanesulfonyl, isopropylsulfonyl, cyclopropylsulfonyl, p-toluenesulfonyl, amino, $C_{1-4}$ monoalkylamino, di($C_{1-4}$ alkyl)amino and $C_{1-4}$ alkanoyl, above groups are optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy, amino, $C_{1-4}$ monoalkylamino, di($C_{1-4}$ alkyl)amino and $C_{1-4}$ alkanoyl;

or $R_{12}$ and $R_{13}$, together with the nitrogen atom directly attached thereto, form 4-6 membered heterocyclyl, above group is optionally further substituted by one or more substituents selected from the group consisting of deuterium, halogen, hydroxy, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{5-8}$ aryl, $C_{5-8}$ aryloxy, 5-8 membered heteroaryl, 5-8 membered heteroaryloxy, amino, $C_{1-4}$ monoalkylamino, di($C_{1-4}$ alkyl)amino and $C_{1-4}$ alkanoyl.

9. The compound of formula (I), the stereoisomer, prodrug or pharmaceutically acceptable salt thereof according to claim 1, which is selected from the group consisting of the following compounds:

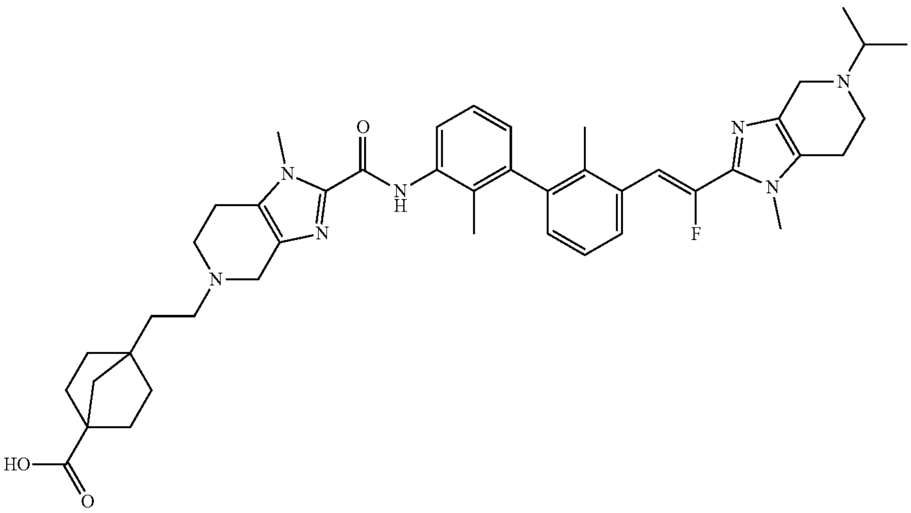
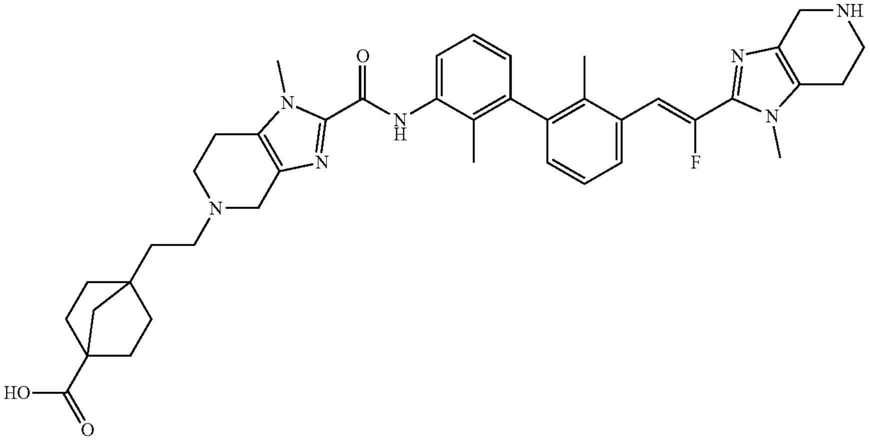
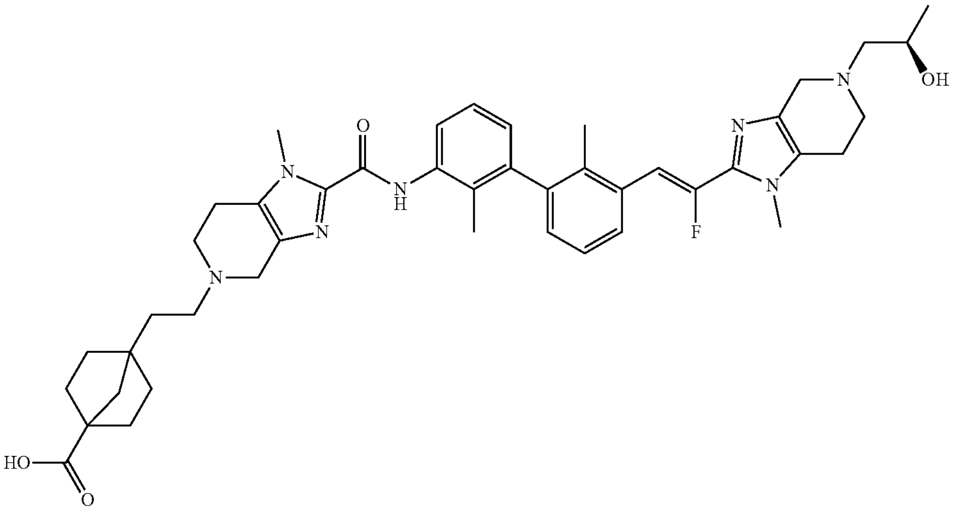

-continued
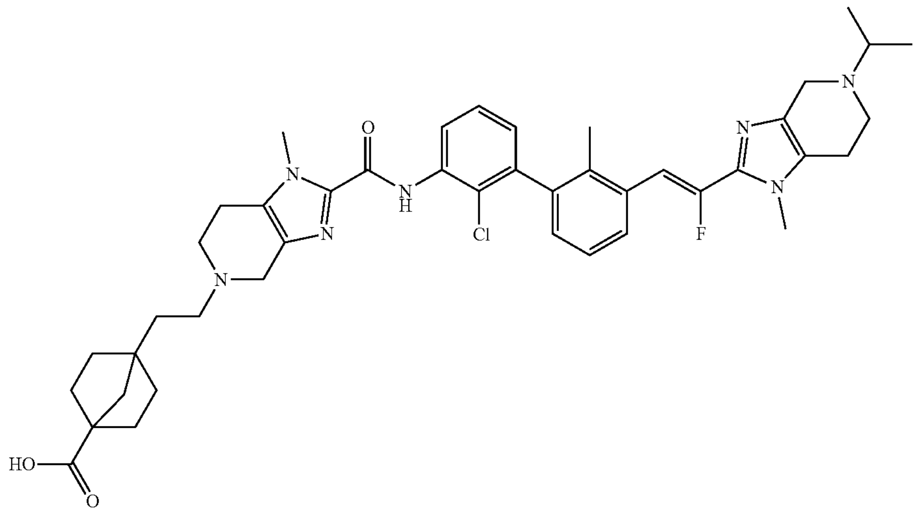
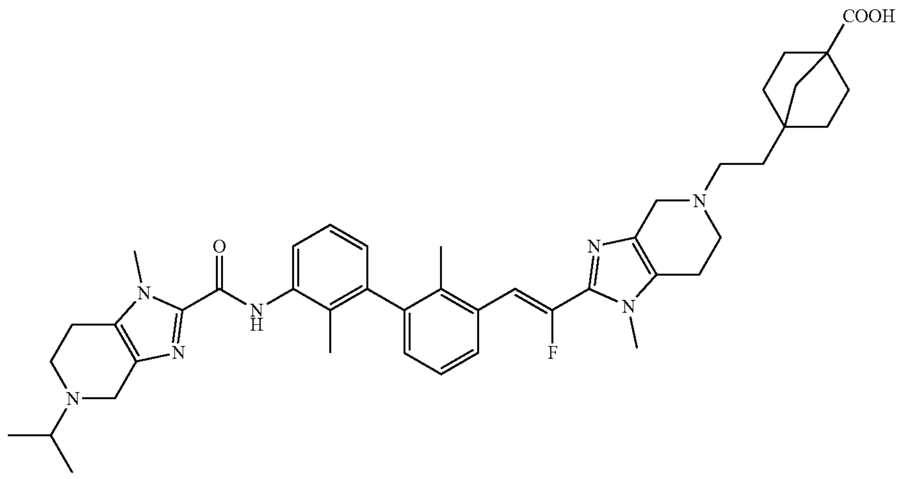
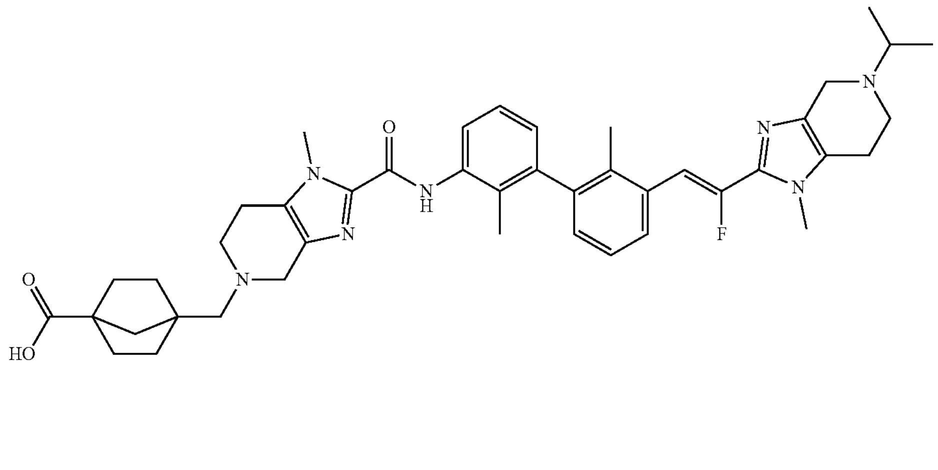

-continued
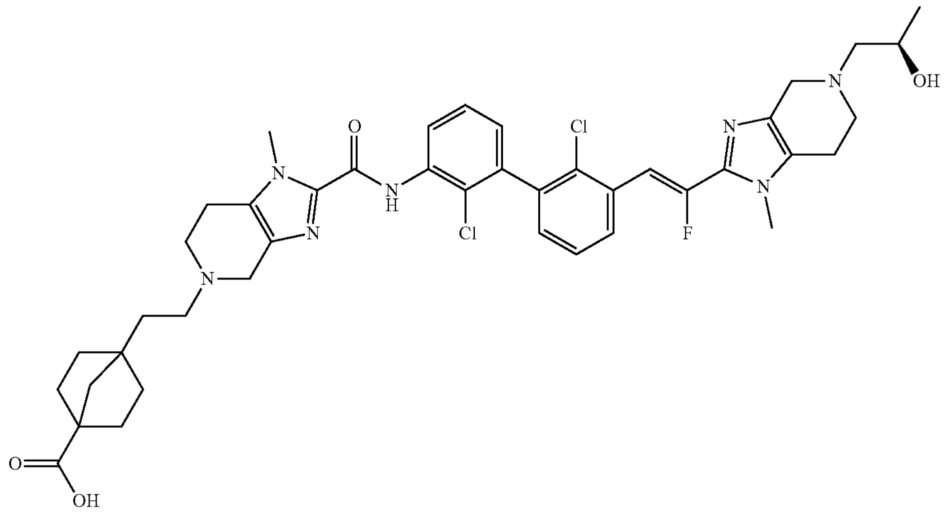
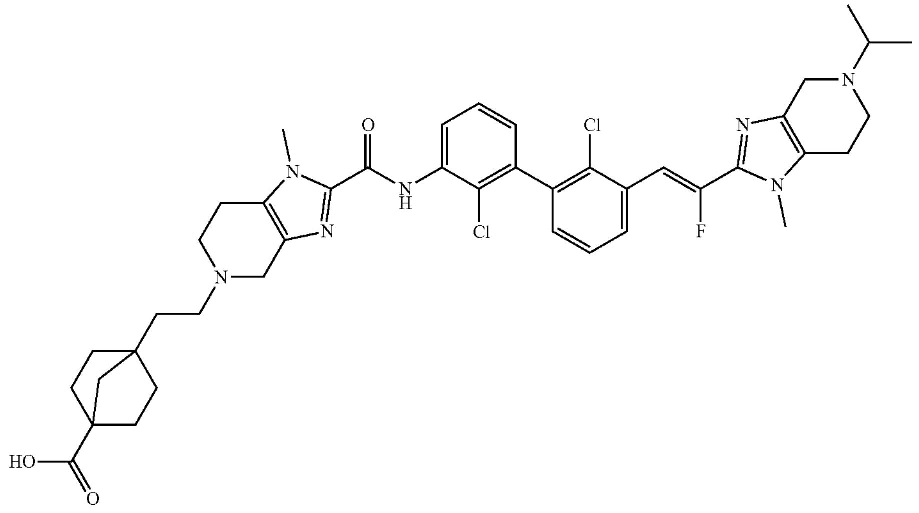
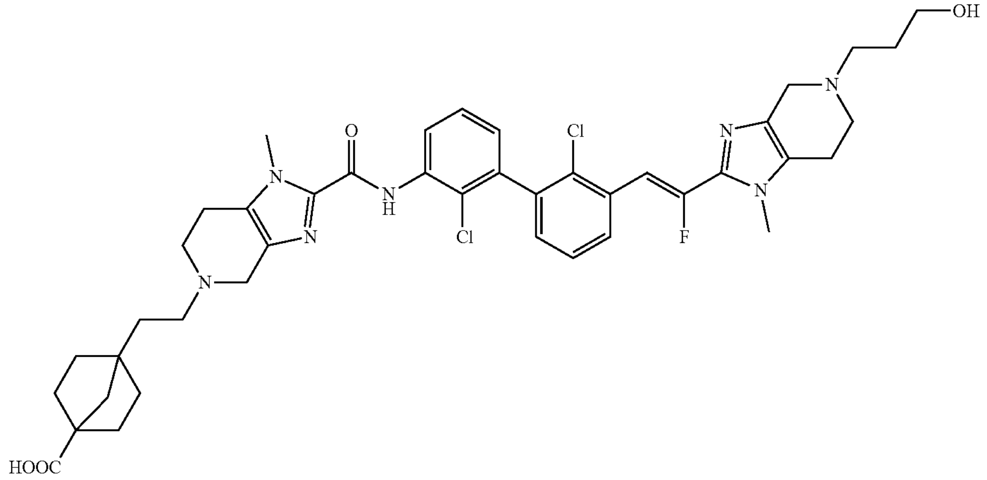

-continued
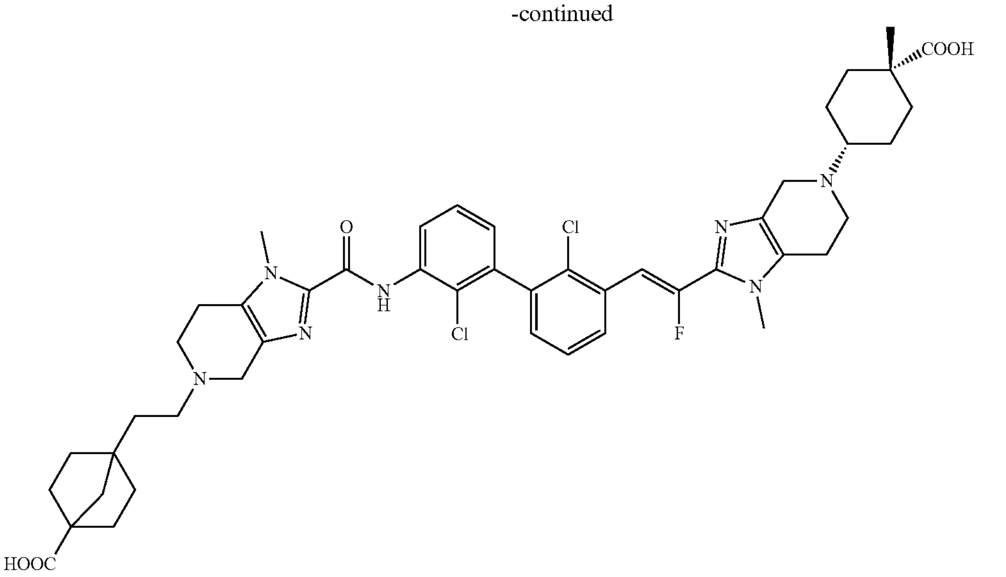
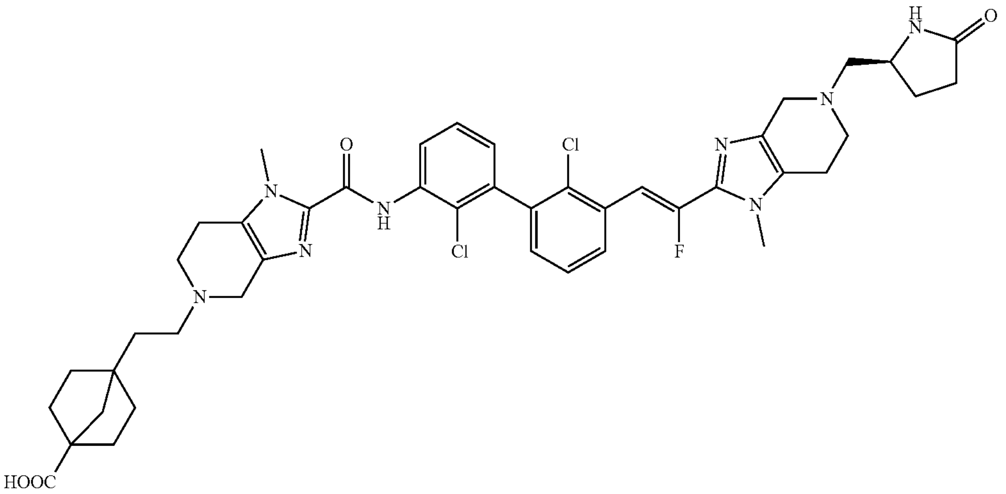
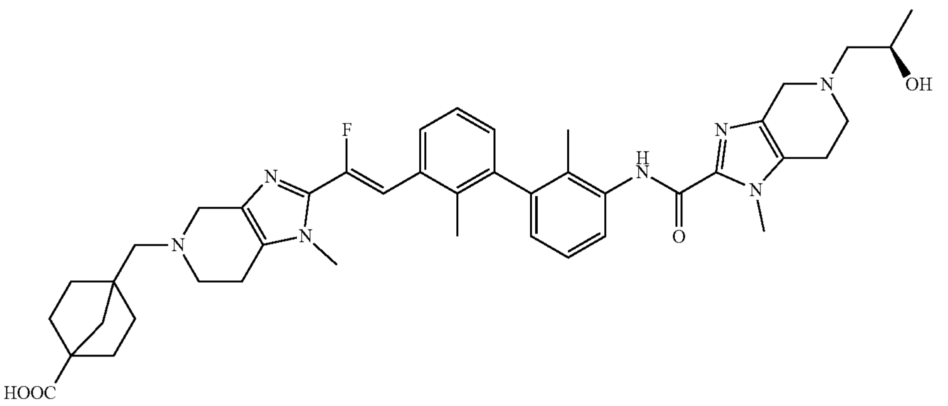

-continued
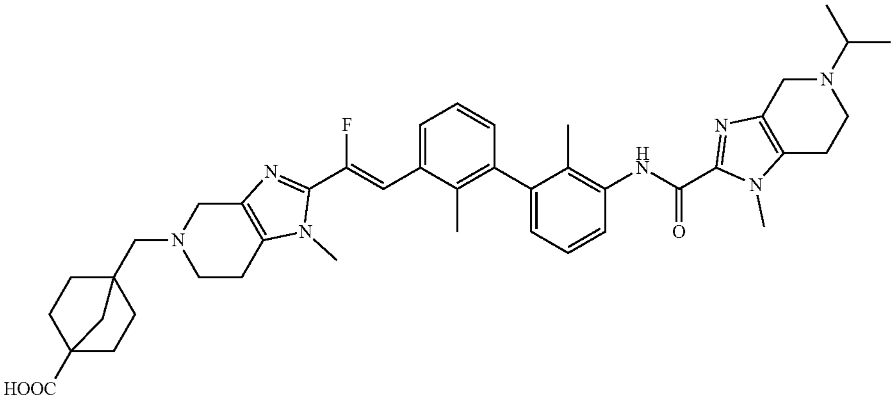
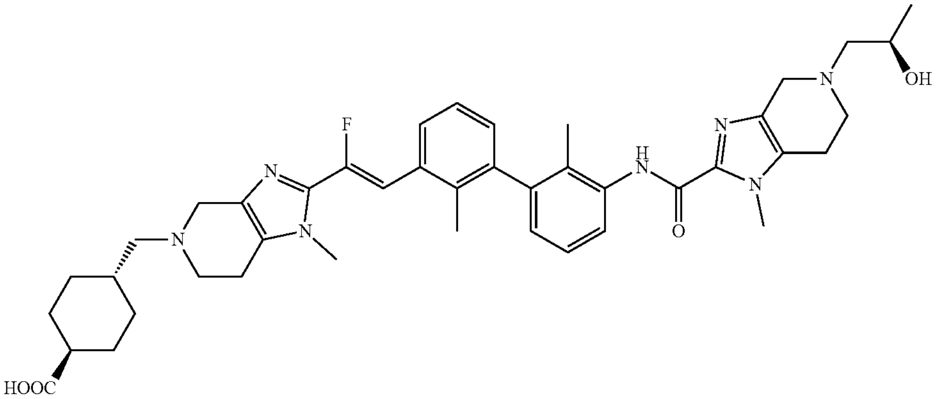
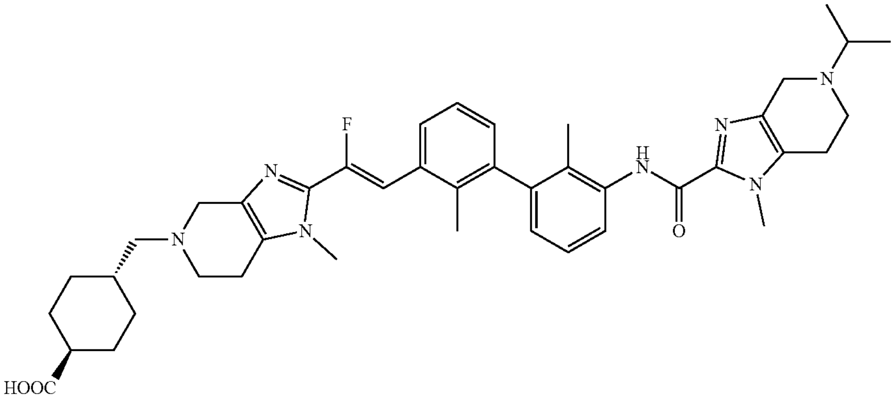
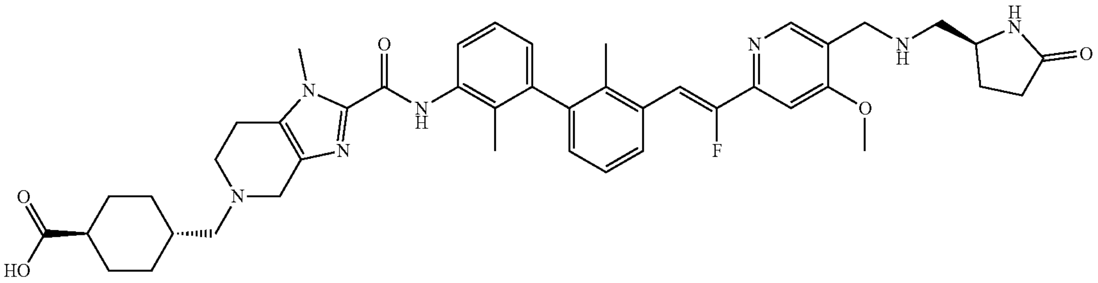

-continued
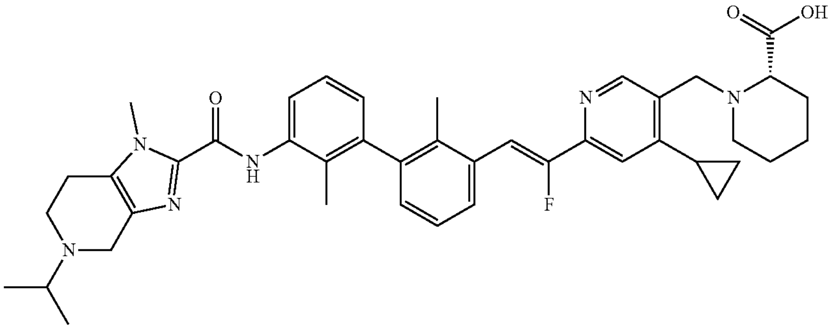
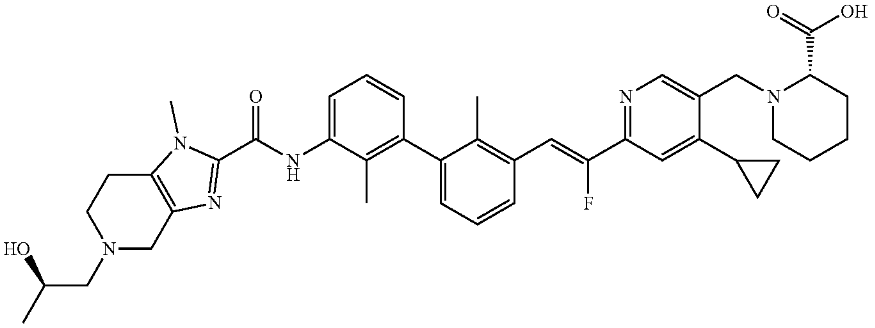
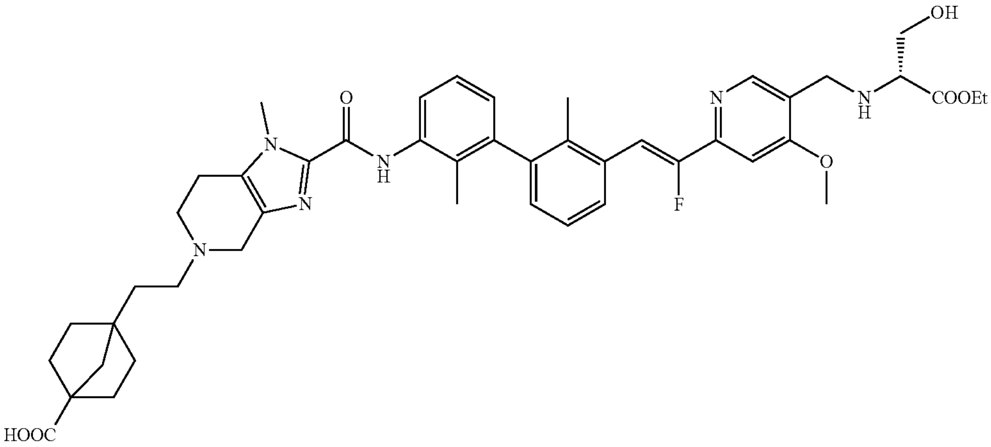
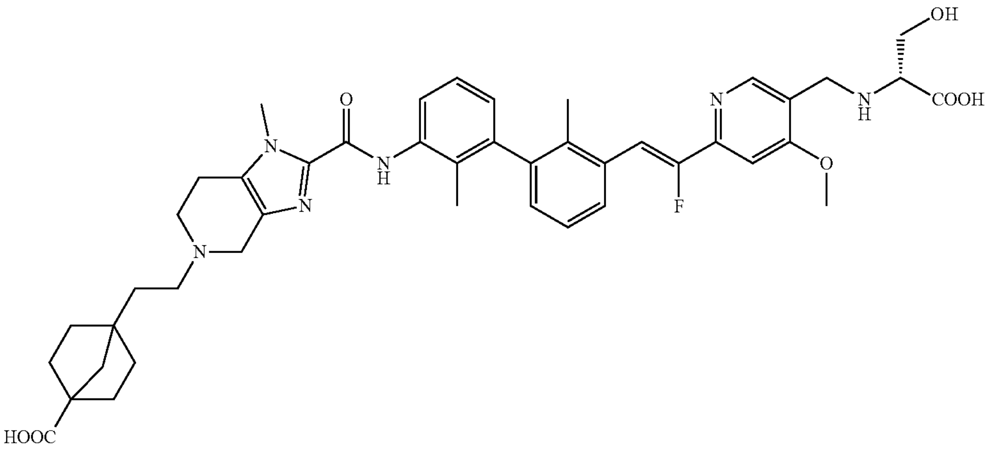

-continued
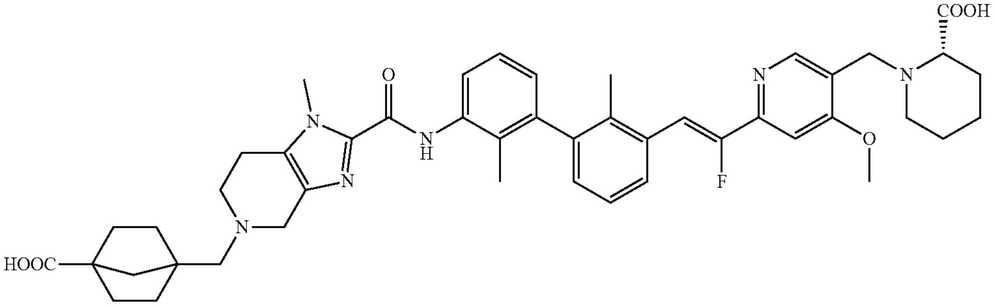
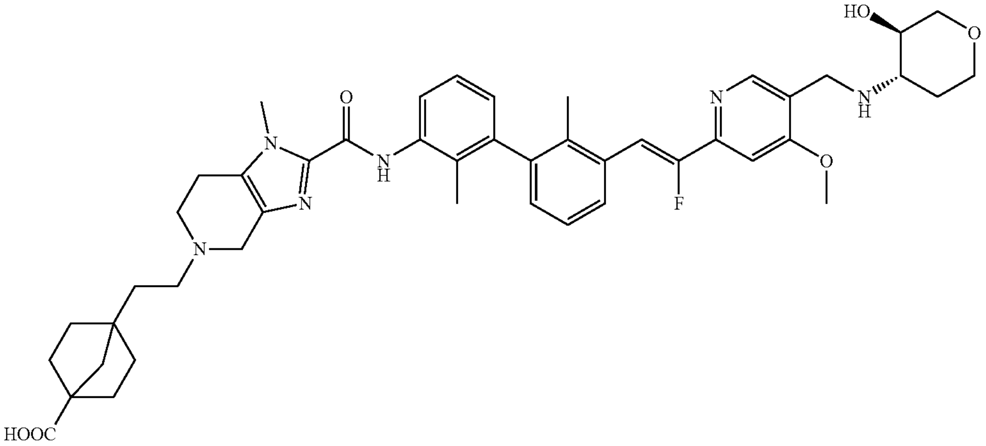
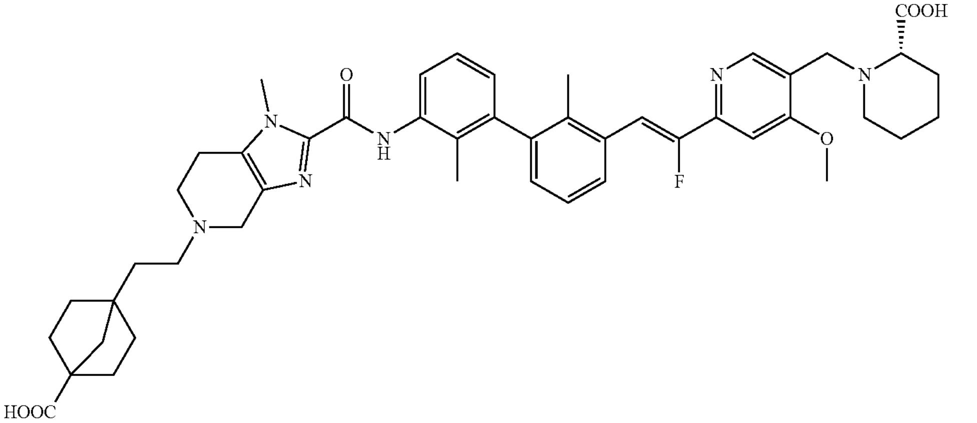
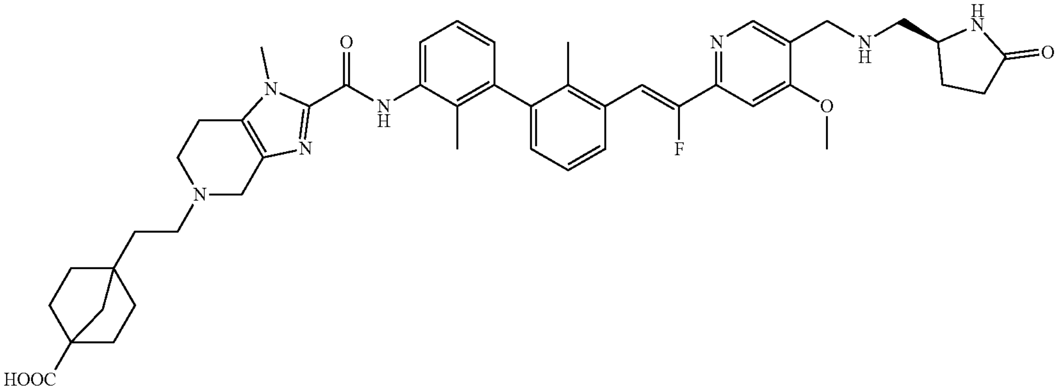

-continued
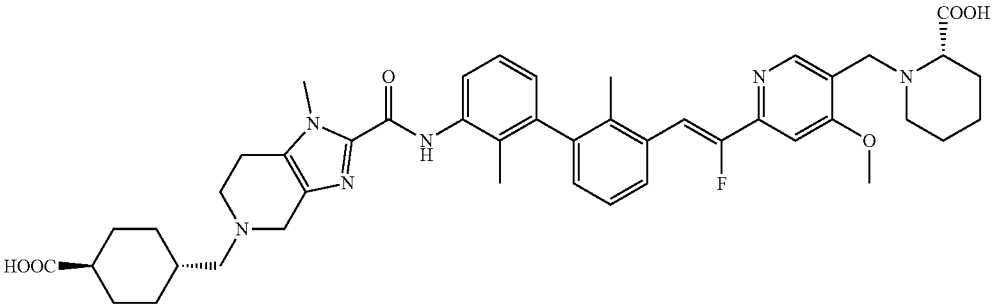
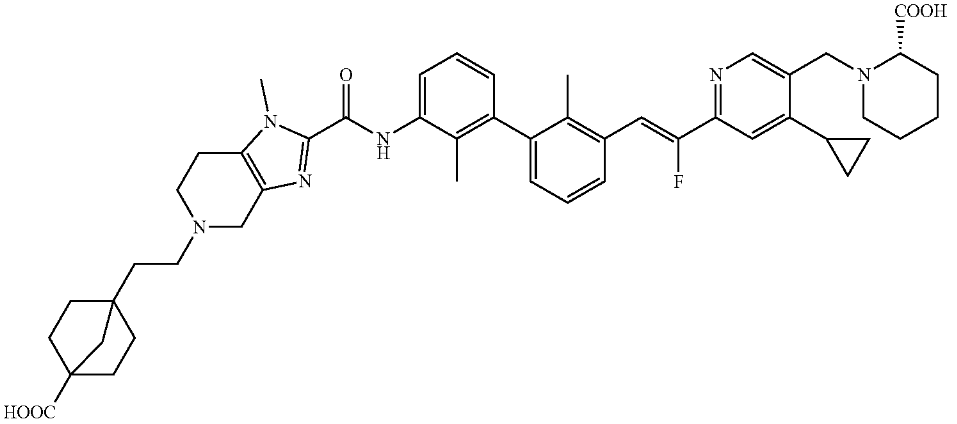
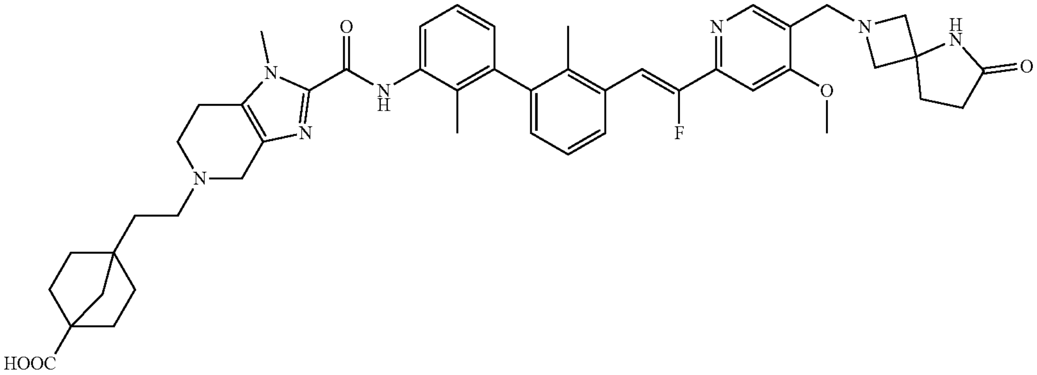
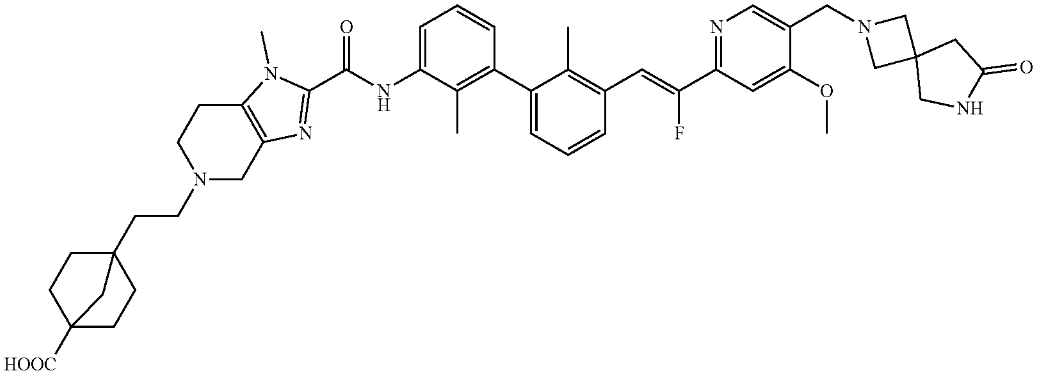

-continued
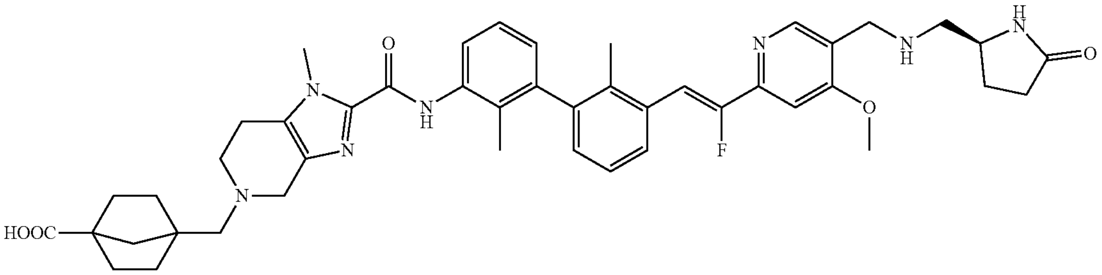
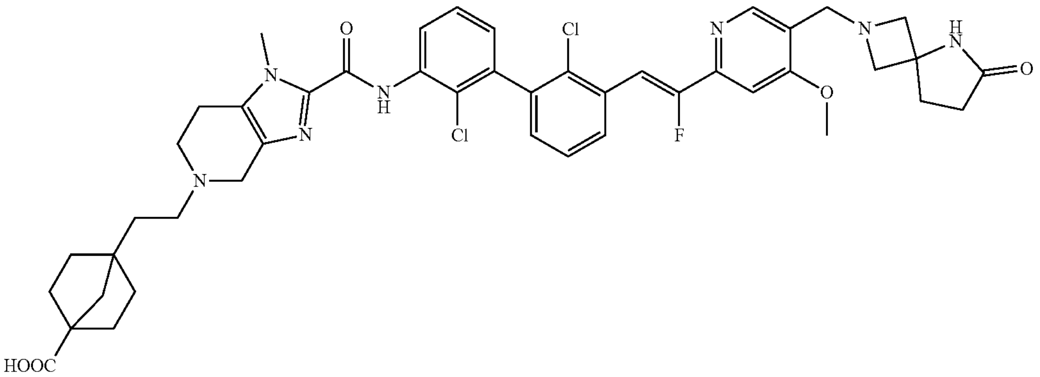
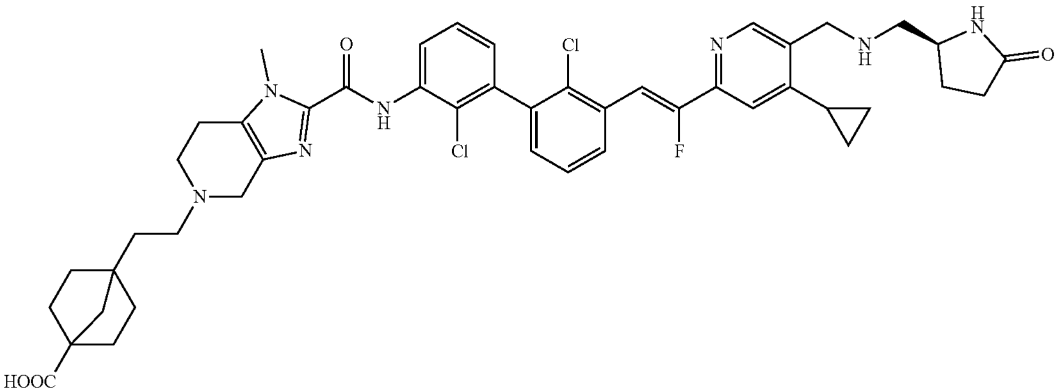
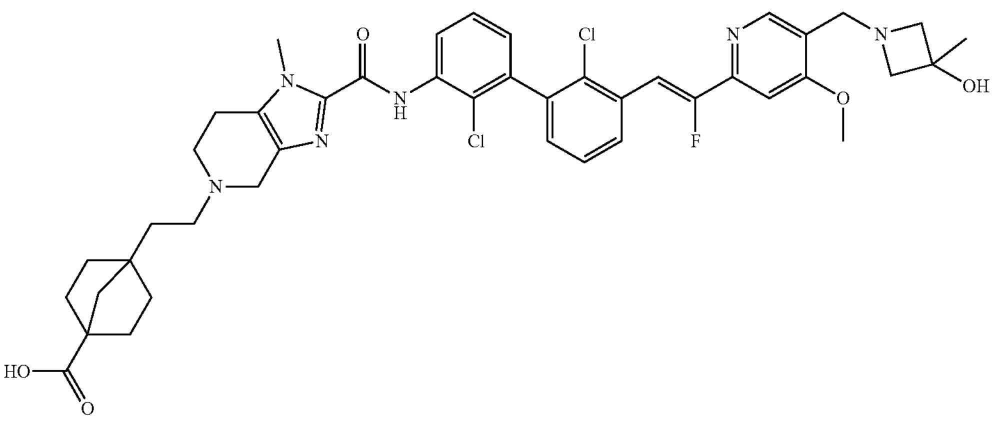

-continued
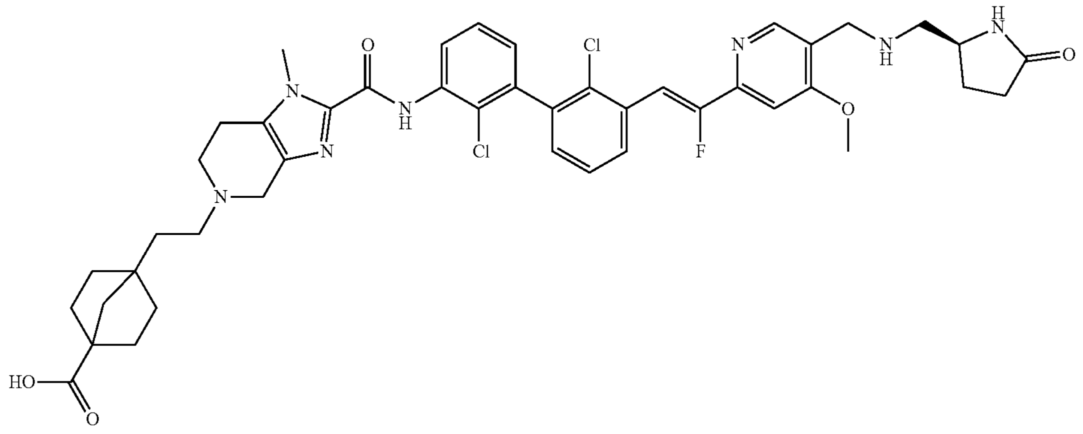
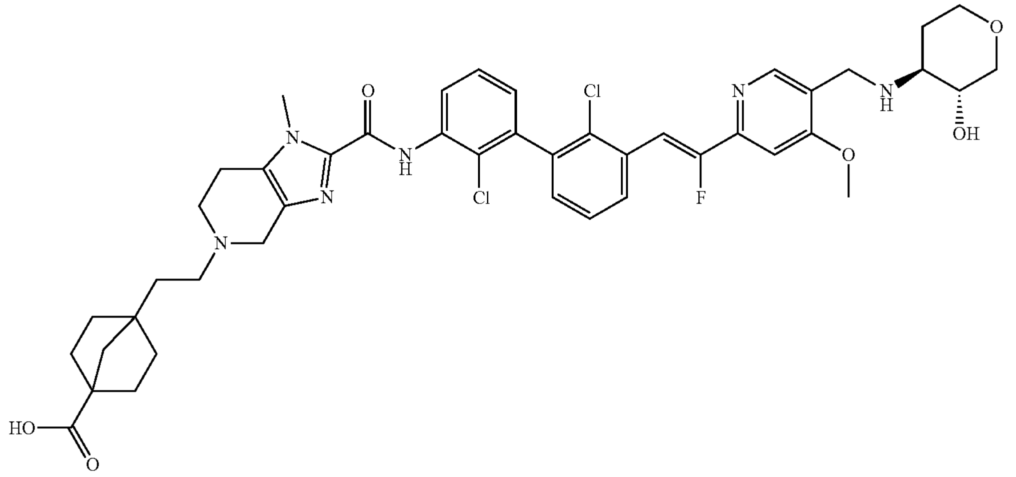
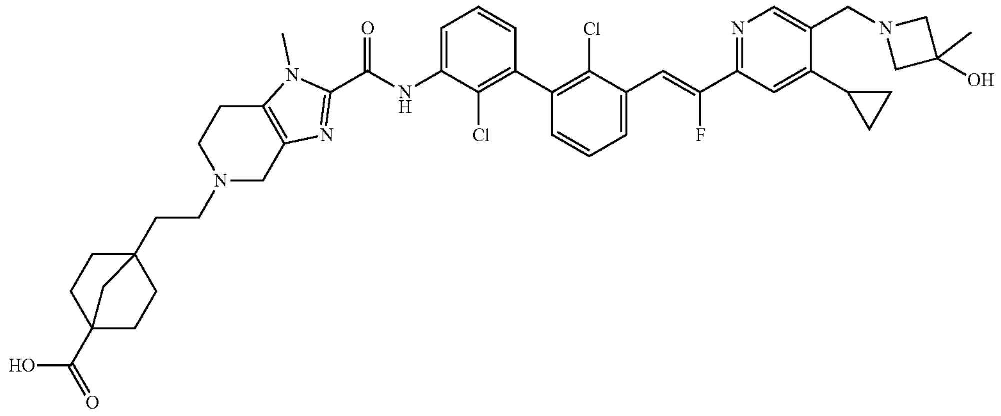

-continued
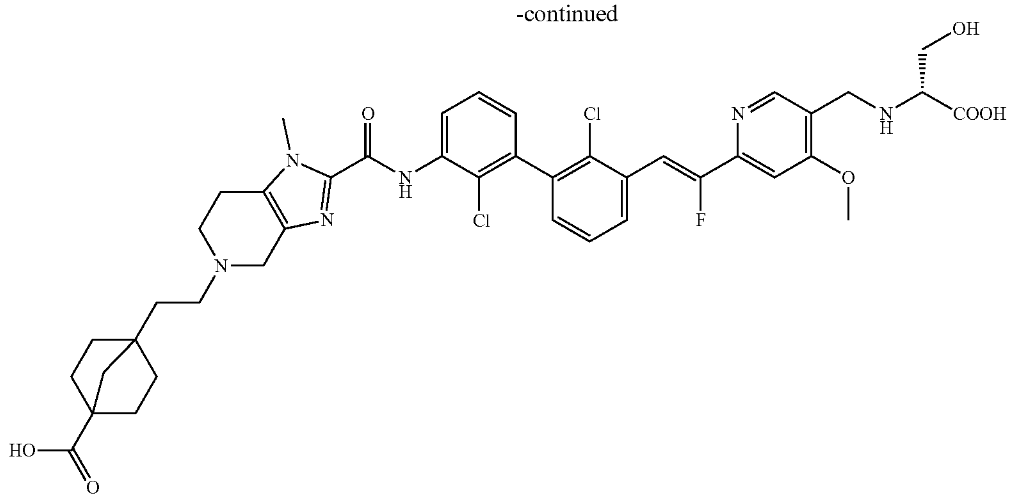
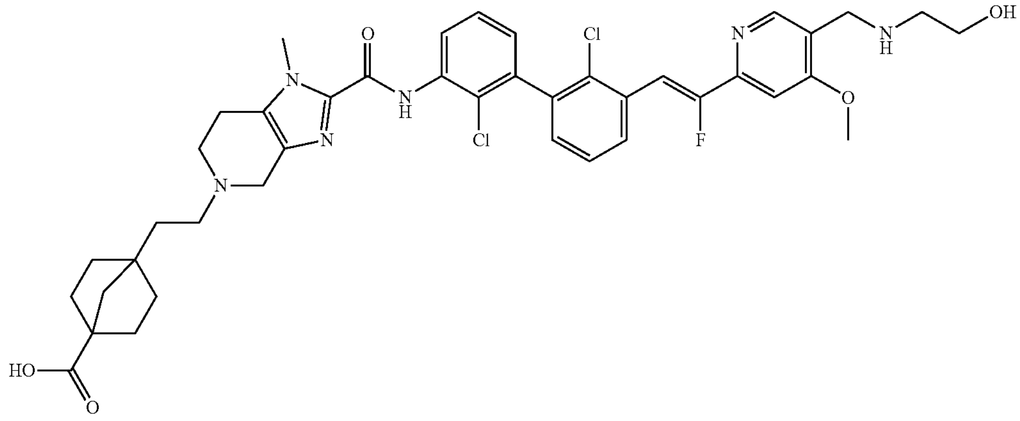
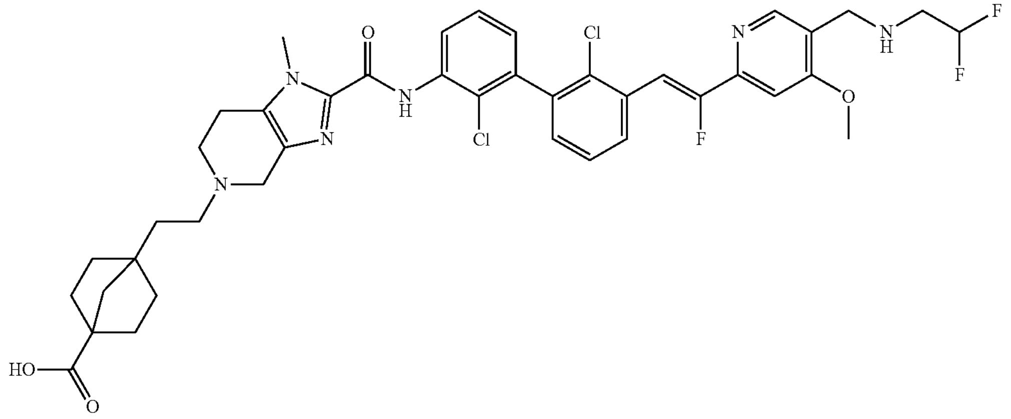
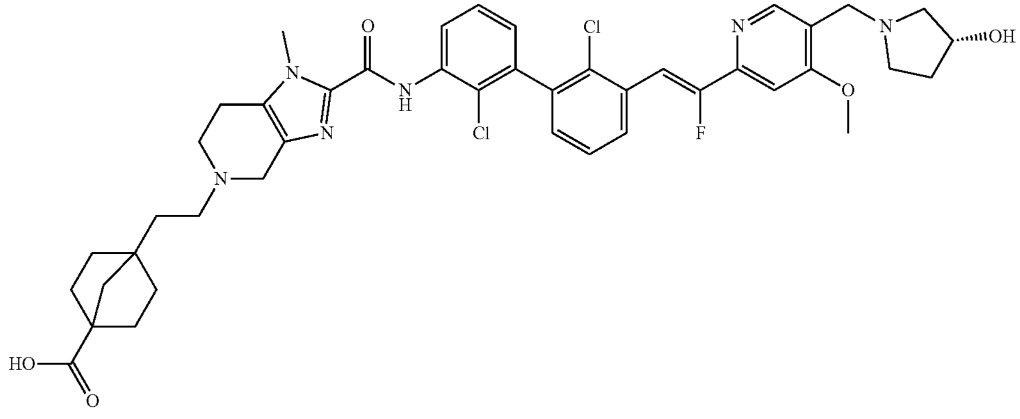

-continued
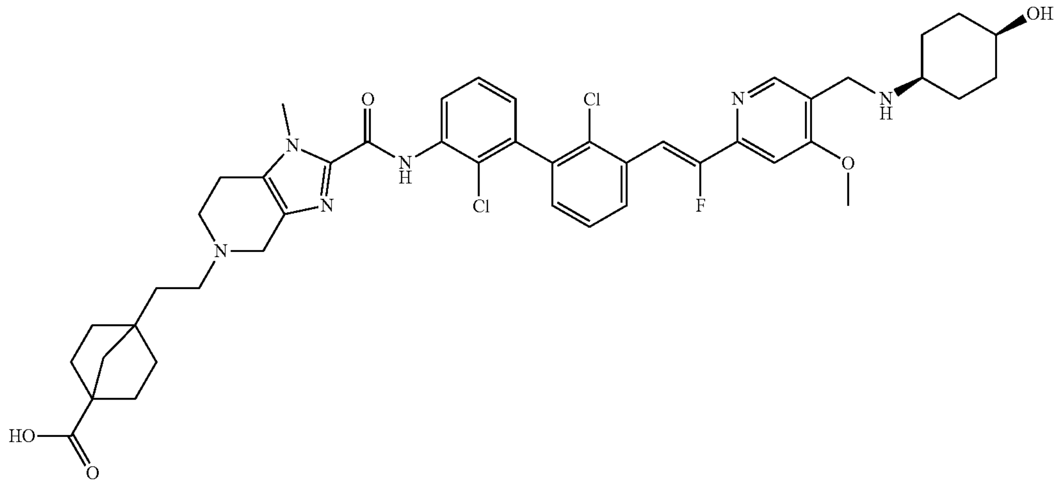
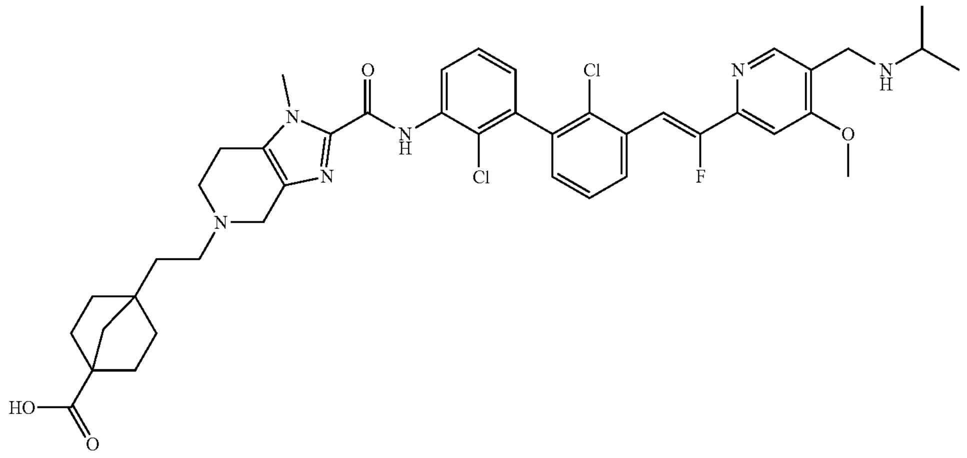
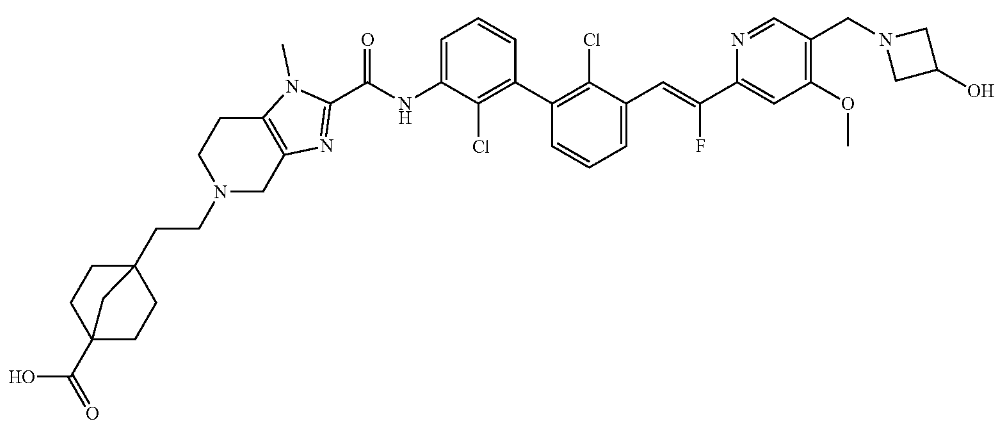

-continued
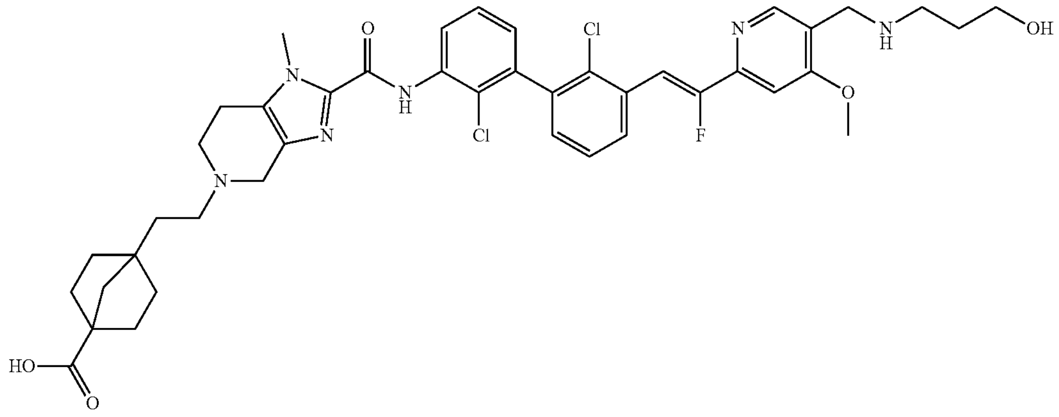
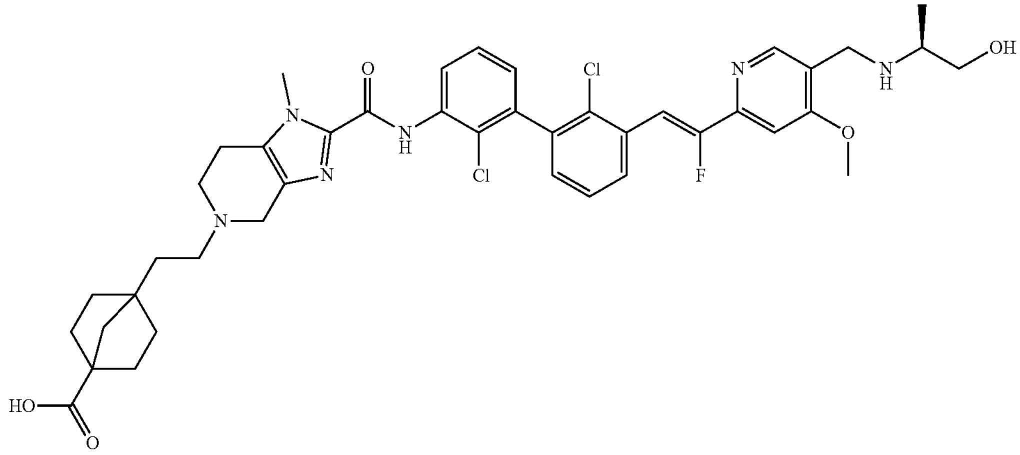
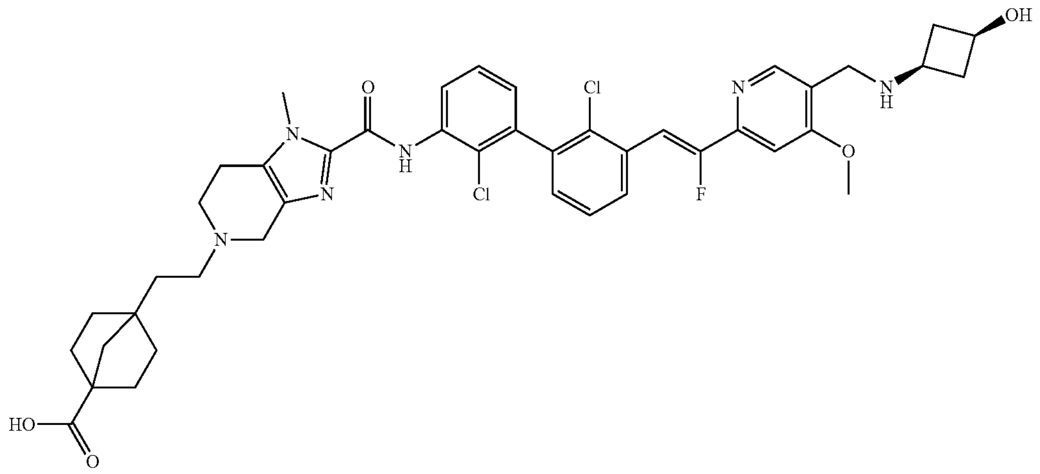

-continued
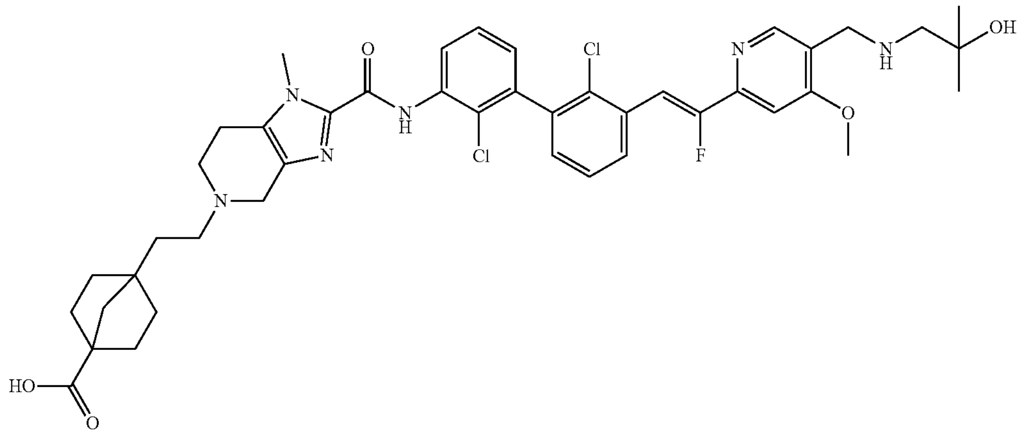
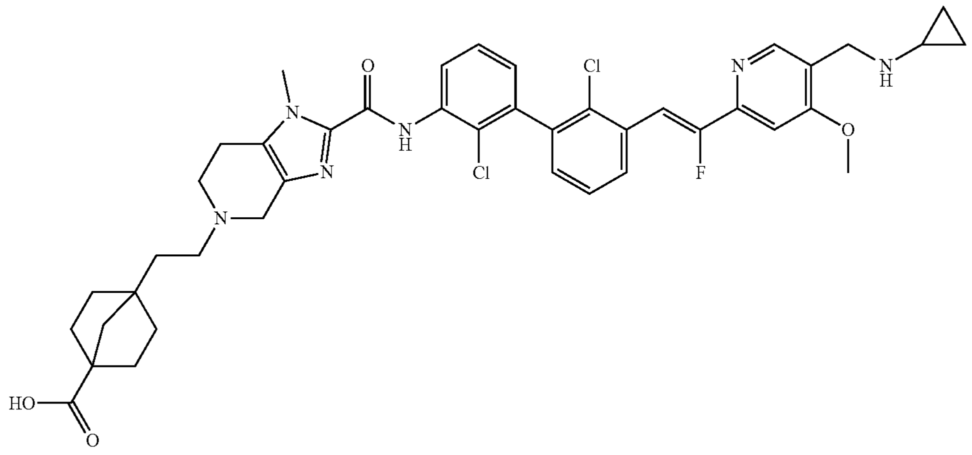
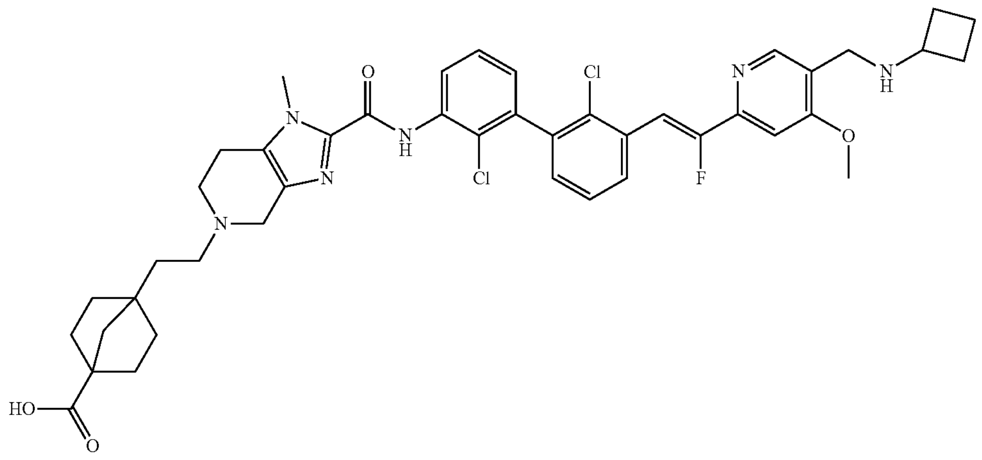

-continued
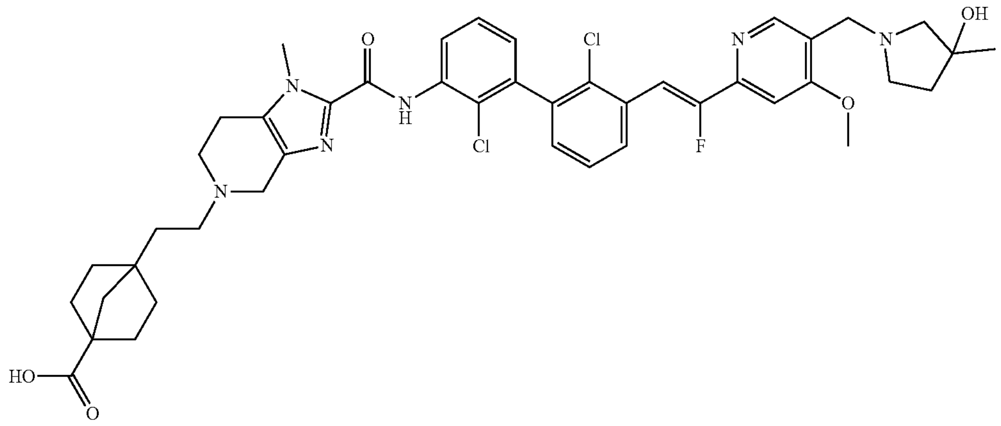
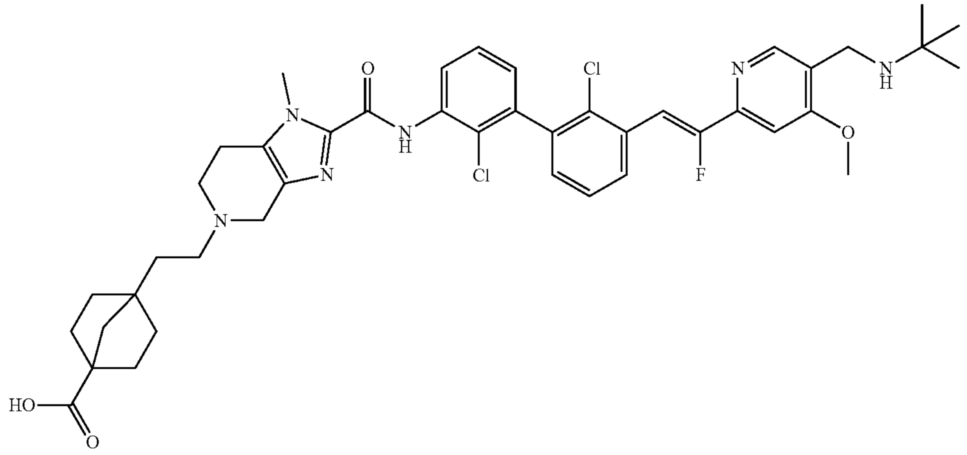
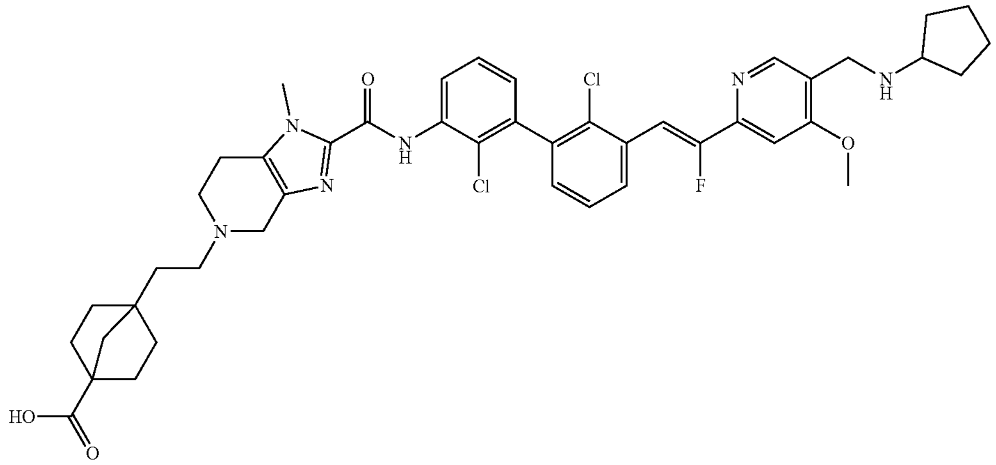

-continued
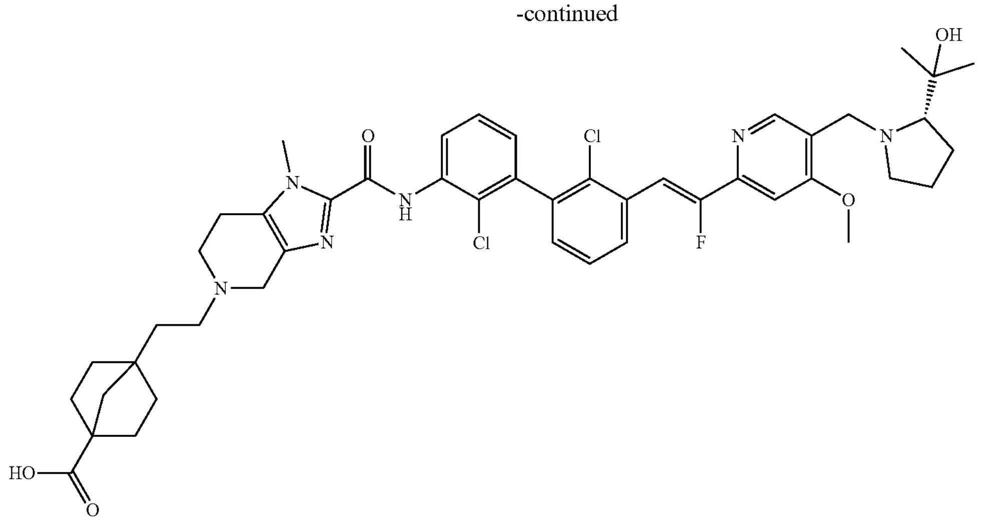
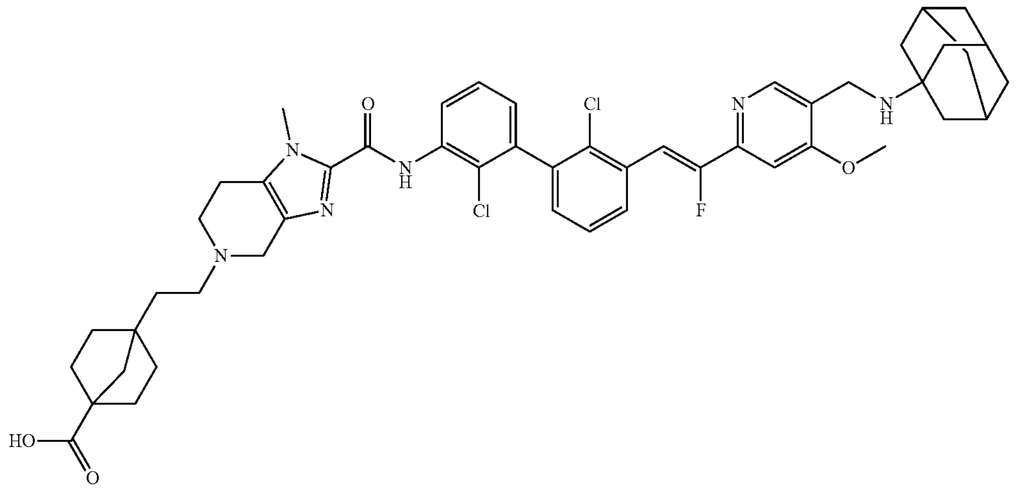
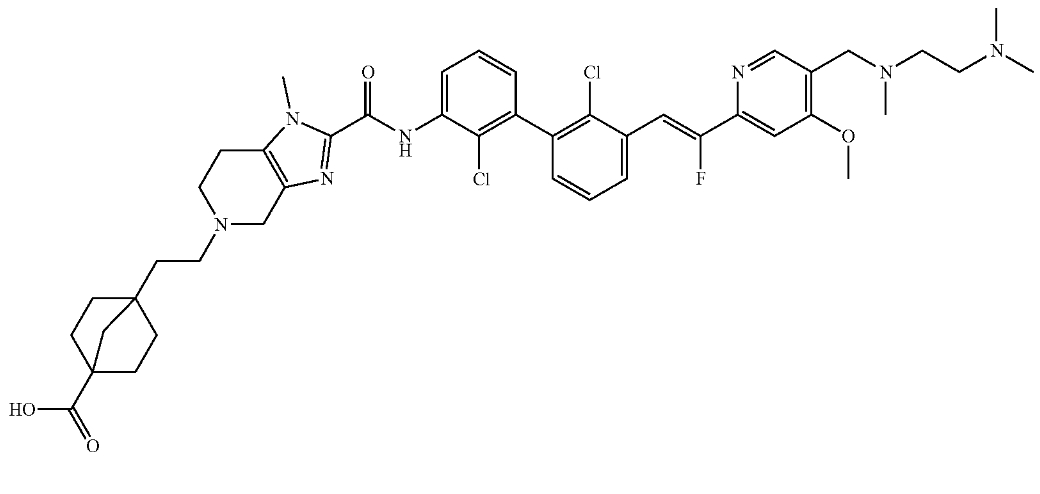

-continued
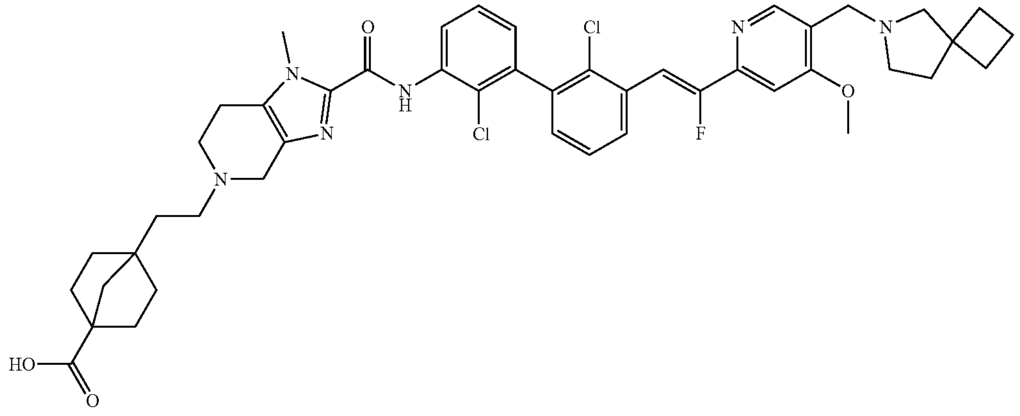
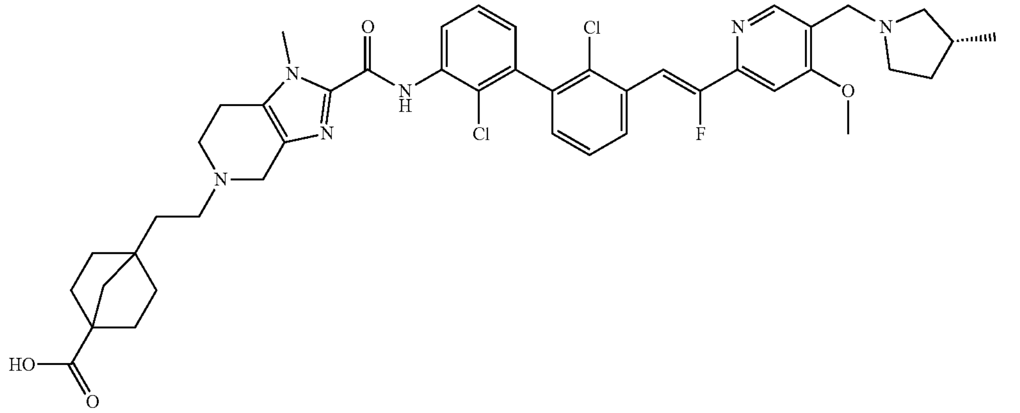
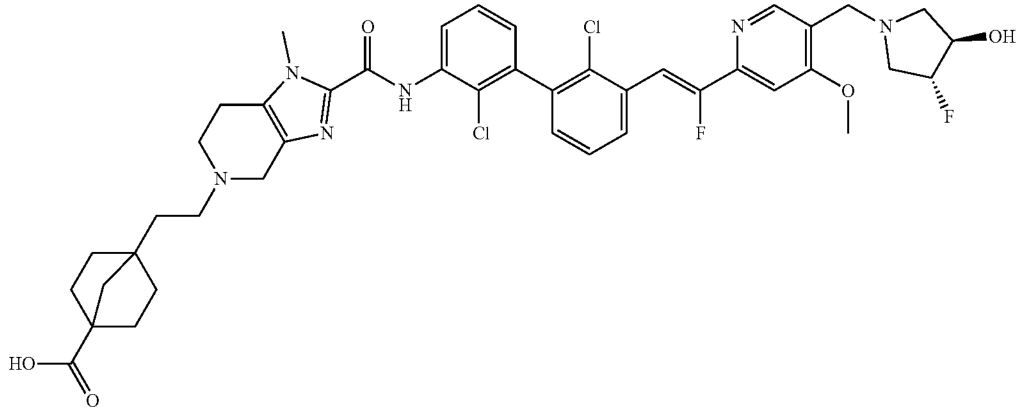
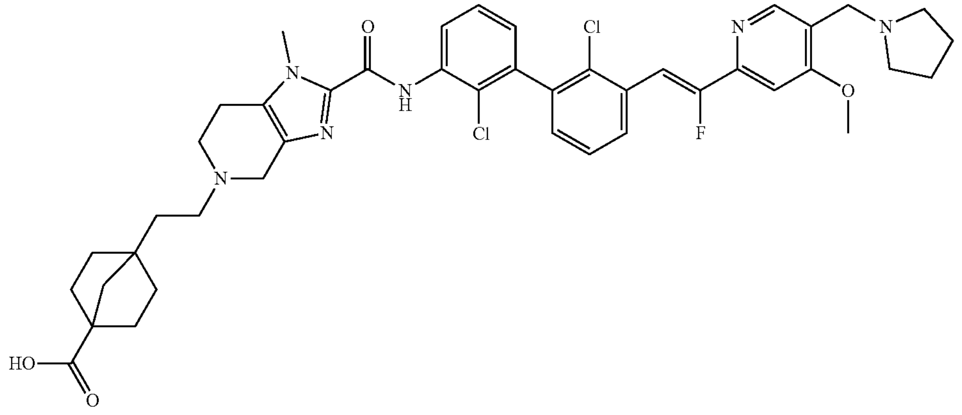

-continued
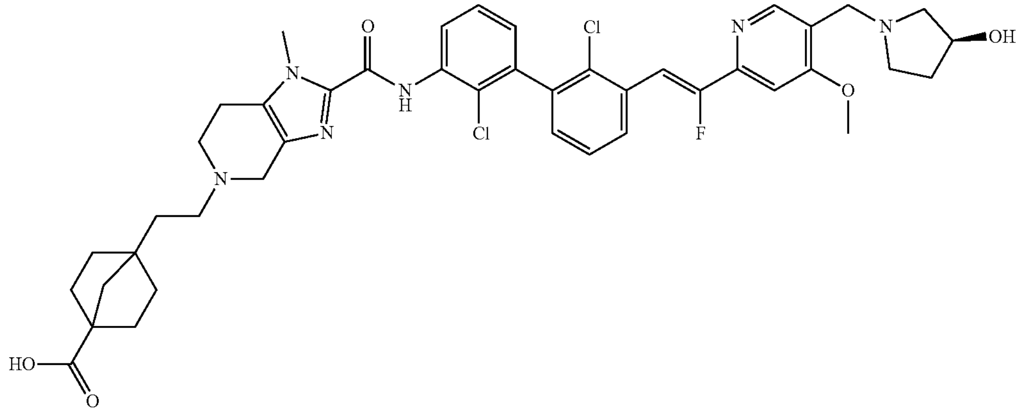
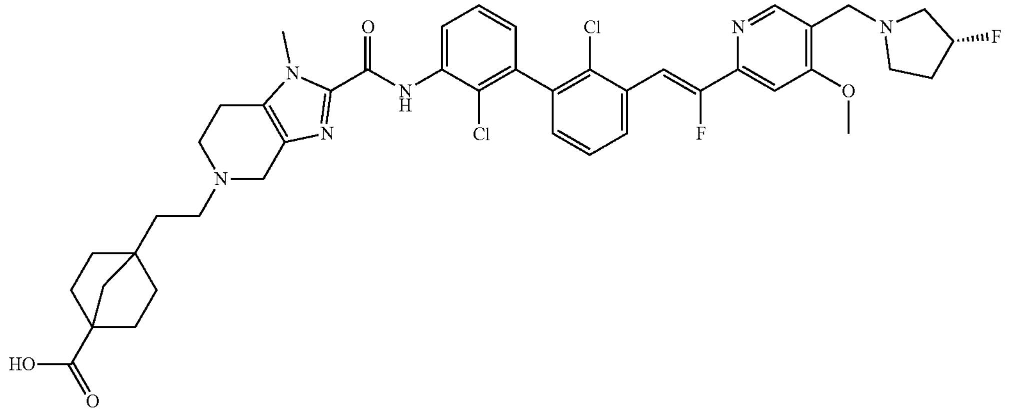
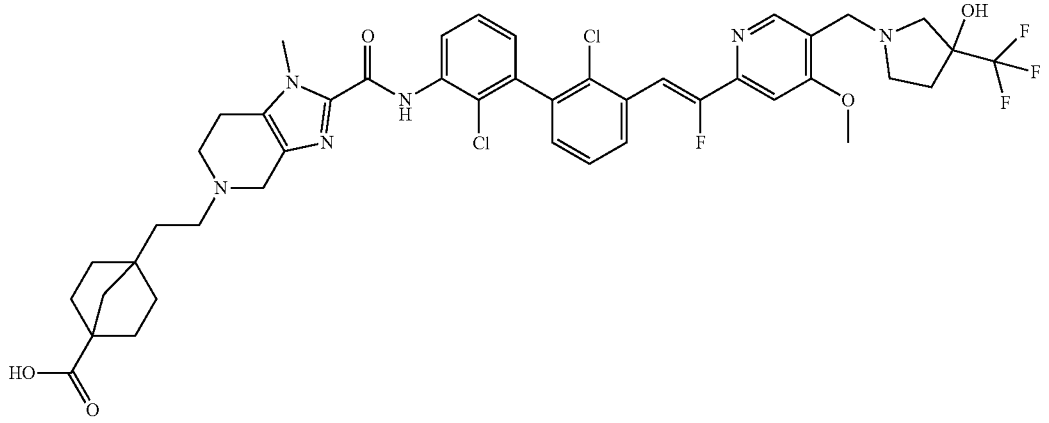
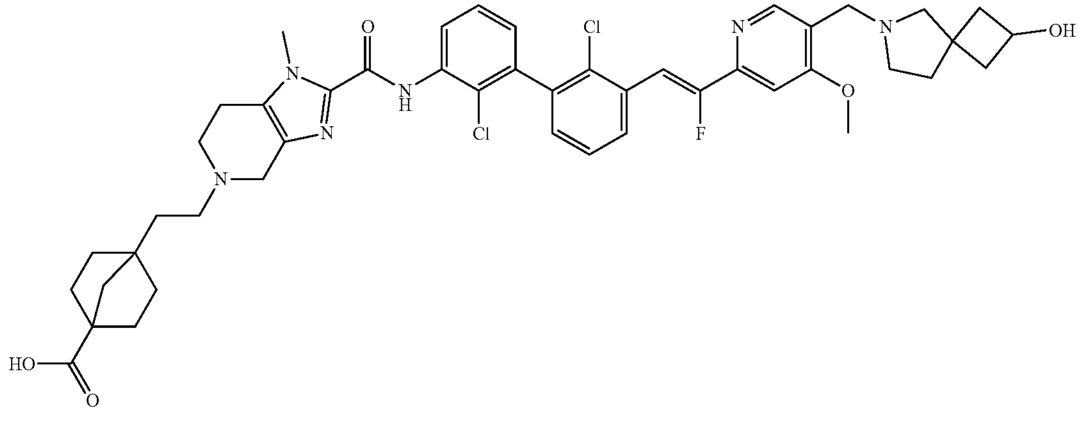

-continued
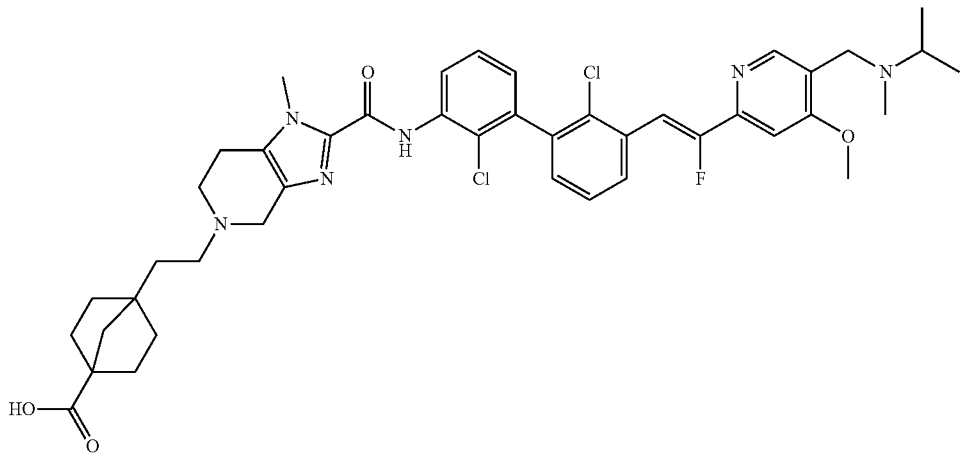
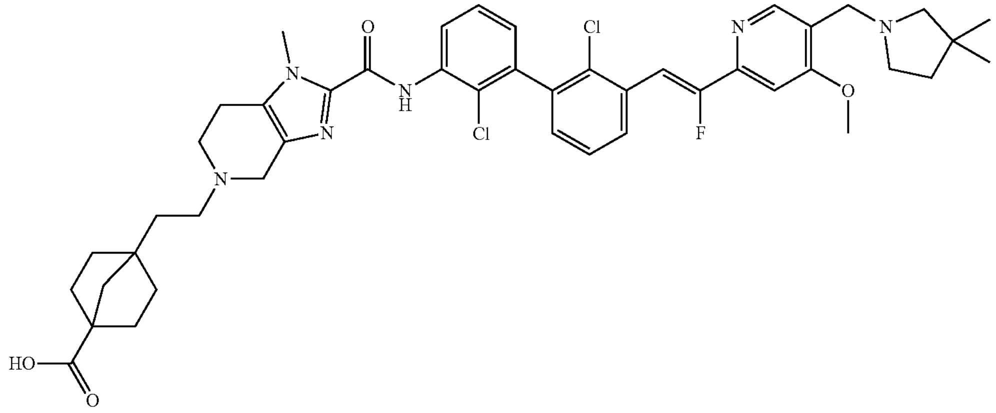
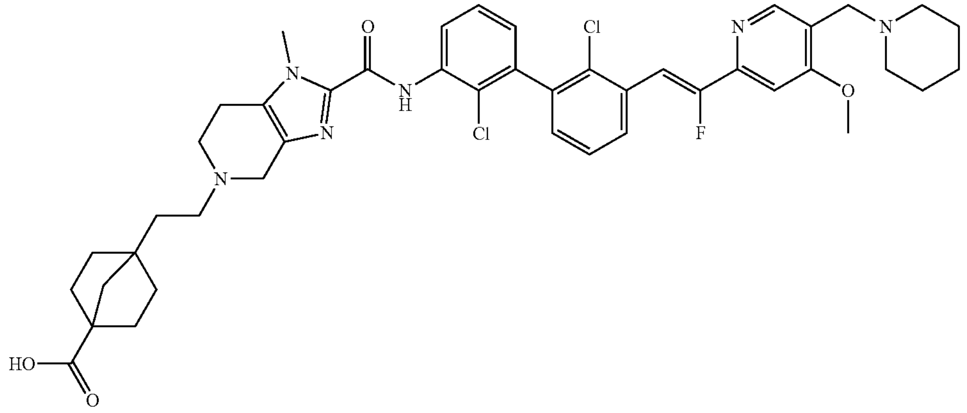
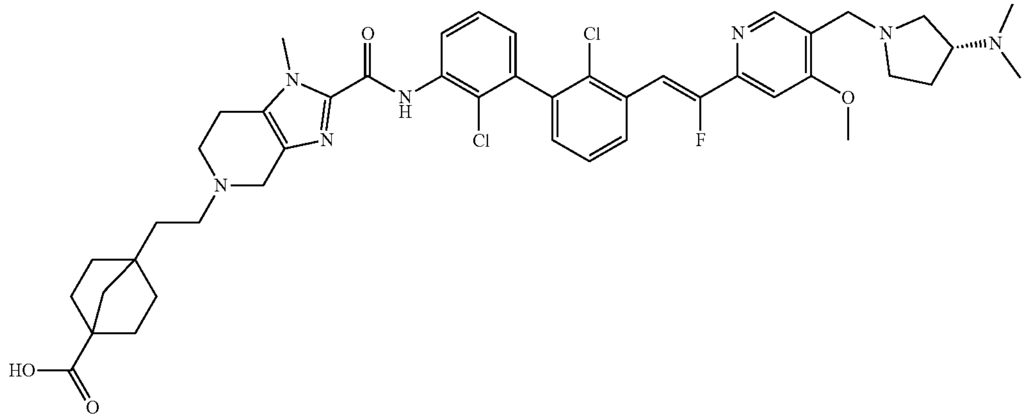

-continued
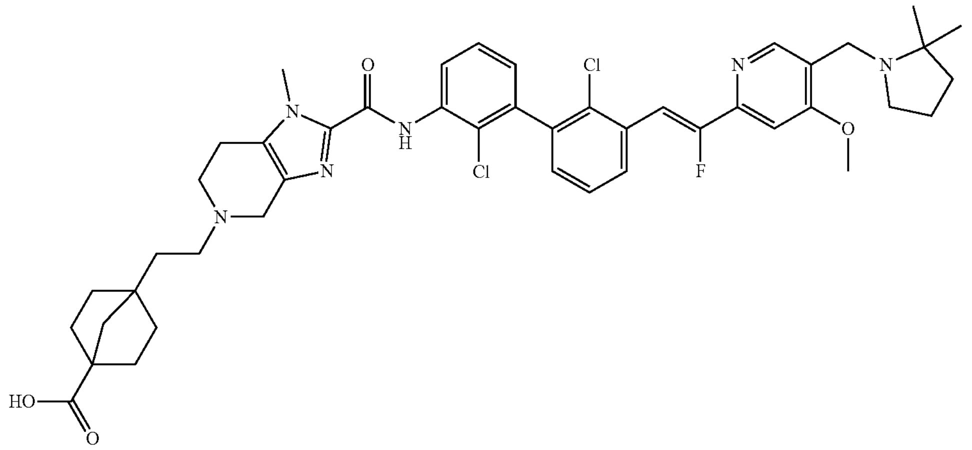
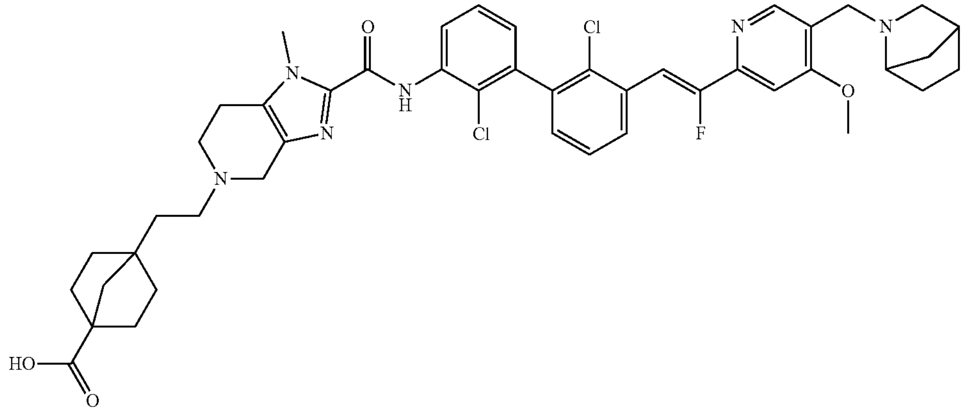
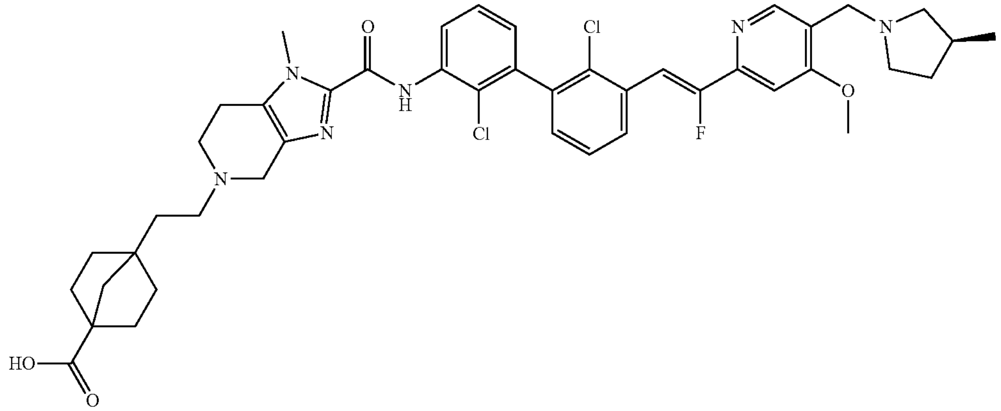
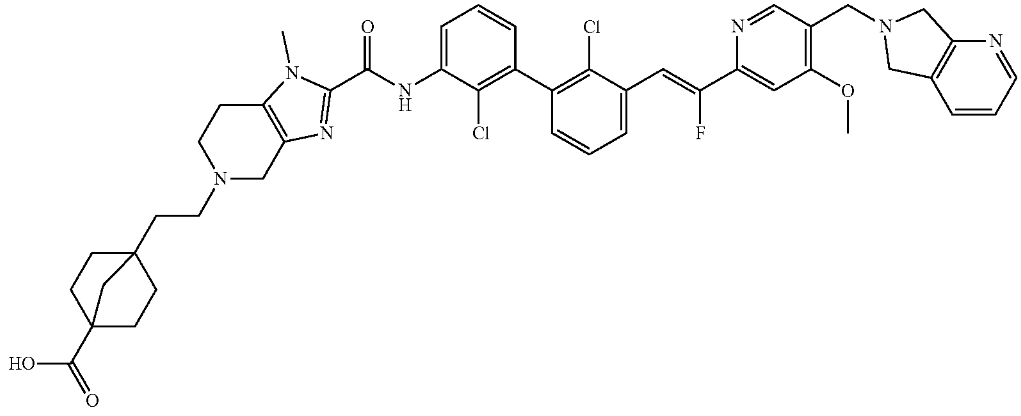

-continued
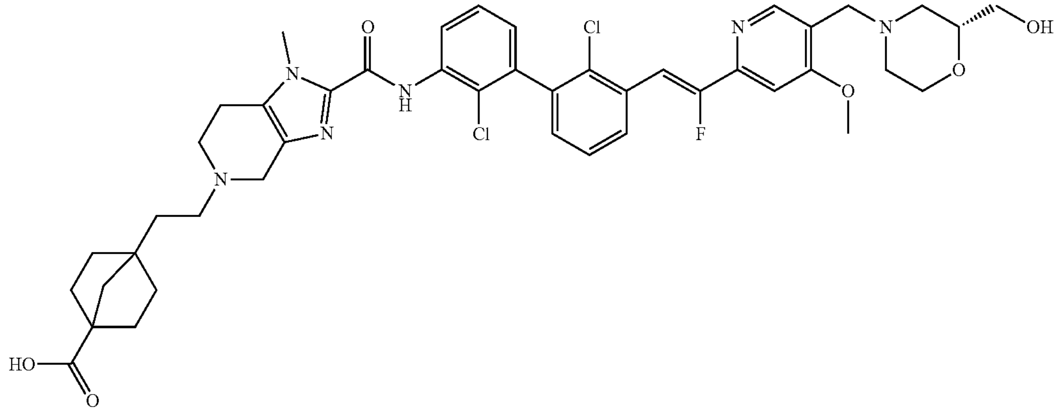
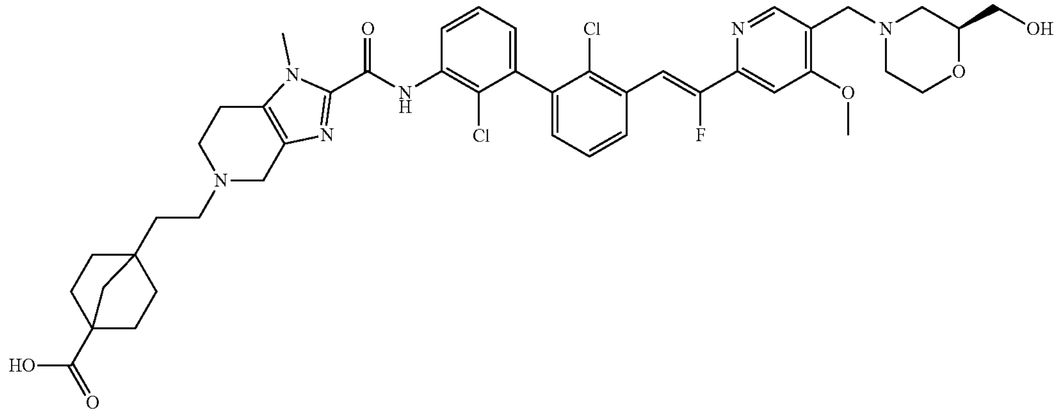
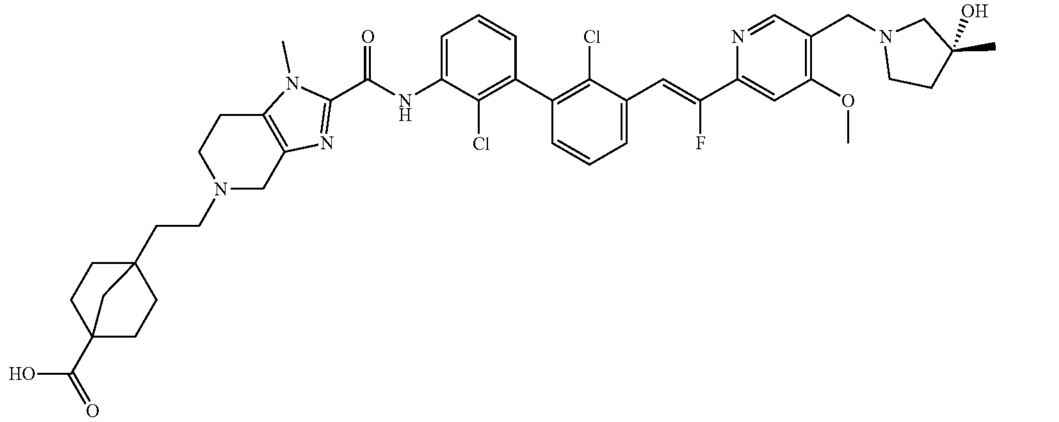
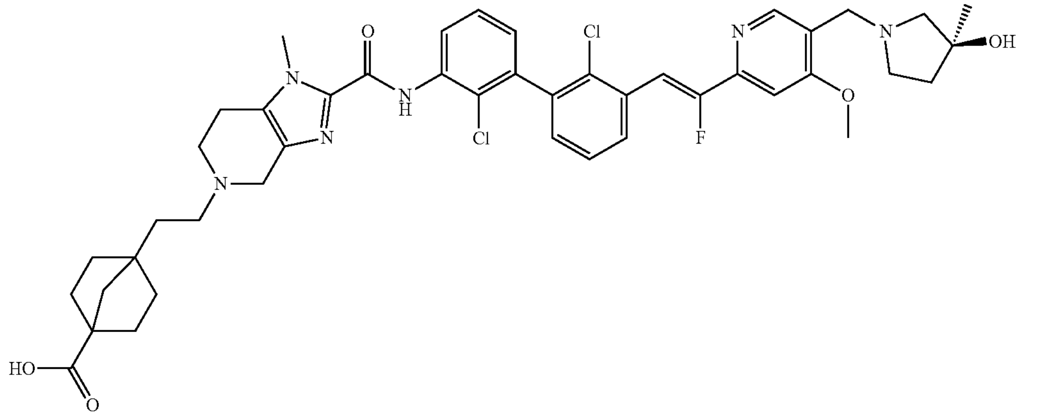

-continued
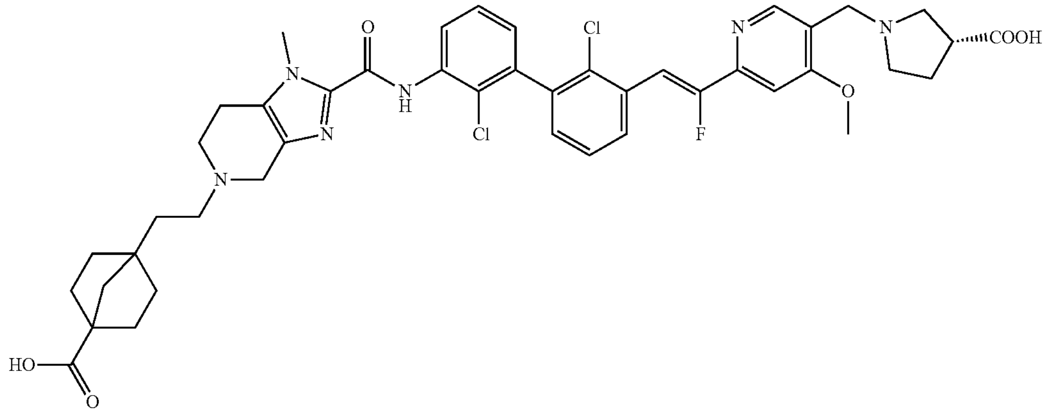
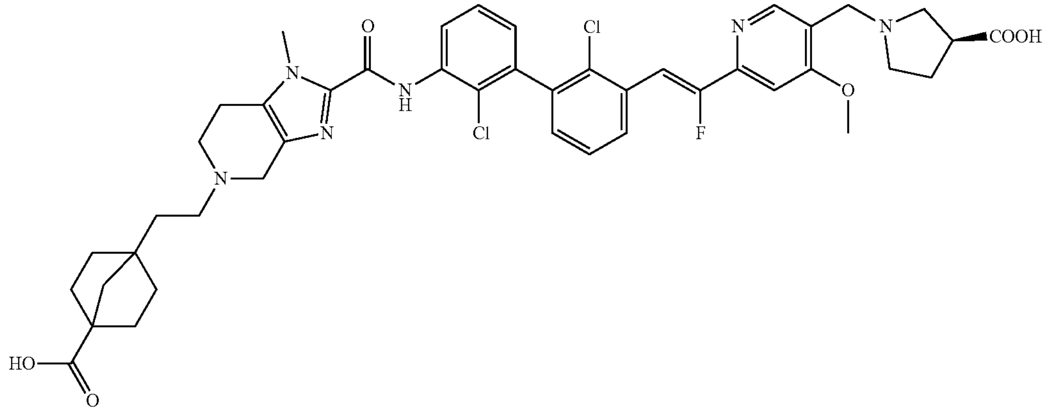
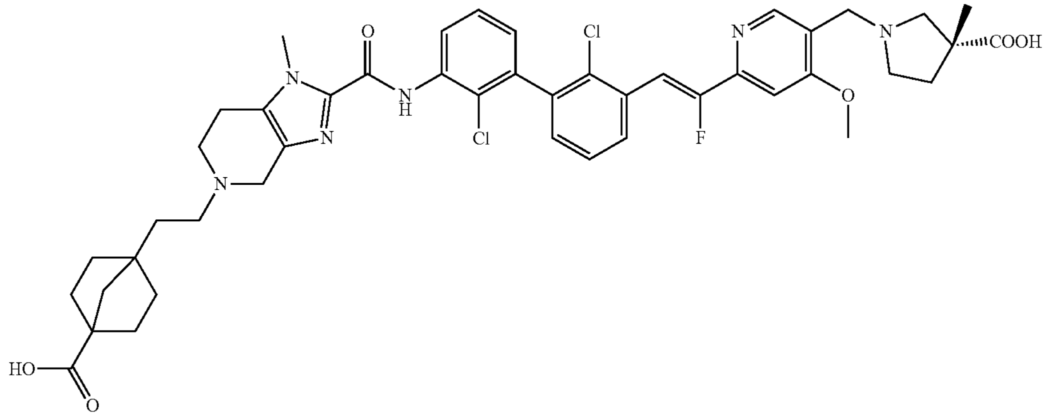
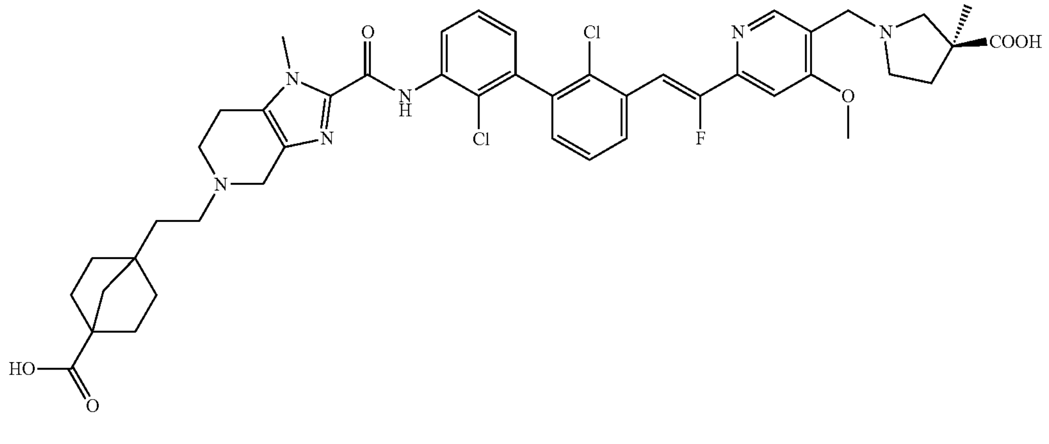
or

-continued

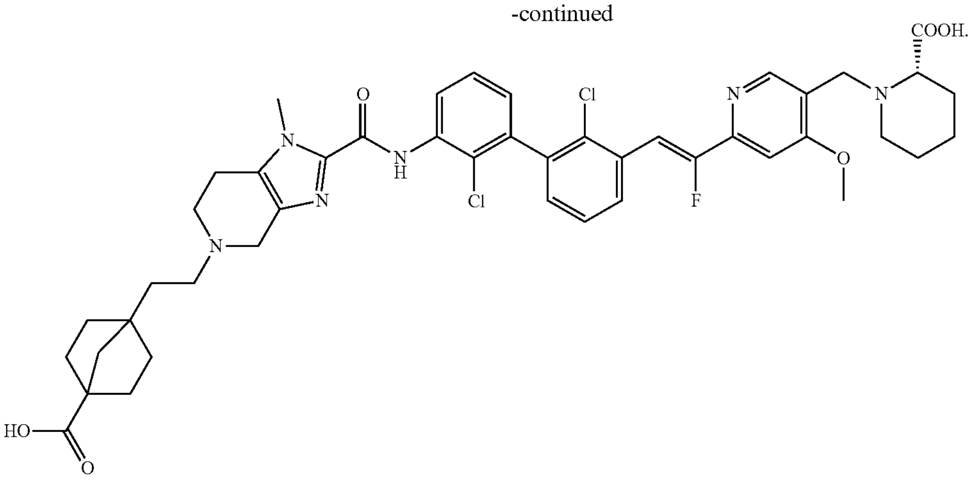

10. A process for preparing the compound of formula (I), the stereoisomer, prodrug or pharmaceutically acceptable salt thereof according to claim 1, comprising the following steps:

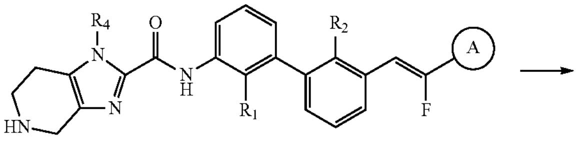

(I')

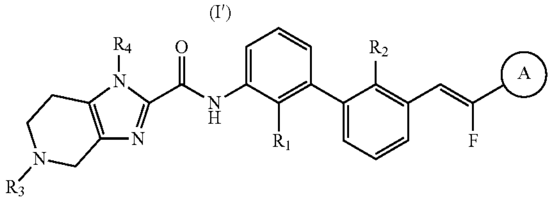

(I)

optionally, further reaction is carried out according to the different substituents to obtain corresponding compound of formula (I).

11. A pharmaceutical composition, comprising the compound of formula (I), the stereoisomer, prodrug or pharmaceutically acceptable salt thereof according to claim 1, and a pharmaceutically acceptable carrier.

12. A method for preventing and/or treating PD-1/PD-L1 signal pathway-mediated disease comprising administering a subject in need thereof the compound of formula (I), the stereoisomer, prodrug or pharmaceutically acceptable salt thereof according to claim 1, wherein the PD-1/PD-L1 signal pathway-mediated disease is cancer or tumor, immune-related disease and disorder, infectious disease or metabolic disease.

13. The method according to claim 12, wherein, the infectious disease is selected from bacterial infectious disease, viral infectious disease, or fungal infectious disease;

the cancer or tumor is selected from the group consisting of lymphoma, sarcoma, melanoma, glioblastoma, synovioma, meningioma, biliary tract tumor, thymic tumor, neuroma, seminoma, nephroblastoma, pleomorphic adenoma, hepatocellular papilloma, renal tubule adenoma, cystadenoma, papilloma, adenoma, leiomyoma, rhabdomyoma, hemangioma, lymphangioma, osteoma, chondroma, lipoma, fibroma, central nervous system tumor, rhachiophyma, brain stem glioma, pituitary adenoma, multiple myeloma, ovarian tumor, myelodysplastic syndrome or mesothelioma, prostate cancer, recurrent prostate cancer or prostate cancer having resistance to existing medicaments, thyroid cancer, parathyroid cancer, anal cancer, testicular cancer, urethral carcinoma, penile cancer, bladder cancer, ureteral cancer, uterine cancer, ovarian cancer, fallopian tube cancer, endometrial cancer, cervical cancer, vaginal cancer, vulvar cancer, adrenal cancer, Merkel cell carcinoma, embryonal carcinoma, chronic or acute leukemia, bronchial carcinoma, esophageal cancer, nasopharyngeal carcinoma, hepatocellular carcinoma, renal cell carcinoma, small cell lung cancer, basal cell carcinoma, lung cancer, breast cancer, adenocarcinoma, papillary carcinoma, cystadenocarcinoma, squamous non-small cell lung cancer, non-squamous non-small cell lung cancer, rectal cancer, colon cancer, colorectal cancer, gastric cancer, pancreatic cancer, head and neck squamous cell carcinoma, head and neck cancer, gastrointestinal cancer, bone cancer, skin cancer, small intestine cancer, endocrine cancer, renal pelvic carcinoma, epidermoid carcinoma, abdominal wall carcinoma, renal cell carcinoma, transitional cell carcinoma, choriocarcinoma, and metastatic tumor;

the immune-related disease and disorder is selected from the group consisting of rheumatic arthritis, renal failure, lupus erythematosus, asthma, psoriasis, ulcerative colitis, pancreatitis, allergy, fibrosis, anemia, fibromyalgia, Alzheimer's disease, congestive heart failure, stroke, aortic valve stenosis, arteriosclerosis, osteoporosis, Parkinson's disease, infection, Crohn's disease, ulcerative colitis, allergic contact dermatitis and eczema, systemic sclerosis or multiple sclerosis;

the infectious disease is selected from the group consisting of sepsis, liver infection, HIV, hepatitis A, hepatitis B, hepatitis C, hepatitis D, herpes virus, papillomavirus or influenza; or the metabolic disease is selected from the group consisting of diabetes, diabetic ketoacidosis, hyperglycemic hyperosmolar syndrome, hypoglycemia, gout, malnutrition, vitamin A deficiency, scurvy, vitamin D deficiency or osteoporosis.

14. The method according to claim 13, wherein, the lymphoma is lymphocytic lymphoma, primary central nervous system lymphoma, T cell lymphoma, diffuse large B cell lymphoma, follicle center lymphoma, Hodgkin lymphoma, non-Hodgkin lymphoma or primary mediastinal large B cell lymphoma;

the sarcoma is Kaposi's sarcoma, fibrosarcoma, liposarcoma, chondrosarcoma, osteosarcoma, leiomyosarcoma, rhabdomyosarcoma, soft tissue sarcoma, angiosarcoma or lymphangiosarcoma;

the chronic or acute leukemia is acute myeloid leukemia, chronic myeloid leukemia, acute lymphoblastic leukemia, chronic granulocytic leukemia or chronic lymphoblastic leukemia; and the metastatic tumor is metastatic tumor expressing PD-L1.

15. The compound of formula (I), the stereoisomer, prodrug or pharmaceutically acceptable salt thereof according to claim 1, wherein, $R_{5a}$ is hydrogen or $C_{1-4}$ alkyl, $R_{5b}$ is selected from the group consisting of hydrogen, deuterium, hydroxy, $C_{1-4}$ alkyl, $C_{2-4}$ alkenyl, $C_{2-4}$ alkynyl, $C_{3-10}$ cycloalkyl, 3-10 membered heterocyclyl, $C_{5-8}$ aryl and 5-8 membered heteroaryl, or $R_{5a}$ and $R_{5b}$, together with the nitrogen atom directly attached thereto, form 4-8 membered heterocyclyl, the formed 4-8 membered heterocyclyl is fused to $C_{5-8}$ aryl or 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, =O, —$S(O)_rR_9$, —O—$R_{10}$, —$C(O)OR_{10}$, —$C(O)R_{11}$, —O—$C(O)R_{11}$, —$NR_{12}R_{13}$, —$C(=NR_{12})R_{11}$, —$N(R_{12})$—$C(=NR_{13})R_{11}$, —$C(O)NR_{12}R_{13}$ and —$N(R_{12})$—$C(O)R_{11}$, above groups are optionally more further substituted by one or more substituents selected from the group consisting of deuterium, halogen, cyano, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —$S(O)_rR_9$, —O—$R_{10}$, —$C(O)OR_{10}$, —$C(O)R_{11}$, —O—$C(O)R_{11}$, —$NR_{12}R_{13}$, —$C(=NR_{12})R_{11}$, —$N(R_{12})$—$C(=NR_{13})R_{11}$, —$C(O)NR_{12}R_{13}$ and —$N(R_{12})$—$C(O)R_{11}$;

$R_6$ is selected from the group consisting of hydrogen, deuterium, halogen, cyano, hydroxy, carboxyl, $C_{1-4}$ alkyl, $C_{3-6}$ cycloalkyl and $C_{1-4}$ alkoxy, above groups are optionally further substituted by one or more substituents selected from the group consisting of deuterium, halogen, cyano, cyclopropyl, hydroxy and $C_{1-4}$ alkoxy;

$R_7$ is selected from the group consisting of hydrogen, deuterium, hydroxy, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl and 5-8 membered heteroaryl, above groups are optionally further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{3-8}$ cycloalkyl, 3-8 membered heterocyclyl, $C_{5-8}$ aryl, 5-8 membered heteroaryl, =O, —$C_{0-4}$—$S(O)_rR_9$, —$C_{0-4}$—O—$R_{10}$, —$C_{0-4}$—$C(O)OR_{10}$, —$C_{0-4}$—$C(O)R_{11}$, —$C_{0-4}$—O—$C(O)R_{11}$, —$C_{0-4}$—$NR_{12}R_{13}$, —$C_{0-4}$—$C(=NR_{12})R_{11}$, —$C_{0-4}$—$N(R_{12})$—$C(=NR_{13})R_{11}$, —$C_{0-4}$—$C(O)NR_{12}R_{13}$ and —$C_{0-4}$—$N(R_{12})$—$C(O)R_{11}$, above groups are optionally more further substituted by one or more substituents selected from the group consisting of deuterium, halogen, cyano, nitro, azido, $C_{1-4}$ alkyl, $C_{2-4}$ alkenyl, $C_{2-4}$ alkynyl, $C_{1-4}$ haloalkyl, $C_{1-4}$ deuterioalkyl, $C_{3-8}$ cycloalkyl, 3-8 membered heterocyclyl, $C_{5-8}$ aryl, 5-8 membered heteroaryl, =O, —$C_{0-4}$—$S(O)_rR_9$, —$C_{0-4}$—O—$R_{10}$, —$C_{0-4}$—$C(O)OR_{10}$, —$C_{0-4}$—$C(O)R_{11}$, —$C_{0-4}$—O—$C(O)R_{11}$, —$C_{0-4}$—$NR_{12}R_{13}$, —$C_{0-4}$—$C(=NR_{12})R_{11}$, —$C_{0-4}$—$N(R_{12})$—$C(=NR_{13})R_{11}$, —$C_{0-4}$—$C(O)NR_{12}R_{13}$ and —$C_{0-4}$—$N(R_{12})$—$C(O)R_{11}$; and $R_8$ is selected from the group consisting of hydrogen, deuterium, hydroxy, $C_{1-4}$ alkyl, and $C_{3-6}$ cycloalkyl, above groups are optionally further substituted by one or more substituents selected from the group consisting of deuterium, halogen, cyano, cyclopropyl, hydroxy and $C_{1-4}$ alkoxy.

* * * * *